(12) United States Patent
Perez et al.

(10) Patent No.: US 12,011,485 B2
(45) Date of Patent: Jun. 18, 2024

(54) SULFOMALEIMIDE-BASED LINKERS AND CORRESPONDING CONJUGATES

(71) Applicant: PIERRE FABRE MEDICAMENT, Boulogne-Billancourt (FR)

(72) Inventors: Michel Perez, Castres (FR); Frédéric Marion, Toulouse (FR); Jean-François Haeuw, Beaumont (FR); Cyrille Dreyfus, Amancy (FR)

(73) Assignee: PIERRE FABRE MEDICAMENT, Paris (FR)

( * ) Notice: Subject to any disclaimer, the term of this patent is extended or adjusted under 35 U.S.C. 154(b) by 698 days.

(21) Appl. No.: 17/280,800

(22) PCT Filed: Sep. 27, 2019

(86) PCT No.: PCT/IB2019/001114
§ 371 (c)(1),
(2) Date: Mar. 26, 2021

(87) PCT Pub. No.: WO2020/065408
PCT Pub. Date: Apr. 2, 2020

(65) Prior Publication Data
US 2022/0023438 A1    Jan. 27, 2022

(30) Foreign Application Priority Data

Sep. 27, 2018    (EP) .................................... 18306270

(51) Int. Cl.
*A61K 47/68* (2017.01)
*A61K 38/07* (2006.01)
(Continued)

(52) U.S. Cl.
CPC .......... *A61K 47/6849* (2017.08); *A61K 38/07* (2013.01); *A61K 38/12* (2013.01);
(Continued)

(58) Field of Classification Search
None
See application file for complete search history.

(56) References Cited

U.S. PATENT DOCUMENTS 4,127,687 A * 11/1978 Dupont ................ C09D 5/1625
106/18.32
5,530,101 A    6/1996 Queen et al.
(Continued)

FOREIGN PATENT DOCUMENTS

CN    101397280 A    4/2009
CN    104230916 A    12/2014
(Continued)

OTHER PUBLICATIONS

Alley et al., "Contribution of Linker Stability to the Activities of Anticancer Immunoconjugates," Bioconjugate Chemistry, vol. 19, No. 3, 2008, pp. 759-765.
(Continued)

*Primary Examiner* — Karl J Puttlitz
(74) *Attorney, Agent, or Firm* — Birch, Stewart, Kolasch & Birch, LLP

(57) ABSTRACT

The present invention relates to a linker of the following formula (I) or a salt thereof: (I). The present invention relates to a linker-drug conjugate of the following formula (II) or a salt thereof: (II). The present invention relates also to a binding unit-drug corrugate, such as an antibody-drug conjugate, of the following formula (III) or (IV) or a salt thereof: (III), (IV), as well as a pharmaceutical composition comprising such a binding unit-drug corrugate and its use in the treatment of cancer.

(Continued)

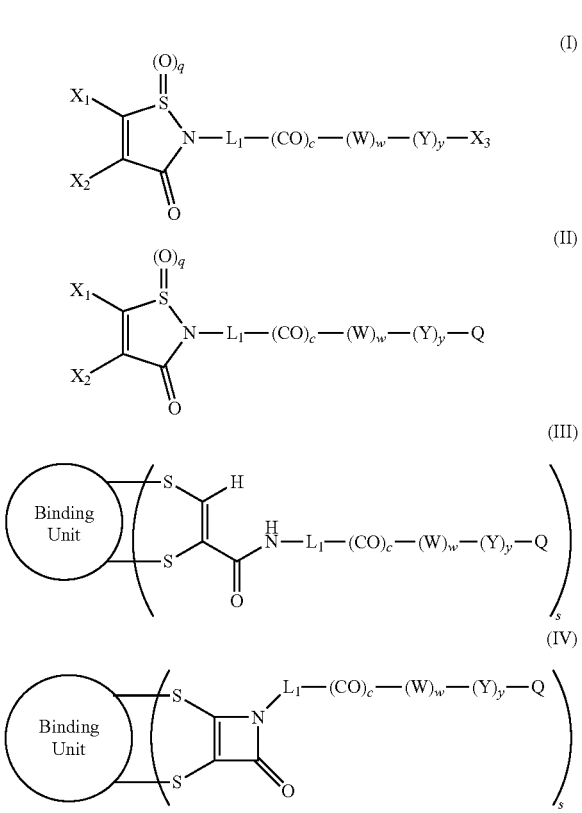

18 Claims, 35 Drawing Sheets

Specification includes a Sequence Listing.

(51) Int. Cl.
A61K 38/12 (2006.01)
A61K 47/54 (2017.01)
A61P 35/00 (2006.01)

(52) U.S. Cl.
CPC ........ A61K 47/545 (2017.08); A61K 47/6809 (2017.08); A61K 47/6811 (2017.08); A61P 35/00 (2018.01)

(56) References Cited

U.S. PATENT DOCUMENTS

| | | | |
|---|---|---|---|
| 5,554,542 A * | 9/1996 | Willingham | G01N 33/54353 436/815 |
| 5,585,089 A | 12/1996 | Queen et al. | |
| 5,639,641 A | 6/1997 | Pedersen et al. | |
| 5,693,761 A | 12/1997 | Queen et al. | |
| 5,877,293 A | 3/1999 | Adair et al. | |
| 5,886,152 A | 3/1999 | Nakatani et al. | |
| 6,054,297 A | 4/2000 | Carter et al. | |
| 6,180,370 B1 | 1/2001 | Queen et al. | |
| 2009/0027774 A1 * | 1/2009 | Sano | C09B 67/0079 106/18.33 |
| 2017/0174689 A1 | 6/2017 | Lee et al. | |

FOREIGN PATENT DOCUMENTS

| | | |
|---|---|---|
| EP | 0 682 040 A1 | 11/1995 |
| EP | 0 939 127 A2 | 9/1999 |
| JP | 4-248881 A | 9/1992 |
| JP | 4-261476 A | 9/1992 |
| JP | 7-294522 A | 11/1995 |
| JP | 2017-510641 A | 4/2017 |
| WO | WO 90/07861 A1 | 7/1990 |
| WO | WO 92/11018 A1 | 7/1992 |
| WO | WO 2006/095622 A1 | 9/2006 |
| WO | 2007001932 * | 1/2007 |
| WO | WO 2007/001932 A2 | 1/2007 |
| WO | WO 2014/174064 A1 | 10/2014 |
| WO | WO 2014/179335 A1 | 11/2014 |
| WO | WO 2014/197866 A1 | 12/2014 |
| WO | WO 2015/151078 A4 | 10/2015 |
| WO | WO 2015/162291 A1 | 10/2015 |
| WO | WO 2015/162293 A1 | 10/2015 |
| WO | WO 2016/059622 A2 | 4/2016 |
| WO | WO 2016/064749 A2 | 4/2016 |
| WO | WO 2016/096174 A1 | 6/2016 |
| WO | WO 2016/145102 A1 | 9/2016 |
| WO | WO 2017/106740 A1 | 6/2017 |
| WO | WO 2018/100558 A2 | 6/2018 |

OTHER PUBLICATIONS

Ghizzoni et al., "Reactivity of isothiazolones and isothiazolone-1-oxides in the inhibition of the PCAF histone acetyltransferase," European Journal of Medicinal Chemistry, vol. 44, No. 12, 2009, pp. 4855-4861.

Haeuw et al., "Proteomics for development of immunotherapies." In Proteomics: Biomedical and Pharmaceutical Applications, Kluwer Academic Publishers, Ed. Hondermarck H., 2014, pp. 243-278.

Kaas et al., "IMGT Colliers de Perles: Standardized Sequence-Structure Representations of the IgSF and MhcSF Superfamily Domains," Current Bioinformatics, vol. 2, No. 1, 2007, pp. 21-30.

Kaas et al., "IMGT/3Dstructure-DB and IMGT/StructuralQuery, a database and a tool for immunoglobulin, T cell receptor and MHC structural data," Nucleic Acids Research, vol. 32, 2004, pp. D208-D210.

Lefranc et al., "IMGT unique numbering for immunoglobulin and T cell receptor variable domains and Ig superfamily V-like domains," Developmental and Comparative Immunology, vol. 27, 2003, pp. 55-77.

Lefranc, "The IMGT Unique Numbering for Immunoglobulins, T-Cell Receptors, and Ig-Like Domains," The Immunologist, vol. 7, No. 4. 1999, pp. 132-136.

Lefranc, "Unique database numbering system for immunogenetic analysis," Immunology Today, vol. 18, No. 11, 1997, p. 509.

Lioux et al., "Design, Synthesis, and Biological Evaluation of Novel Cyclic Adenosine-Inosine Monophosphate (cAIMP) Analogs That Activate Stimulator of Interferon Genes (STING)," Journal of Medicinal Chemistry, vol. 59, No. 22, 2016 (published Oct. 26, 2016), pp. 10253-10267.

Neddleman et al., "A General Method Applicable to the Search for Similarities in the Amino Acid Sequence of Two Proteins," J. Mol. Biol., vol. 48, 1970, pp. 443-453.

Pearson et al., "Improved tools for biological sequence comparison," Proc. Natl. Acad. Sci. USA, vol. 85, Apr. 1988, pp. 2444-2448.

Ruiz et al., "IMGT gene identification and Colliers de Perles of human immunoglobulins with known 3D structures," Immunogenetics, vol. 53, 2002 (published online Jan. 30, 2002), pp. 857-883.

Smith et al., "Comparison of Biosequences," Advances in Applied Mathmatics, vol. 2, 1981, pp. 482-489.

Tatusova et al., "Blast 2 sequences, a new tool for comparing protein and nucleotide sequences," FEMS Microbiology Letters, vol. 174, 1999, pp. 247-250.

Wisastra et al., "Isothiazolones; thiol-reactive inhibitors of cysteine protease cathepsin B and histone acetyltransferase PCAF," Organic & Biomolecular Chemistry, vol. 9, No. 6. 2011, pp. 1817-1822.

* cited by examiner

SEQUENCE LISTING

```
<160> NUMBER OF SEQ ID NOS: 81

<210> SEQ ID NO 1
<211> LENGTH: 8
<212> TYPE: PRT
<213> ORGANISM: artificial
<220> FEATURE:
<223> OTHER INFORMATION: Consensus CDR -H1
<220> FEATURE:
<221> NAME/KEY: MISC_FEATURE
<222> LOCATION: (3)..(3)
<223> OTHER INFORMATION: Thr may be replaced by Ser
<220> FEATURE:
<221> NAME/KEY: MISC_FEATURE
<222> LOCATION: (8)..(8)
<223> OTHER INFORMATION: Tyr may be replaced by Phe

<400> SEQUENCE: 1

Gly Tyr Thr Phe Thr Ser Tyr Tyr
1               5

<210> SEQ ID NO 2
<211> LENGTH: 8
<212> TYPE: PRT
<213> ORGANISM: artificial
<220> FEATURE:
<223> OTHER INFORMATION: Consensus CDR-H2

<400> SEQUENCE: 2

Ile Trp Pro Gly Asp Gly Ser Thr
1               5

<210> SEQ ID NO 3
<211> LENGTH: 13
<212> TYPE: PRT
<213> ORGANISM: artificial
<220> FEATURE:
<223> OTHER INFORMATION: Consensus CDR-H3

<400> SEQUENCE: 3

Ala Ser Pro Met Ile Thr Pro Asn Tyr Ala Met Asp Tyr
1               5                   10

<210> SEQ ID NO 4
<211> LENGTH: 6
<212> TYPE: PRT
<213> ORGANISM: artificial
<220> FEATURE:
<223> OTHER INFORMATION: Consensus CDR-L1
<220> FEATURE:
<221> NAME/KEY: MISC_FEATURE
<222> LOCATION: (4)..(4)
<223> OTHER INFORMATION: Ser may be replaced by Asn

<400> SEQUENCE: 4

Gln Asp Ile Ser Lys Tyr
1               5
```

-continued

```
<210> SEQ ID NO 5
<211> LENGTH: 3
<212> TYPE: PRT
<213> ORGANISM: artificial
<220> FEATURE:
<223> OTHER INFORMATION: Consensus CDR-L2

<400> SEQUENCE: 5

Tyr Thr Ser
1

<210> SEQ ID NO 6
<211> LENGTH: 9
<212> TYPE: PRT
<213> ORGANISM: artificial
<220> FEATURE:
<223> OTHER INFORMATION: Consensus CDR-L3
<220> FEATURE:
<221> NAME/KEY: MISC_FEATURE
<222> LOCATION: (5)..(5)
<223> OTHER INFORMATION: Thr may be replaced by Ala

<400> SEQUENCE: 6

Gln Gln Gly Ser Thr Leu Pro Tyr Thr
1               5

<210> SEQ ID NO 7
<211> LENGTH: 8
<212> TYPE: PRT
<213> ORGANISM: artificial
<220> FEATURE:
<223> OTHER INFORMATION: CDR-H1

<400> SEQUENCE: 7

Gly Tyr Thr Phe Thr Ser Tyr Tyr
1               5

<210> SEQ ID NO 8
<211> LENGTH: 8
<212> TYPE: PRT
<213> ORGANISM: artificial
<220> FEATURE:
<223> OTHER INFORMATION: CDR-H1

<400> SEQUENCE: 8

Gly Tyr Ser Phe Thr Ser Tyr Phe
1               5

<210> SEQ ID NO 9
<211> LENGTH: 6
<212> TYPE: PRT
<213> ORGANISM: artificial
<220> FEATURE:
<223> OTHER INFORMATION: CDR-L1

<400> SEQUENCE: 9

Gln Asp Ile Ser Lys Tyr
1               5

<210> SEQ ID NO 10
<211> LENGTH: 6
<212> TYPE: PRT
<213> ORGANISM: artificial
<220> FEATURE:
<223> OTHER INFORMATION: CDR-L1

<400> SEQUENCE: 10

Gln Asp Ile Asn Lys Tyr
```

<210> SEQ ID NO 11
<211> LENGTH: 9
<212> TYPE: PRT
<213> ORGANISM: artificial
<220> FEATURE:
<223> OTHER INFORMATION: CDR-L3

<400> SEQUENCE: 11

Gln Gln Gly Ser Thr Leu Pro Tyr Thr
1               5

<210> SEQ ID NO 12
<211> LENGTH: 9
<212> TYPE: PRT
<213> ORGANISM: artificial
<220> FEATURE:
<223> OTHER INFORMATION: CDR-L3

<400> SEQUENCE: 12

Gln Gln Gly Ser Ala Leu Pro Tyr Thr
1               5

<210> SEQ ID NO 13
<211> LENGTH: 120
<212> TYPE: PRT
<213> ORGANISM: artificial
<220> FEATURE:
<223> OTHER INFORMATION: c208F2, heavy chain, VH

<400> SEQUENCE: 13

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Lys Asp Lys Thr Thr Leu Thr Ala Asp Lys Ser Ser Asn Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser
        115                 120

<210> SEQ ID NO 14
<211> LENGTH: 120
<212> TYPE: PRT
<213> ORGANISM: artificial
<220> FEATURE:
<223> OTHER INFORMATION: c212A11, heavy chain, VH

<400> SEQUENCE: 14

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile

```
            35                  40                  45

Gly Trp Ile Trp Pro Gly Asp Gly Ser Thr Lys Tyr Asn Glu Lys Phe
 50                  55                  60

Lys Gly Lys Thr Thr Leu Thr Ala Asp Lys Ser Ser Thr Ala Tyr
 65                  70                  75                  80

Met Phe Leu Ser Ser Leu Thr Ser Glu Asp Ser Ala Val Tyr Phe Cys
                 85                  90                  95

Ala Ser Pro Met Ile Thr Pro Asn Tyr Ala Met Asp Tyr Trp Gly Gln
                100                 105                 110

Gly Ala Ser Val Thr Val Ser Ser
            115                 120

<210> SEQ ID NO 15
<211> LENGTH: 120
<212> TYPE: PRT
<213> ORGANISM: artificial
<220> FEATURE:
<223> OTHER INFORMATION: c214F8, heavy chain, VH

<400> SEQUENCE: 15

Gln Val Gln Leu Gln Gln Ser Gly Ser Glu Leu Val Lys Pro Gly Ala
 1               5                   10                  15

Ser Val Lys Leu Ser Cys Lys Ala Ser Gly Tyr Thr Phe Thr Ser Tyr
                20                  25                  30

Tyr Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Arg Phe
 50                  55                  60

Lys Gly Lys Thr Thr Leu Thr Ala Asp Lys Ser Ser Thr Ala Tyr
 65                  70                  75                  80

Met Phe Leu Ser Ser Leu Thr Ser Glu Asp Ser Ala Val Tyr Phe Cys
                 85                  90                  95

Ala Ser Pro Met Ile Thr Pro Asn Tyr Ala Met Asp Tyr Trp Gly Gln
                100                 105                 110

Gly Ala Ser Val Thr Val Ser Ser
            115                 120

<210> SEQ ID NO 16
<211> LENGTH: 120
<212> TYPE: PRT
<213> ORGANISM: artificial
<220> FEATURE:
<223> OTHER INFORMATION: c219D6, heavy chain, VH

<400> SEQUENCE: 16

Gln Val Gln Leu Gln Gln Ser Gly Pro Glu Leu Val Lys Pro Gly Asp
 1               5                   10                  15

Ser Val Lys Met Ser Cys Lys Ala Ser Gly Tyr Ser Phe Thr Ser Tyr
                20                  25                  30

Phe Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Lys Phe
 50                  55                  60

Lys Gly Lys Thr Thr Leu Thr Asp Lys Ser Ser Ser Thr Ala Tyr
 65                  70                  75                  80

Met Phe Leu Asn Ser Leu Thr Ser Glu Asp Ser Ala Val Tyr Phe Cys
                 85                  90                  95
```

```
Ala Ser Pro Met Ile Thr Pro Asn Tyr Ala Met Asp Tyr Trp Gly Gln
            100                 105                 110

Gly Ala Ser Val Thr Val Ser Ser
        115                 120
```

<210> SEQ ID NO 17
<211> LENGTH: 120
<212> TYPE: PRT
<213> ORGANISM: artificial
<220> FEATURE:
<223> OTHER INFORMATION: c213B10, heavy chain, VH

<400> SEQUENCE: 17

```
Gln Val Gln Leu Gln Gln Ser Gly Ser Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Arg Phe
    50                  55                  60

Lys Gly Lys Thr Thr Leu Thr Ala Asp Lys Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser
        115                 120
```

<210> SEQ ID NO 18
<211> LENGTH: 107
<212> TYPE: PRT
<213> ORGANISM: artificial
<220> FEATURE:
<223> OTHER INFORMATION: c208F2, light chain, VL

<400> SEQUENCE: 18

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Val Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105
```

<210> SEQ ID NO 19
<211> LENGTH: 107
<212> TYPE: PRT
<213> ORGANISM: artificial
<220> FEATURE:
<223> OTHER INFORMATION: c212A11, light chain, VL

```
<400> SEQUENCE: 19

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 20
<211> LENGTH: 107
<212> TYPE: PRT
<213> ORGANISM: artificial
<220> FEATURE:
<223> OTHER INFORMATION: c214F8, light chain, VL

<400> SEQUENCE: 20

Asp Ile Gln Met Thr Gln Thr Thr Ser Ser Leu Ser Ala Ser Leu Gly
1               5                   10                  15

Asp Arg Val Thr Phe Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys
            100                 105

<210> SEQ ID NO 21
<211> LENGTH: 107
<212> TYPE: PRT
<213> ORGANISM: artificial
<220> FEATURE:
<223> OTHER INFORMATION: c219D6, light chain, VL

<400> SEQUENCE: 21

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Glu Gln
65                  70                  75                  80
```

```
Glu Asp Ile Ala Thr Tyr Phe Cys Gln Gln Gly Ser Thr Leu Pro Tyr
             85                  90                  95

Thr Phe Gly Gly Gly Thr Lys Leu Glu Ile Lys
            100                 105

<210> SEQ ID NO 22
<211> LENGTH: 107
<212> TYPE: PRT
<213> ORGANISM: artificial
<220> FEATURE:
<223> OTHER INFORMATION: c213B10, light chain, VL

<400> SEQUENCE: 22

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
             85                  90                  95

Thr Phe Gly Gly Gly Thr Lys Leu Glu Ile Lys
            100                 105

<210> SEQ ID NO 23
<211> LENGTH: 449
<212> TYPE: PRT
<213> ORGANISM: artificial
<220> FEATURE:
<223> OTHER INFORMATION: c208F2, heavy chain, full length

<400> SEQUENCE: 23

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Leu
        35                  40                  45

Gly Trp Ile Trp Pro Gly Asp Gly Ser Thr Lys Tyr Asn Glu Lys Phe
50                  55                  60

Lys Asp Lys Thr Thr Leu Thr Ala Asp Lys Ser Ser Asn Thr Ala Tyr
65                  70                  75                  80

Met Phe Leu Ser Ser Leu Thr Ser Glu Asp Ser Ala Val Tyr Phe Cys
             85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175
```

-continued

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 24
<211> LENGTH: 449
<212> TYPE: PRT
<213> ORGANISM: artificial
<220> FEATURE:
<223> OTHER INFORMATION: c212A11, heavy chain, full length

<400> SEQUENCE: 24

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Lys Phe
        50                  55                  60

Lys Gly Lys Thr Thr Leu Thr Ala Asp Lys Ser Ser Ser Thr Ala Tyr
65                  70                  75                  80
```

```
Met Phe Leu Ser Ser Leu Thr Ser Glu Asp Ser Ala Val Tyr Phe Cys
                 85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 25
<211> LENGTH: 449
<212> TYPE: PRT
<213> ORGANISM: artificial
<220> FEATURE:
<223> OTHER INFORMATION: c214F8, heavy chain, full length
```

```
<400> SEQUENCE: 25

Gln Val Gln Leu Gln Gln Ser Gly Ser Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Arg Phe
    50                  55                  60

Lys Gly Lys Thr Thr Leu Thr Ala Asp Lys Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

-continued

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 26
<211> LENGTH: 449
<212> TYPE: PRT
<213> ORGANISM: artificial
<220> FEATURE:
<223> OTHER INFORMATION: c219D6, heavy chain, full length

<400> SEQUENCE: 26

Gln Val Gln Leu Gln Gln Ser Gly Pro Glu Leu Val Lys Pro Gly Asp
1               5                   10                  15

Ser Val Lys Met Ser Cys Lys Ala Ser Gly Tyr Ser Phe Thr Ser Tyr
                20                  25                  30

Phe Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Lys Phe
50                  55                  60

Lys Gly Lys Thr Thr Leu Thr Thr Asp Lys Ser Ser Ser Thr Ala Tyr
65                  70                  75                  80

Met Phe Leu Asn Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

```
Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly

<210> SEQ ID NO 27
<211> LENGTH: 449
<212> TYPE: PRT
<213> ORGANISM: artificial
<220> FEATURE:
<223> OTHER INFORMATION: c213B10, heavy chain, full length

<400> SEQUENCE: 27

Gln Val Gln Leu Gln Gln Ser Gly Ser Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Arg Phe
    50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
```

```
               225                 230                 235                 240
        Pro Ser Val Phe Leu Phe Pro Lys Pro Lys Asp Thr Leu Met Ile
                        245                 250                 255

Ser Arg Thr Pro Glu Val Thr Cys Val Val Val Asp Val Ser His Glu
                        260                 265                 270

Asp Pro Glu Val Lys Phe Asn Trp Tyr Val Asp Gly Val Glu Val His
                        275                 280                 285

Asn Ala Lys Thr Lys Pro Arg Glu Glu Gln Tyr Asn Ser Thr Tyr Arg
                        290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                        340                 345                 350

Thr Leu Pro Pro Ser Arg Glu Glu Met Thr Lys Asn Gln Val Ser Leu
                        355                 360                 365

Thr Cys Leu Val Lys Gly Phe Tyr Pro Ser Asp Ile Ala Val Glu Trp
                        370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                        435                 440                 445

Gly

<210> SEQ ID NO 28
<211> LENGTH: 214
<212> TYPE: PRT
<213> ORGANISM: artificial
<220> FEATURE:
<223> OTHER INFORMATION: c208F2, light chain, full length

<400> SEQUENCE: 28

Asp Ile Gln Met Thr Gln Thr Thr Ser Ser Leu Ser Ala Ser Leu Gly
        1               5                   10                  15

Asp Arg Val Thr Ile Ser Cys Arg Ala Ser Gln Asp Ile Ser Lys Tyr
                        20                  25                  30

Leu Asn Trp Tyr Gln Gln Pro Asp Gly Thr Ile Lys Leu Leu Ile
                        35                  40                  45

Tyr Tyr Thr Ser Arg Leu His Ser Gly Val Pro Ser Arg Phe Ser Gly
                50                  55                  60

Arg Gly Ser Gly Thr Asp Tyr Ser Leu Thr Ile Ser Asn Val Glu Gln
        65                  70                  75                  80

Glu Asp Ile Ala Thr Tyr Phe Cys Gln Gln Gly Ser Thr Leu Pro Tyr
                        85                  90                  95

Thr Phe Gly Gly Gly Thr Lys Leu Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 214
<212> TYPE: PRT
<213> ORGANISM: artificial
<220> FEATURE:
<223> OTHER INFORMATION: c212A11, light chain, full length

<400> SEQUENCE: 29

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Lys Tyr
                20                  25                  30

Leu Asn Trp Tyr Gln Gln Pro Asp Gly Thr Val Lys Leu Leu Ile
            35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 214
<212> TYPE: PRT
<213> ORGANISM: artificial
<220> FEATURE:
<223> OTHER INFORMATION: c214F8, light chain, full length

<400> SEQUENCE: 30

Asp Ile Gln Met Thr Gln Thr Thr Ser Ser Leu Ser Ala Ser Leu Gly
```

-continued

```
                1               5                  10                  15
        Asp Arg Val Thr Phe Ser Cys Arg Ala Ser Gln Asp Ile Ser Lys Tyr
                        20                  25                  30

Leu Asn Trp Tyr Gln Gln Pro Asp Gly Thr Ile Lys Leu Leu Ile
                    35                  40                  45

Tyr Tyr Thr Ser Arg Leu His Ser Gly Val Pro Ser Arg Phe Ser Gly
                50                  55                  60

Arg Gly Ser Gly Thr Asp Tyr Ser Leu Thr Ile Thr Asn Leu Glu Gln
        65                  70                  75                  80

Glu Asp Ile Ala Thr Tyr Phe Cys Gln Gln Gly Ser Ala Leu Pro Tyr
                        85                  90                  95

Thr Phe Gly Gly Gly Thr Lys Leu Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                    130                 135                 140

Lys Val Gln Trp Lys Val Asp Asn Ala Leu Gln Ser Gly Asn Ser Gln
        145                 150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
                    210
```

<210> SEQ ID NO 31
<211> LENGTH: 214
<212> TYPE: PRT
<213> ORGANISM: artificial
<220> FEATURE:
<223> OTHER INFORMATION: c219D6, light chain, full length

<400> SEQUENCE: 31

```
        Asp Ile Gln Met Thr Gln Thr Thr Ser Ser Leu Ser Ala Ser Leu Gly
        1                   5                   10                  15

Asp Arg Val Thr Ile Ser Cys Arg Ala Ser Gln Asp Ile Ser Lys Tyr
                        20                  25                  30

Leu Asn Trp Tyr Gln Gln Pro Asp Gly Thr Val Lys Leu Leu Ile
                    35                  40                  45

Tyr Tyr Thr Ser Arg Leu His Ser Gly Val Pro Ser Arg Phe Ser Gly
                50                  55                  60

Arg Gly Ser Gly Thr Asp Tyr Ser Leu Thr Ile Ser Asn Leu Glu Gln
        65                  70                  75                  80

Glu Asp Ile Ala Thr Tyr Phe Cys Gln Gln Gly Ser Thr Leu Pro Tyr
                        85                  90                  95

Thr Phe Gly Gly Gly Thr Lys Leu Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 32
<211> LENGTH: 214
<212> TYPE: PRT
<213> ORGANISM: artificial
<220> FEATURE:
<223> OTHER INFORMATION: c213B10, light chain, full length

<400> SEQUENCE: 32

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Pro Asp Gly Thr Ile Lys Leu Leu Ile
            35                  40                  45

Tyr Tyr Thr Ser Arg Leu His Ser Gly Val Pro Ser Arg Phe Ser Gly
        50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 33
<211> LENGTH: 120
<212> TYPE: PRT
<213> ORGANISM: artificial
<220> FEATURE:
<223> OTHER INFORMATION: hz208F2 (var.1) heavy chain, VH

<400> SEQUENCE: 33

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Trp Pro Gly Asp Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 34
<211> LENGTH: 120
<212> TYPE: PRT
<213> ORGANISM: artificial
<220> FEATURE:
<223> OTHER INFORMATION: hz208F2 (var. 3), VH

<400> SEQUENCE: 34

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Ser Asn Thr Ala Tyr
65                  70                  75                  80

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 35
<211> LENGTH: 107
<212> TYPE: PRT
<213> ORGANISM: artificial
<220> FEATURE:
<223> OTHER INFORMATION: hz208F2 (var. 1), VL

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Gly Ser Thr Leu Pro Tyr
                85                  90                  95

Thr Phe Gly Gly Gly Thr Lys Val Glu Ile Lys
            100                 105

<210> SEQ ID NO 36
<211> LENGTH: 107
<212> TYPE: PRT
<213> ORGANISM: artificial
<220> FEATURE:
<223> OTHER INFORMATION: hz208F2 (var.3), VL

<400> SEQUENCE: 36

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
            100                 105

<210> SEQ ID NO 37
<211> LENGTH: 449
<212> TYPE: PRT
<213> ORGANISM: artificial
<220> FEATURE:
<223> OTHER INFORMATION: hz208F2 (var. 1), heavy chain, full length

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Trp Pro Gly Asp Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                165                 170                 175
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 38
<211> LENGTH: 449
<212> TYPE: PRT
<213> ORGANISM: artificial
<220> FEATURE:
<223> OTHER INFORMATION: hz208F2 (var.3), heavy chain full length

<400> SEQUENCE: 38

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Ser Asn Thr Ala Tyr
65                  70                  75                  80
```

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 39
<211> LENGTH: 214
<212> TYPE: PRT
<213> ORGANISM: artificial
<220> FEATURE:
<223> OTHER INFORMATION: hz208F2 (var. 1), light chain, full length

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 40
<211> LENGTH: 214
<212> TYPE: PRT
<213> ORGANISM: artificial
<220> FEATURE:
<223> OTHER INFORMATION: hz208F2 (var.3), light chain, full length

<400> SEQUENCE: 40

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 120
<212> TYPE: PRT
<213> ORGANISM: artificial
<220> FEATURE:
<223> OTHER INFORMATION: hz208F2 (var.2) heavy chain, VH
<220> FEATURE:
<221> NAME/KEY: MISC_FEATURE
<222> LOCATION: (20)..(20)
<223> OTHER INFORMATION: Met may be replaced by Val
<220> FEATURE:
<221> NAME/KEY: MISC_FEATURE
<222> LOCATION: (34)..(34)
<223> OTHER INFORMATION: Ile may be replaced by Met
<220> FEATURE:
<221> NAME/KEY: MISC_FEATURE
<222> LOCATION: (35)..(35)
<223> OTHER INFORMATION: Tyr may be replaced by His
<220> FEATURE:
<221> NAME/KEY: MISC_FEATURE
<222> LOCATION: (38)..(38)
<223> OTHER INFORMATION: Lys may be replaced by Arg
<220> FEATURE:
<221> NAME/KEY: MISC_FEATURE
<222> LOCATION: (48)..(48)
<223> OTHER INFORMATION: Leu may be replaced by Met
<220> FEATURE:
<221> NAME/KEY: MISC_FEATURE
<222> LOCATION: (50)..(50)
<223> OTHER INFORMATION: Trp may be replaced by Ile
<220> FEATURE:
<221> NAME/KEY: MISC_FEATURE
<222> LOCATION: (59)..(59)
<223> OTHER INFORMATION: Lys may be replaced by Ser
<220> FEATURE:
<221> NAME/KEY: MISC_FEATURE
<222> LOCATION: (61)..(61)
<223> OTHER INFORMATION: Asn may be replaced by Ala
<220> FEATURE:
<221> NAME/KEY: MISC_FEATURE
<222> LOCATION: (62)..(62)
<223> OTHER INFORMATION: Glu may be replaced by Gln
<220> FEATURE:
<221> NAME/KEY: MISC_FEATURE
<222> LOCATION: (70)..(70)
<223> OTHER INFORMATION: Leu may be replaced by Met
<220> FEATURE:
<221> NAME/KEY: MISC_FEATURE
<222> LOCATION: (72)..(72)
<223> OTHER INFORMATION: Ala may be replaced by Arg
<220> FEATURE:
<221> NAME/KEY: MISC_FEATURE
<222> LOCATION: (74)..(74)
<223> OTHER INFORMATION: Lys may be replaced by Thr
<220> FEATURE:
<221> NAME/KEY: MISC_FEATURE
<222> LOCATION: (76)..(76)
<223> OTHER INFORMATION: Ser may be replaced by Thr
<220> FEATURE:
<221> NAME/KEY: MISC_FEATURE
```

<222> LOCATION: (77)..(77)
<223> OTHER INFORMATION: Asn may be replaced by Ser
<220> FEATURE:
<221> NAME/KEY: MISC_FEATURE
<222> LOCATION: (79)..(79)
<223> OTHER INFORMATION: Ala may be replaced by Val
<220> FEATURE:
<221> NAME/KEY: MISC_FEATURE
<222> LOCATION: (82)..(82)
<223> OTHER INFORMATION: Phe may be replaced by Glu
<220> FEATURE:
<221> NAME/KEY: MISC_FEATURE
<222> LOCATION: (95)..(95)
<223> OTHER INFORMATION: Phe may be replaced by Tyr

<400> SEQUENCE: 41

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
50                  55                  60

Gln Gly Arg Val Thr Leu Thr Ala Asp Lys Ser Ser Asn Thr Ala Tyr
65                  70                  75                  80

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 42
<211> LENGTH: 107
<212> TYPE: PRT
<213> ORGANISM: artificial
<220> FEATURE:
<223> OTHER INFORMATION: hz208F2 (var. 2), light chain, VL
<220> FEATURE:
<221> NAME/KEY: MISC_FEATURE
<222> LOCATION: (22)..(22)
<223> OTHER INFORMATION: Ser may be replaced by Thr
<220> FEATURE:
<221> NAME/KEY: MISC_FEATURE
<222> LOCATION: (53)..(53)
<223> OTHER INFORMATION: Arg may be replaced by Ser
<220> FEATURE:
<221> NAME/KEY: MISC_FEATURE
<222> LOCATION: (55)..(55)
<223> OTHER INFORMATION: His may be replaced by Gln
<220> FEATURE:
<221> NAME/KEY: MISC_FEATURE
<222> LOCATION: (65)..(65)
<223> OTHER INFORMATION: Arg may be replaced by Ser
<220> FEATURE:
<221> NAME/KEY: MISC_FEATURE
<222> LOCATION: (71)..(71)
<223> OTHER INFORMATION: Tyr may be replaced by Phe
<220> FEATURE:
<221> NAME/KEY: MISC_FEATURE
<222> LOCATION: (72)..(72)
<223> OTHER INFORMATION: Ser may be replaced by Thr
<220> FEATURE:
<221> NAME/KEY: MISC_FEATURE
<222> LOCATION: (77)..(77)
<223> OTHER INFORMATION: Asn may be replaced by Ser
<220> FEATURE:
<221> NAME/KEY: MISC_FEATURE
<222> LOCATION: (87)..(87)

<223> OTHER INFORMATION: Phe may be replaced by Tyr

<400> SEQUENCE: 42

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
            100                 105
```

<210> SEQ ID NO 43
<211> LENGTH: 329
<212> TYPE: PRT
<213> ORGANISM: artificial
<220> FEATURE:
<223> OTHER INFORMATION: Constant domain (VH) IgG1

<400> SEQUENCE: 43

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 44
<211> LENGTH: 326
<212> TYPE: PRT
<213> ORGANISM: artificial
<220> FEATURE:
<223> OTHER INFORMATION: Constant domain (VH) IgG4 (S228P)

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 45
<211> LENGTH: 107
<212> TYPE: PRT
<213> ORGANISM: artificial
<220> FEATURE:
<223> OTHER INFORMATION: Domain kappa (VL)

<400> SEQUENCE: 45

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 46
<211> LENGTH: 98
<212> TYPE: PRT
<213> ORGANISM: artificial
<220> FEATURE:
<223> OTHER INFORMATION: Human germline IGHV1-46*01

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 47
<211> LENGTH: 95
<212> TYPE: PRT
<213> ORGANISM: artificial

```
<220> FEATURE:
<223> OTHER INFORMATION: Human germline IGKV1-39*01

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 48
<211> LENGTH: 15
<212> TYPE: PRT
<213> ORGANISM: artificial
<220> FEATURE:
<223> OTHER INFORMATION: Human germline IGHJ4*01

<400> SEQUENCE: 48

Tyr Phe Asp Tyr Trp Gly Gln Gly Thr Leu Val Thr Val Ser Ser
1               5                   10                  15

<210> SEQ ID NO 49
<211> LENGTH: 12
<212> TYPE: PRT
<213> ORGANISM: artificial
<220> FEATURE:
<223> OTHER INFORMATION: Human germline IGKJ4*01

<400> SEQUENCE: 49

Leu Thr Phe Gly Gly Gly Thr Lys Val Glu Ile Lys
1               5                   10

<210> SEQ ID NO 50
<211> LENGTH: 1367
<212> TYPE: PRT
<213> ORGANISM: artificial
<220> FEATURE:
<223> OTHER INFORMATION: IGF-1R (human)

<400> SEQUENCE: 50

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110
```

```
Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
        130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525
```

-continued

Glu Ala Pro Phe Lys Asn Val Thr Glu Tyr Asp Gly Gln Asp Ala Cys
530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
930                 935                 940

Leu Leu Ile Val Gly Gly Leu Val Ile Met Leu Tyr Val Phe His Arg

-continued

```
945                 950                 955                 960
Lys Arg Asn Asn Ser Arg Leu Gly Asn Gly Val Leu Tyr Ala Ser Val
                965                 970                 975
Asn Pro Glu Tyr Phe Ser Ala Ala Asp Val Tyr Val Pro Asp Glu Trp
                980                 985                 990
Glu Val Ala Arg Glu Lys Ile Thr Met Ser Arg Glu Leu Gly Gln Gly
                995                 1000                1005
Ser Phe Gly Met Val Tyr Glu Gly Val Ala Lys Gly Val Val Lys
    1010                1015                1020
Asp Glu Pro Glu Thr Arg Val Ala Ile Lys Thr Val Asn Glu Ala
    1025                1030                1035
Ala Ser Met Arg Glu Arg Ile Glu Phe Leu Asn Glu Ala Ser Val
    1040                1045                1050
Met Lys Glu Phe Asn Cys His His Val Val Arg Leu Leu Gly Val
    1055                1060                1065
Val Ser Gln Gly Gln Pro Thr Leu Val Ile Met Glu Leu Met Thr
    1070                1075                1080
Arg Gly Asp Leu Lys Ser Tyr Leu Arg Ser Leu Arg Pro Glu Met
    1085                1090                1095
Glu Asn Asn Pro Val Leu Ala Pro Pro Ser Leu Ser Lys Met Ile
    1100                1105                1110
Gln Met Ala Gly Glu Ile Ala Asp Gly Met Ala Tyr Leu Asn Ala
    1115                1120                1125
Asn Lys Phe Val His Arg Asp Leu Ala Ala Arg Asn Cys Met Val
    1130                1135                1140
Ala Glu Asp Phe Thr Val Lys Ile Gly Asp Phe Gly Met Thr Arg
    1145                1150                1155
Asp Ile Tyr Glu Thr Asp Tyr Tyr Arg Lys Gly Gly Lys Gly Leu
    1160                1165                1170
Leu Pro Val Arg Trp Met Ser Pro Glu Ser Leu Lys Asp Gly Val
    1175                1180                1185
Phe Thr Thr Tyr Ser Asp Val Trp Ser Phe Gly Val Val Leu Trp
    1190                1195                1200
Glu Ile Ala Thr Leu Ala Glu Gln Pro Tyr Gln Gly Leu Ser Asn
    1205                1210                1215
Glu Gln Val Leu Arg Phe Val Met Glu Gly Gly Leu Leu Asp Lys
    1220                1225                1230
Pro Asp Asn Cys Pro Asp Met Leu Phe Glu Leu Met Arg Met Cys
    1235                1240                1245
Trp Gln Tyr Asn Pro Lys Met Arg Pro Ser Phe Leu Glu Ile Ile
    1250                1255                1260
Ser Ser Ile Lys Glu Glu Met Glu Pro Gly Phe Arg Glu Val Ser
    1265                1270                1275
Phe Tyr Tyr Ser Glu Glu Asn Lys Leu Pro Glu Pro Glu Glu Leu
    1280                1285                1290
Asp Leu Glu Pro Glu Asn Met Glu Ser Val Pro Leu Asp Pro Ser
    1295                1300                1305
Ala Ser Ser Ser Ser Leu Pro Leu Pro Asp Arg His Ser Gly His
    1310                1315                1320
Lys Ala Glu Asn Gly Pro Gly Pro Gly Val Leu Val Leu Arg Ala
    1325                1330                1335
Ser Phe Asp Glu Arg Gln Pro Tyr Ala His Met Asn Gly Gly Arg
    1340                1345                1350
```

-continued

Lys Asn Glu Arg Ala Leu Pro Leu Pro Gln Ser Ser Thr Cys
              1355              1360              1365

<210> SEQ ID NO 51
<211> LENGTH: 932
<212> TYPE: PRT
<213> ORGANISM: artificial
<220> FEATURE:
<223> OTHER INFORMATION: IGF-1R ECD (human)

<400> SEQUENCE: 51

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

```
Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
                435                 440                 445

Ala Phe Asn Pro Lys Leu Cys Val Ser Glu Ile Tyr Arg Met Glu Glu
                450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
                500                 505                 510

Arg Pro Pro Asp Tyr Arg Asp Leu Ile Ser Phe Thr Val Tyr Tyr Lys
                515                 520                 525

Glu Ala Pro Phe Lys Asn Val Thr Glu Tyr Asp Gly Gln Asp Ala Cys
                530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
                580                 585                 590

His Ile Arg Gly Ala Lys Ser Glu Ile Leu Tyr Ile Arg Thr Asn Ala
                595                 600                 605

Ser Val Pro Ser Ile Pro Leu Asp Val Leu Ser Ala Ser Asn Ser Ser
                610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
                660                 665                 670

Tyr Ala Asp Gly Thr Ile Asp Ile Glu Glu Val Thr Glu Asn Pro Lys
                675                 680                 685

Thr Glu Val Cys Gly Gly Glu Lys Gly Pro Cys Cys Ala Cys Pro Lys
                690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
                740                 745                 750

Arg Ser Arg Asn Thr Thr Ala Ala Asp Thr Tyr Asn Ile Thr Asp Pro
                755                 760                 765
```

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn
        930

<210> SEQ ID NO 52
<211> LENGTH: 512
<212> TYPE: PRT
<213> ORGANISM: artificial
<220> FEATURE:
<223> OTHER INFORMATION: IGF-1R ECD Nterminal (human)

<400> SEQUENCE: 52

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

```
Glu Lys Thr Thr Ile Asn Asn Glu Tyr Asn Tyr Arg Cys Trp Thr Thr
            195                 200                 205
Asn Arg Cys Gln Lys Met Cys Pro Ser Thr Cys Gly Lys Arg Ala Cys
        210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
                245                 250                 255
Ala Gly Val Cys Val Pro Ala Cys Pro Asn Thr Tyr Arg Phe Glu
            260                 265                 270
Gly Trp Arg Cys Val Asp Arg Asp Phe Cys Ala Asn Ile Leu Ser Ala
            275                 280                 285
Glu Ser Ser Asp Ser Glu Gly Phe Val Ile His Asp Gly Glu Cys Met
    290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Lys
                325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
        355                 360                 365
Asn Ile Ala Ser Glu Leu Glu Asn Phe Met Gly Leu Ile Glu Val Val
    370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
            435                 440                 445
Ala Phe Asn Pro Lys Leu Cys Val Ser Glu Ile Tyr Arg Met Glu Glu
    450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Ile Thr Trp His Arg Tyr
            500                 505                 510

<210> SEQ ID NO 53
<211> LENGTH: 4
<212> TYPE: PRT
<213> ORGANISM: artificial
<220> FEATURE:
<223> OTHER INFORMATION: tetrapeptide (linker)

<400> SEQUENCE: 53

Gly Phe Leu Gly
1

<210> SEQ ID NO 54
<211> LENGTH: 4
<212> TYPE: PRT
<213> ORGANISM: artificial
<220> FEATURE:
```

<223> OTHER INFORMATION: tetrapeptide (linker)

<400> SEQUENCE: 54

Ala Leu Ala Leu
1

<210> SEQ ID NO 55
<211> LENGTH: 5
<212> TYPE: PRT
<213> ORGANISM: artificial
<220> FEATURE:
<223> OTHER INFORMATION: tetrapeptide (linker)

<400> SEQUENCE: 55

Pro Val Gly Val Val
1               5

<210> SEQ ID NO 56
<211> LENGTH: 120
<212> TYPE: PRT
<213> ORGANISM: artificial
<220> FEATURE:
<223> OTHER INFORMATION: hz208F2 heavy chain H037, VH

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 57
<211> LENGTH: 107
<212> TYPE: PRT
<213> ORGANISM: artificial
<220> FEATURE:
<223> OTHER INFORMATION: hz208F2 light chain L018, VL

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Arg Gly Ser Gly Thr Asp Tyr Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
            100                 105

<210> SEQ ID NO 58
<211> LENGTH: 449
<212> TYPE: PRT
<213> ORGANISM: artificial
<220> FEATURE:
<223> OTHER INFORMATION: hz208F2 heavy chain H037 full length

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 59
<211> LENGTH: 214
<212> TYPE: PRT
<213> ORGANISM: artificial
<220> FEATURE:
<223> OTHER INFORMATION: hz208F2 light chain L018 full length

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Arg Gly Ser Gly Thr Asp Tyr Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 60
<211> LENGTH: 107
<212> TYPE: PRT
```

<213> ORGANISM: artificial
<220> FEATURE:
<223> OTHER INFORMATION: hz208F2 light chain L021, VL

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Phe Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
            100                 105

<210> SEQ ID NO 61
<211> LENGTH: 214
<212> TYPE: PRT
<213> ORGANISM: artificial
<220> FEATURE:
<223> OTHER INFORMATION: hz208F2 light chain L021 full length

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Phe Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 62
<211> LENGTH: 120
<212> TYPE: PRT
<213> ORGANISM: artificial
<220> FEATURE:
<223> OTHER INFORMATION: hz208F2 heavy chain H047, VH

<400> SEQUENCE: 62
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Thr Ser Ser Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

```
<210> SEQ ID NO 63
<211> LENGTH: 449
<212> TYPE: PRT
<213> ORGANISM: artificial
<220> FEATURE:
<223> OTHER INFORMATION: hz208F2 heavy chain H047 full length

<400> SEQUENCE: 63
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Thr Ser Ser Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 64
<211> LENGTH: 120
<212> TYPE: PRT
<213> ORGANISM: artificial
<220> FEATURE:
<223> OTHER INFORMATION: hz208F2 heavy chain H049, VH

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Ser Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
            115                 120

<210> SEQ ID NO 65
<211> LENGTH: 449
<212> TYPE: PRT
<213> ORGANISM: artificial
<220> FEATURE:
<223> OTHER INFORMATION: hz208F2 heavy chain H049 full length

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 66
<211> LENGTH: 120
<212> TYPE: PRT
<213> ORGANISM: artificial
<220> FEATURE:
<223> OTHER INFORMATION: hz208F2 heavy chain H051, VH

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Ser Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 67
<211> LENGTH: 449
<212> TYPE: PRT
<213> ORGANISM: artificial
<220> FEATURE:
<223> OTHER INFORMATION: hz208F2 heavy chain H051 full length

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60
```

```
Gln Gly Arg Val Thr Met Thr Arg Asp Thr Ser Ser Asn Thr Val Tyr
 65                  70                  75                  80

Met Glu Leu Ser Ser Leu Arg Ser Glu Asp Thr Ala Val Tyr Phe Cys
                 85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 68
<211> LENGTH: 120
<212> TYPE: PRT
<213> ORGANISM: artificial
```

<220> FEATURE:
<223> OTHER INFORMATION: hz208F2 heavy chain H052, VH

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
            115                 120

<210> SEQ ID NO 69
<211> LENGTH: 449
<212> TYPE: PRT
<213> ORGANISM: artificial
<220> FEATURE:
<223> OTHER INFORMATION: hz208F2 heavy chain H052 full length

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp

```
                210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 70
<211> LENGTH: 120
<212> TYPE: PRT
<213> ORGANISM: artificial
<220> FEATURE:
<223> OTHER INFORMATION: hz208F2 heavy chain H057, VH

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
        50                  55                  60

Gln Gly Arg Val Thr Met Thr Arg Asp Lys Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120
```

<210> SEQ ID NO 71
<211> LENGTH: 449
<212> TYPE: PRT
<213> ORGANISM: artificial
<220> FEATURE:
<223> OTHER INFORMATION: hz208F2 heavy chain H057 full length

<400> SEQUENCE: 71

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly

<210> SEQ ID NO 72
<211> LENGTH: 120
<212> TYPE: PRT
<213> ORGANISM: artificial
<220> FEATURE:
<223> OTHER INFORMATION: hz208F2 heavy chain H068, VH

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
                100                 105                 110

Gly Thr Leu Val Thr Val Ser Ser
        115                 120

<210> SEQ ID NO 73
<211> LENGTH: 449
<212> TYPE: PRT
<213> ORGANISM: artificial
<220> FEATURE:
<223> OTHER INFORMATION: hz208F2 heavy chain H068 full length

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Phe Cys
                85                  90                  95
```

Ala Ser Pro Met Ile Thr Pro Asn Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 74
<211> LENGTH: 120
<212> TYPE: PRT
<213> ORGANISM: artificial
<220> FEATURE:
<223> OTHER INFORMATION: hz208F2 heavy chain H070, VH

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Ser Pro Met Ile Thr Pro Asn Tyr Ala Met Asp Tyr Trp Gly Gln
            100                 105                 110

Gly Thr Leu Val Thr Val Ser Ser
            115                 120

<210> SEQ ID NO 75
<211> LENGTH: 449
<212> TYPE: PRT
<213> ORGANISM: artificial
<220> FEATURE:
<223> OTHER INFORMATION: hz208F2 heavy chain H070 full length

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 76
<211> LENGTH: 120
<212> TYPE: PRT
<213> ORGANISM: artificial
<220> FEATURE:
<223> OTHER INFORMATION: hz208F2 heavy chain H071, VH

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 77
<211> LENGTH: 449
<212> TYPE: PRT
```

<213> ORGANISM: artificial
<220> FEATURE:
<223> OTHER INFORMATION: hz208F2 heavy chain H071 full length

<400> SEQUENCE: 77

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
```

```
385                 390                 395                 400
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 78
<211> LENGTH: 120
<212> TYPE: PRT
<213> ORGANISM: artificial
<220> FEATURE:
<223> OTHER INFORMATION: hz208F2 heavy chain H076, VH

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
                100                 105                 110

Gly Thr Leu Val Thr Val Ser Ser
        115                 120

<210> SEQ ID NO 79
<211> LENGTH: 449
<212> TYPE: PRT
<213> ORGANISM: artificial
<220> FEATURE:
<223> OTHER INFORMATION: hz208F2 heavy chain H076 full length

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
                100                 105                 110

Gly Thr Leu Val Thr Val Ser Ser Ala Ser Thr Lys Gly Pro Ser Val
```

```
            115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 80
<211> LENGTH: 120
<212> TYPE: PRT
<213> ORGANISM: artificial
<220> FEATURE:
<223> OTHER INFORMATION: hz208F2 heavy chain H077, VH

<400> SEQUENCE: 80

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
```

Tyr Ile His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Phe Cys
                 85                  90                  95

Ala Ser Pro Met Ile Thr Pro Asn Tyr Ala Met Asp Tyr Trp Gly Gln
            100                 105                 110

Gly Thr Leu Val Thr Val Ser Ser
            115                 120

<210> SEQ ID NO 81
<211> LENGTH: 449
<212> TYPE: PRT
<213> ORGANISM: artificial
<220> FEATURE:
<223> OTHER INFORMATION: hz208F2 heavy chain H077 full length

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Phe Cys
                 85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

```
Asp Pro Glu Val Lys Phe Asn Trp Tyr Val Asp Gly Val Glu Val His
    275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly
```

SULFOMALEIMIDE-BASED LINKERS AND CORRESPONDING CONJUGATES

TECHNICAL FIELD

The present invention relates to a sulfomaleimide-based linker useful in the preparation of conjugates such as antibody-drug conjugates (ADCs) by covalently linking drug molecule(s) to a binding unit, which is advantageously an antibody.

BACKGROUND

ADCs are all controlled mixtures of different drug-loaded species (from 0 to 8 drug molecules per antibody=DAR) and have a typical average DAR of 3.5 or 4. Unconjugated species are generally not active and are in competition with the drug-loaded species for binding to the antigen. In addition, species that have a DAR of more than 4 have been shown to lead to lower tolerability, higher plasma clearance rates and decreased efficacy. Most of the ADCs that are currently on the market and in clinical trials share common structural features, such as a thiosuccinimide linkage, which is formed through the reaction of thiols and alkyl maleimides. This type of chemistry is widely used because the reaction of maleimides and thiols is very rapid under physiological conditions and is quantitative (without a large excess of both original species). However, thiosuccinimide formation is slowly reversible under physiological conditions. ADCs that contain alkyl maleimides can result in measurable drug loss during prolonged circulation. The pharmacological consequences of this maleimide elimination from ADCs (via a retro-Michael reaction) include diminished antitumour activity due to reduced exposure to the antibody-conjugated form of the drug and greater toxicity, which arises from the non-targeted release of the drug and the linker. This has been described both for cysteine linked ADCs and lysine-linked ADCs via the thioether linker SMCC (succinimidyl 4-(N-maleimidomethyl)cyclohexane-1-carboxylate).

The present invention relates thus to compounds useful for the conjugation of drug to binding units, the obtained conjugates being more stable and more efficient.

SUMMARY OF THE INVENTION

The present invention thus relates to a linker of the following formula (I):

$$X_1 \text{—} \underset{\underset{O}{\|}}{\overset{(O)_q}{\overset{\|}{S}}} \text{—} N\text{—}L_1\text{—}(CO)_c\text{—}(W)_w\text{—}(Y)_y\text{—}X_3, \quad (I)$$

(with $X_2$ on the ring)

preferably of the following formula (Ia):

$$X_1 \text{—} \underset{\underset{O}{\|}}{\overset{O\underset{\|}{\searrow}\nearrow O}{\overset{\|}{S}}} \text{—} N\text{—}L_1\text{—}(CO)_c\text{—}(W)_w\text{—}(Y)_y\text{—}X_3, \quad (Ia)$$

or a salt thereof, wherein:

$X_1$ and $X_2$ represent, independently of each other, H, a halogen atom, a $(C_1\text{-}C_6)$alkoxy, an aryloxy optionally substituted, or —O—$(CH_2CH_2O)_r$H (—O-PEG), provided that $X_1$ and $X_2$ do not represent H at the same time;

$L_1$ represents a group of formula $L_1'$-(CO—Z')$_{z'}$ with $L_1'$ being —$(CH_2)_n$—, —$(CH_2CH_2O)_m$—$CH_2$—$CH_2$—, arylene, heteroarylene, cycloalkanediyl, —$(CH_2)_n$-arylene-, —$(CH_2)_n$-heteroarylene-, —$(CH_2)_n$-cycloalkanediyl-, -arylene-$(CH_2)_p$—, -heteroarylene-$(CH_2)_p$—, -cycloalkanediyl-$(CH_2)_p$—, —$(CH_2)_n$-arylene-$(CH_2)_p$—, —$(CH_2)_n$-heteroarylene-$(CH_2)_p$—, —$(CH_2)_n$-cycloalkanediyl-$(CH_2)_p$—, —$(CH_2CH_2O)_m$—$CH_2$—$CH_2$-arylene-$(CH_2)_p$—, —$(CH_2CH_2O)_m$—$CH_2$—$CH_2$-heteroarylene-$(CH_2)_p$—, —$(CH_2CH_2O)_m$—$CH_2$—$CH_2$-cycloalkanediyl-$(CH_2)_p$—, —$(CH_2)_n$-arylene-$CH_2$—$CH_2$—$(OCH_2CH_2)_m$—, —$(CH_2)_n$-heteroarylene-$CH_2$—$CH_2$—$(OCH_2CH_2)_m$—, or —$(CH_2)_n$-cycloalkanediyl-$CH_2$—$CH_2$—$(OCH_2CH_2)_m$—;

each W independently represents an amino acid unit;

Y is -PAB-CO—(Z)$_z$—, with PAB being $$\text{(4-aminobenzyl structure: } {-}\text{NH-C}_6\text{H}_4\text{-CH}_2\text{-O-}{-}\text{)}$$

(the oxygen of the PAB unit being linked to CO—(Z)$_z$);

Z is —NR$_4$—$(CH_2)_u$—NR$_5$— or —NR$_4$—$(CH_2)_u$—NR$_5$—CO—, or even else —NR$_4$—$(CH_2)_u$—NR$_5$—CO—$(CH_2)_v$— or —NR$_4$—$(CH_2)_u$—NR$_5$—CO—$(CH_2)_v$—CO— (the NR$_4$ group being linked to the CO group of PAB-CO);

Z' is —NR$_4$—$(CH_2)_u$—NR$_5$— or —NR$_4$—$(CH_2)_u$—NR$_5$—CO—$(CH_2)_v$— (the NR$_4$ group being linked to the CO group of CO—Z');

R$_4$ and R$_5$ are independently H or a $(C_1\text{-}C_6)$alkyl group;

c is 0 or 1, preferably 1;
m is an integer from 1 to 15;
n is an integer from 1 to 6;
p is an integer from 1 to 6;
q is 0.1 or 2, preferably 2;
r is an integer from 1 to 24, notably from 1 to 12;
u is an integer from 1 to 6;
v is an integer from 1 to 6;
w is an integer from 0 to 5, preferably 0 or 2;
y is 0 or 1 (preferably y is 0 when w is 0 and y is 0 or 1 when w is an integer from 1 to 5);
z is 0 or 1;
z' is 0 or 1, notably 0; and $X_3$ represents H when y=z=1 and Z is —$NR_4$—$(CH_2)_u$—$NR_5$— or when c=w=y=0, z'=1 and Z' is —$NR_4$—$(CH_2)_u$—$NR_5$— and in the other cases, $X_3$ represents OH, $NH_2$ or a leaving group.

The leaving group is more particularly a halogen atom, a sulfonate of formula —$OSO_2$—$R_{LG}$, N-succinimidyloxy, 4-nitro-phenyloxy, pentafluorophenoxy or N-benzotriazoloxy, $R_{LG}$ representing a $(C_1-C_6)$alkyl, aryl, aryl-$(C_1-C_6)$alkyl or $(C_1-C_6)$alkyl-aryl group, the said group being optionally substituted with one or several halogen atoms such as fluorine atoms.

Preferably, the compound of formula (I) is not a compound of formula (I) for which:

$X_1$ is Cl, $X_2$ is H, q is 0, $L_1$ is

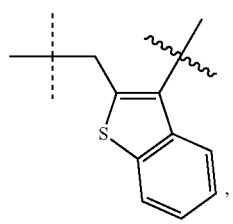

c is 0, w is 0, y is 0 and $X_3$ is Cl;
$X_1$ is Cl, $X_2$ is Cl, q is 0, $L_1$ is

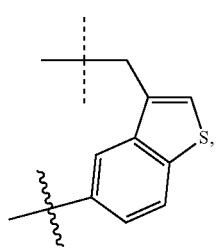

c is 0, w is 0, y is 0 and $X_3$ is Cl;
$X_1$ is Cl, $X_2$ is H, q is 0, $L_1$ is

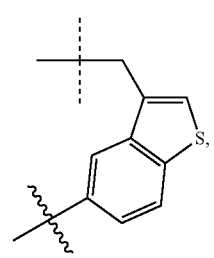

c is 0, w is 0, y is 0 and $X_3$ is Cl;
$X_1$ is Cl, $X_2$ is H, q is 0, $L_1$ is

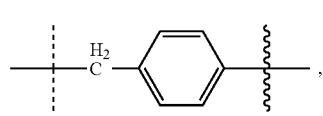

c is 0, w is 0, y is 0 and $X_3$ is Cl;
$X_1$ is Cl, $X_2$ is H, q is 0, $L_1$ is

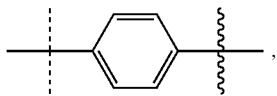

c is 0, w is 0, y is 0 and $X_3$ is Cl;
$X_1$ is Cl, $X_2$ is H, q is 0, $L_1$ is

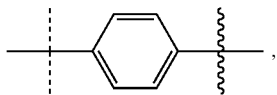

c is 0, w is 0, y is 0 and $X_3$ is Br;
$X_1$ is Cl, $X_2$ is H, q is 0, $L_1$ is

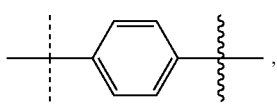

c is 0, w is 0, y is 0 and $X_3$ is I;
$X_1$ is H, $X_2$ is Cl, q is 0, $L_1$ is

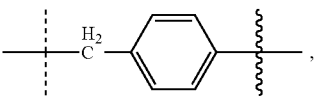

c is 0, w is 0, y is 0 and $X_3$ is Cl;
$X_1$ is H, $X_2$ is Br, q is 0, $L_1$ is

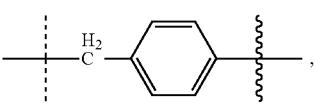

c is 0, w is 0, y is 0 and $X_3$ is Cl;
$X_1$ is H, $X_2$ is Br, q is 0, $L_1$ is

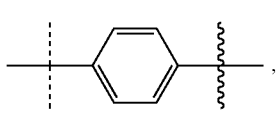

c is 0, w is 0, y is 0 and $X_3$ is Cl;
$X_1$ is Cl, $X_2$ is Cl, q is 0, $L_1$ is

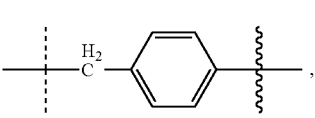

c is 0, w is 0, y is 0 and $X_3$ is Cl;
$X_1$ is Cl, $X_2$ is Cl, q is 0, $L_1$ is

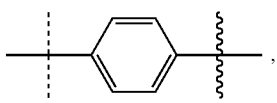

c is 0, w is 0, y is 0 and $X_3$ is Cl;
$X_1$ is Cl, $X_2$ is Cl, q is 0, $L_1$ is

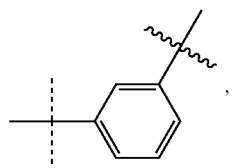

c is 0, w is 0, y is 0 and $X_3$ is Cl;
$X_1$ is Cl, $X_2$ is Br, q is 0, $L_1$ is

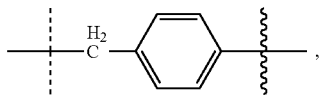

c is 0, w is 0, y is 0 and $X_3$ is Cl;
$X_1$ is Cl, $X_2$ is Br, q is 0, $L_1$ is

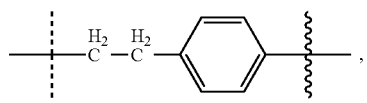

c is 0, w is 0, y is 0 and $X_3$ is Cl;
$X_1$ is Cl, $X_2$ is Br, q is 0, $L_1$ is

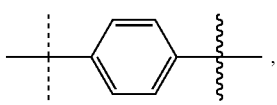

c is 0, w is 0, y is 0 and $X_3$ is Cl; or
$X_1$ is Br, $X_2$ is Br, q is 0, $L_1$ is

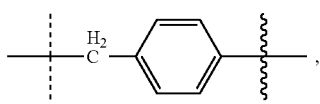

c is 0, w is 0, y is 0 and $X_3$ is Cl;
wherein the dashed line indicates the point of attachment of $L_1$ to the nitrogen atom of

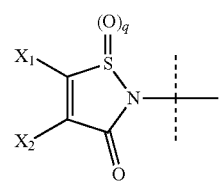

and the wavy line indicates the point of attachment of $L_1$ to $X_3$.

These compounds are disclosed in WO 2007/001932 or in U.S. Pat. No. 4,127,687 but not as a linker which is more particularly intended to the preparation of conjugates such as ADCs.

The present invention relates also to a linker-drug conjugate of the following formula (II):

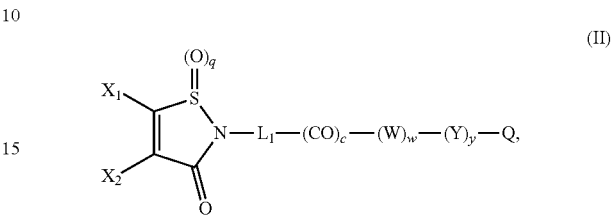

preferably of the following formula (IIa):

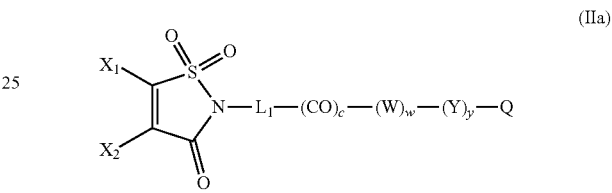

or a salt thereof,
wherein:
$X_1$ and $X_2$ represent, independently of each other, H, a halogen atom, a $(C_1\text{-}C_6)$alkoxy, an aryloxy optionally substituted, or —O—$(CH_2CH_2O)_r$H, provided that $X_1$ and $X_2$ do not represent H at the same time;
$L_1$ represents a group of formula $L_1'$-(CO—Z')$_z$ with $L_1'$ being —$(CH_2)_n$—, —$(CH_2CH_2O)_m$—$CH_2$—$CH_2$—, arylene, heteroarylene, cycloalkanediyl, —$(CH_2)_n$-arylene-, —$(CH_2)_n$-heteroarylene-, —$(CH_2)_n$-cycloalkanediyl-, -arylene-$(CH_2)_p$—, -heteroarylene-$(CH_2)_p$—, -cycloalkanediyl-$(CH_2)_p$—, —$(CH_2)_n$-arylene-$(CH_2)_p$—, —$(CH_2)_n$-heteroarylene-$(CH_2)_p$—, —$(CH_2)_n$-cycloalkanediyl-$(CH_2)_p$—, —$(CH_2CH_2O)_m$—$CH_2$—$CH_2$-arylene-$(CH_2)_p$—, —$(CH_2CH_2O)_m$—$CH_2$—$CH_2$-heteroarylene-$(CH_2)_p$—, —$(CH_2CH_2O)_m$—$CH_2$—$CH_2$-cycloalkanediyl-$(CH_2)_p$—, —$(CH_2)_n$-arylene-$CH_2$—$CH_2$—$(OCH_2CH_2)_m$—, —$(CH_2)_n$-heteroarylene-$CH_2$—$CH_2$—$(OCH_2CH_2)_m$—, or —$(CH_2)_n$-cycloalkanediyl-$CH_2$—$CH_2$—$(OCH_2CH_2)_m$—;
each W independently represents an amino acid unit;
Y is -PAB-CO—(Z)$_z$—, with PAB being

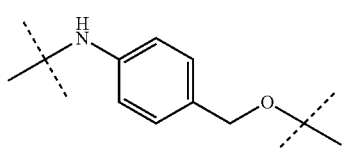

(the oxygen of the PAB unit being linked to CO—(Z)$_z$);
Z is —$NR_4$—$(CH_2)_u$—$NR_5$— or —$NR_4$—$(CH_2)_u$—$NR_5$—CO—, or even else —$NR_4$—$(CH_2)_u$—$NR_5$—CO—$(CH_2)_v$— or —$NR_4$—$(CH_2)_u$—$NR_5$—CO—$(CH_2)_v$—CO— (the $NR_4$ group being linked to the CO group of PAB-CO);

Z' is —NR$_4$—(CH$_2$)$_u$—NR$_5$— or —NR$_4$—(CH$_2$)$_u$—NR$_5$—CO—(CH$_2$)$_v$— (the NR$_4$ group being linked to the CO group of CO—Z');

R$_4$ and R$_5$ are independently H or a (C$_1$-C$_6$)alkyl group;

Q represents a drug moiety;

c is 0 or 1, preferably 1;

m is an integer from 1 to 15;

n is an integer from 1 to 6;

p is an integer from 1 to 6;

q is 0, 1 or 2, preferably 2;

r is an integer from 1 to 24, notably from 1 to 12;

u is an integer from 1 to 6;

v is an integer from 1 to 6;

w is an integer from 0 to 5, preferably 0 or 2;

y is 0 or 1 (preferably y is 0 when w is 0 and y is 0 or 1 when w is an integer from 1 to 5);

z is 0 or 1; and z' is 0 or 1, notably 0.

The present invention relates also to a binding unit-drug conjugate of the following formula (III) or (IV):

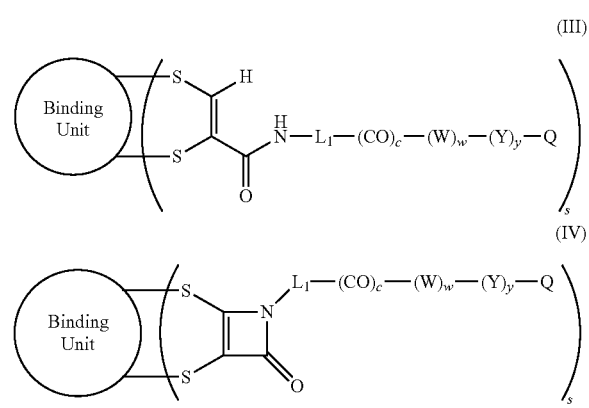

or a salt thereof, preferably a pharmaceutically acceptable salt thereof, wherein:

the binding unit is a peptide, a protein (e.g, an engineered protein), an antibody, (e.g., a monoclonal antibody) or an antigen binding fragment thereof;

L$_1$ represents a group of formula L$_1$'-(CO—Z')$_z$ with L$_1$' being —(CH$_2$)$_n$—, —(CH$_2$CH$_2$O)$_m$—CH$_2$—CH$_2$—, arylene, heteroarylene, cycloalkanediyl. —(CH$_2$)$_n$-arylene-, —(CH$_2$)$_n$-heteroarylene-, —(CH$_2$)$_n$-cycloalkanediyl-, -arylene-(CH$_2$)$_p$—, -heteroarylene-(CH$_2$)$_p$—, -cycloalkanediyl-(CH$_2$)$_p$—, —(CH$_2$)$_n$-arylene-(CH$_2$)$_p$—, —(CH$_2$)$_n$-heteroarylene-(CH$_2$)$_p$—, —(CH$_2$)$_n$-cycloalkanediyl-(CH$_2$)$_p$—, —(CH$_2$CH$_2$O)$_m$—CH$_2$—CH$_2$-arylene-(CH$_2$)$_p$—, —(CH$_2$CH$_2$O)$_m$—CH$_2$—CH$_2$-heteroarylene-(CH$_2$)$_p$—, —(CH$_2$CH$_2$O)$_m$—CH$_2$—CH$_2$-cycloalkanediyl-(CH$_2$)$_p$—, —(CH$_2$)$_n$-arylene-CH$_2$—CH$_2$—(OCH$_2$CH$_2$)$_m$—, —(CH$_2$)$_n$-heteroarylene-CH$_2$—CH$_2$—(OCH$_2$CH$_2$)$_m$—, or —(CH$_2$)$_n$-cycloalkanediyl-CH$_2$—CH$_2$—(OCH$_2$CH$_2$)$_m$—;

each W independently represents an amino acid unit;

Y is -PAB-CO—(Z)$_z$—, with PAB being

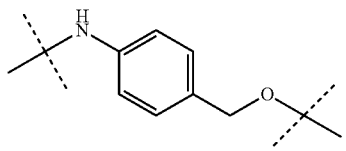

(the oxygen of the PAB unit being linked to CO—(Z)$_z$;

Z is —NR$_4$—(CH$_2$)$_u$—NR$_5$— or —NR$_4$—(CH$_2$)$_u$—NR$_5$—CO—, or even else —NR$_4$—(CH$_2$)$_u$—NR$_5$—CO—(CH$_2$)$_v$— or —NR$_4$—(CH$_2$)$_u$—NR$_5$—CO—(CH$_2$)$_v$—CO— (the NR$_4$ group being linked to the CO group of PAB-CO);

Z' is —NR$_4$—(CH$_2$)$_u$—NR$_5$— or —NR$_4$—(CH$_2$)$_u$—NR$_5$—CO—(CH$_2$)$_v$— (the NR$_4$ group being linked to the CO group of CO—Z');

R$_4$ and R$_5$ are independently H or a (C$_1$-C$_6$)alkyl group;

Q represents a drug moiety;

c is 0 or 1, preferably 1;

m is an integer from 1 to 15;

n is an integer from 1 to 6;

p is an integer from 1 to 6;

s is an integer from 1 to 8;

u is an integer from 1 to 6;

v is an integer from 1 to 6;

w is an integer from 0 to S, preferably 0 or 2;

y is 0 or 1 (preferably y is 0 when w is 0 and y is 0 or 1 when w is an integer from 1 to 5);

z is 0 or 1; and z' is 0 or 1, notably 0.

According to a preferred embodiment, the binding unit is an IGF-1R antibody, a HER2 antibody (e.g, trastuzumab) or an antigen binding fragment thereof.

The present invention relates also to the use of a linker of formula (I) or a drug-linker conjugate of formula (II), preferably in which q=2, for covalently linking a drug to a binding unit, such as an antibody (e.g., a monoclonal antibody) or an antigen binding fragment thereof. Such a covalent link is thus made by means of a linker moiety.

Indeed, the compounds of formula (I) or (II), preferably for which q=2, are useful for covalently linking a drug to a binding unit, such as an antibody (e.g., a monoclonal antibody) or an antigen binding fragment thereof.

The compounds of formula (I) or (II) for which q=0 or 1 can also be used as synthesis intermediates for preparing compounds of formula (I) or (II) for which q=2. In consequence, the present invention relates also to the compounds of formula (I) or (II) as defined above, for which q=0 or 1, as synthesis intermediate.

The present invention relates also to methods for preparing the linker of formula (I) or the conjugates of formula (II), (III) or (IV).

The present invention relates also to a pharmaceutical composition comprising a binding unit-drug conjugate of formula (III) or (IV) and at least one pharmaceutically acceptable excipient.

The present invention relates also to a binding unit-drug conjugate of formula (III) or (IV) or a pharmaceutical composition comprising a binding unit-drug conjugate of formula (III) or (IV) and at least one pharmaceutically acceptable excipient for use in the treatment of cancer.

The present invention relates also to the use of a binding unit-drug conjugate of formula (III) or (IV) for the manufacture of a medicament intended to be used in the treatment of cancer.

The present invention relates also to a method for treating cancer comprising the administration to a person in need thereof of an effective amount of a binding unit-drug conjugate of formula (III) or (IV) or of a pharmaceutical composition comprising a binding unit-drug conjugate of formula (III) or (IV) and at least one pharmaceutically acceptable excipient.

Definitions

For the purpose of the invention, the term "pharmaceutically acceptable" is intended to mean what is useful to the preparation of a pharmaceutical composition, and what is generally safe and non toxic, for a pharmaceutical use.

The term "pharmaceutically acceptable salt" is intended to mean, in the framework of the present invention, a salt of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphthalenesulfonic, propionic, succinic, dibenzoyl-L-tartaric, tartaric, p-toluenesulfonic, trimethylacetic, and trifluoroacetic acid and the like, and (2) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine. N-methylglucamine, triethanolamine, tromethamine and the like. Acceptable inorganic bases comprise aluminium hydroxide, calcium hydroxide, potassium hydroxide, sodium carbonate and sodium hydroxide.

The term "halogen", as used in the present invention, refers to a fluorine, bromine, chlorine or iodine atom.

The term "$(C_1-C_6)$alkyl", as used in the present invention, refers to a monovalent straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "$(C_1-C_6)$alkoxy", as used in the present invention, refers to a $(C_1-C_6)$alkyl group as defined above bound to the molecule via an oxygen atom, including, but not limited to, methoxy, ethoxy, n-propoxy, iso-propoxy, n-butoxy, iso-butoxy, sec-butoxy, t-butoxy, n-pentoxy, n-hexoxy, and the like.

The term "$(C_2-C_6)$alkenyl", as used in the present invention, refers to a straight or branched monovalent unsaturated hydrocarbon chain containing from 2 to 6 carbon atoms and comprising at least one double bond including, but not limited to, ethenyl, propenyl, butenyl, pentenyl, hexenyl and the like.

The term "cycloalkanediyl", as used in the present invention, refers to a bivalent saturated hydrocarbon ring having advantageously 4 to 10 carbon atoms, notably 5 or 6 carbon atoms including, but not limited to, cyclopentanediyl, cyclohexanediyl and the like. Preferably, it is a cyclohexanediyl group.

The term "aryl", as used in the present invention, refers to a monovalent aromatic hydrocarbon group comprising preferably 6 to 10 carbon atoms and comprising one or more fused rings, such as, for example, a phenyl or naphtyl group. Advantageously, it will be a phenyl group.

The term "aryl-$(C_1-C_6)$alkyl", as used in the present invention, refers to a $(C_1-C_6)$alkyl group as defined above substituted with an aryl group as defined above. In particular, it can be a benzyl group.

The term "$(C_1-C_6)$alkyl-aryl", as used in the present invention, refers to an aryl group as defined above substituted with a $(C_1-C_6)$alkyl group as defined above. In particular, it can be a tolyl group ($CH_3Ph$).

The term "aryloxy", as used in the present invention, refers to an aryl group as defined above bound to the molecule via an oxygen atom, including, but not limited to phenyloxy.

The term "arylene", as used in the present invention, refers to a bivalent aromatic hydrocarbon group comprising preferably 6 to 10 carbon atoms and comprising one or more fused rings, such as, for example, a phenylene or naphthylene group. Advantageously, it will be a phenylene group.

The term "heteroarylene", as used in the present invention, refers to a bivalent aromatic group comprising one or several, notably one or two, fused hydrocarbon cycles in which one or several, notably one to four, advantageously one to three, carbon atoms each have been replaced with a heteroatom selected from a sulfur atom, an oxygen atom and a nitrogen atom, preferably selected from an oxygen atom and a nitrogen atom, more preferably a nitrogen atom. Advantageously, it is a bivalent 1,2,3-triazole, such as a bivalent 1H-1,2,3-triazole.

The term "leaving group" as used in the present invention refers to a chemical group which can be easily replaced with a nucleophile (such as an amine or an alcohol respectively bearing a functional group NH or OH) during a nucleophile substitution reaction. Such a leaving group can be in particular a halogen atom, a sulfonate, N-succinimidyloxy, 4-nitro-phenyloxy, pentafluorophenoxy or N-benzotriazoloxy. The sulfonate is in particular a group —$OSO_2$—$R_{LG}$ with $R_{LG}$ representing a $(C_1-C_6)$alkyl, aryl, aryl-$(C_1-C_6)$alkyl or $(C_1-C_6)$alkyl-aryl group, the said group being optionally substituted with one or several halogen atoms such as fluorine atoms. The sulfonate can be notably a mesylate (OMs, $CH_3$—$S(O_2)O$—), a triflate (OTf, $CF_3$—$S(O)_2O$—) or a tosylate (OTs, p-Me-$C_6H_4$—$S(O)_2O$—). The leaving group can be in particular Cl, Br, I, OTf, OMs, OTf, N-succinimidyloxy, 4-nitro-phenyloxy or N-benzotriazoloxy.

The term "trialkylsilyl group", as used in the present invention, refers to a group —$SiAlk_1Alk_2Alk_3$ in which $Alk_1$, $Alk_2$ and $Alk_3$, identical or different, represent a $(C_1-C_6)$-alkyl group as defined above. For example, it can be a trimethylsilyl or triethylsilyl group.

The term "protected form" of a molecule means that at least an OH or NH function present on said molecule is protected with an O-protecting group or an N-protecting group respectively.

The term "protecting group", as used in the present invention, refers to a chemical group which selectively blocks a reactive site in a multifunctional compound so as to allow selectively performing a chemical reaction on another unprotected reactive site.

The term "O-protecting group" as used in the present invention refers to a substituent which protects hydroxyl groups (OH) against undesirable reactions during synthetic procedures such as those O-protecting groups disclosed in "Greene's Protective Groups In Organic Synthesis", $4^{th}$ edition, 2007, John Wiley & Sons, Hoboken, New Jersey A hydroxyl group protected by a O-protecting group can be for example an ether, an ester, a carbonate, an acetal and the like. In particular. O-protecting groups can be a ($C_1$-$C_6$)alkyl optionally substituted with one or several (notably 1 to 3) halogen atoms (such as chlorine atoms), such as methyl, ethyl, tert-butyl or 2,2,2-trichloroethyl; an aryl-($C_1$-$C_6$)alkyl, such as a benzyl, the aryl moiety being optionally substituted with one or several methoxy groups, such as benzyl (Bn) or p-methoxybenzyl (PMB); a trityl derivative of formula —$CAr_1Ar_2Ar_3$ such as triphenylmethyl (also called trityl—Tr), (4-methoxyphenyl)diphenylmethyl (also called methoxytrityl—NMT) or bis-(4-methoxyphenyl)phenylmethyl (also called dimethoxytrityl—DMT); a substituted methyl group of formula —$CH_2OR_{GP2}$ or —$CH_2SR_{GP2}$ (in particular —$CH_2OR_{GP2}$), for example, methoxymethyl (MOM), benzyloxymethyl, 2-methoxyethoxymethyl (MEM), 2-(trimethylsilyl)ethoxymethyl or methylthiomethyl; a substituted ethyl group of formula —$CH_2CH_2OR_{GP2}$ or —$CH_2CH_2SR_{GP2}$ (in particular —$CH_2CH_2OR_{GP2}$), for example, ethoxyethyl (EE); a silyl group of formula —$SiR_{GP3}R_{GP4}R_{GP5}$, for example, trimethylsilyl (TMS), triethylsilyl (TES), t-butyldimethylsilyl (TBS or TBDMS) and t-butyldiphenylsilyl (TBDPS); a carbonylated group of formula —CO—$R_{GP6}$ such as acetyl (Ac), pivaloyl (Piv or Pv) or benzoyl (Bz) or of formula —$CO_2$—$R_{GP7}$ such as allyloxycarbonyl (Alloc) or 9-fluorenylmethyloxycarbonyl (Fmoc); or a tetrahydropyranyl

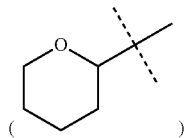

(THP) or tetrahydrofuranyl

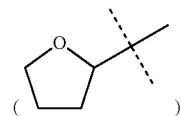

group;
with $Ar_1$, $Ar_2$ and $Ar_3$ representing, independently from one another, an aryl, such as a phenyl, optionally substituted with one or several methoxy groups: $R_{GP2}$ representing a ($C_1$-$C_6$)alkyl (such as methyl or ethyl) optionally substituted with an aryl (such as phenyl), a ($C_1$-$C_6$)alkoxy (such as methoxy) or a trialkylsilyl group (such as $SiMe_3$); $R_{GP3}$, $R_{GP4}$ and $R_{GP5}$ representing, independently from one another, a ($C_1$-$C_6$)alkyl or aryl (such as phenyl) group; and $R_{GP6}$ and $R_{GP7}$ representing, independently of each other, a ($C_1$-$C_6$)alkyl, a ($C_2$-$C_6$)alkenyl, an aryl, an aryl-($C_1$-$C_6$)alkyl or a 9-fluorenylmethyl group.

The term "N-protecting group", as used in the present invention, refers to those groups intended to protect an amine function (notably a primary amine function) against undesirable reactions during synthetic procedures. Commonly used N-protecting groups are disclosed in "Greene's Protective Groups In Organic Synthesis", $4^{th}$ edition, 2007, John Wiley & Sons, Hoboken, New Jersey An amine function protected by a N-protecting group can be a carbamate, an amide, a sulfonamide, an N-alkyl derivative, an amino acetal derivative, a N-benzyl derivative, an imine derivative, an enamine derivative or a N-heteroatom derivative. In particular. N-protecting groups can be formyl; an aryl, such as a phenyl, optionally substituted with one or several methoxy groups such as p-methoxyphenyl (PMP); an aryl-($C_1$-$C_6$)alkyl, such as a benzyl, the aryl moiety being optionally substituted with one or several methoxy groups, such as benzyl (Bn), p-methoxybenzyl (PMB) or 3,4-dimethoxybenzyl (DMPM); —CO—$R_{GP1}$ such as acetyl (Ac), pivaloyl (Piv or Pv), benzoyl (Bz) or p-methoxybenzylcarbonyl (Moz); —$CO_2$—$R_{GP1}$ such as tbutyloxycarbonyl (Boc), trichloroethoxycarbonyl (TROC), allyloxycarbonyl (Alloc), benzyloxycarbonyl (Cbz or Z) or 9-fluorenylmethyloxycarbonyl (Fmoc); —$SO_2$—$R_{GP1}$ such as phenylsulfonyl, tosyl (Ts or Tos) or 2-nitrobenzenesulfonyl (also called nosyl— Nos or Ns); and the like,
with $R_{GP1}$ representing a ($C_1$-$C_6$)alkyl optionally substituted with one or several halogen atoms such as F or Cl; a ($C_2$-$C_6$)alkenyl such as an allyl; an aryl, such as a phenyl, optionally substituted with one or several groups chosen among OMe (methoxy) and $NO_2$ (nitro); an aryl-($C_1$-$C_6$) alkyl, such as a benzyl, the aryl moiety being optionally substituted with one or several methoxy groups; or a 9-fluorenylmethyl group.

The terms "antibody", "antibodies" "ab", "Ab", "MAb" or "immunoglobulin" are used interchangeably in the broadest sense and include monoclonal antibodies, isolated, engineered or recombinant antibodies (e.g, full length or intact monoclonal antibodies), polyclonal antibodies, multivalent antibodies or multispecific antibodies (e.g, bispecific antibodies) and also antibody fragment thereof, so long as they exhibit the desired biological activity.

The term "recombinant antibody" refers to an antibody that results from the expression of recombinant DNA within living cells. A recombinant antibody according to the invention is obtained by using laboratory methods of genetic recombination, well known by a person skilled in the art, creating DNA sequences that would not be found in biological organisms.

The term "antigen binding fragment" of an antibody according to the invention is intended to indicate any peptide, polypeptide, or protein retaining the ability to bind to the target (also generally referred as antigen) of the antibody.

By "binding", "binds", or the like, it is intended that the antibody, or any antigen binding fragment thereof, forms a complex with an antigen that is relatively stable under physiologic conditions. Specific binding can be characterized by an equilibrium dissociation constant of at least about $1 \times 10^{-6}$ M. Methods for determining whether two molecules bind are well known in the art and include, for example, equilibrium dialysis, surface plasmon resonance, radiolabelled assays and the like. For the avoidance of doubt, it does not mean that the said antibody could not bind or interfere, at a low level, to another antigen. Nevertheless, as an embodiment, the said antibody binds only to the said antigen.

As used in the present specification, the expression "IGF-1R antibody" should be interpreted as similar to "anti-IGF-1R antibody" and means an antibody capable of binding to IGF-1R.

As used in the present specification, the expression "HER2 antibody" should be interpreted as similar to "anti-HER2 antibody" and means an antibody capable of binding to HER2.

The term half maximal effective concentration ($EC_{50}$) corresponds to the concentration of a drug, antibody or toxicant which induces a response halfway between the baseline and maximum after some specified exposure time.

It is commonly used as a measure of drug's potency. The $EC_{50}$ of a graded dose response curve therefore represents the concentration of a compound where 50% of its maximal effect is observed. The $EC_{50}$ of a quantal dose response curve represents the concentration of a compound where 50% of the population exhibits a response, after specified exposure duration. Concentration measures typically follow a sigmoidal curve, increasing rapidly over a relatively small change in concentration. This can be determined mathematically by derivation of the best-fit line.

As a preferred embodiment, the $EC_{50}$, determined in the present invention, characterizes the potency of antibody to bind on the IGF-1R ECD exposed on human tumor cells. The $EC_{50}$ parameter is determined using FACS analysis. The $EC_{50}$ parameter reflects the antibody concentration for which 50% of the maximal binding on the human IGF-1R expressed on human tumor cells is obtained. Each $EC_{50}$ value was calculated as the midpoint of the dose response curve using a four-parameter regression curve fitting program (Prism Software). This parameter has been selected as to be representative of physiological/pathological conditions.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "monoclonal antibody" or "Mab" as used herein refers to an antibody obtained from a population of substantially homogeneous antibodies, i.e, the individual antibodies of the population are identical except for possible naturally occurring mutations that may be present in minor amounts. Monoclonal antibodies are highly specific, being directed against a single epitope. Such monoclonal antibody may be produced by a single clone of B cells or hybridoma. Monoclonal antibodies may also be recombinant, i.e, produced by protein engineering or chemical synthesis. Monoclonal antibodies may also be isolated from phage antibody libraries. In addition, in contrast with preparations of polyclonal antibodies which typically include various antibodies directed against various determinants, or epitopes, each monoclonal antibody is directed against a single epitope of the antigen. The monoclonal antibody herein includes murine, chimeric and humanized antibody.

The term "chimeric antibody" relates to an antibody containing a natural variable region (light chain and heavy chain) derived from an antibody of a given species in combination with constant regions of the light chain and the heavy chain of an antibody of a species heterologous to said given species. The chimeric antibodies can be prepared by using the techniques of recombinant genetics. For example, the chimeric antibody could be produced by cloning recombinant DNA containing a promoter and a sequence coding for the variable region of a nonhuman monoclonal antibody, notably murine, and a sequence coding for heterologous species antibody constant region, preferably human. A chimeric antibody according to the invention coded by one such recombinant gene could be, for example, a mouse-human chimera, the specificity of this antibody being determined by the variable region derived from the murine DNA and its isotype determined by the constant region derived from human DNA.

The term "humanized antibodies" means an antibody that contains CDR regions derived from an antibody of nonhuman origin, the other parts of the antibody molecule being derived from one (or several) human antibodies. In addition, some of the skeleton segment residues (called FR) can be modified to preserve binding affinity. The humanized antibodies or fragments of same can be prepared by techniques known to a person skilled in the art. Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents and patent applications EP 0 451 216, EP 0 682 040, EP 0 939 127, EP 0 566 647, U.S. Pat. Nos. 5,530,101, 6,180,370, 5,585,089, 5,693,761, 5,639,641, 6,054,297, 5,886,152 and 5,877,293 can also be cited.

Without contradictory specification in the present specification, complementarity-determining regions or CDRs, mean the hypervariable regions of the heavy and light chains of immunoglobulins as defined according to the IMGT numbering system.

Nevertheless. CDRs can also be defined according to the Kabat numbering system (Kabat et al., Sequences of proteins of immunological interest, $5^{th}$ Ed., U.S. Department of Health and Human Services, NIH, 1991, and later editions). There are three heavy chain CDRs and three light chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes. In order to simplify the reading of the present application, the CDRs according to Kabat are not defined. Nevertheless, it would be obvious for the person skilled in the art, using the definition of the CDRs according to IMGT, to define the CDRs according to Kabat.

In the sense of the present invention, the "identity" or "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package. Genetics Computer Group, 575 Science Dr., Madison, WI, or by the comparison software BLAST NR or BLAST P).

Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences.

For example, the BLAST program. "BLAST 2 sequences" (Tatusova et al., "Blast 2 sequences—a new tool for comparing protein and nucleotide sequences", FEMS Microbiol., 1999. Lett. 174:247-250) available on the site http://www.ncbi.nlm.nih.gov/gorf/bl2.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

By the expressions "back-mutation" or "back mutation" it is meant a mutation or replacement of the human residue present in the germline by the corresponding residue initially present in the murine sequence.

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

The term "peptide" relates to a chain of amino acid monomers linked to each other by peptide (amide) bonds. The covalent peptide bonds (amides) are formed by reacting the carboxyl group (COOH) of one amino acid with the amino group ($NH_2$) of another amino acid. The term peptide includes oligopeptide and polypeptide.

The term "protein" is an assembly of one or several peptides as defined above that have undergone post-translational modifications and protein folding so that they are arranged in a biologically functional way.

The term "amino acid" as used in the present invention refers to natural α-amino acids (e.g. Alanine (Ala), Arginine (Arg), Asparagine (Asn), Aspartic acid (Asp), Cysteine (Cys), Glutamine (Gln), Glutamic acid (Glu). Glycine (Gly), Histidine (His), Isoleucine (Ile). Leucine (Leu), Lysine (Lys), Methionine (Met), Phenylalanine (Phe), Proline (Pro), Serine (Ser), Threonine (Thr), Tryptophan (Trp), Tyrosine (Tyr) and Valine (Val)) in the D or L form, as well as non-natural amino acid (e.g. β-alanine, allylglycine, tert-leucine, 3-amino-adipic acid, 2-aminobenzoic acid, 3-aminobenzoic acid, 4-aminobenzoic acid, 2-aminobutanoic acid, 4-amino-1-carboxymethyl piperidine, 1-amino-1-cyclobutanecarboxylic acid, 4-aminocyclohexaneacetic acid, 1-amino-1-cyclohexanecarboxyilic acid, (1R,2R)-2-aminocyclohexanecarboxylic acid, (1R,2S)-2-aminocyclohexanecarboxylic acid, (1S,2R)-2-aminocyclohexanecarboxylic acid, (1S,2S)-2-aminocyclohexanecarboxylic acid, 3-aminocyclohexanecarboxylic acid, 4-aminocyclohexanecarboxylic acid, (1R,2R)-2-aminocyclopentanecarboxylic acid, (1R,2S)-2-aminocyclopentanecarboxyilic acid, 1-amino-1-cyclopentanecarboxylic acid, 1-amino-1-cyclopropanecarboxylic acid, 4-(2-aminoethoxy)-benzoic acid, 3-aminomethylbenzoic acid, 4-aminomethylbenzoic acid, 2-aminobutanoic acid, 4-aminobutanoic acid, 6-aminohexanoic acid, 1-aminoindane-1-carboxylic acid, 4-aminomethyl-phenylacetic acid, 4-aminophenylacetic acid, 3-amino-2-napthoic acid, 4-aminophenylbutanoic acid, 4-amino-5-(3-indolyl)-pentanoic acid, (4R,5S)-4-amino-5-methylheptanoic acid, (R)-4-amino-5-methylhexanoic acid, (R)-4-amino-6-methylthiohexanoic acid. (S)-4-amino-pentanoic acid, (R)-4-amino-5-phenylpentanoic acid, 4-amino-phenylpropionic acid, (R)-4-aminopimeric acid, (4R,5R)-4-amino-5-hydroxyhexanoic acid, (R)-4-amino-5-hydroxypentanoic acid, (R)-4-amino-5-(p-hydroxyphenyl)-pentanoic acid, 8-aminooctanoic acid, (2S,4R)-4-amino-pyrrolidine-2-carboxylic acid, (2S,4S)-4-amino-pyrrolidine-2-carboxylic acid, azetidine-2-carboxylic acid, (2S,4R)-4-benzyl-pyrrolidine-2-carboxylic acid, (S)-4,8-diaminooctanoic acid, ten-butylglycine acid, γ-carboxyglutamate, β-cyclohexylalanine, citrulline, 2,3-diamino propionic acid, hippuric acid, homocyclohexylalanine, moleucine, homophenylalanine, 4-hydroxyproline, indoline-2-carboxylic acid, isonipecotic acid, α-methyl-alanine, nicopetic acid, norleucine, norvaline, octahydroindole-2-carboxylic acid, ornithine, penicillamine, phenylglycine, 4-phenyl-pyrrolidine-2-carboxylic acid, pipecolic acid, propargylglycine, 3-pyridinylalanine, 4-pyridinylalanine, 1-pyrrolidine-3-carboxylic acid, sarcosine, statines, tetrahydroisoquinoline-1-carboxylic acid, 1,2,3,4-tetrahydroisoquinoline-3-carboxylic acid, or tranexamic acid).

DETAILED DESCRIPTION

Linker Moiety

The linker moiety according to the present invention enables to covalently attach an antibody to at least one drug moiety.

The linker moiety may be "non cleavable" or "cleavable"

In a preferred embodiment, it consists in a "cleavable" linker moiety facilitating the release of the drug in the cell.

For example, in some embodiments, the linker is cleavable by a cleaving agent that is present in the intracellular environment (e.g., within a lysosome or endosome or caveolea). The linker can be, for example, a peptidyl linker that is cleaved by an intracellular peptidase or protease enzyme, including, but not limited to, a lysosomal or endosomal protease. Typically, the peptidyl linker comprises at least two successive amino acids or at least three successive amino acids. Cleaving agents can include cathepsins B and D and plasmin, all of which are known to hydrolyse dipeptide drug derivatives resulting in the release of active drug inside target cells. For example, a peptidyl linker that is cleavable by the thiol-dependent protease cathepsin-B, which is highly expressed in cancerous tissue, can be used (e.g, a linker comprising Phe-Leu or Gly-Phe-Leu-Gly). In specific embodiments, the peptidyl linker cleavable by an intracellular protease comprises or is Val-Cit, Phe-Lys or Val-Ala. One advantage of using intracellular proteolytic release of the drug is that the drug is typically attenuated when conjugated and the serum stabilities of the conjugates are typically high.

The group -$L_1$-(CO)$_c$— represents the stretcher unit of the linker moiety, which is necessarily present. The group -$L_1$-(CO)$_c$— is a group of formula -$L_1$'-(CO—Z')$_z$—(CO)$_c$ — with z' and c being 0 or 1, such as a group -$L_1$'-(CO)$_c$— when z' is 0. Preferably, when at least one of w and y is not 0, then z' is 0 and, in the other cases, z' is 0 or 1.

$L_1$' represents —(CH$_2$)$_n$—, —(CH$_2$CH$_2$O)$_m$—CH$_2$—CH$_2$—, arylene, heteroarylene, cycloalkanediyl, —(CH$_2$)$_n$-arylene-, —(CH$_2$)$_n$-heteroarylene-, —(CH$_2$)$_n$-cycloalkanediyl-, -arylene-(CH$_2$)$_p$—, -heteroarylene-(CH$_2$)$_p$—, -cycloalkanediyl-(CH$_2$)$_p$—, —(CH$_2$)$_n$-arylene-(CH$_2$)$_p$—, —(CH$_2$)$_n$-heteroarylene-(CH$_2$)$_p$—, —(CH$_2$)$_n$-cycloalkanediyl-(CH$_2$)$_p$—, (CH$_2$CH$_2$O)$_m$—CH$_2$—CH$_2$-arylene-(CH$_2$)$_p$—, —(CH$_2$CH$_2$O)$_m$—CH$_2$—CH$_2$-heteroarylene-(CH$_2$)$_p$—, —(CH$_2$CH$_2$O)$_m$—CH$_2$—CH$_2$-cycloalkanediyl-(CH$_2$)$_p$—, —(CH$_2$)$_n$-arylene-CH$_2$—CH$_2$—(OCH$_2$CH$_2$)$_m$—, —(CH$_2$)$_n$-heteroarylene-CH$_2$—CH$_2$—(OCH$_2$ $CH_2)_m$—, or —$(CH_2)_n$-cycloalkanediyl-$CH_2$—$CH_2$—$(OCH_2CH_2)_m$—. More particularly, the arylene is a phenylene; the cycloalkanediyl is a cyclohexanediyl, such as a para-cyclohexanediyl; and the heteroarylene is a bivalent 1,2,3-triazole, such as a bivalent 1H-1,2,3-triazole.

According to a particular embodiment. $L_1'$ represents —$(CH_2)_n$—, —$(CH_2CH_2O)_m$—$CH_2$—$CH_2$—, arylene, -cycloalkanediyl-, —$(CH_2)_n$-arylene-, -arylene-$(CH_2)_n$—, —$(CH_2)_n$-cycloalkanediyl-, -cycloalkanediyl-$(CH_2)_n$—,

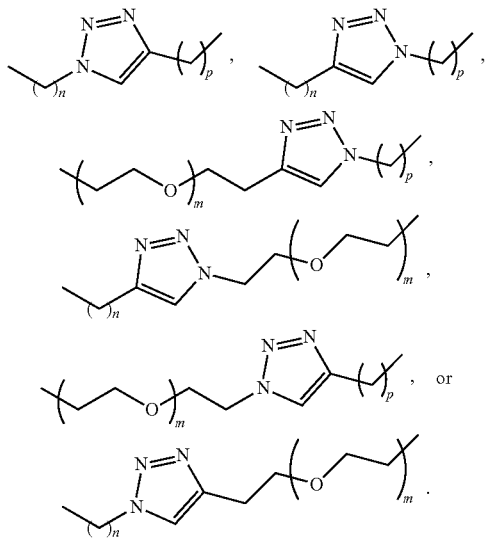

More particularly, the arylene is a phenylene; and the cycloalkanediyl is a cyclohexanediyl, such as a para-cyclohexanediyl.

According to another particular embodiment, $L_1'$ represents —$(CH_2)_n$— or —$(CH_2CH_2O)_m$—$CH_2$—$CH_2$—, notably —$(CH_2)_n$—such as —$(CH_2)_5$—.

The $L_1'$ stretcher unit moiety can be completed with a stretcher unit moiety CO—Z' with Z' being —CO—$NR_4$—$(CH_2)_u$—$NR_5$— or —CO—$NR_4$—$(CH_2)_u$—$NR_5$—CO—$(CH_2)_v$—, when z'=1. $R_4$ and $R_5$ are independently H or $(C_1$-$C_6)$alkyl, such as H or Me, u and v are independently an integer from 1 to 6, such as from 1 to 4, notably 1 or 2, e.g. 2.

$(W)_w$ represents the amino acid unit of the linker.

The amino acid unit of the linker can be enzymatically cleaved by an enzyme including, but not limited to, a tumor-associated protease to liberate the drug.

The amino acid unit can be designed and optimized in its selectivity for enzymatic cleavage by a particular tumor-associated protease. The suitable units are those whose cleavage is catalysed by the proteases, cathepsin B. C and D, and plasmin.

$(W)_w$ may be absent (w=0) or may be a dipeptide, tripeptide, tetrapeptide or pentapeptide unit (w=1, 2, 3, 4 or 5), wherein the amino acids forming the peptide can be different from one another.

Thus $(W)_w$ can be represented by the following formula: $(W1)_{w1}(W2)_{w2}(W3)_{w3}(W4)_{w4}(W5)_{w5}$, wherein each W1 to W5 represents, independently from one another, an amino acid unit and each w1 to w5 is 0 or 1.

In some embodiments, the amino acid unit $(W)_w$ may comprise amino acid residues such as those occurring naturally, as well as minor amino acids and non-naturally occurring amino acid analogs, such as citrulline.

The amino acid residues of the amino acid unit $(W)_w$ include, without limitation, alanine, valine, leucine, isoleucine, methionine, phenylalanine, tryptophan, proline, lysine protected or not with acetyl or formyl, arginine, arginine protected or not with tosyl or nitro group(s), histidine, ornithine, ornithine protected with acetyl or formyl, and citrulline. Exemplary amino acid linker components include preferably a dipeptide or a tripeptide.

Exemplary dipeptides include: Val-Cit, Ala-Val, Ala-Ala, Val-Ala, Lys-Lys, Cit-Cit, Val-Lys, Ala-Phe, Phe-Lys, Ala-Lys. Phe-Cit, Leu-Cit. Ile-Cit, Trp-Cit, Phe-Ala, Phe-$N^9$-tosyl-Arg, and Phe-$N^9$-Nitro-Arg, preferably Val-Cit or Val-Ala.

Exemplary tripeptides include: Val-Ala-Val, Ala-Asn-Val. Val-Leu-Lys, Ala-Ala-Asn, Phe-Phe-Lys, Gly-Gly-Gly. D-Phe-Phe-Lys, Gly-Phe-Lys.

Exemplary tetrapeptide include: Gly-Phe-Leu-Gly (SEQ ID NO. 53), Ala-Leu-Ala-Leu (SEQ ID NO. 54).

Exemplary pentapeptide include: Pro-Val-Gly-Val-Val (SEQ ID NO. 55).

According to a particular embodiment, $(W)_w$ can be a dipeptide (i.e, w=2) such as Val-Cit or Val-Ala, preferably Val-Cit, or the linker lacks an amino acid unit (w=0). When the linker lacks an amino acid unit, preferably it lacks also a spacer unit Y (y=0).

According to a preferred embodiment, w=0 (i.e. $(W)_w$ is a single bond) or w=2 (i.e. $(W)_w$ is a dipeptide) and $(W)_w$ can thus be selected from:

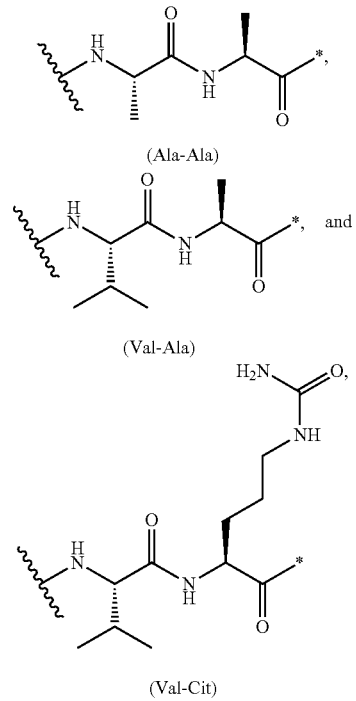

(Ala-Ala)

(Val-Ala)

(Val-Cit)

and in particular is Val-Cit,
wherein
the asterisk indicates the point of attachment to the spacer unit $(Y)_y$; and
the wavy line indicates the point of attachment to -$L_1$-$(CO)_c$— (CO if c=1 or $L_1$ if c=0).

Y represents the spacer unit of the linker.

Spacer units are of two general types: self-immolative and non self-immolative. A non self-immolative spacer unit is one in which part or all of the spacer unit remains bound to the drug after enzymatic cleavage of an amino acid unit from the antibody-drug conjugate. Examples of a non self-immolative spacer unit include, but are not limited to a (glycine-glycine) spacer unit and a glycine spacer unit. To liberate the drug, an independent hydrolysis reaction should take place within the target cell to cleave the glycine-drug unit bond. A self-immolative spacer unit can release the drug without the need for a separate hydrolysis step. In these embodiments, (Y) is a residue of p-aminobenzyl alcohol unit (PAB) that is linked to $(W)_w$ via the nitrogen atom of the PAB group, and connected directly to the drug via an ester, carbonate, carbamate or ether group. Such a linker comprising a PAB moiety can also be considered as a traceless linker.

In the present invention, the spacer unit (Y) is -PAB-CO—$(Z)_z$— with PAB being

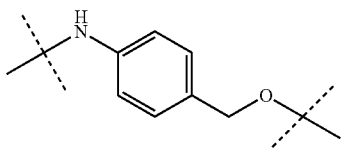

(the oxygen of the PAB unit being linked to the carbonyl), also called -para-aminobenzyl-O—CO—, and y=1 or the linker lacks a spacer unit (y=0).

The spacer -para-aminobenzyl-O—CO— can be completed with a spacer Z which is —$NR_4$—$(CH_2)_u$—$NR_5$— or —$NR_4$—$(CH_2)_u$—$NR_5$—CO— or even —$NR_4$—$(CH_2)_u$—$NR_5$—CO—$(CH_2)_v$— or —$NR_4$—$(CH_2)_u$—$NR_5$—CO—$(CH_2)_v$—CO—, when z=1. $R_4$ and $R_5$ are independently H or ($C_1$-$C_6$)alkyl, such as H or Me, u and v are independently an integer from 1 to 6, such as from 1 to 4, notably 1 or 2, e.g. 2.

Advantageously, y is 0 when w is 0 and y is 0 or 1 when w is an integer from 1 to 5, meaning that the spacer unit Y may be present only when an amino acid unit W is present.

Preferably, y is 0 when w is 0 and y is 1 when w is an integer from 1 to 5, meaning that the spacer unit Y is present when an amino acid unit $(W)_w$ is present and is absent when the amino unit $(W)_w$ is absent.

According to a particular embodiment, the group -$L_1$-$(CO)_c$—$(W)_w$—$(Y)_y$— represents —$(CH_2)_n$—, —$(CH_2)_n$—CO—, —$(CH_2CH_2O)_m$—$CH_2$—$CH_2$—, —$(CH_2CH_2O)_m$—$CH_2$—$CH_2$—CO—, —$CH_2$-para-cyclohexyl-CO—, -aryl-$(CH_2)_n$—, —$(CH_2)_n$—Val-Cit-para-aminobenzyl-O—CO—, —$(CH_2)_n$—CO-Val-Cit-para-aminobenzyl-O—CO—, —$(CH_2CH_2O)_m$—$CH_2$—$CH_2$—Val-Cit-para-aminobenzyl-O—CO—, —$(CH_2CH_2O)_m$—$CH_2$—$CH_2$—CO-Val-Cit-para-aminobenzyl-O—CO—, —$CH_2$-para-cyclohexyl-CO-Val-Cit-para-aminobenzyl-O—CO—, -aryl-$(CH_2)_n$—Val-Cit-para-aminobenzyl-O—CO—, -aryl-CO-Val-Cit-para-aminobenzyl-O—CO—, —$(CH_2)_n$-Val-Ala-para-aminobenzyl-O—CO—, —$(CH_2)_n$—CO-Val-Ala-para-aminobenzyl-O—CO—, —$(CH_2CH_2O)_m$—$CH_2$—$CH_2$-Val-Ala-para-aminobenzyl-O—CO—, —$(CH_2CH_2O)_m$—$CH_2$—$CH_2$—CO-Val-Ala-para-aminobenzyl-O—CO—, —$CH_2$-para-cyclohexyl-CO-Val-Ala-para-aminobenzyl-O—CO—, -aryl-$(CH_2)_n$—Val-Ala-para-aminobenzyl-O—CO—, -aryl-CO-Val-Ala-para-aminobenzyl-O—CO—, —$(CH_2)_n$-Val-Cit-para-aminobenzyl-O—CO—NH—$(CH_2)_u$—NH—, —$(CH_2)_n$—CO-Val-Cit-para-aminobenzyl-O—CO—NH—$(CH_2)_u$—NH—, —$(CH_2CH_2O)_m$—$CH_2$—$CH_2$—Val-Cit-para-aminobenzyl-O—CO—NH—$(CH_2)_u$—NH—, —$(CH_2CH_2O)_m$—$CH_2$—$CH_2$—CO-Val-Cit-para-aminobenzyl-O—CO—NH—$(CH_2)_u$—NH—, —$CH_2$-para-cyclohexyl-CO-Val-Cit-para-aminobenzyl-O—CO—NH—$(CH_2)_u$—NH—, -aryl-$(CH_2)_n$—Val-Cit-para-aminobenzyl-O—CO—NH—$(CH_2)_u$—NH—, -aryl-CO-Val-Cit-para-aminobenzyl-O—CO—NH—$(CH_2)_u$—NH—, —$(CH_2)_n$—Val-Ala-para-aminobenzyl-O—CO—NH—$(CH_2)_u$—NH—, —$(CH_2)_n$—CO-Val-Ala-para-aminobenzyl-O—CO—NH—$(CH_2)_u$—NH—, —$(CH_2CH_2O)_m$—$CH_2$—$CH_2$—Val-Ala-para-aminobenzyl-O—CO—NH—$(CH_2)_u$—NH—, —$(CH_2CH_2O)_m$—$CH_2$—$CH_2$—CO-Val-Ala-para-aminobenzyl-O—CO—NH—$(CH_2)_u$—NH—, —$CH_2$-para-cyclohexyl-CO-Val-Ala-para-aminobenzyl-O—CO—NH—$(CH_2)_u$—NH—, -aryl-$(CH_2)_n$-Val-Ala-para-aminobenzyl-O—CO—NH—$(CH_2)_u$—NH—, -aryl-CO-Val-Ala-para-aminobenzyl-O—CO—NH—$(CH_2)_u$—NH—, —$(CH_2)_n$-Val-Cit-para-aminobenzyl-O—CO—$NCH_3$—$(CH_2)_u$—$NCH_3$—CO—, —$(CH_2)_n$—CO-Val-Cit-para-aminobenzyl-O—CO—$NCH_3$—$(CH_2)_u$—$NCH_3$—CO—, —$(CH_2CH_2O)_m$—$CH_2$—$CH_2$—Val-Cit-para-aminobenzyl-O—CO—$NCH_3$—$(CH_2)_u$—$NCH_3$—CO—, —$(CH_2CH_2O)_m$—$CH_2$—$CH_2$—CO-Val-Cit-para-aminobenzyl-O—CO—$NCH_3$—$(CH_2)_u$—$NCH_3$—CO—, —$CH_2$-para-cyclohexyl-CO-Val-Cit-para-aminobenzyl-O—CO—$NCH_3$—$(CH_2)_u$—$NCH_3$—CO—, -aryl-$(CH_2)_n$—Val-Cit-para-aminobenzyl-O—CO—$NCH_3$—$(CH_2)_u$—$NCH_3$—CO—, -aryl-CO-Val-Cit-para-aminobenzyl-O—CO—$NCH_3$—$(CH_2)_u$—$NCH_3$—CO—, —$(CH_2)_n$—Val-Ala-para-aminobenzyl-O—CO—$NCH_3$—$(CH_2)_u$—$NCH_3$—CO—, —$(CH_2)_n$—CO-Val-Ala-para-aminobenzyl-O—CO—$NCH_3$—$(CH_2)_u$—$NCH_3$—CO—, —$(CH_2CH_2O)_m$—$CH_2$—$CH_2$-Val-Ala-para-aminobenzyl-O—CO—$NCH_3$—$(CH_2)_u$—$NCH_3$—CO—, —$(CH_2CH_2O)_m$—$CH_2$—$CH_2$—CO-Val-Ala-para-aminobenzyl-O—CO—$NCH_3$—$(CH_2)_u$—$NCH_3$—CO—, —$CH_2$-para-cyclohexyl-CO-Val-Ala-para-aminobenzyl-O—CO—$NCH_3$—$(CH_2)_u$—$NCH_3$—CO—, -aryl-$(CH_2)_n$—Val-Ala-para-aminobenzyl-O—CO—$NCH_3$—$(CH_2)_u$—$NCH_3$—CO—, -aryl-CO-Val-Ala-para-aminobenzyl-O—CO—$NCH_3$—$(CH_2)_u$—$NCH_3$—CO—,

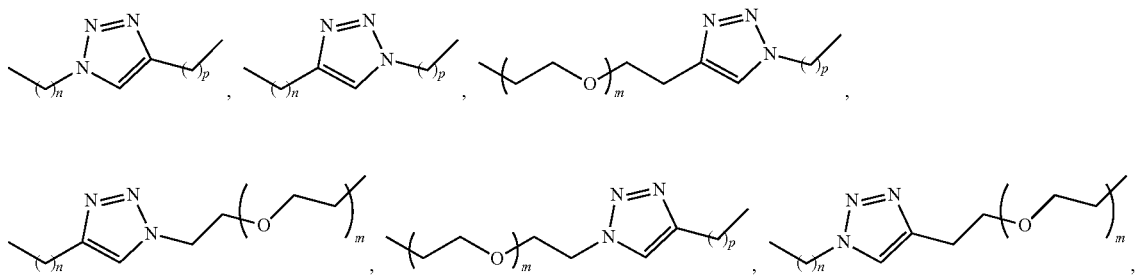

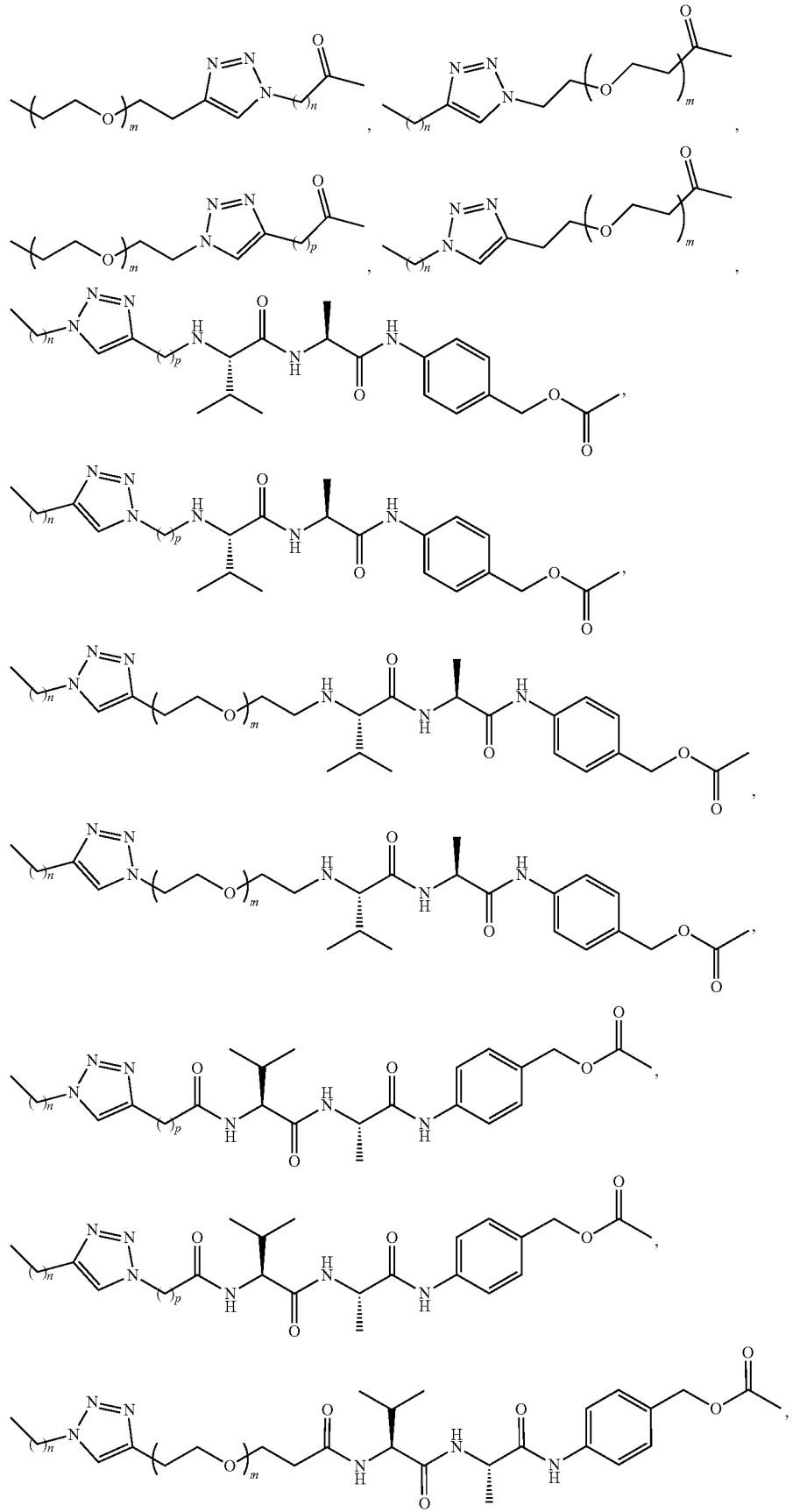

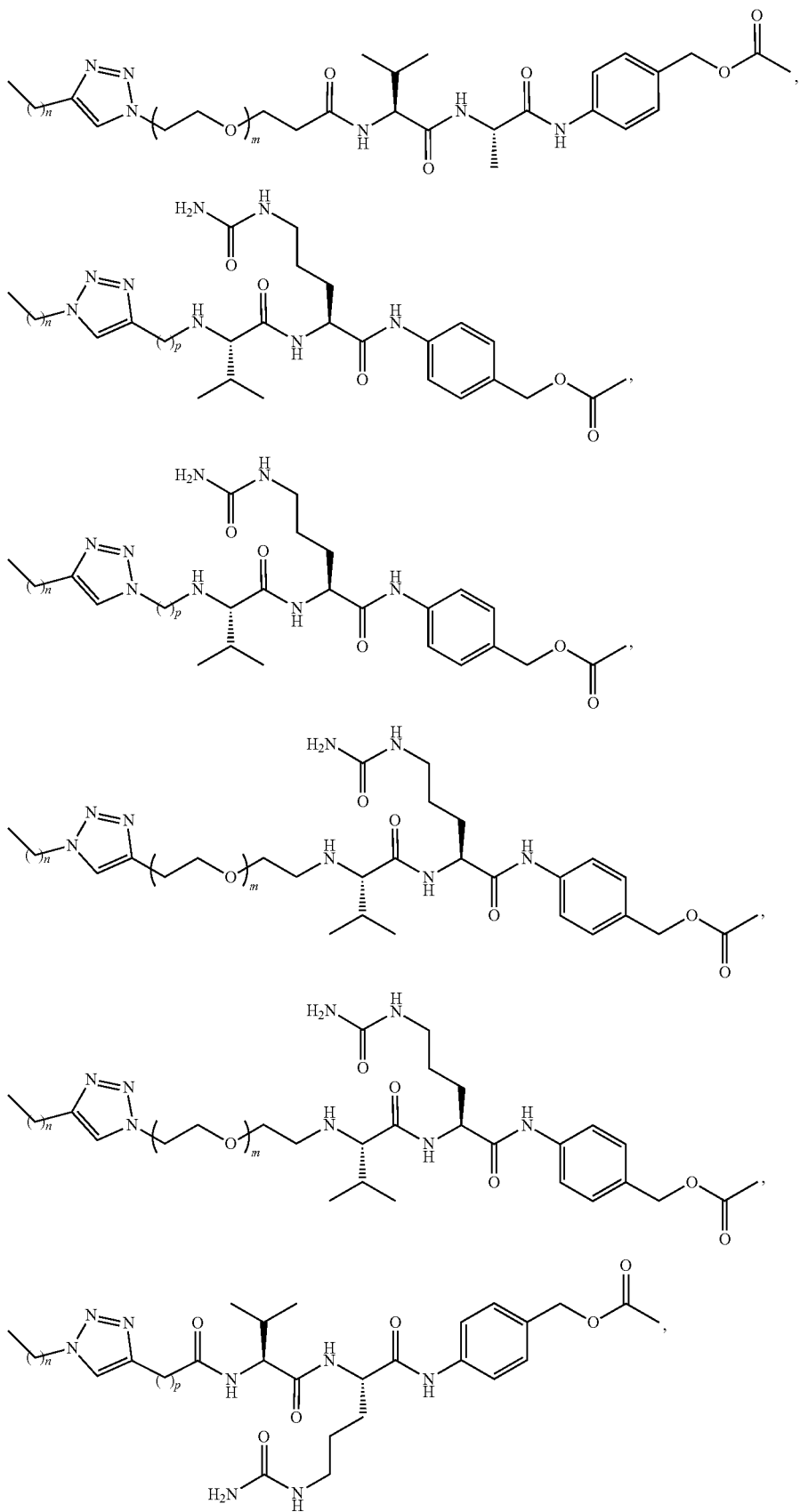

-continued

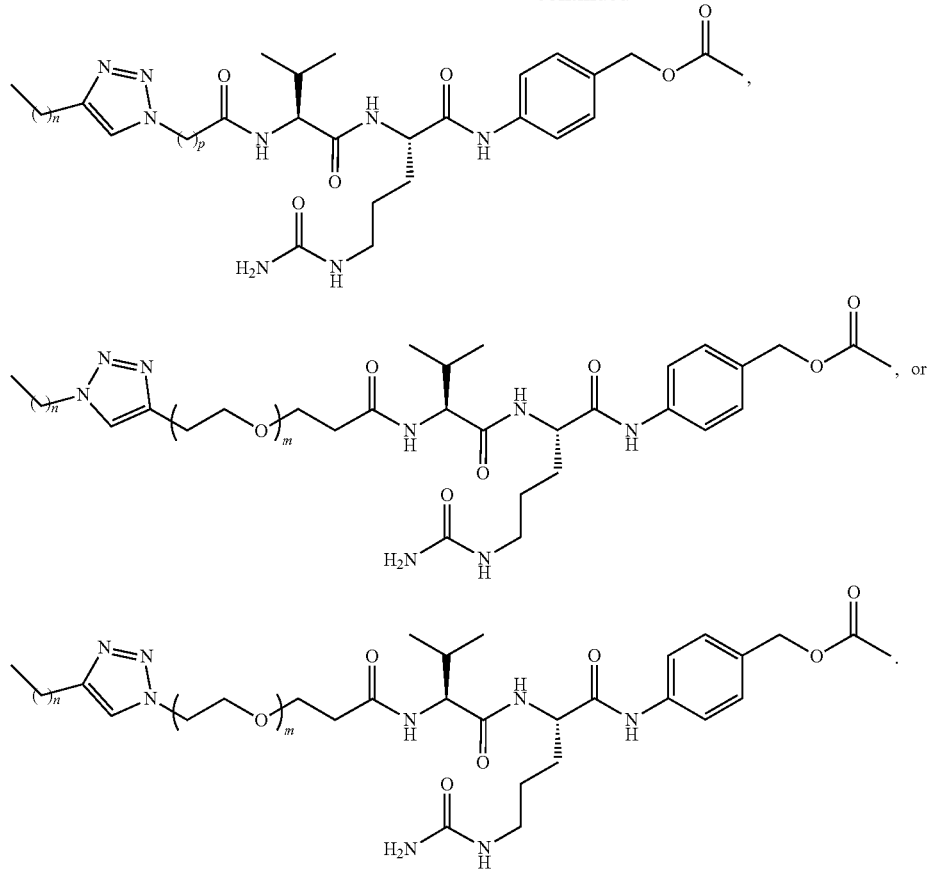

The group -L$_1$-(CO)$_c$—(W)$_w$—(Y)$_y$— can also represent —(CH$_2$)$_n$—CO—NCH$_3$—(CH$_2$)$_u$—NCH$_3$—CO—(CH$_2$)$_v$—, —(CH$_2$)$_n$—CO—NCH$_3$—(CH$_2$)$_u$—NCH$_3$—CO—(CH$_2$)$_v$—CO—, —(CH$_2$CH$_2$O)$_m$—CH$_2$—CH$_2$—CO—NCH$_3$—(CH$_2$)$_u$—NCH$_3$—CO—(CH$_2$)$_v$—, —(CH$_2$CH$_2$O)$_m$—CH$_2$—CH$_2$—CO—NCH$_3$—(CH$_2$)$_u$—NCH$_3$—CO—(CH$_2$)$_n$—CO—, —CH$_2$-para-cyclohexyl-CO—NCH$_3$—(CH$_2$)$_u$—NCH$_3$—CO—(CH$_2$)$_v$—, —CH$_2$-para-cyclohexyl-CO—NCH$_3$—(CH$_2$)$_u$—NCH$_3$—CO—(CH$_2$)$_v$—CO—, -aryl-(CH$_2$)$_n$—CO—NCH$_3$—(CH$_2$)$_u$—NCH$_3$—CO—(CH$_2$)$_v$—, -aryl-(CH$_2$)$_n$—CO—NCH$_3$—(CH$_2$)$_u$—NCH$_3$—CO—(CH$_2$)$_v$—CO—, —(CH$_2$)$_n$—CO—NCH$_3$—(CH$_2$)$_u$—NCH$_3$—, —(CH$_2$)$_n$—CO—NCH$_3$—(CH$_2$)$_u$—NCH$_3$—CO—, —(CH$_2$CH$_2$O)$_m$—CH$_2$—CH$_2$—CO—NCH$_3$—(CH$_2$)$_u$—NCH$_3$—, —(CH$_2$CH$_2$O)$_m$—CH$_2$—CH$_2$—CO—NCH$_3$—(CH$_2$)$_u$—NCH$_3$—, —(CH$_2$CH$_2$O)$_m$—CH$_2$—CH$_2$—CO—NCH$_3$—(CH$_2$)$_u$—NCH$_3$—CO—, —CH$_2$-para-cyclohexyl-CO—NCH$_3$—(CH$_2$)$_u$—NCH$_3$—, —CH$_2$-para-cyclohexyl-CO—NCH$_3$—(CH$_2$)$_u$—NCH$_3$—CO—, -aryl-(CH$_2$)$_n$—CO—NCH$_3$—(CH$_2$)$_u$—NCH$_3$—, -aryl-(CH$_2$)$_n$—CO—NCH$_3$—(CH$_2$)$_u$—NCH$_3$—, -aryl-(CH$_2$)$_n$—CO—NCH$_3$—(CH$_2$)$_u$—NCH$_3$—CO—, —(CH$_2$)$_n$—CO—NH—(CH$_2$)$_u$—NH—, —(CH$_2$)$_n$—CO—NH—(CH$_2$)$_u$—NH—CO—, —(CH$_2$CH$_2$O)$_m$—CH$_2$—CH$_2$—CO—NH—(CH$_2$)$_u$—NH—, —(CH$_2$CH$_2$O)$_m$—CH$_2$—CH$_2$—CO—NH—(CH$_2$)$_u$—NH—CO—, —CH$_2$-para-cyclohexyl-CO—NH—(CH$_2$)$_u$—NH—, —CH$_2$-para-cyclohexyl-CO—NH—(CH$_2$)$_u$—NH—CO—, -aryl-(CH$_2$)$_n$—CO—NH—(CH$_2$)$_u$—NH—, -aryl-(CH$_2$)$_n$—CO—NH—(CH$_2$)$_u$—NH—CO—, —(CH$_2$)$_n$—Val-Cit-para-aminobenzyl-O—CO—NCH$_3$—(CH$_2$)$_u$—NCH$_3$—CO—(CH$_2$)$_v$—, —(CH$_2$)$_n$-Val-Cit-para-aminobenzyl-O—CO—NCH$_3$—(CH$_2$)$_u$—NCH$_3$—CO—(CH$_2$)$_v$—CO—, —(CH$_2$)$_n$—CO-Val-Cit-para-aminobenzyl-O—CO—NCH$_3$—(CH$_2$)$_u$—NCH$_3$—CO—(CH$_2$)$_v$—, —(CH$_2$)$_n$—CO-Val-Cit-para-aminobenzyl-O—CO—NCH$_3$—(CH$_2$)$_u$—NCH$_3$—CO—(CH$_2$)$_v$—CO—, —(CH$_2$CH$_2$O)$_m$—CH$_2$—CH$_2$-Val-Cit-para-aminobenzyl-O—CO—NCH$_3$—(CH$_2$)$_u$—NCH$_3$—CO—(CH$_2$)$_v$—, —(CH$_2$CH$_2$O)$_m$—CH$_2$—CH$_2$—Val-Cit-para-aminobenzyl-O—CO—NCH$_3$—(CH$_2$)$_u$—NCH$_3$—CO—(CH$_2$)$_v$—CO—, —(CH$_2$CH$_2$O)$_m$—CH$_2$—CH$_2$—CO-Val-Cit-para-aminobenzyl-O—CO—NCH$_3$—(CH$_2$)$_u$—NCH$_3$—CO—(CH$_2$)$_v$—, —(CH$_2$CH$_2$O)$_m$—CH$_2$—CH$_2$—CO-Val-Cit-para-aminobenzyl-O—CO—NCH$_3$—(CH$_2$)$_u$—NCH$_3$—CO—(CH$_2$)$_v$—CO—, —CH$_2$-para-cyclohexyl-CO-Val-Cit-para-aminobenzyl-O—CO—NCH$_3$—(CH$_2$)$_u$—NCH$_3$—CO—(CH$_2$)$_v$—, —CH$_2$-para-cyclohexyl-CO-Val-Cit-para-aminobenzyl-O—CO—NCH$_3$—(CH$_2$)$_u$—NCH$_3$—CO—(CH$_2$)$_v$—CO—, -aryl-(CH$_2$)$_n$—Val-Cit-para-aminobenzyl-O—CO—NCH$_3$—(CH$_2$)$_u$—NCH$_3$—CO—(CH$_2$)$_v$—, -aryl-(CH$_2$)$_n$-Val-Cit-para-aminobenzyl-O—CO—NCH$_3$—(CH$_2$)$_u$—NCH$_3$—CO—(CH$_2$)$_v$—CO—, -aryl-CO-Val-Cit-para-aminobenzyl-O—CO—NCH$_3$—(CH$_2$)$_u$—NCH$_3$—CO—(CH$_2$)$_v$—, -aryl-CO-Val-Cit-para-aminobenzyl-O—CO—NCH$_3$—(CH$_2$)$_u$—NCH$_3$—CO—(CH$_2$)$_v$—CO—, —(CH$_2$)$_n$-Val-Ala-para-aminobenzyl-O—CO—NCH$_3$—(CH$_2$)$_u$—NCH$_3$—CO—(CH$_2$)$_v$—, —(CH$_2$)$_n$-Val-Ala-para-aminobenzyl-O—CO—NCH$_3$—(CH$_2$)$_u$—NCH$_3$—CO—(CH$_2$)$_v$—CO—, —(CH$_2$)$_n$—CO-Val-Ala-para-aminobenzyl-O—CO—NCH$_3$—(CH$_2$)$_u$—NCH$_3$—CO—

$(CH_2)_v$—, —$(CH_2)_n$—CO-Val-Ala-para-aminobenzyl-O—CO—NCH$_3$—$(CH_2)_u$—NCH$_3$—CO—$(CH_2)_v$—CO—, —$(CH_2CH_2O)_m$—CH$_2$—CH$_2$-Val-Ala-para-aminobenzyl-O—CO—NCH$_3$—$(CH_2)_u$—NCH$_3$—CO—$(CH_2)_v$—, —$(CH_2CH_2O)_m$—CH$_2$—CH$_2$—Val-Ala-para-aminobenzyl-O—CO—NCH$_3$—$(CH_2)_u$—NCH$_3$—CO—$(CH_2)_v$—CO—, $(CH_2CH_2O)_m$—CH$_2$—CH$_2$—CO-Val-Ala-para-aminobenzyl-O—CO—NCH$_3$—$(CH_2)_u$—NCH$_3$—CO—$(CH_2)_v$—, —$(CH_2CH_2O)_m$—CH$_2$—CH$_2$—CO-Val-Ala-para-aminobenzyl-O—CO—NCH$_3$—$(CH_2)_u$—NCH$_3$—CO—$(CH_2)_v$—CO—, —CH$_2$-para-cyclohexyl-CO-Val-Ala-para-aminobenzyl-O—CO—NCH$_3$—$(CH_2)_u$—NCH$_3$—CO—$(CH_2)_v$—, —CH$_2$-para-cyclohexyl-CO-Val-Ala-para-aminobenzyl-O—CO—NCH$_3$—$(CH_2)_u$—NCH$_3$—CO—$(CH_2)_v$—CO—, -aryl-$(CH_2)_n$-Val-Ala-para-aminobenzyl-O—CO—NCH$_3$—$(CH_2)_u$—NCH$_3$—CO—$(CH_2)_v$—, -aryl-$(CH_2)_n$-Val-Ala-para-aminobenzyl-O—CO—NCH$_3$—$(CH_2)_u$—NCH$_3$—CO—$(CH_2)_v$—CO—, -aryl-CO-Val-Ala-para-aminobenzyl-O—CO—NCH$_3$—$(CH_2)_u$—NCH$_3$—CO—$(CH_2)_v$— or -aryl-CO-Val-Ala-para-aminobenzyl-O—CO—NCH$_3$—$(CH_2)_u$—NCH$_3$—CO—$(CH_2)_v$—CO—.

According to another particular embodiment, the group -L$_1$-(CO)$_c$—(W)$_w$—(Y)$_y$— represents —$(CH_2)_n$—, —$(CH_2)_n$—CO—, —$(CH_2)_n$—Val-Cit-para-aminobenzyl-O—CO—, —$(CH_2)_n$—CO-Val-Cit-para-aminobenzyl-O—CO—, —$(CH_2)_n$—Val-Ala-para-aminobenzyl-O—CO—, —$(CH_2)_n$—CO-Val-Ala-para-aminobenzyl-O—CO—, —$(CH_2)_n$-Val-Cit-para-aminobenzyl-O—CO—NH—$(CH_2)_u$—NH—, —$(CH_2)_n$—CO-Val-Cit-para-aminobenzyl-O—CO—NH—$(CH_2)_u$—NH—, —$(CH_2)_n$-Val-Ala-para-aminobenzyl-O—CO—NH—$(CH_2)_u$—NH—, —$(CH_2)_n$—CO-Val-Ala-para-aminobenzyl-O—CO—NH—$(CH_2)_u$—NH—, —$(CH_2)_n$—Val-Cit-para-aminobenzyl-O—CO—NCH$_3$—$(CH_2)_u$—NCH$_3$—CO—, —$(CH_2)_n$—CO-Val-Cit-para-aminobenzyl-O—CO—NCH$_3$—$(CH_2)_u$—NCH$_3$—CO—, —$(CH_2)_n$-Val-Ala-para-aminobenzyl-O—CO—NCH$_3$—$(CH_2)_u$—NCH$_3$—CO—, or —$(CH_2)_n$—CO-Val-Ala-para-aminobenzyl-O—CO—NCH$_3$—$(CH_2)_u$—NCH$_3$—CO—, with n and u as defined previously and notably with n=5 and u=2.

The group -L$_1$-(CO)$_c$—(W)$_w$—(Y)$_y$— can also represent —$(CH_2)_n$—CO—NH—$(CH_2)_u$—NH—, —$(CH_2)_n$—CO—NH—$(CH_2)_u$—NH—CO—, —$(CH_2)_n$—CO—NCH$_3$—$(CH_2)_u$—NCH$_3$—, —$(CH_2)_n$—CO—NCH$_3$—$(CH_2)_u$—NCH$_3$—CO—, —$(CH_2)_n$—CO—NCH$_3$—$(CH_2)_u$—NCH$_3$—CO—$(CH_2)_v$—, —$(CH_2)_n$—CO—NCH$_3$—$(CH_2)_u$—NCH$_3$—CO—$(CH_2)_v$—CO—, —$(CH_2)_n$—Val-Cit-para-aminobenzyl-O—CO—NCH$_3$—$(CH_2)_u$—NCH$_3$—CO—$(CH_2)_v$—, —$(CH_2)_n$—Val-Cit-para-aminobenzyl-O—CO—NCH$_3$—$(CH_2)_u$—NCH$_3$—CO—$(CH_2)_v$—CO—, —$(CH_2)_n$—CO-Val-Cit-para-aminobenzyl-O—CO—NCH$_3$—$(CH_2)_u$—NCH$_3$—CO—$(CH_2)_v$—, —$(CH_2)_n$—CO-Val-Cit-para-aminobenzyl-O—CO—NCH$_3$—$(CH_2)_u$—NCH$_3$—CO—$(CH_2)_v$—CO—, —$(CH_2)_n$—Val-Ala-para-aminobenzyl-O—CO—NCH$_3$—$(CH_2)_u$—NCH$_3$—CO—$(CH_2)_v$—, —$(CH_2)_n$-Val-Ala-para-aminobenzyl-O—CO—NCH$_3$—$(CH_2)_u$—NCH$_3$—CO—$(CH_2)_v$—CO—, —$(CH_2)_n$—CO-Val-Ala-para-aminobenzyl-O—CO—NCH$_3$—$(CH_2)_u$—NCH$_3$—CO—$(CH_2)_v$—, or —$(CH_2)_n$—CO-Val-Ala-para-aminobenzyl-O—CO—NCH$_3$—$(CH_2)_u$—NCH$_3$—CO—$(CH_2)_v$—CO—, with n, u and v as defined previously and notably with n=5 and u=v=2.

According to a preferred embodiment, the group -L$_1$-(CO)$_c$—(W)$_w$(Y)$_y$— represents —$(CH_2)_n$—CO—, —$(CH_2)_n$—CO-Val-Cit-para-aminobenzyl-O—CO—, —$(CH_2)_n$—CO-Val-Ala-para-aminobenzyl-O—CO—, —$(CH_2)_n$—CO-Val-Cit-para-aminobenzyl-O—CO—NH—$(CH_2)_u$—NH—, —$(CH_2)_n$—CO-Val-Ala-para-aminobenzyl-O—CO—NH—$(CH_2)_u$—NH—, —$(CH_2)_n$—CO-Val-Cit-para-aminobenzyl-O—CO—NCH$_3$—$(CH_2)_u$—NCH$_3$—CO—, or —$(CH_2)_n$—CO-Val-Ala-para-aminobenzyl-O—CO—NCH$_3$—$(CH_2)_u$—NCH$_3$—CO—, with n and u as defined previously and notably with n=5 and u=2.

The group -L$_1$-(CO)$_c$—(W)$_w$—(Y)$_y$— can also represent —$(CH_2)_n$—CO—NH—$(CH_2)_u$—NH—, —$(CH_2)_n$—CO—NH—$(CH_2)_u$—NH—CO—, —$(CH_2)_n$—CO—NCH$_3$—$(CH_2)_u$—NCH$_3$—, —$(CH_2)_n$—CO—NCH$_3$—$(CH_2)_u$—NCH$_3$—CO—, —$(CH_2)_n$—CO—NCH$_3$—$(CH_2)_u$—NCH$_3$—CO—$(CH_2)_v$—, —$(CH_2)_n$—CO—NCH$_3$—$(CH_2)_u$—NCH$_3$—CO—$(CH_2)_v$—CO—, —$(CH_2)_n$—CO-Val-Cit-para-aminobenzyl-O—CO—NCH$_3$—$(CH_2)_u$—NCH$_3$—CO—$(CH_2)_v$—, —$(CH_2)_n$—CO-Val-Cit-para-aminobenzyl-O—CO—NCH$_3$—$(CH_2)_u$—NCH$_3$—CO—$(CH_2)_v$—CO—, —$(CH_2)_n$—CO-Val-Ala-para-aminobenzyl-O—CO—NCH$_3$—$(CH_2)_u$—NCH$_3$—CO—$(CH_2)_v$—, or —$(CH_2)_n$—CO-Val-Ala-para-aminobenzyl-O—CO—NCH$_3$—$(CH_2)_u$—NCH$_3$—CO—$(CH_2)_v$—CO—, with n, u and v as defined previously and notably with n=5 and u=v=2.

The group

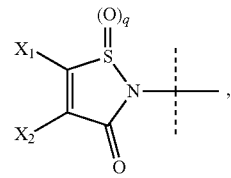

preferably

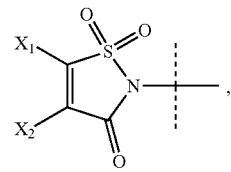

is the functional group which will react with the binding unit, such as an antibody, to attach a drug moiety on it, thanks to sulfhydryl groups present on said binding unit. Sulfhydryl groups can be generated by reduction of intramolecular disulfide bonds of the binding unit, if present, in particular in antibodies. Alternatively, sulfhydryl groups can be generated by reaction of an amino group of a lysine moiety of the binding unit with 2-iminothiolane or other sulfhydryl generating reagents. In specific embodiments, the binding unit, such as an antibody, is engineered to carry one or more lysines. More preferably, the binding unit, such as an antibody, can be engineered to carry one or more cysteines (cf. ThioMabs).

$X_1$ and $X_2$ represent, independently of each other, H, a halogen atom such as Cl or Br, a ($C_1$-$C_6$)alkoxy, an aryloxy optionally substituted, or —O—$(CH_2CH_2O)_r$H, provided that $X_1$ and $X_2$ do not represent H at the same time. The aryloxy is more particularly optionally substituted with one or several groups (e.g, one) selected from halogen, CN, NO; and an aryloxy (e.g, phenyloxy) optionally substituted with one or several halogen atoms such as fluorine atoms. In particular the aryloxy is optionally substituted with one or several (e.g, one) groups selected from CN, NO; and pentafluorophenyloxy, notably optionally substituted with CN. The aryloxy can be in particular a phenyloxy.

According to a particular embodiment, $X_1$ and $X_2$ represent, independently of each other, H, a halogen atom such as Cl or Br, a $(C_1$-$C_6)$alkoxy or an aryloxy optionally substituted, provided that $X_1$ and $X_2$ do not represent H at the same time. The aryloxy is more particularly optionally substituted with one or several groups (e.g, one) selected from halogen, CN, $NO_2$ and an aryloxy (e.g, phenyloxy) optionally substituted with one or several halogen atoms such as fluorine atoms. In particular the aryloxy is optionally substituted with one or several (e.g, one) groups selected from CN, $NO_2$ and pentafluorophenyloxy, notably optionally substituted with CN. The aryloxy can be in particular a phenyloxy.

According to another particular embodiment, $X_1$ and $X_2$ represent, independently of each other, H, Cl, Br, a methoxy or a phenyloxy substituted with CN, notably H, Cl or Br, provided that $X_1$ and $X_2$ do not represent H at the same time.

Advantageously, $X_1$ and $X_2$ are identical and not H or one of $X_1$ and $X_2$ is H and the other is not H. When $X_1$ and/or $X_2$ is not H, it is a halogen atom such as Cl or Br, a $(C_1$-$C_6)$alkoxy, an aryloxy optionally substituted, or —O—$(CH_2CH_2O)_rH$; in particular a halogen atom such as Cl or Br, a $(C_1$-$C_6)$alkoxy or an aryloxy optionally substituted; preferably Cl, Br, a methoxy or a phenyloxy substituted with CN; in particular Cl or Br, q represents 0, 1 or 2. Preferably, q represents 2.

$X_3$ represents a functional group (optionally with the terminal nitrogen of Z when y=z=1 and Z is —$NR_4$—$(CH_2)_u$—$NR_5$— or with the terminal nitrogen of Z' when c=w=y=0 and z'=1 and Z' is —$NR_4$—$(CH_2)_u$—$NR_5$—) which aims to react with the drug (QH or Q-OH) in order ultimately to covalently link the drug to the binding unit, such as an antibody.

It could also be envisaged to introduce first the spacer unit Y and the amino acid unit $(W)_w$, when present, on the drug moiety, before linking the stretcher unit bearing the sulfomaleimide function. In this case, a compound of formula (I) with w=y=0 (i.e, comprising only the stretcher unit and the sulfomaleimide function) will be used and $X_3$ represents in this case a functional group which will react with the amino acid unit $(W)_w$ or the spacer unit Y already attached on the drug unit.

$X_3$ represents H when y=z=1 and Z is —$NR_4$—$(CH_2)_u$—$NR_5$— or when c=w=y=0, z'=1 and T is —$NR_4$—$(CH_2)_u$—$NR_5$— (and form a NH functional group with the terminal nitrogen of the Z or Z' group) and in the other cases, $X_3$ represents OH, $NH_2$ or a leaving group, such as OH or a leaving group. The leaving group can be a halogen atom (e.g. Cl, Br, I), a sulfonate (e.g. OTf, OMs, OTs), N-succinimidyloxy, 4-nitro-phenyloxy, pentafluorophenyloxy or N-benzotriazoloxy. In particular, $X_3$ represents H when y=z=1 and Z is —$NR_4$—$(CH_2)_u$—$NR_5$— or when c=w=y=0, z'=1 and Z' is —$NR_4$—$(CH_2)_u$—$NR_5$— and in the other cases, $X_3$ can be more particularly OH, Cl or N-succinimidyloxy.

Drug Moiety

The drug moiety (Q) is a residue of a drug QH or of a drug Q-OH.

The drug according to the present invention can be any drug useful in human or veterinary therapy, notably for the treatment of cancer. It can be notably a cytotoxic agent. Advantageously, such a drug comprises a functional group to be able to link this drug to the linker moiety. It can also be envisaged to add such a functional group onto the drug to perform the linking. This functional group can be for example OH, SH, NH or COOH and will react with the $X_3$ end of the linker to link the drug to the linker moiety. The coupling reaction can be for example a nucleophilic substitution (e.g, reaction of OH, SH, NH or COOH with $X_3$=leaving group), a peptide coupling (e.g, reaction of COOH with $X_3$=$NH_2$ or $ZX_3$ or $Z'X_3$ ending by NH), an esterification (reaction between COOH and OH), a Mitsunobu reaction, etc.

The drug moiety Q can be for example:

a residue of an auristatin derivative such as a residue of monomethyl auristatin F (MMAF) (linked by its terminal NH or COOH group), monomethyl auristatin E (MMAE) (linked by its terminal NH or OH group), monomethyl dolastatin-10 (linked by its terminal NH group) or a derivative thereof such as a drug moiety of formula (C) as defined below;

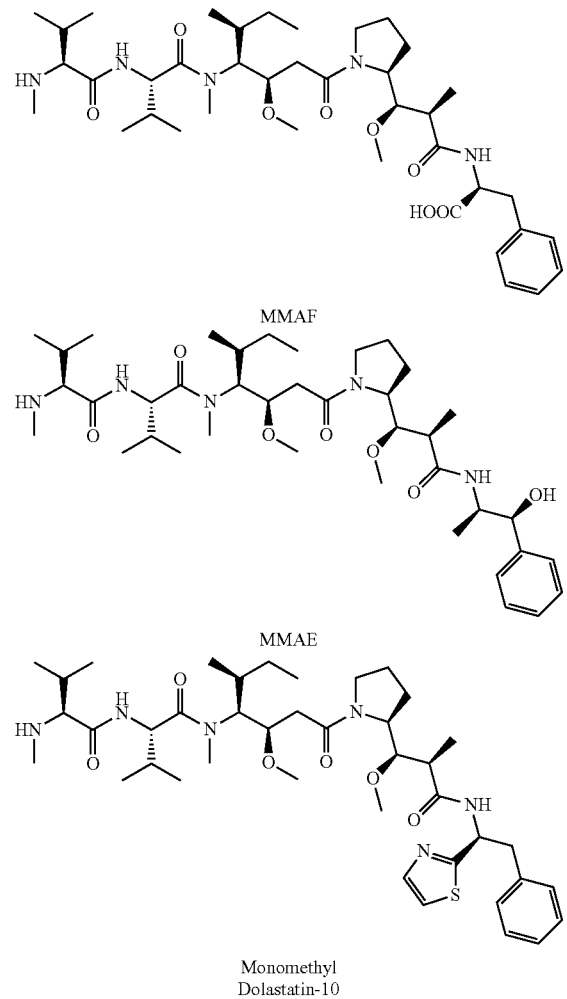

MMAF

MMAE

Monomethyl Dolastatin-10 a residue of an anthracycline, such as a residue of daunorubicine, doxorubicine, epirubicine or idarubicine (linked by an $NH_2$ group or the OH group of —$COCH_2OH$), or a derivative thereof such as 2-pyrrolinodoxorubicine or pro-2-pyrrolinodoxorubicine (linked by the OH group of —$COCH_2OH$), or PNU-159682 (linked by the OH group of —$COCH_2OH$) or a derivative thereof; in particular a residue of doxorubicine (linked by an $NH_2$ group or the OH group of —$COCH_2OH$), 2-pyrrolinodoxorubicine, pro-2-pyrrolinodoxorubicine (linked by the OH group of —COCH$_2$OH) or PNU-159682 (linked by the OH group of —COCH$_2$OH) or a derivative of PNU-159682 notably as illustrated below; preferably a residue of PNU-159682 (linked by the OH group of —COCH$_2$OH) or a residue of a derivative of PNU-159682 as illustrated below (linked by COOH);
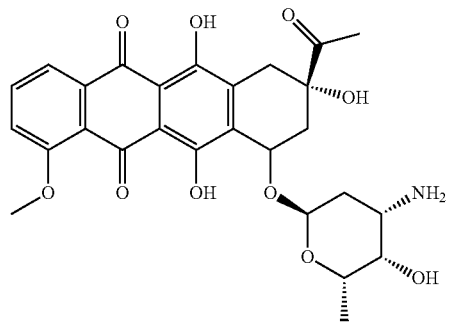
Daunorubicine
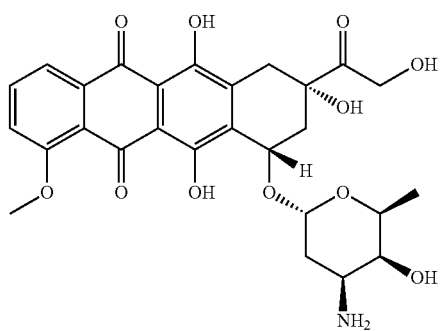
Doxorubicine
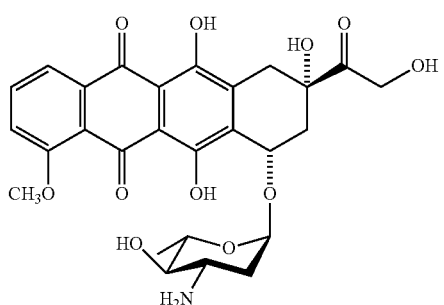
Epirubicine
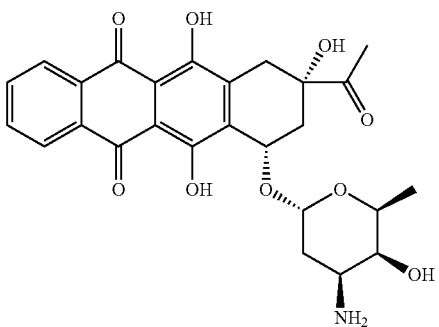
Ibarubicine
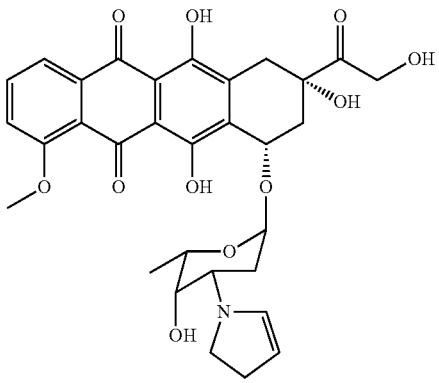
2-Pyrrolino-doxorubicine
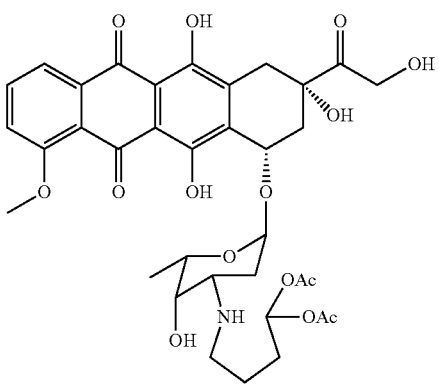
Pro-2-pyrrolino-doxorubicine

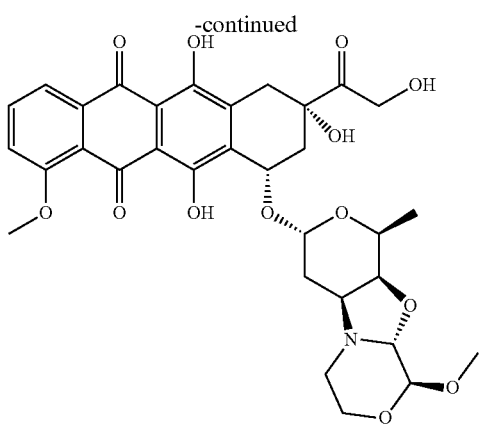
PNU-159682
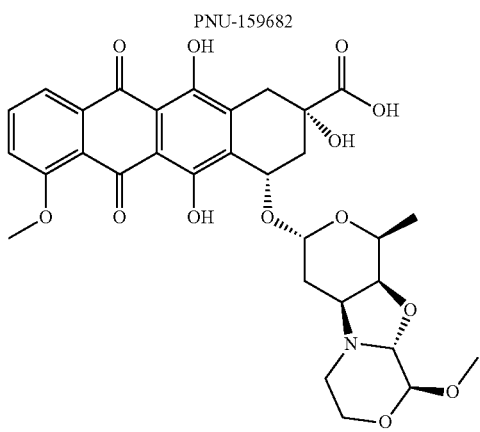
Derivative of PNU-159682
a residue of camptothecin or a derivative thereof such as SN-38 (linked by its OH group);
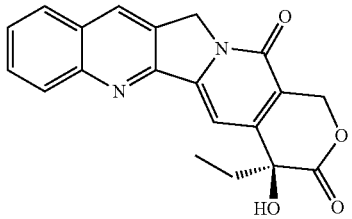
Camptothecin
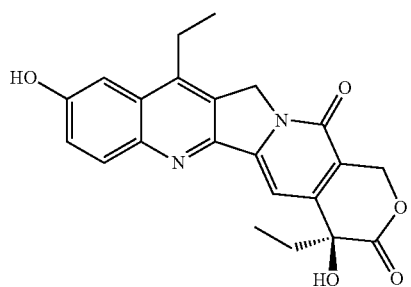
SN-38
a residue of a tubulysin, such as tubulysin A, tubulysin B, tubulysin C or tubulysin D (linked by a COOH group or an OH group when present);
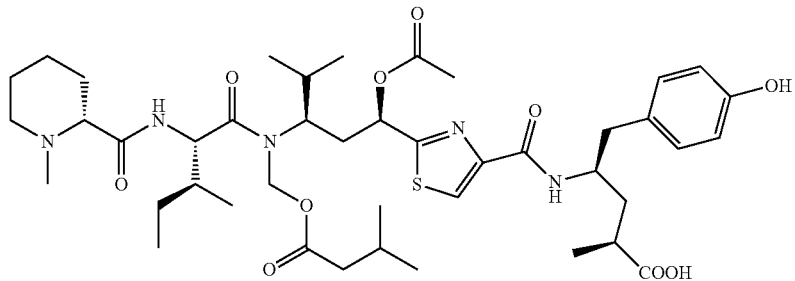
Tubulysin A
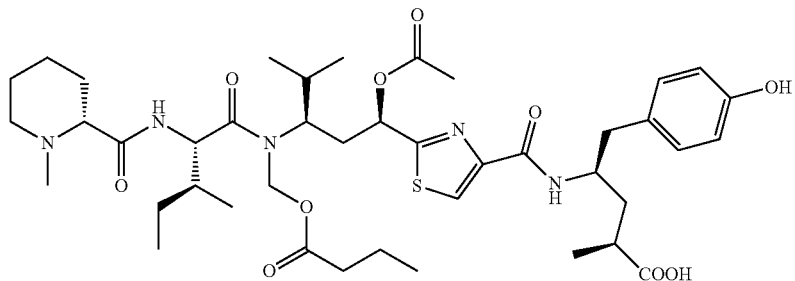
Tubulysin B

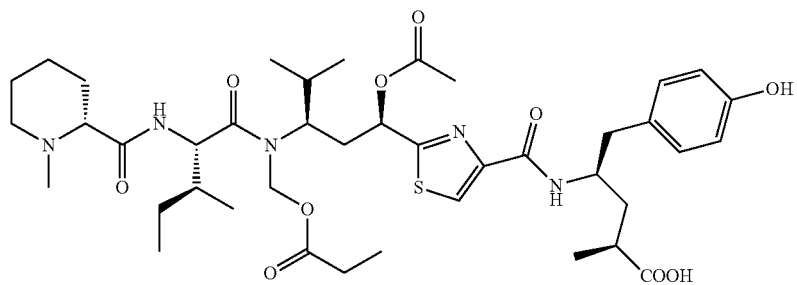
Tubulysin C
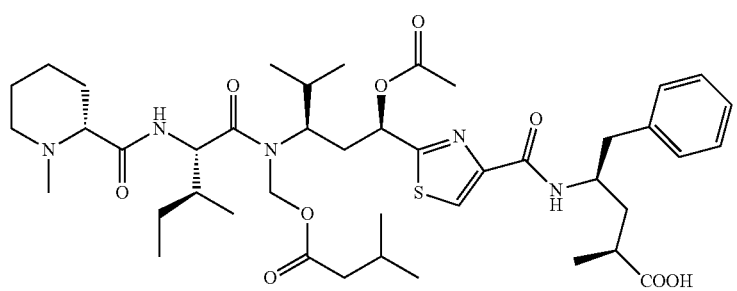
Tubulysin D
a residue of a calicheamicin, such as esperamicin or calicheamicin γ1, or a derivative thereof such as N-acetyl dimethyl hydrazide calicheamicin (linked by its hydrazide moiety);
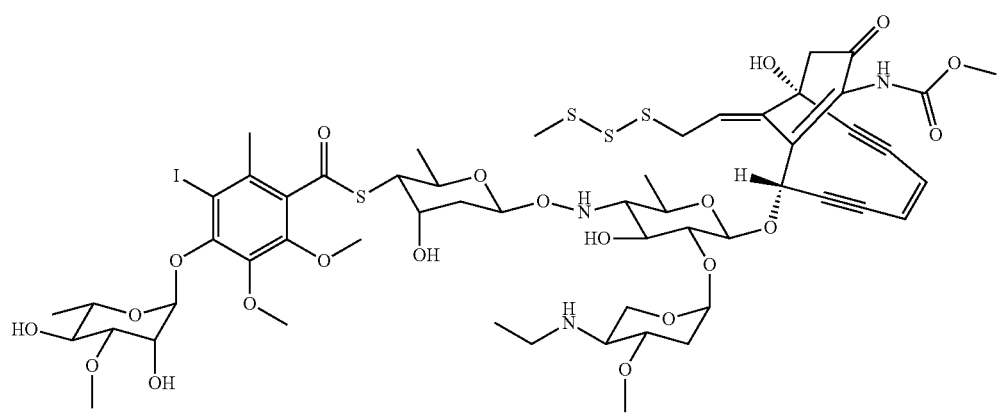
Calicheamicin γ1

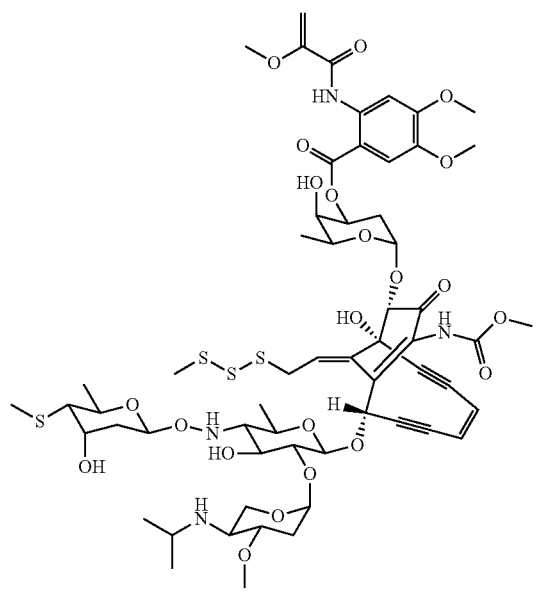
Esperamicin
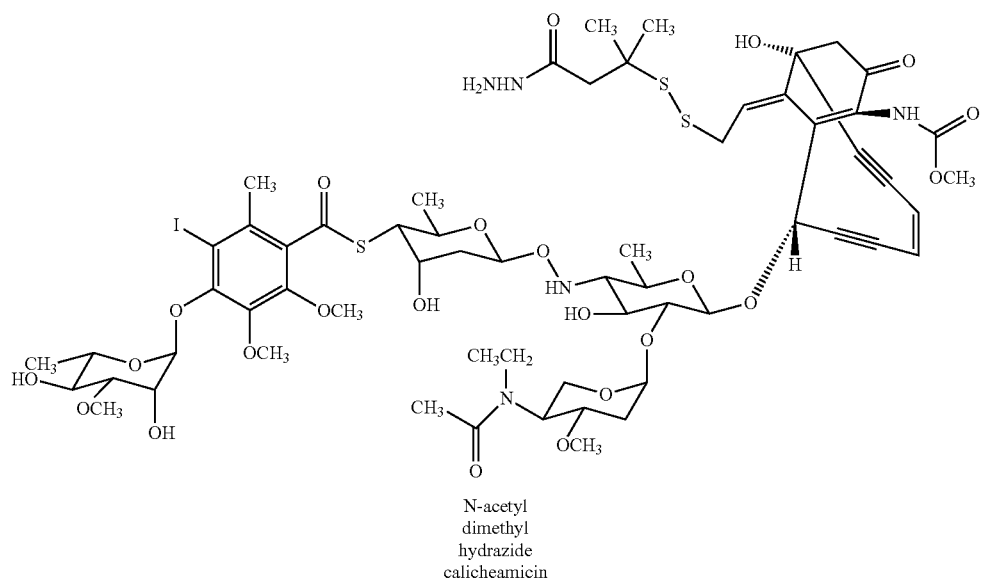
N-acetyl dimethyl hydrazide calicheamicin a residue of a maytansinoid, such as maytansine (also called maitansine) or a derivative thereof such as DM1 or DM4 (linked by a SH group); in particular a residue of DM1 or DM4 (linked by a SH group);

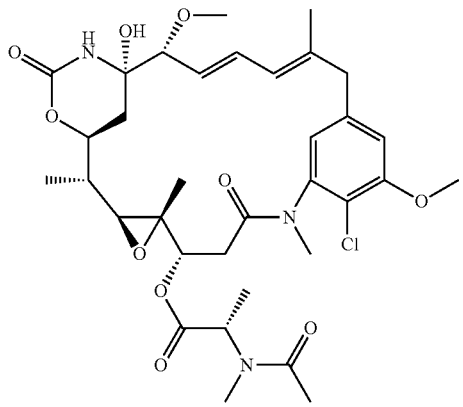
Maytansine

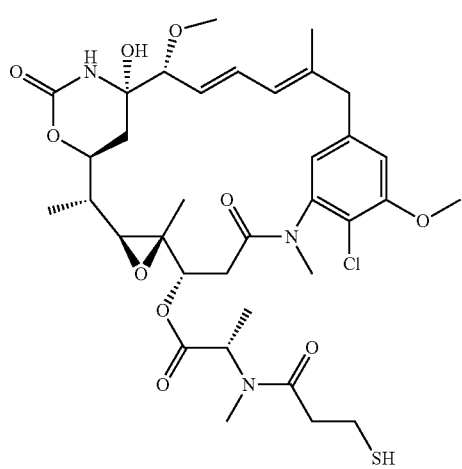
DM1

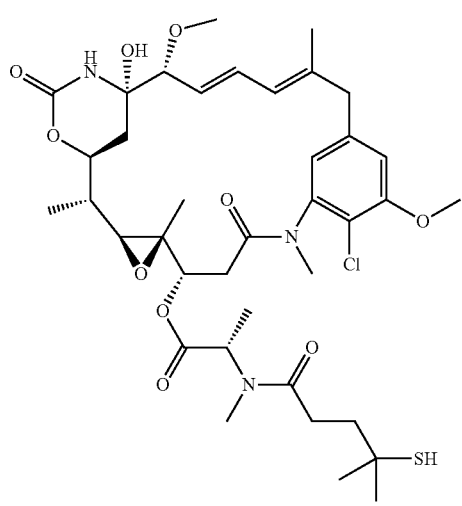
DM4 a residue of a duocarmycin such as duocarmycin A, duocarmycin B1, duocarmycin B2, duocarmycin C1, duocarmycin C2, duocarmycin D duocarmycin SA, or CC-1065 (linked by a CONH$_2$ group); in particular a residue of CC-1065 (linked by a CONH$_2$ group);

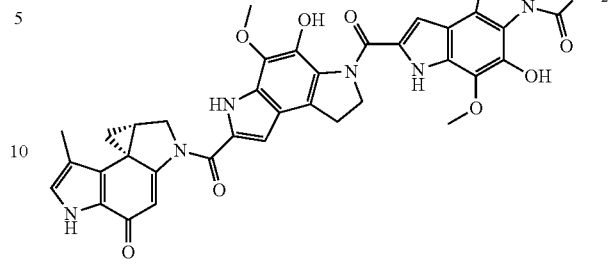
CC-1065 a residue of an amanitine (linked by an OH, NH, COOH or CONH$_2$ group, in particular an OH group) such as α-amanitine, β-amanitine, γ-amanitine or ε-amanitine; in particular a residue of α-amanitine (linked notably by a CH$_2$OH group);

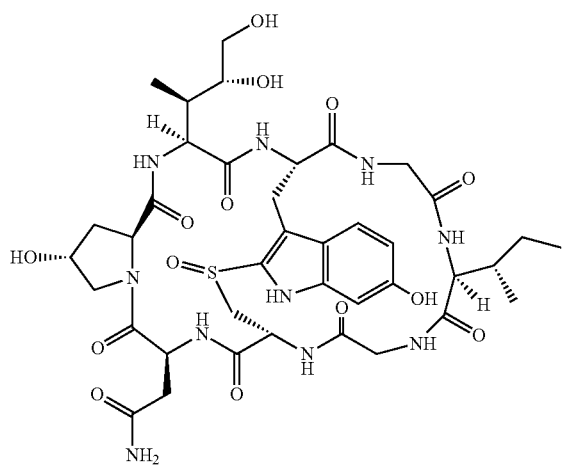
α-Amanitine

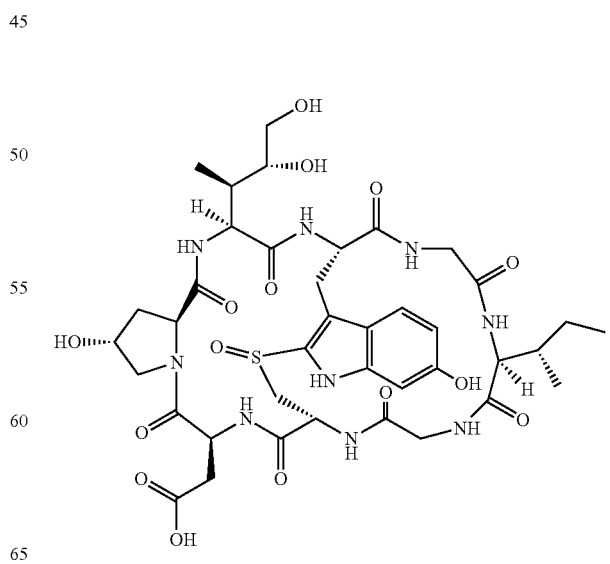
β-Amanitine

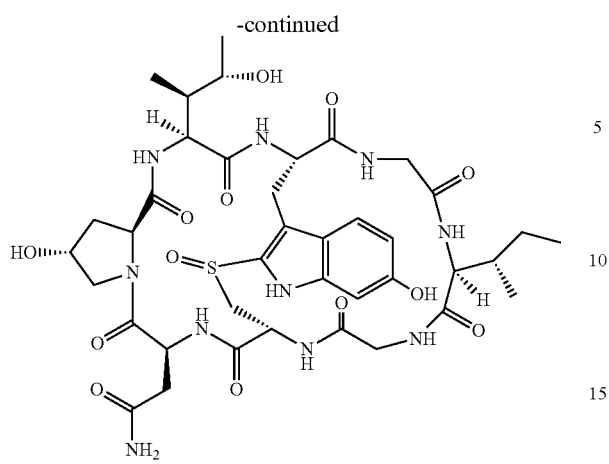
γ-Amanitine
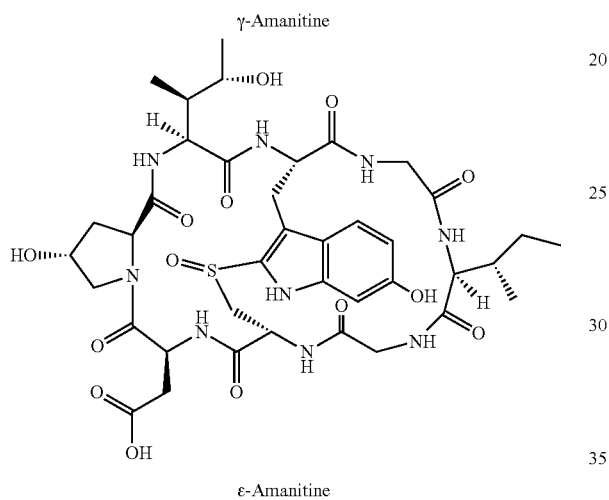
ε-Amanitine
a residue of a pyrrolobenzodiazepine (PBD) such as anthramycin (linked by its OH or NH$_2$ group) or SGD-1882 (linked by its NH$_2$ group); in particular a residue of SGD-1882 (linked by its NH$_2$ group);
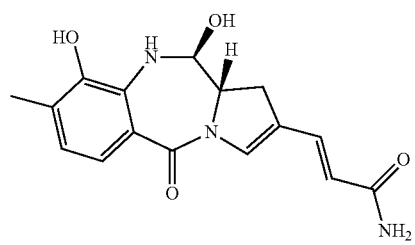
Anthramycin
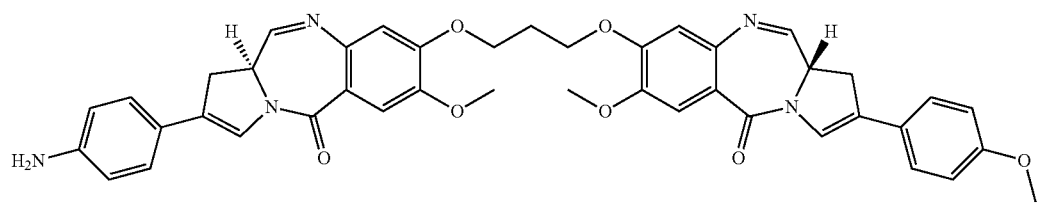
SGD-1882 a residue of an activator of Immune check point such as a residue of a STING (stimulator of interferon genes) agonist advantageously of formula (D) as defined below (linked by OH, SH or NH) or a residue of an IDO (indoleamine 2,3-dioxygenase) inhibitor such as epacadostat (INCB024360) or BMS-986205.

Advantageously, the drug moiety Q is:

a residue of an auristatin derivative such as a residue of MMAF (linked by its terminal NH or COOH group), MMAE (linked by its terminal NH or OH group), or monomethyl dolastatin-10 (linked by its terminal NH group) or a drug moiety of formula (C) as defined below;

a residue of a STING agonist, notably of formula (D) as defined below; or a residue of an anthracycline, such as defined above and preferably a residue of PNU-159682 or a derivative thereof as illustrated below:

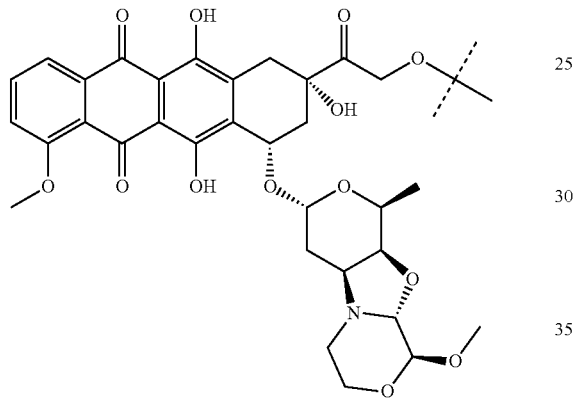

Residue of
PNU-159682

The drug moiety Q is in particular a residue of an anthracycline, such as defined above and preferably a residue of PNU-159682 or a derivative thereof as illustrated below:

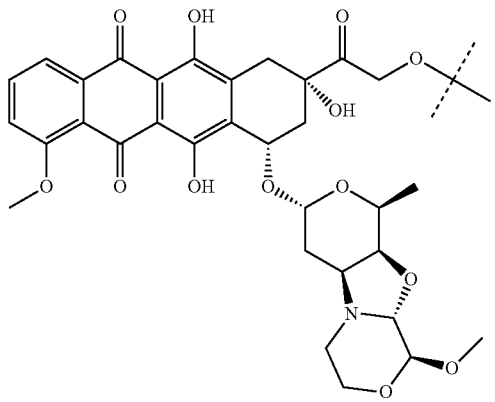

Residue of
PNU-159682

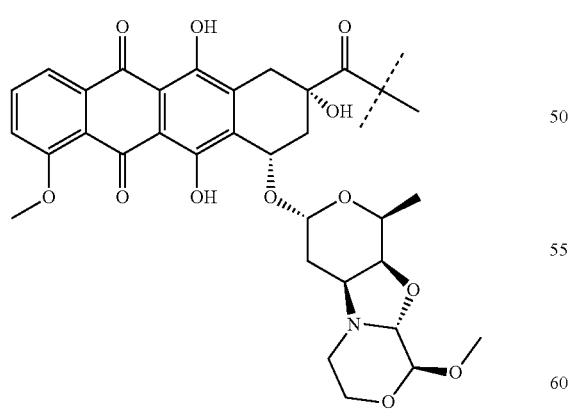

Residue of
a derivative of
PNU-159682

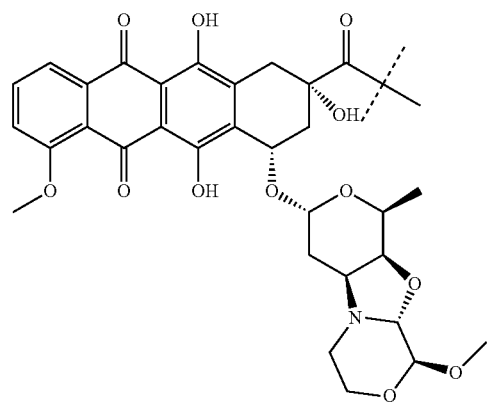

Residue of
a derivative of
PNU-159682

According to a first embodiment, the residue of an auristatin derivative has the following formula (C):

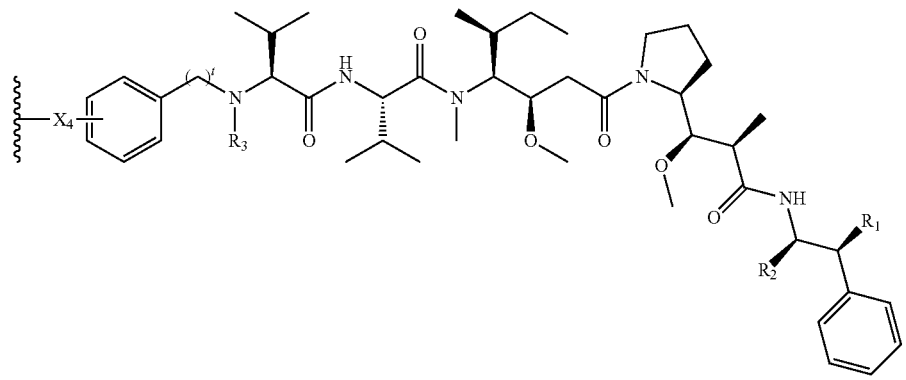

(C)

where:
- $R_1$ is H or OH,
- $R_2$ is a $(C_1-C_6)$alkyl (e.g, methyl), COOH, COO—$((C_1-C_6)$alkyl) (such as COOMe) or a thiazolyl (such as thiazol-2-yl),
- $R_3$ is H or a $(C_1-C_6)$alkyl (such as methyl), in particular a $(C_1-C_6)$alkyl group,
- $X_4$ is O or $NR_9$,
- $R_9$ is H or $(C_1-C_6)$alkyl (such as methyl), and
- t is an integer from 1 and 8, in particular from 1 to 6, advantageously from 1 to 4, preferably is 1 or 2.

According to a particular embodiment:
- $R_1$ is OH and $R_2$ is $(C_1-C_6)$alkyl such as methyl; or
- $R_1$ is H and $R_2$ is thiazolyl such as thiazol-2-yl, COO—$(C_1-C_6)$alkyl such as COOMe, or COOH.

Advantageously, $R_1$ is H and $R_2$ is thiazolyl such as thiazol-2-yl, COO—$(C_1-C_6)$alkyl such as COOMe, or COOH. Preferably $R_1$ is H and $R_2$ is COOH or COOMe, in particular COOH.

t is an integer from 1 and 8, in particular from 1 to 6, advantageously from 1 to 4, preferably is 1 or 2.

Advantageously. $R_3$ is a $(C_1-C_6)$alkyl group and preferably a methyl group.

According to a particular embodiment, $R_1$ is H, $R_2$ is COOH or COOMe (preferably COOH), $R_3$ is methyl and t is 1 or 2.

Advantageously, $X_4$ is $NR_9$ with $R_9$ being H or $(C_1-C_6)$ alkyl, preferably being H or methyl.

In a preferred embodiment:
- $R_1$ is H, $R_2$ is COOH, $R_3$ is methyl, $X_4$ is $NR_9$, $R_9$ is methyl and t is 1 or 2, or
- $R_1$ is H, $R_2$ is COOH, $R_3$ is methyl, $X_4$ is $NR_9$, $R_9$ is H and t is 1 or 2.

According to a preferred embodiment, the $X_4$ group is located on the phenyl ring in a para position in relation to the $(CH_2)_t$ group.

Advantageously, the residue of an auristatin of formula (C) is chosen from among the following moieties:

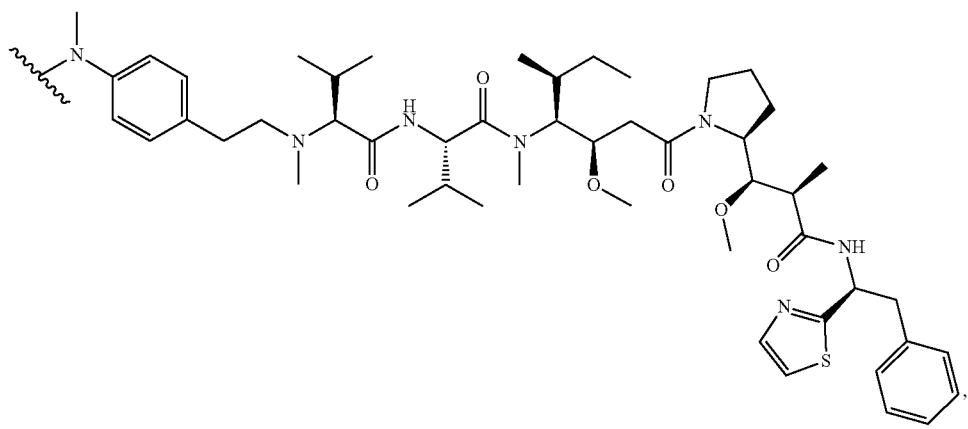

-continued
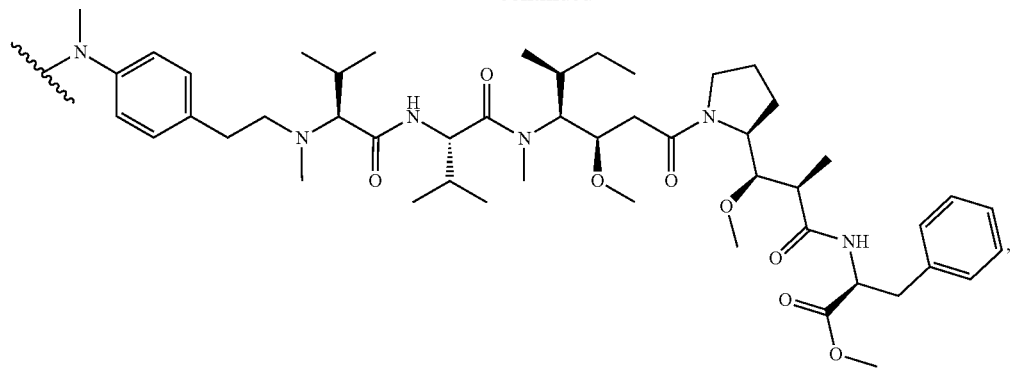
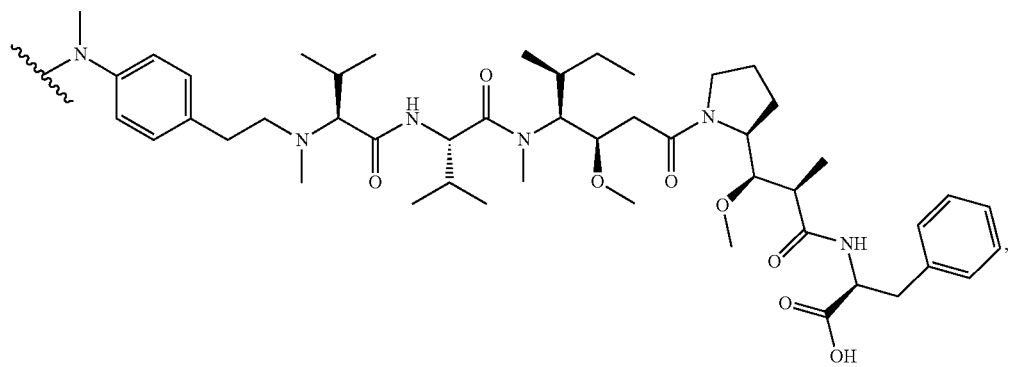
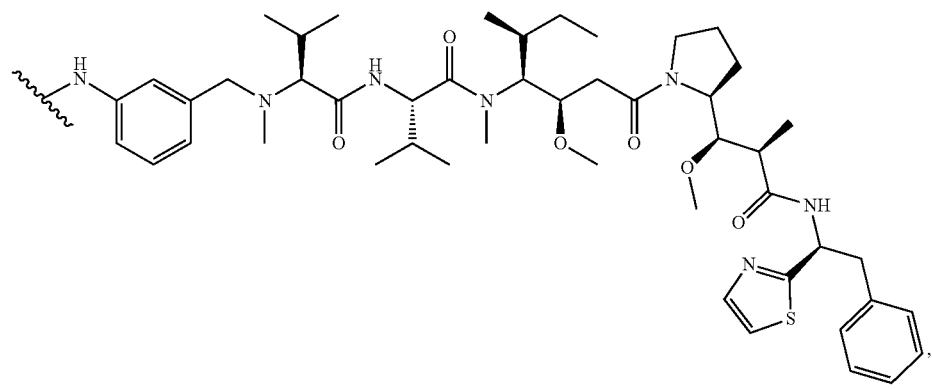
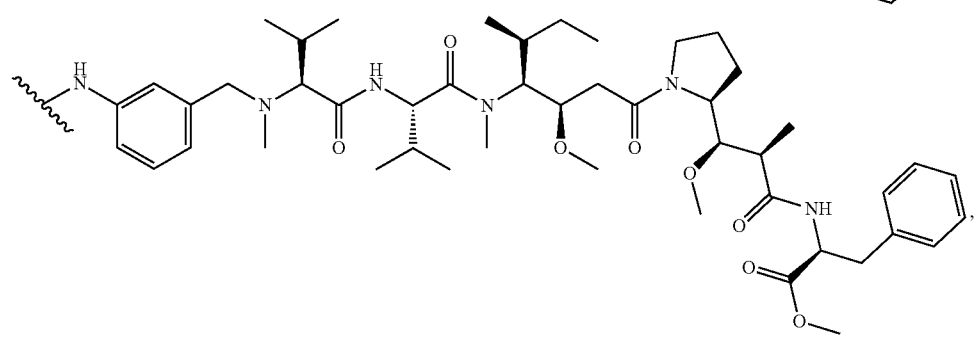

-continued
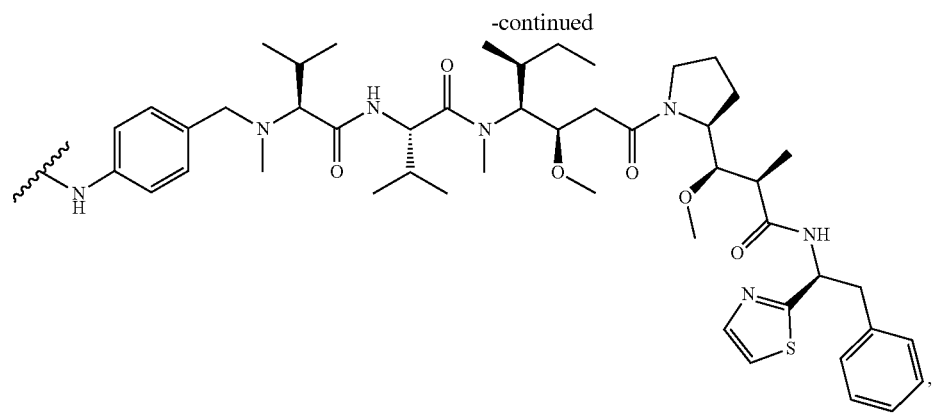
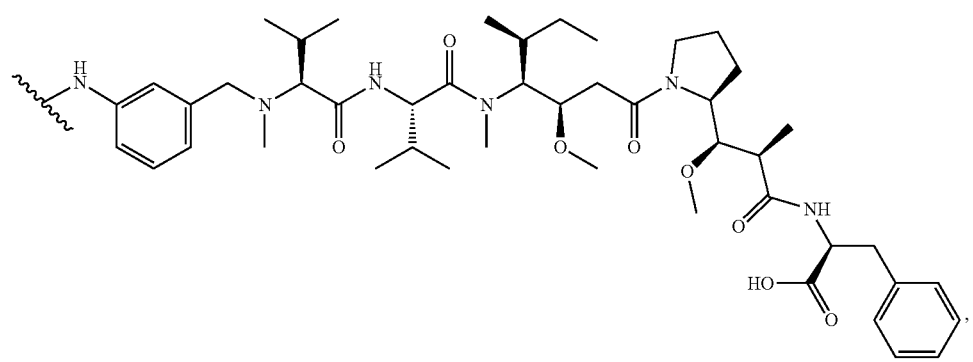
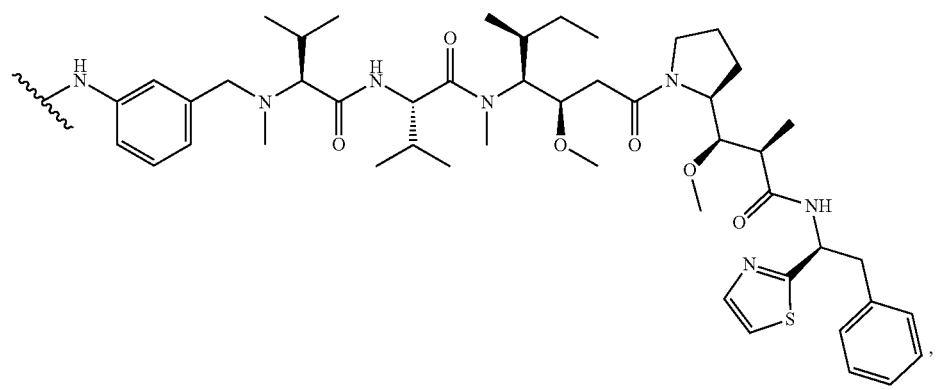
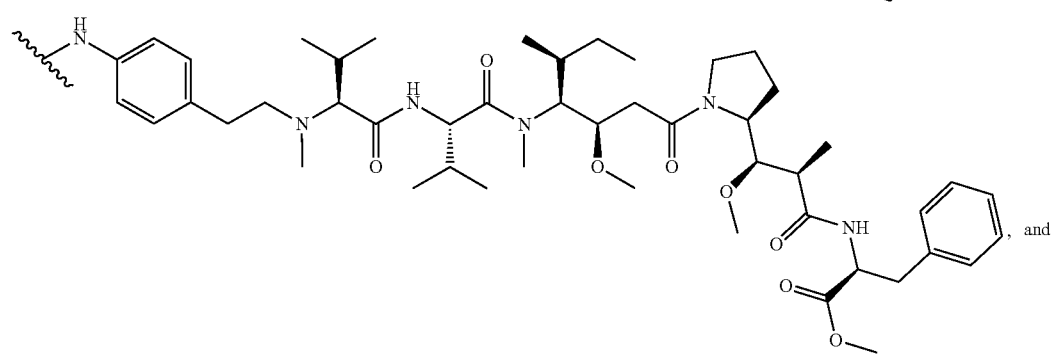

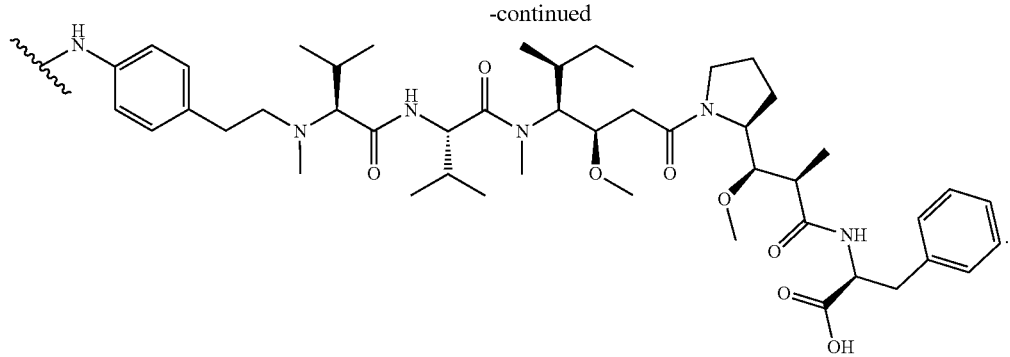

The preparation of such an auristatin derivative is disclosed in WO2014/174064 or WO2015/162293 for example.

According to a second embodiment, the STING agonist has the following formula (X):

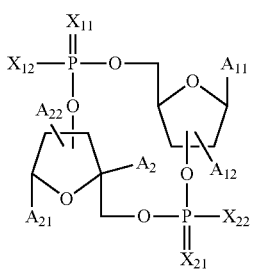

(X)

where:

$X_{11}$ and $X_{21}$ are independently O or S, preferably O, $X_{12}$ and $X_{22}$ are independently OH or SH, preferably SH, $A_{11}$ and $A_{21}$ are independently a group of formula:

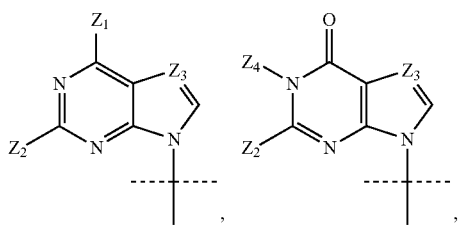

preferably

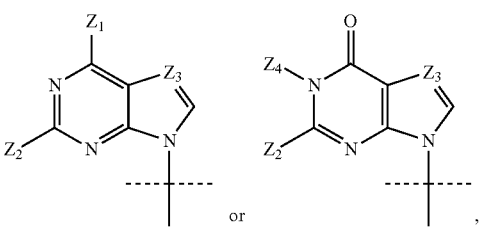

or where:

$Z_1$ is $OR_{11}$ or $NR_{11}R_{12}$, with $R_{11}$ and $R_{12}$ being independently H, $R_{13}$ or $COR_{13}$, with $R_{13}$ being $(C_1-C_6)$alkyl, aryl or aryl$(C_1-C_6)$alkyl, $Z_2$ is H or $NR_{21}R_{22}$, with $R_{21}$ and $R_{22}$ being independently H, $R_{23}$ or $COR_{23}$, with $R_{23}$ being $(C_1-C_6)$alkyl, aryl or aryl$(C_1-C_6)$alkyl, $Z_3$ is N or $CR_{33}$, preferably N, with $R_{33}$ being H or a halogen atom such as F or Cl, and $Z_4$ is H or a $(C_1-C_6)$alkyl, $A_{12}$ and $A_{22}$ are independently H, OH or F, and $A_2$ is H or $A_2$ and $A_{22}$ are linked together with $A_2$ being $CH_2$ and $A_{22}$ being O.

When, $Z_1$ is OH or $Z_4$ is H, the following tautomer forms can be obtained:

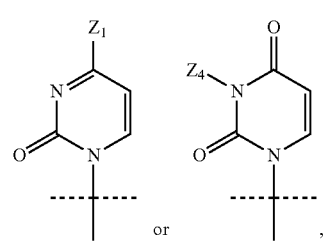

or

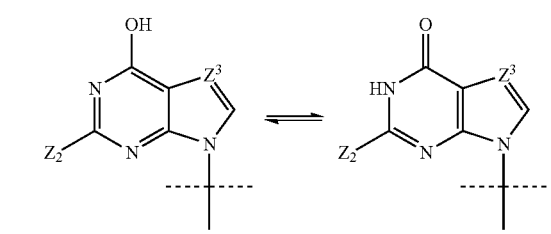

According to a particular embodiment, the STING agonist has one of the following formulas:

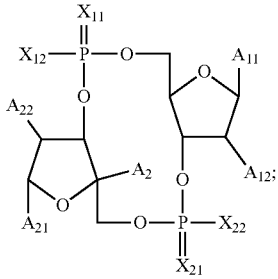
(X-1)

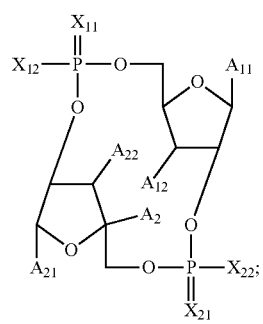
(X-2)

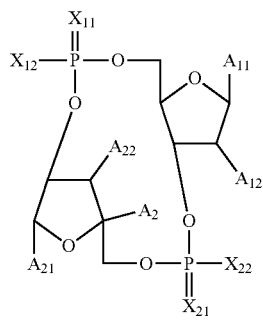
(X-3)

where $X_{11}$, $X_{21}$, $X_{12}$, $X_{22}$, $A_{11}$, $A_{21}$, $A_{12}$, $A_{22}$ and $A_2$ are as defined above or below.

According to another particular embodiment, the STING agonist has one of the following formulas:

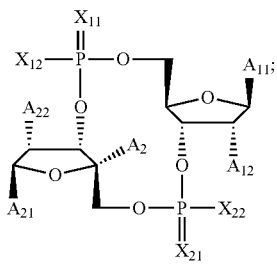
(X-1a)

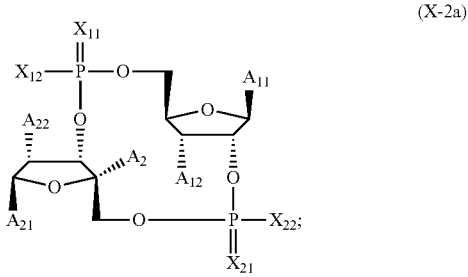
(X-2a)

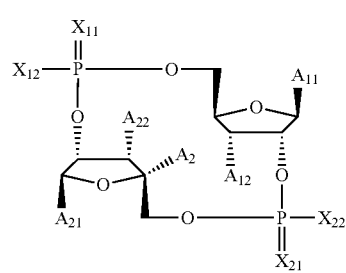
(X-3a)

where $X_{11}$, $X_{21}$, $X_{12}$, $X_{22}$, $A_{11}$, $A_{21}$, $A_{12}$, $A_{22}$ and $A_2$ are as defined above or below.

Advantageously. Xn and $X_{21}$ both are O. Advantageously, at least one of $X_{12}$ and $X_{22}$ is SH and preferably $X_{12}$ and $X_{22}$ both are SH. Preferably, $X_{11}$ and $X_{21}$ both are O and $X_{12}$ and $X_{22}$ both are SH.

In particular, Rn and $R_1$: both are H and advantageously $R_{11}$, $R_{12}$, $R_{21}$ and $R_{22}$ each are H.

$Z_3$ in particular is N. Advantageously, $Z_1$ is OH or $NH_2$; $Z_2$ is H or $NH_2$; $Z_3$ is N; and $Z_4$ is H.

Preferably, $A_{11}$ and $A_{21}$ are independently selected from

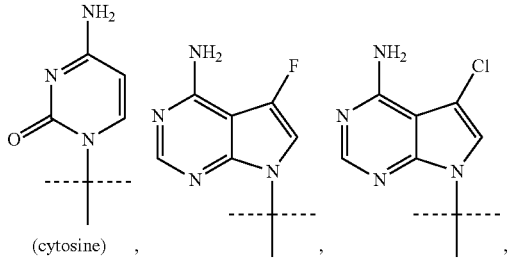
(cytosine), , ,

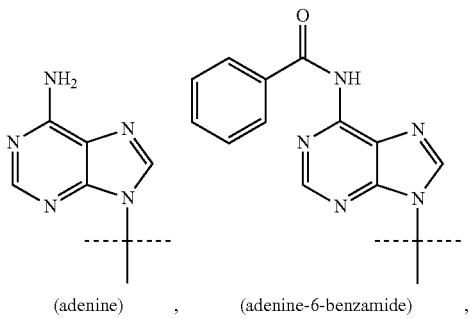
(adenine), (adenine-6-benzamide), ,

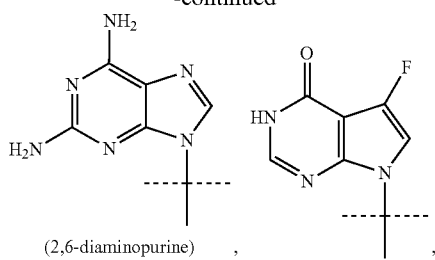

(2,6-diaminopurine),

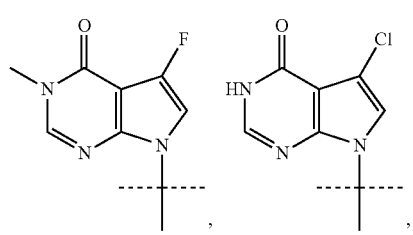

,

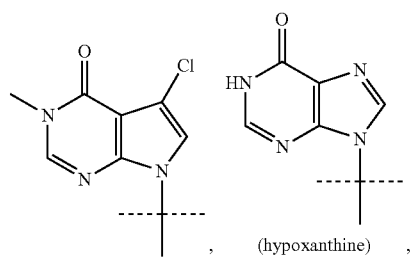

, (hypoxanthine) ,

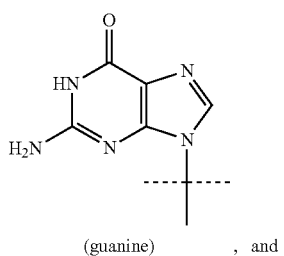

(guanine) , and

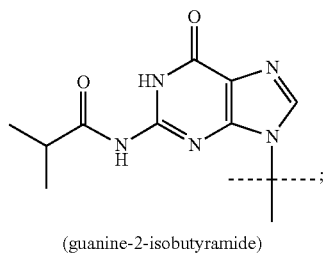

(guanine-2-isobutyramide);

more preferably selected from cytosine, adenine, adenine-6-benzamide, 2,6-diaminopurine, hypoxanthine, guanine and guanine-2-isobutyramide; most preferably selected from adenine, hypoxanthine and guanine.

It can be in particular ADU-S100 of following formula:

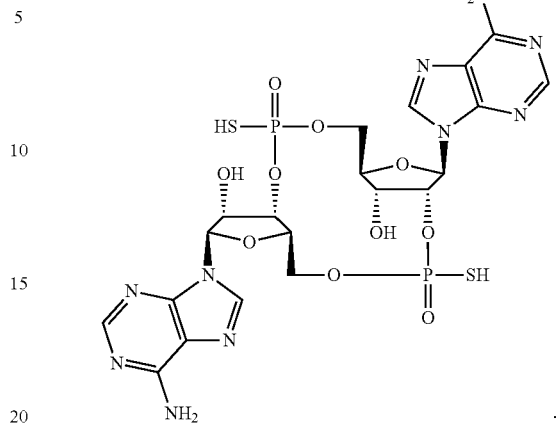

.

Alternatively it can be in particular one of the compounds specifically disclosed in Lioux et al. J. Med. Chem., 2016, 59 (22), pp 10253-10267.

The preparation of such a STING agonist is disclosed in WO2014/179335, WO2016/096174, WO2016/145102, WO2017/106740 or WO2018/100558 for example.

The said STING agonist is linked to the linker moiety by a SH, OH or NH group present on the molecule, i.e, by the group $X_{12}$ (OH or SH), $X_{22}$ (OH or SH), $Z_1$ when at least one of $R_{11}$ and $R_{12}$ is H (OH, $NHR_{11}$ or $NHR_{12}$), or $Z_2$ when at least one of $R_{21}$ and $R_{22}$ is H ($NHR_{21}$ or $NHR_{22}$). Preferably, at least one of $X_{12}$ and $X_{22}$ is SH and the STING agonist is linked by this SH group.

In consequence, the residue of STING agonist has advantageously the following formula (D), (D-1), (D-2), (D-3), (D-1a), (D-2a) or (D-3a):

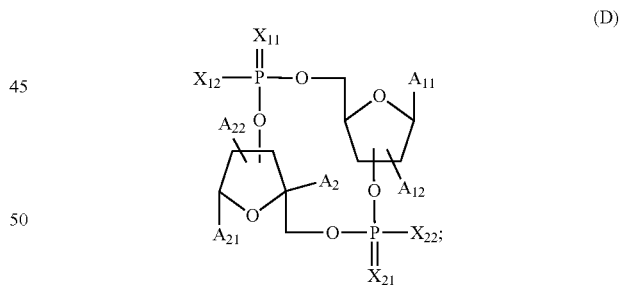

(D)

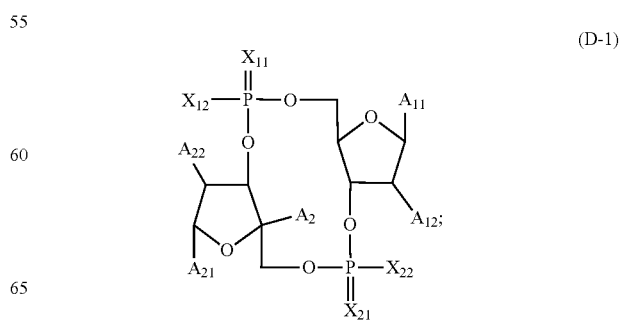

(D-1)

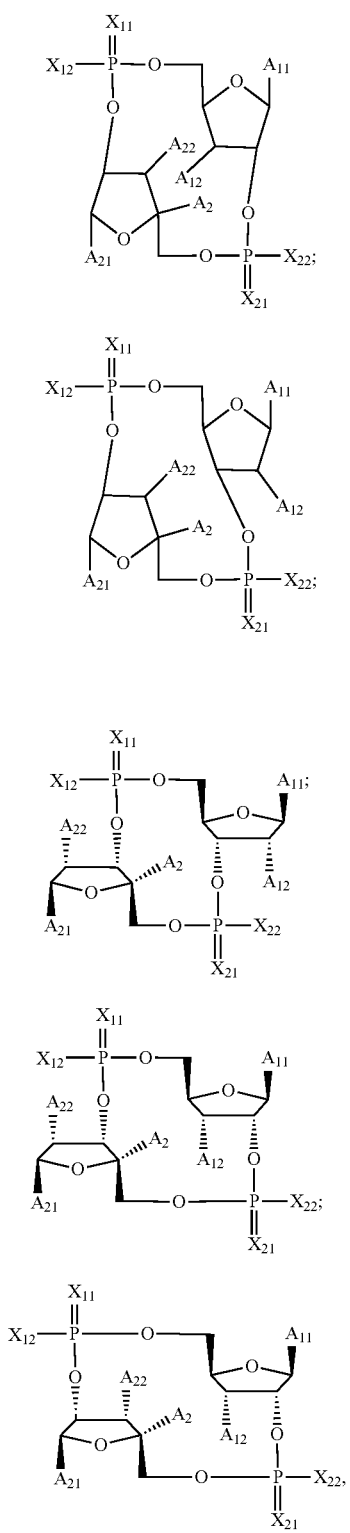

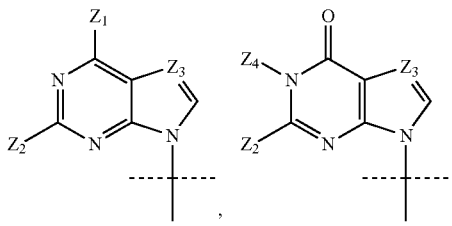

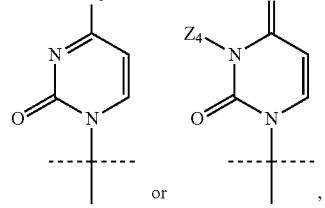

preferably

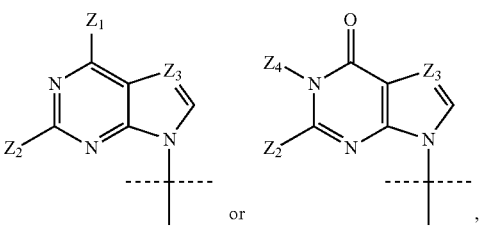

where:
- $Z_1$ is as defined above or O or $NR_{11}$,
- $Z_2$ is as defined above or $NR_{21}$,
- $Z_3$ is as defined above, and
- $Z_4$ is as defined above,
- $A_{12}$ and $A_{22}$ are as defined above, and
- $A_2$ is as defined above, wherein:
when $X_{12}$ is O or S, then $X_{22}$ is not O and is not S, $Z_1$ is not O and is not $NR_{11}$, $Z_2$ is not $NR_{21}$, and the residue of the STING agonist is linked to the rest of the molecule by $X_{12}$;

when $X_{22}$ is O or S, then $X_2$ is not O and is not S, $Z_1$ is not O and is not $NR_{11}$, $Z_2$ is not $NR_{21}$, and the residue of the STING agonist is linked to the rest of the molecule by $X_{22}$;

when $Z_1$ is O or $NR_{11}$, then $X_2$ is not O and is not S, $X_{22}$ is not O and is not S, $Z_2$ is not $NR_{21}$, and the residue of the STING agonist is linked to the rest of the molecule by $Z_1$;

when $Z_2$ is $NR_{21}$, then $X_2$ is not O and is not S, $X_{22}$ is not O and is not S, $Z_1$ is not O and is not $NR_{11}$, and the residue of the STING agonist is linked to the rest of the molecule by $Z_2$.

Binding Unit Moiety

The binding unit is a peptide, a protein (e.g, an engineered protein), an antibody (e.g, a monoclonal antibody) or an antigen binding fragment thereof.

Preferably, the binding unit according to the invention is an antibody or an antigen binding fragment thereof, and thus, the binding unit-drug conjugate according to the invention is an antibody-drug conjugate (ADC). In an embodiment, the antibody of the invention consists of a recombinant antibody. In another embodiment, the antibody of the ADC of the invention consists of a chemically synthesized antibody.

where:
- $X_{11}$ and $X_{21}$ are as defined above,
- $X_{12}$ and $X_{22}$ are as defined above or O or S,
- $A_{11}$ and $A_{21}$ are as defined above, i.e, independently a group of formula:

More particularly, such a molecule consists of a glycoprotein comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CH1, $CH_2$ and $CH_3$. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g, effector cells) and the first component (C1q) of the classical complement system.

In an embodiment, the "antigen binding fragments" are selected in the group consisting of Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of the antibody according to the invention. Preferably, said "antigen binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of the affinity of the antibody from which it is descended, with respect to the target. More preferably, said "antigen binding fragments" will be constituted of or will comprise at least the three CDRs CDR-H1, CDR-H2 and CDR-H3 of the heavy variable chain and the three CDRs CDR-L1, CDR-L2 and CDR-L3 of the light variable chain of the antibody from which they are derived.

According to a preferred embodiment, the binding unit is an IGF-1R antibody, a HER2 antibody or an antigen binding fragment thereof.

The HER2 antibody is more particularly trastuzumab.

In an embodiment of the present application, the antibody is an IGF-1R antibody and the epitope of the antibody is preferentially localized into the extracellular domain of the human IGF-1R (also referred as IGF-1R ECD).

In a particular embodiment, the antibody, or any antigen binding fragment thereof, is capable of binding to IGF-1R with an $EC_{50}$ comprised between $10 \times 10^{-10}$ to $1 \times 10^{-10}$, and more preferentially between $8 \times 10^{-10}$ to $2 \times 10^{-10}$.

The competition for binding to IGF-1R can be determined by any methods or techniques known by the person skilled in the art such as, without limitation, radioactivity, Biacore, ELISA, Flow cytometry, etc. As "which competes for binding to IGF-1R" it is meant a competition of at least 20%, preferentially at least 30% and more preferentially at least 70%.

The determination of the binding to the same epitope can be determined by any methods or techniques known by the person skilled in the art such as, without limitation, radioactivity, Biacore, ELISA, Flow cytometry, etc. As "which bind to the same epitope of IGF-1R, it is meant a competition of at least 20%, preferentially at least 30% and more preferentially at least 70%.

As above mentioned, and contrary to the general knowledge, the present invention focuses on specific IGF-1R antibodies presenting a high ability to be internalized following IGF-1R binding. As used herein, an antibody that "is internalized" or that "internalized" (the two expressions being similar) is one that is taken up by (meaning it "enters") the cell upon binding to IGF-1R on a mammalian cell. Such an antibody is interesting as part of the ADC, so it addresses or directs the linked cytotoxic into the targeted cancer cells. Once internalized the cytotoxic triggers cancer cell death.

Advantageously, the IGF-1R antibodies according to the invention are all presenting the same sequences for the CDR-H2, CDR-H3 and CDR-L2, the other 3 CDRs being different. This observation seems coherent as it is part of the general knowledge that, regarding the binding specificity of an antibody, the CDR-H3 is described as being the most important and the most implicated with the recognition of the epitope.

Important keys to success with ADC therapy are thought to be the target antigen specificity and the internalization of the antigen-antibody complexes into the cancer cells. Obviously non-internalizing antigens are less effective than internalizing antigens to delivers cytotoxic agents. Internalization processes are variable across antigens and depend on multiple parameters that can be influenced by antibodies.

In the ADC, the drug moiety confers the cytotoxic activity and the used antibody is responsible for the specificity against cancer cells, as well as a vector for entering within the cells to correctly address the cytotoxic. Thus, to improve the ADC, the antibody can exhibit high ability to internalize into the targeted cancer cells. The efficiency of the antibody mediated internalisation differs significantly depending on the epitope targeted. Selection of potent internalizing IGF-1R antibodies requires various experimental data studying not only IGF-1R downregulation but also following IGF-1R antibody internalization into the cells.

In an embodiment, the internalization of the antibody of the ADC according to the invention can be evaluated by immunofluorescence or FACS (Flow Cytometry) (as exemplified hereinafter in the present application) or any method or process known by the person skilled in the art specific for the internalization mechanism. In a preferred embodiment, the antibody of the ADC according to the invention can induce internalization after binding to IGF-1R of at least 30%, preferentially 50% and more preferentially 80%.

The complex IGF-1R/antibody is internalized after binding of the antibody to the ECD of said IGF-1R, and a reduction in the quantity of IGF-1R at the surface of the cells is induced. This reduction can be quantified by any method known by the person skilled in the art such as non limitative examples western-blot, FACS, and immunofluorescence.

In one embodiment, this reduction, thus reflecting the internalization, can be preferably measured by FACS and expressed as the difference or delta between the Mean Fluorescence Intensity (MFI) measured at 4° C., with the MFI measured at 37° C., after 4 hours incubation with the antibody.

As non limitative example, this delta is determined based on MFIs obtained with untreated cells and cells treated with the antibody using i) breast cancer cells MCF7 after a 4 hour incubation period with the antibody herein described and ii) a secondary antibody labelled with Alexa488. This parameter is defined as calculated with the following formula: $\Delta(MFI_{4°\,C.}-MFI_{37°\,C.})$.

This difference between MFIs reflects the IGF-1R down-regulation as MFIs are proportional to IGF-1R expressed on the cell-surface.

In an advantageous aspect, the antibodies consist of antibodies triggering a $\Delta(MFI_{4°\,C.}-MFI_{37°\,C.})$ on MCF-7 of at least 280, preferably of at least 400.

In more details, the above mentioned delta can be measured according to the following process, which must be considered as an illustrative and non limitative example:
 a) Treating and incubating tumor cells of interest with the antibody of the invention in either cold (4° C.) or warm (37° C.) complete culture medium;
 b) Treating the treated cells of step a) and, in parallel, untreated cells with a secondary antibody;
 c) Measuring the MFI (representative of the quantity of IGF-1R present at the surface) for the treated and the non-treated cells with a secondary labeled antibody capable of binding to the antibody of the invention; and
 d) Calculating the delta as the subtraction of the MFI obtained with the treated cells from the MFI obtained with the non-treated cells.

From this delta MFI, an internalization percentage can be determined as: $100 \times (MFI_{4°\,C.}-MFI_{37°\,C.})/MFI_{4°\,C.}$ The antibodies of the ADC according to the invention, present, preferably, on MCF7 an internalization percentage comprised between 50% and 99%, 70% and 90%, preferentially between 75% and 87%.

A particular advantage of the antibodies herein described relies on their rate of internalization.

It is generally known that, for an ADC, it is desirable that the used antibodies exhibit a rapid rate of internalization, preferably within 24 hours from administration of the antibody and, more preferably within 12 hours and, even more preferably within 6 hours.

In the present invention, the internalization rate, also referred as cell surface bound antibody decrease or cell surface antibody decay, is expressed as t½ (half-life) and corresponds as the time necessary to obtain a decrease of 50% of the ΔMFI (this aspect will be clearly understood regarding the following examples).

A particular advantage is that the antibodies of the ADC of the invention have a t½ comprised between 5 and 25 minutes, and preferentially between 10 and 20 minutes.

According to a particular embodiment of the invention, the antibody comprises the three heavy chain CDRs of sequences SEQ ID Nos. 1, 2 and 3 and the three light chain CDRs of sequences SEQ ID Nos. 4, 5 and 6.

According to a particular embodiment of the invention, the antibody comprises the three heavy chain CDRs comprising or consisting of the sequences SEQ ID Nos. 1, 2 and 3, or any sequence exhibiting at least 80%, preferably 85%, 90%, 95% and 98% identity with SEQ ID Nos. 1, 2 or 3; and the three light chain CDRs comprising or consisting of the sequences SEQ ID Nos. 4, 5 and 6, or any sequence exhibiting at least 80%, preferably 85%, 90%, 95% and 98% identity with SEQ ID Nos. 4, 5 or 6.

According to a particular embodiment of the invention, the binding unit is an antibody, or an antigen binding fragment thereof, capable of binding to the human IGF-1R selected from:
 i) an antibody which comprises three heavy chain CDRs with CDR-H2 of sequence SEQ ID No. 2 and CDR-H3 of sequence SEQ ID No. 3, and three light chain CDRs with CDR-L2 of sequence SEQ ID No. 5;
 ii) an antibody that competes for binding to IGF-1R with the antibody of i); and
 iii) an antibody that binds to the same epitope of IGF-1R as the antibody of i).

According to a particular embodiment of the invention, the binding unit is an antibody, or an antigen binding fragment thereof, capable of binding to the human IGF-1R selected from:
 i) an antibody which comprises the three heavy chain CDRs of sequence SEQ ID No. 1, 2 and 3 and the three light chain CDRs of sequence SEQ ID No. 4, 5 and 6;
 ii) an antibody that competes for binding to IGF-1R with the antibody of i); and
 iii) an antibody that binds to the same epitope of IGF-1R as the antibody of i).

In another embodiment, the antibody, or any antigen binding fragment thereof, comprises the three heavy chain CDRs comprising the sequences SEQ ID Nos. 1, 2 and 3; and the three light chain CDRs comprising the sequences SEQ ID Nos. 4, 5 and 6.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier. E., Truong. L., Thouvenin-Contet, V, and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M, and Lefranc, M.-P., Immunogenetics, 53, 857-883 (2002)/Kaas, Q, and Lefranc, M.-P., Current Bioinformatics, 2, 21-30 (2007)], and in 3D structures in IMGT/3Dstructure-DB [Kaas, Q., Ruiz, M, and Lefranc, M.-P., T cell receptor and MHC structural data. Nucl. Acids. Res., 32. D208-D210 (2004)].

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

As a non-limiting example, table 1 below summarizes the possible substitutions likely to be carried out without resulting in a significant modification of the biological activity of the corresponding modified antibody; inverse substitutions are naturally possible under the same conditions.

TABLE 1

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

A particular aspect of the invention is that the antibody does not bind to the Insulin receptor (IR). This aspect is of interest as the antibody herein described will not have any negative impact on the IR, meaning the Insulin metabolism.

In another embodiment, still another advantageous aspect of the antibody is that it is capable of binding not only to the human IGF-1R but also to the monkey IGF-1R, and more particularly to the cynomolgus IGF-1R. This aspect is also of interest as it will facilitate the toxicity assessment required for clinical trials.

In still another embodiment, the antibody consists of a monoclonal antibody. The monoclonal antibody herein includes murine, chimeric and humanized antibody, such as described after.

The antibody is preferably derived from an hybridoma of murine origin filed within the French collection for microorganism cultures (CNCM, Pasteur Institute, 25 rue du Docteur Roux, 75724 Paris Cedex 15, France), said hybridoma being obtained by the fusion of Balb/C immunized mice splenocytes/lymphocytes and cells of the myeloma Sp 2/O—Ag 14 cell line.

In an embodiment, the IGF-1R antibody consists of a murine antibody, then referred as m [name of the antibody].

In an embodiment, the IGF-1R antibody consists of a chimeric antibody, then referred as c [name of the antibody].

In an embodiment, the IGF-1R antibody consists of a humanized antibody, then referred as hz [name of the antibody].

For the avoidance of doubt, in the following specification, the expressions "IGF-1R antibody" and "[name of the antibody]" are similar and include (without contrary specification) the murine, the chimeric and the humanized versions of the said IGF-1R antibody or of the said "[name of the antibody]". When necessary, the prefix m- (murine), c- (chimeric) or hz- (humanized) is used.

For more clarity, the following table 2 illustrates the CDR sequences, defined according to IMGT, for the preferred antibodies.

TABLE 2

|  | Heavy chain | Light chain | SEQ ID No. |
|---|---|---|---|
| Consensus | CDR-H1 |  | 1 |
|  | CDR-H2 |  | 2 |
|  | CDR-H3 |  | 3 |
|  |  | CDR-L1 | 4 |
|  |  | CDR-L2 | 5 |
|  |  | CDR-L3 | 6 |
| 208F2 | CDR-H1 |  | 7 |
|  | CDR-H2 |  | 2 |
|  | CDR-H3 |  | 3 |
|  |  | CDR-L1 | 9 |
|  |  | CDR-L2 | 5 |
|  |  | CDR-L3 | 11 |
| 212A11 | CDR-H1 |  | 7 |
|  | CDR-H2 |  | 2 |
|  | CDR-H3 |  | 3 |
|  |  | CDR-L1 | 10 |
|  |  | CDR-L2 | 5 |
|  |  | CDR-L3 | 11 |
| 214F8 & 213B10 | CDR-H1 |  | 7 |
|  | CDR-H2 |  | 2 |
|  | CDR-H3 |  | 3 |
|  |  | CDR-L1 | 9 |
|  |  | CDR-L2 | 5 |
|  |  | CDR-L3 | 12 |
| 219D6 | CDR-H1 |  | 8 |
|  | CDR-H2 |  | 2 |
|  | CDR-H3 |  | 3 |
|  |  | CDR-L1 | 9 |
|  |  | CDR-L2 | 5 |
|  |  | CDR-L3 | 11 |

It will be obvious for the man skilled in the art that any combination of 6 CDRs as above described should be considered as part of the present invention.

As can be observed from this table 2, all the antibodies herein described have the same sequences for the CDR-H2, CDR-H3 and CDR-L2, this property being of particular interest as above described.

According to a specific aspect, the antibody is a murine antibody characterized in that said antibody also comprises light chain and heavy chain constant regions derived from an antibody of a species heterologous with the mouse, notably man.

According to another specific aspect, the antibody is a chimeric (c) antibody characterized in that said antibody also comprises light chain and heavy chain constant regions derived from an antibody of a species heterologous with the mouse, notably human.

A chimeric antibody is one containing a natural variable region (light chain and heavy chain) derived from an antibody of a given species in combination with constant regions of the light chain and the heavy chain of an antibody of a species heterologous to said given species.

The chimeric antibodies can be prepared by using the techniques of recombinant genetics. For example, the chimeric antibody could be produced by cloning recombinant DNA containing a promoter and a sequence coding for the variable region of a nonhuman monoclonal antibody, notably murine, and a sequence coding for heterologous species antibody constant region, preferably human. A chimeric antibody of the ADC according to the invention coded by one such recombinant gene could be, for example, a mouse-human chimera, the specificity of this antibody being determined by the variable region derived from the murine DNA and its isotype determined by the constant region derived from human DNA.

According to an embodiment of the invention, the antibody is selected from:

a) an antibody comprising the three heavy chain CDRs of sequence SEQ ID No. 7, 2 and 3 and the three light chain CDRs of sequence SEQ ID No. 9, 5 and 11;
b) an antibody comprising the three heavy chain CDRs of sequence SEQ ID No. 7, 2 and 3 and the three light chain CDRs of sequence SEQ ID No. 10, 5 and 11;
c) an antibody comprising the three heavy chain CDRs of sequence SEQ ID No. 7, 2 and 3 and the three light chain CDRs of sequence SEQ ID No. 9, 5 and 12; and
d) an antibody comprising the three heavy chain CDRs of sequence SEQ ID No. 8, 2 and 3 and the three light chain CDRs of sequence SEQ ID No. 9, 5 and 11.

In a preferred, but not limitative, embodiment, the antibody is selected from:
a) an antibody comprising a heavy chain variable domain of sequence SEQ ID No. 13 or any sequence exhibiting at least 80% identity with SEQ ID No. 13 and the three light chain CDRs of sequences SEQ ID Nos. 9, 5 and 11;
b) an antibody comprising a heavy chain variable domain of sequence SEQ ID No. 14 or any sequence exhibiting at least 80% identity with SEQ ID No. 14 and the three light chain CDRs of sequences SEQ ID Nos. 10, 5 and 11;
c) an antibody comprising a heavy chain variable domain of sequence SEQ ID No. 15 or any sequence exhibiting at least 80% identity with SEQ ID No. 15 and the three light chain CDRs of sequences SEQ ID Nos. 9, 5 and 12;
d) an antibody comprising a heavy chain variable domain of sequence SEQ ID No. 16 or any sequence exhibiting at least 80% identity with SEQ ID No. 16 and the three light chain CDRs of sequences SEQ ID Nos. 9, 5 and 11; and
e) an antibody comprising a heavy chain variable domain of sequence SEQ ID No. 17 or any sequence exhibiting at least 80% identity with SEQ ID No. 17 and the three light chain CDRs of sequences SEQ ID Nos. 9, 5 and 12.

By "any sequence exhibiting at least 80%, preferably 85%, 90%, 95% and 98% identity with SEQ ID No. 13 to 17", its is intended to designate the sequences exhibiting the three heavy chain CDRs SEQ ID Nos. 1, 2 and 3 and, in addition, exhibiting at least 80%, preferably 85%, 90%, 95% and 98%, identity with the full sequence SEQ ID No. 13 to 17 outside the sequences corresponding to the CDRs (i.e. SEQ ID No. 1, 2 and 3).

According to an embodiment of the invention, the antibody is selected from:
a) an antibody comprising a heavy chain variable domain of sequence SEQ ID No. 13 and the three light chain CDRs of sequence SEQ ID No. 9, 5 and 11;
b) an antibody comprising a heavy chain variable domain of sequence SEQ ID No. 14 and the three light chain CDRs of sequence SEQ ID No. 10, 5 and 11;
c) an antibody comprising a heavy chain variable domain of sequence SEQ ID No. 15 and the three light chain CDRs of sequence SEQ ID No. 9, 5 and 12;
d) an antibody comprising a heavy chain variable domain of sequence SEQ ID No. 16 and the three light chain CDRs of sequence SEQ ID No. 9, 5 and 11; and
e) an antibody comprising a heavy chain variable domain of sequence SEQ ID No. 17 and the three light chain CDRs of sequence SEQ ID No. 9, 5 and 12.

In another preferred, but not limitative, embodiment, the antibody is selected from:

a) an antibody comprising a light chain variable domain of sequence SEQ ID No. 18 or any sequence exhibiting at least 80% identity with SEQ ID No. 18 and the three heavy chain CDRs of sequences SEQ ID Nos. 7, 2 and 3;
b) an antibody comprising a light chain variable domain of sequence SEQ ID No. 19 or any sequence exhibiting at least 80% identity with SEQ ID No. 19 and the three heavy chain CDRs of sequences SEQ ID Nos. 7, 2 and 3;
c) an antibody comprising a light chain variable domain of sequence SEQ ID No. or any sequence exhibiting at least 80% identity with SEQ ID No. 20 and the three heavy chain CDRs of sequences SEQ ID Nos. 7, 2 and 3;
d) an antibody comprising a light chain variable domain of sequence SEQ ID No. 21 or any sequence exhibiting at least 80% identity with SEQ ID No. 21 and the three heavy chain CDRs of sequences SEQ ID Nos. 8, 2 and 3; and
e) an antibody comprising a light chain variable domain of sequence SEQ ID No. 22 or any sequence exhibiting at least 80% identity with SEQ ID No. 22 and the three heavy chain CDRs of sequences SEQ ID Nos. 7, 2 and 3.

By "any sequence exhibiting at least 80%, preferably 85%, 90%, 95% and 98% identity with SEQ ID No. 18 to 22", its is intended to designate respectively the sequences exhibiting the three light chain CDRs SEQ ID Nos. 4, 5 and 6 and, in addition, exhibiting at least 80%, preferably 85%, 90%, 95% and 98%, identity with the full sequence SEQ ID No. 18 to 22 outside the sequences corresponding to the CDRs (i.e. SEQ ID No. 4, 5 and 6).

According to an embodiment of the invention, the antibody is selected from:
a) an antibody comprising a light chain variable domain of sequence SEQ ID No. 18 and the three heavy chain CDRs of sequence SEQ ID No. 7, 2 and 3;
b) an antibody comprising a light chain variable domain of sequence SEQ ID No. 19 and the three heavy chain CDRs of sequence SEQ ID No. 7, 2 and 3;
c) an antibody comprising a light chain variable domain of sequence SEQ ID No. 20 and the three heavy chain CDRs of sequence SEQ ID No. 7, 2 and 3;
d) an antibody comprising a light chain variable domain of sequence SEQ ID No. 21 and the three heavy chain CDRs of sequence SEQ ID No. 8, 2 and 3; and
e) an antibody comprising a light chain variable domain of sequence SEQ ID No. 22 and the three heavy chain CDRs of sequence SEQ ID No. 7, 2 and 3.

According to an embodiment of the invention, the antibody is an antibody selected from:
a) an antibody comprising a heavy chain variable domain of sequence SEQ ID No. 13 or any sequence exhibiting at least 80% identity with SEQ ID No. 13 and a light chain variable domain of sequence SEQ ID No. 18 or any sequence exhibiting at least 80% identity with SEQ ID No. 18;
b) an antibody comprising a heavy chain variable domain of sequence SEQ ID No. 14 or any sequence exhibiting at least 80% identity with SEQ ID No. 14 and a light chain variable domain of sequence SEQ ID No. 19 or any sequence exhibiting at least 80% identity with SEQ ID NO. 19;
c) an antibody comprising a heavy chain variable domain of sequence SEQ ID No. 15 or any sequence exhibiting at least 80% identity with SEQ ID No. 15 and a light chain variable domain of sequence SEQ ID No. 20 or any sequence exhibiting at least 80% identity with SEQ ID No. 20;

d) an antibody comprising a heavy chain variable domain of sequence SEQ ID No. 16 or any sequence exhibiting at least 80% identity with SEQ ID No. 16 and a light chain variable domain of sequence SEQ ID No. 21 or any sequence exhibiting at least 80% identity with SEQ ID No. 21; and e) an antibody comprising a heavy chain variable domain of sequence SEQ ID No. 17 or any sequence exhibiting at least 80% identity with SEQ ID No. 17 and a light chain variable domain of sequence SEQ ID No. 22 or any sequence exhibiting at least 80% identity with SEQ ID No. 22.

Chimeric antibodies herein described can be also characterized by the constant domain and, more particularly, said chimeric antibodies can be selected or designed such as, without limitation, IgG1, IgG2. IgG3, IgM, IgA, IgD or IgE. More preferably, in the context of the present invention, said chimeric antibodies are IgG1 or IgG4.

According to an embodiment of the invention, the antibody is a chimeric antibody comprising variable domains VH and VL as above described in the format IgG1. More preferably, said chimeric antibody comprises a constant domain for the VH of sequence SEQ ID No. 43 and a Kappa domain for the VL of sequence SEQ ID No. 4S.

According to an embodiment of the invention, the antibody is a chimeric antibody comprising variable domains VH and VL as above described in the format IgG4. More preferably, said chimeric antibody comprises a constant domain for the VH of sequence SEQ ID No. 44 and a Kappa domain for the VL of sequence SEQ ID No. 45.

In another preferred, but not limitative, embodiment, the antibody is selected from:

a) an antibody comprising or consisting of a heavy chain of sequence SEQ ID No. 23 or any sequence exhibiting at least 80% identity with SEQ ID No. 23 and a light chain of sequence SEQ ID No. 28 or any sequence exhibiting at least 80% identity with SEQ ID No. 28;

b) an antibody comprising or consisting of a heavy chain of sequence SEQ ID No. 24 or any sequence exhibiting at least 80% identity with SEQ ID No. 24 and a light chain of sequence SEQ ID No. 29 or any sequence exhibiting at least 80% identity with SEQ ID No. 29;

c) an antibody comprising or consisting of a heavy chain of sequence SEQ ID No. or any sequence exhibiting at least 80% identity with SEQ ID No. 25 and a light chain of sequence SEQ ID No. 30 or any sequence exhibiting at least 80% identity with SEQ ID No. 30;

d) an antibody comprising or consisting of a heavy chain of sequence SEQ ID No. 26 or any sequence exhibiting at least 80% identity with SEQ ID No. 26 and a light chain of sequence SEQ ID No. 31 or any sequence exhibiting at least 80% identity with SEQ ID No. 31; and e) an antibody comprising or consisting of a heavy chain of sequence SEQ ID No. 27 or any sequence exhibiting at least 80% identity with SEQ ID No. 27 and a light chain of sequence SEQ ID No. 32 or any sequence exhibiting at least 80% identity with SEQ ID No. 32.

For more clarity, the following table 3 illustrates the sequences of the VH and VL, respectively, for the preferred chimeric antibodies.

TABLE 3

|  | Heavy Chain | Light chain | SEQ ID No. |
|---|---|---|---|
| c208F2 | Variable domain (VH) |  | 13 |
|  |  | Variable domain (VL) | 18 |
|  | Full length |  | 23 |
|  |  | Full length | 28 |
| c212A11 | Variable domain (VH) |  | 14 |
|  |  | Variable domain (VL) | 19 |
|  | Full length |  | 24 |
|  |  | Full length | 29 |
| c214F8 | Variable domain (VH) |  | 15 |
|  |  | Variable domain (VL) | 20 |
|  | Full length |  | 25 |
|  |  | Full length | 30 |
| c219D6 | Variable domain (VH) |  | 16 |
|  |  | Variable domain (VL) | 21 |
|  | Full length |  | 26 |
|  |  | Full length | 31 |
| c213B10 | Variable domain (VH) |  | 17 |
|  |  | Variable domain (VL) | 22 |
|  | Full length |  | 27 |
|  |  | Full length | 32 |

According to another specific aspect of the present invention, the antibody is a humanized antibody characterized in that the constant regions of the light chain and the heavy chain derived from human antibody are, respectively, the lambda or kappa region and the gamma-1, gamma-2 or gamma-4 region.

The humanized antibodies or fragments of same can be prepared by techniques known to a person skilled in the art. Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents EP 0 451 216, EP 0 682 040, EP 0 939 127. EP 0 566 647 or U.S. Pat. Nos. 5,530,101, 6,180,370, 5,585,089 and 5,693,761. U.S. Pat. No. 5,639,641 or 6,054,297, 5,886,152 and 5,877,293 can also be cited.

In a preferred embodiment, the antibody comprises a heavy chain variable domain (VH) having:
  i) the CDR-H1, CDR-H2 and CDR-H3 of sequences SEQ ID Nos. 7, 2 and 3, respectively, and
  ii) the FR1, FR2 and FR3 derived from the human germline IGHV1-46*01 (SEQ ID No. 46), and
  iii) the FR4 derived from the human germline IGHJ4*01 (SEQ ID No. 48).

In a preferred embodiment, the antibody comprises a light chain variable domain (VL) having:
  i) the CDR-L1, CDR-L2 and CDR-L3 of sequences SEQ ID Nos. 9, 5 and 11, respectively, and
  ii) the FR1, FR2 and FR3 derived from the human germline IGKV1-39*01 (SEQ ID No. 47), and
  iii) the FR4 derived from the human germline IGKJ4*01 (SEQ ID No. 49).

In a preferred, but not limitative, embodiment of the invention, the antibody comprises:
  a) a heavy chain having CDR-H1, CDR-H2 and CDR-H3 of sequences SEQ ID Nos. 7, 2 and 3, respectively, and FR1, FR2 and FR3 derived from the human germline IGHV1-46*01 (SEQ ID No. 46), and the FR4 derived from the human germline IGHJ4*01 (SEQ ID No. 48); and
  b) a light chain having CDR-L1, CDR-L2 and CDR-L3 of sequences SEQ ID Nos. 9, 5 and 11, respectively, and FR1, FR2 and FR3 derived from the human germline IGKV1-39*01 (SEQ ID No. 47), and the FR4 derived from the human germline IGKJ4*01 (SEQ ID No. 49).

In an embodiment, the antibody comprises a heavy chain variable domain (VH) of sequence SEQ ID No. 33 and a light chain variable domain (VL) of sequence SEQ ID No. 35. Said humanized antibody will be called thereinafter hz208F2 ("Variant 1" or "Var. 1").

In another embodiment, the antibody comprises a heavy chain variable domain (VH) of sequence SEQ ID No. 33 wherein said sequence SEQ ID No. 33 comprises at least 1 back-mutation selected from the residues 20, 34, 35, 38, 48, 50, 59, 61, 62, 70, 72, 74, 76, 77, 79, 82 and 95.

In another embodiment, the antibody comprises a heavy chain variable domain (VH) of sequence SEQ ID No. 33 wherein said sequence SEQ ID No. 33 comprises 2, 3, 4, 5, 6, 7, 8, 9, 10, 11, 12, 13, 14, 15, 16 or 17 back-mutations selected from the residues 20, 34, 35, 38, 48, 50, 59, 61, 62, 70, 72, 74, 76, 77, 79, 82 and 95.

For more clarity, the following table 4 illustrates the preferred back-mutations.

TABLE 4

| No résidu | 20 | 34 | 35 | 38 | 48 | 50 | 59 | 61 | 62 | 70 | 72 | 74 | 76 | 77 | 79 | 82 | 95 |
|---|---|---|---|---|---|---|---|---|---|---|---|---|---|---|---|---|---|
| Murin | M | I | Y | K | L | W | K | N | E | L | A | K | S | N | A | F | F |
| humain | V | M | H | R | M | I | S | A | Q | M | R | T | T | S | V | E | Y |

In an embodiment, the antibody comprises a light chain variable domain (VL) of sequence SEQ ID No. 35, wherein said sequence SEQ ID No. 35 comprises at least 1 back-mutation selected from the residues 22, 53, 55, 65, 71, 72, 77 and 87.

In an embodiment, the antibody comprises a light chain variable domain (VL) of sequence SEQ ID No. 35, wherein said sequence SEQ ID No. 35 comprises 2, 3, 4, 5, 6, 7 or 8 back-mutations selected from the residues 22, 53, 55, 65, 71, 72, 77 or 87.

In another embodiment, the antibody comprises:
a) a heavy chain variable domain (VH) of sequence SEQ ID No. 33 wherein said sequence SEQ ID No. 33 comprises at least 1 back-mutation selected from the residues 20, 34, 35, 38, 48, 50, 59, 61, 62, 70, 72, 74, 76, 77, 79, 82 and 95; and
b) a light chain variable domain (VL) of sequence SEQ ID No. 35, wherein said sequence SEQ ID No. 35 comprises at least 1 back-mutation selected from the residues 22, 53, 55, 65, 71, 72, 77 and 87.

For more clarity, the following table 5 illustrates the preferred back-mutations.

TABLE 5

| No résidu | 22 | 53 | 55 | 65 | 71 | 72 | 77 | 87 |
|---|---|---|---|---|---|---|---|---|
| Murin | S | R | H | R | Y | S | N | F |
| humain | T | S | Q | S | F | T | S | Y |

In such an embodiment, the antibody comprises all the back-mutations above mentioned and corresponds to an antibody comprising a heavy chain variable domain (VH) of sequence SEQ ID No. 34 and a light chain variable domain (VL) of sequence SEQ ID No. 36. Said humanized antibody will be called thereinafter hz208F2 ("Variant 3" or "Var. 3").

In another embodiment, all the humanized forms comprised between the Variant 1 and the Variant 3 are also encompassed by the present invention. In other words, the antibody corresponds to an antibody comprising a heavy chain variable domain (VH) of "consensus" sequence SEQ ID No. 41 and a light chain variable domain (VL) of "consensus" sequence SEQ ID No. 42. Said humanized antibody, as a whole, will be called thereinafter hz208F2 ("Variant2" or "Var. 2").

In a preferred, but not limitative, embodiment, the antibody is selected from:
a) an antibody comprising a heavy chain variable domain of sequence SEQ ID No. 33 or any sequence exhibiting at least 80%, preferably 85%, 90%, 95% and 98% identity with SEQ ID No. 33 and the three light chain CDRs of sequences SEQ ID Nos. 9, 5 and 11; and
b) an antibody comprising a heavy chain variable domain of sequence SEQ ID No. 34 or any sequence exhibiting at least 80%, preferably 85%, 90%, 95% and 98% identity with SEQ ID No. 34 and the three light chain CDRs of sequences SEQ ID Nos. 9, 5 and 11.

By "any sequence exhibiting at least 80%, preferably 85%, 90%, 95% and 98% identity with SEQ ID No. 33 or 34", it is intended to designate the sequences exhibiting the three heavy chain CDRs SEQ ID Nos. 1, 2 and 3 and, in addition, exhibiting at least 80%, preferably 85%, 90%, 95% and 98%, identity with the full sequence SEQ ID No. 33 or 34 outside the sequences corresponding to the CDRs (i.e. SEQ ID Nos. 1, 2 and 3).

In an embodiment of the invention, the antibody is selected from:
a) an antibody comprising a heavy chain variable domain of sequence SEQ ID No. 33 or any sequence exhibiting at least 80% identity with SEQ ID No. 33 and the three light chain CDRs of sequences SEQ ID Nos. 9, 5 and 11; and
b) an antibody comprising a heavy chain variable domain of sequence SEQ ID No. 34 or any sequence exhibiting at least 80% identity with SEQ ID No. 34 and the three light chain CDRs of sequences SEQ ID Nos. 9, 5 and 11.

If not indicated in the concerned paragraphs, in the present description, by any sequence or by a sequence exhibiting at least 80% with a particular sequence, it must be understood that said sequence exhibits at least 80% and preferably 85%, 90%, 95% and 98% identity with the referenced sequence. Whether these sequences contain CDR sequences, it is intended to designate that the sequences exhibiting at least these CDRs identically to the reference sequence CDRs, the 80%, preferably 85%, 90%, 95% and 98%, identity with the full sequence having to be calculated for the remaining sequence located outside the sequences corresponding to these CDRs.

In a preferred, but not limitative, embodiment, the antibody is selected from:
a) an antibody comprising a light chain variable domain of sequence SEQ ID No. 35 or any sequence exhibiting at least 80%, preferably 85%, 90%, 95% and 98% identity with SEQ ID No. 35 and the three heavy chain CDRs of sequences SEQ ID Nos. 7, 2 and 3; and
b) an antibody comprising a light chain variable domain of sequence SEQ ID No. 36 or any sequence exhibiting at least 80%, preferably 85%, 90%, 95% and 98% identity with SEQ ID No. 36 and the three heavy chain CDRs of sequences SEQ ID Nos. 7, 2 and 3.

By "any sequence exhibiting at least 80%, preferably 85%, 90%, 95% and 98% identity with SEQ ID No. 35 or 36", it is intended to designate the sequences exhibiting the three light chain CDRs SEQ ID Nos. 4, 5 and 6 and, in addition, exhibiting at least 80%, preferably 85%, 90%, 95% and 98%, identity with the full sequence SEQ ID No. or 36 outside the sequences corresponding to the CDRs (i.e. SEQ ID Nos. 4, 5 and 6).

In an embodiment of the invention, the antibody is selected from:
a) an antibody comprising a light chain variable domain of sequence SEQ ID No. 35 or any sequence exhibiting at least 80% identity with SEQ ID No. 35 and the three heavy chain CDRs of sequences SEQ ID Nos. 7, 2 and 3; and
b) an antibody comprising a heavy chain variable domain of sequence SEQ ID No. 36 or any sequence exhibiting at least 80% identity with SEQ ID No. 36 and the three heavy chain CDRs of sequences SEQ ID Nos. 7, 2 and 3.

Humanized antibodies herein described can be also characterized by the constant domain and, more particularly, said humanized antibodies can be selected or designed such as, without limitation, IgG1, IgG2, IgG3, IgM, IgA, IgD or IgE. More preferably, in the context of the present invention, said humanized antibodies are IgG1 or IgG4.

According to an embodiment of the invention, the antibody is a humanized antibody comprising variable domains VH and VL as above described in the format IgG1. More preferably, said humanized antibody comprises a constant domain for the VH of sequence SEQ ID No. 43 and a Kappa domain for the VL of sequence SEQ ID No. 45.

According to an embodiment of the invention, the antibody is a humanized antibody comprising variable domains VH and VL as above described in the format IgG4. More preferably, said humanized antibody comprises a constant domain for the VH of sequence SEQ ID No. 44 and a Kappa domain for the VL of sequence SEQ ID No. 45.

According to still another embodiment of the invention, the antibody is selected from:
a) an antibody comprising or consisting of a heavy chain of sequence SEQ ID No. 37 or any sequence exhibiting at least 80% identity with SEQ ID No. 37 and a light chain of sequence SEQ ID No. 39 or any sequence exhibiting at least 80% identity with SEQ ID No. 39; and
b) an antibody comprising or consisting of a heavy chain of sequence SEQ ID No. 38 or any sequence exhibiting at least 80% identity with SEQ ID No. 38 and a light chain of sequence SEQ ID No. 40 or any sequence exhibiting at least 80% identity with SEQ ID No. 40.

For more clarity, the following table 6a illustrates non limitative examples of sequences of the VH and VL for the variant 1 (Var. 1) and the variant 3 (Var. 3) of the humanized antibody hz208F2. It also comprises the consensus sequence for the variant 2 (Var. 2).

TABLE 6a

|  | Heavy Chain | Light chain | SEQ ID No. |
|---|---|---|---|
| hz208F2 (var. 1) | Variable domain (VH) |  | 33 |
|  |  | Variable domain (VL) | 35 |
|  | Full length |  | 37 |
|  |  | Full length | 39 |
| hz208F2 (Var. 3) | Variable domain (VH) |  | 34 |
|  |  | Variable domain (VL) | 36 |
|  | Full length |  | 38 |
|  |  | Full length | 40 |
| hz208F2 (Var. 2) | Variable domain (VH) |  | 41 |
|  |  | Variable domain (VL) | 42 |

In another preferred, but not limitative, embodiment, the antibody is selected from:
a) an antibody comprising a heavy chain variable domain of sequence selected from SEQ ID Nos. 56, 62, 64, 66, 68, 70, 72, 74, 76, 78 and 80 or any sequence with at least 80%, preferably 85%, 90%, 95% and 98% identity with SEQ ID No. 56, 62, 64, 66, 68, 70, 72, 74, 76, 78 and 80; and the three light chain CDRs of sequences SEQ ID Nos. 9, 5 and 11;
b) an antibody comprising a light chain variable domain of sequence selected from SEQ ID Nos. 57 or 60 or any sequence with at least 80%, preferably 85%, 90%, 95% and 98% identity with SEQ ID Nos. 57 or 60; and the three heavy chain CDRs of sequences SEQ ID Nos. 7, 2 and 3; and
c) an antibody comprising a heavy chain variable domain of sequence selected from SEQ ID Nos. 56, 62, 64, 66, 68, 70, 72, 74, 76, 78 and 80 or any sequence with at least 80%, preferably 85%, 90%, 95% and 98% identity with SEQ ID Nos. 56, 62, 64, 66, 68, 70, 72, 74, 76, 78 and 80; and a light chain variable domain of sequence selected from SEQ ID Nos. 57 or 60 or any sequence with at least 80%, preferably 85%, 90%, 95% and 98% identity with SEQ ID Nos. 57 or 60.

According to still another embodiment of the invention, the antibody is selected from:
a) an antibody comprising a heavy chain of sequence SEQ ID Nos. 56, 62, 64, 66, 68, 70, 72, 74, 76, 78 and 80 or any sequence exhibiting at least 80% identity with SEQ ID No. 56, 62, 64, 66, 68, 70, 72, 74, 76, 78 or 80, and a light chain of sequence SEQ ID No. 57 or any sequence exhibiting at least 80% identity with SEQ ID No. 57; and
b) an antibody comprising a heavy chain of sequence SEQ ID Nos. 56, 64, 68 and 78 or any sequence exhibiting at least 80% identity with SEQ ID No. 56, 64, 68 or 78 and a light chain of sequence SEQ ID No. 60, or any sequence exhibiting at least 80% identity with SEQ ID No. 60.

According to still another embodiment of the invention, the antibody is selected from:
a) an antibody comprising or consisting of a heavy chain of sequence SEQ ID No. 58 or any sequence exhibiting at least 80% identity with SEQ ID No. 58 and a light chain of sequence SEQ ID No. 59 or any sequence exhibiting at least 80% identity with SEQ ID No. 59;
b) an antibody comprising or consisting of a heavy chain of sequence SEQ ID No. 58 or any sequence exhibiting at least 80% identity with SEQ ID No. 58 and a light chain of sequence SEQ ID No. 61 or any sequence exhibiting at least 80% identity with SEQ ID No. 61;
c) an antibody comprising or consisting of a heavy chain of sequence SEQ ID No. 63 or any sequence exhibiting at least 80% identity with SEQ ID No. 63 and a light chain of sequence SEQ ID No. 59 or any sequence exhibiting at least 80% identity with SEQ ID No. 59;
d) an antibody comprising or consisting of a heavy chain of sequence SEQ ID No. 65 or any sequence exhibiting at least 80% identity with SEQ ID No. 65 and a light chain of sequence SEQ ID No. 59 or any sequence exhibiting at least 80% identity with SEQ ID No. 59;
e) an antibody comprising or consisting of a heavy chain of sequence SEQ ID No. 65 or any sequence exhibiting at least 80% identity with SEQ ID No. 65 and a light chain of sequence SEQ ID No. 61 or any sequence exhibiting at least 80% identity with SEQ ID No. 61;
f) an antibody comprising or consisting of a heavy chain of sequence SEQ ID No. 67 or any sequence exhibiting at least 80% identity with SEQ ID No. 67 and a light chain of sequence SEQ ID No. 59 or any sequence exhibiting at least 80% identity with SEQ ID No. 59;
g) an antibody comprising or consisting of a heavy chain of sequence SEQ ID No. 69 or any sequence exhibiting at least 80% identity with SEQ ID No. 69 and a light chain of sequence SEQ ID No. 59 or any sequence exhibiting at least 80% identity with SEQ ID No. 59;
h) an antibody comprising or consisting of a heavy chain of sequence SEQ ID No. 69 or any sequence exhibiting at least 80% identity with SEQ ID No. 69 and a light chain of sequence SEQ ID No. 61 or any sequence exhibiting at least 80% identity with SEQ ID No. 61;
i) an antibody comprising or consisting of a heavy chain of sequence SEQ ID No. 71 or any sequence exhibiting at least 80% identity with SEQ ID No. 71 and a light chain of sequence SEQ ID No. 59 or any sequence exhibiting at least 80% identity with SEQ ID No. 59;
j) an antibody comprising or consisting of a heavy chain of sequence SEQ ID No. 73 or any sequence exhibiting at least 80% identity with SEQ ID No. 73 and a light chain of sequence SEQ ID No. 59 or any sequence exhibiting at least 80% identity with SEQ ID No. 59;
k) an antibody comprising or consisting of a heavy chain of sequence SEQ ID No. 75 or any sequence exhibiting at least 80% identity with SEQ ID No. 75 and a light chain of sequence SEQ ID No. 59 or any sequence exhibiting at least 80% identity with SEQ ID No. 59;
l) an antibody comprising or consisting of a heavy chain of sequence SEQ ID No. 77 or any sequence exhibiting at least 80% identity with SEQ ID No. 77 and a light chain of sequence SEQ ID No. 59 or any sequence exhibiting at least 80% identity with SEQ ID No. 59;
m) an antibody comprising or consisting of a heavy chain of sequence SEQ ID No. 79 or any sequence exhibiting at least 80% identity with SEQ ID No. 79 and a light chain of sequence SEQ ID No. 59 or any sequence exhibiting at least 80% identity with SEQ ID No. 59;
n) an antibody comprising or consisting of a heavy chain of sequence SEQ ID No. 79 or any sequence exhibiting at least 80% identity with SEQ ID No. 79 and a light chain of sequence SEQ ID No. 61 or any sequence exhibiting at least 80% identity with SEQ ID No. 61; and
o) an antibody comprising or consisting of a heavy chain of sequence SEQ ID No. 81 or any sequence exhibiting at least 80% identity with SEQ ID No. 81 and a light chain of sequence SEQ ID No. 59 or any sequence exhibiting at least 80% identity with SEQ ID No. 59.

In other words, the antibody can be an antibody comprising:
a) a heavy chain of sequence selected from SEQ ID Nos. 58, 63, 65, 67, 69, 71, 73, 75, 77, 79 and 81 or any sequence with at least 80% identity with SEQ ID Nos. 58, 63, 65, 67, 69, 71, 73, 75, 77, 79 and 81; and
b) a light chain of sequence selected from SEQ ID Nos. 59 and 61 or any sequence with at least 80% identity with SEQ ID Nos. 59 and 61.

In an embodiment of the invention, the antibody is selected from:
a) a heavy chain of sequence selected from SEQ ID Nos. 58, 63, 65, 67, 69, 71, 73, 75, 77, 79 and 81 or any sequence with at least 80% identity with SEQ ID Nos. 58, 63, 65, 67, 69, 71, 73, 75, 77, 79 or 81; and
b) a light chain of sequence selected from SEQ ID Nos. 59 and 61 or any sequence with at least 80% identity with SEQ ID Nos. 59 or 61.

For more clarity, the following table 6b illustrates non limitative examples of sequences of the VH and VL (variable domain and full length) for different variants of the humanized antibody hz208F2.

TABLE 6b

| | Heavy Chain | Light chain | SEQ ID NO. |
|---|---|---|---|
| hz208F2 H037/L018 | Variable domain (VH) | Variable domain (VL) | 56 57 |
| | Full length | | 58 |
| | | Full length | 59 |
| Hz208F2 H037/L021 | Variable domain (VH) | Variable domain (VL) | 56 60 |
| | Full length | | 58 |
| | | Full length | 61 |
| Hz208F2 H047/L018 | Variable domain (VH) | Variable domain (VL) | 62 57 |
| | Full length | | 63 |
| | | Full length | 59 |
| Hz208F2 H049/L018 | Variable domain (VH) | Variable domain (VL) | 64 57 |
| | Full length | | 65 |
| | | Full length | 59 |
| Hz208F2 H049/L021 | Variable domain (VH) | Variable domain (VL) | 64 60 |
| | Full length | | 65 |
| | | Full length | 61 |
| Hz208F2 H051/L018 | Variable domain (VH) | Variable domain (VL) | 66 57 |
| | Full length | | 67 |
| | | Full length | 59 |
| Hz208F2 H052/L018 | Variable domain (VH) | Variable domain (VL) | 68 57 |
| | Full length | | 69 |
| | | Full length | 59 |
| Hz208F2 H052/L021 | Variable domain (VH) | Variable domain (VL) | 68 60 |
| | Full length | | 69 |
| | | Full length | 61 |
| Hz208F2 H057/L018 | Variable domain (VH) | Variable domain (VL) | 70 57 |
| | Full length | | 71 |
| | | Full length | 59 |
| Hz208F2 H068/L018 | Variable domain (VH) | Variable domain (VL) | 72 57 |
| | Full length | | 73 |
| | | Full length | 59 |
| Hz208F2 H070/L018 | Variable domain (VH) | Variable domain (VL) | 74 57 |
| | Full length | | 75 |
| | | Full length | 59 |
| Hz208F2 H071/L018 | Variable domain (VH) | Variable domain (VL) | 76 57 |
| | Full length | | 77 |
| | | Full length | 59 |
| Hz208F2 H076/L018 | Variable domain (VH) | Variable domain (VL) | 78 57 |
| | Full length | | 79 |
| | | Full length | 59 |

TABLE 6b-continued

| | Heavy Chain | Light chain | SEQ ID NO. |
|---|---|---|---|
| Hz208F2 H076/L021 | Variable domain (VH) | | 78 |
| | | Variable domain (VL) | 60 |
| | Full length | | 79 |
| | | Full length | 61 |
| Hz208F2 H077/L018 | Variable domain (VH) | | 80 |
| | | Variable domain (VL) | 57 |
| | Full length | | 81 |
| | | Full length | 59 |

According to another aspect of the present invention, the antibody is an antibody selected from i) an antibody produced by the hybridoma I-4757, I-4773, I-4775, I-4736 or I-4774 deposited at the CNCM, Institut Pasteur France on the 30 May 2013, 26 Jun. 2013, 26 Jun. 2013, 24 Apr. 2013 and 26 Jun. 2013, respectively, or ii) an antibody which competes for binding to IGF-1R with the antibody of i); or iii) an antibody which binds to the same epitope of IGF-1R as does the antibody of i).

According to a particular aspect, the binding unit is an antibody, or an antigen binding fragment thereof, as above described for use as an addressing vehicle for delivering a cytotoxic agent at a host target site, said host target site consisting of an epitope localized into IGF-1R, preferably the IGF-1R extracellular domain, more preferably the human IGF-1R (SEQ ID No. 50) and still more preferably the human IGF-1R extracellular domain (SEQ ID No. 51), and still more preferably to the N-terminal of the human IGF-1R extracellular domain (SEQ ID No. 52), or any natural variant sequence thereof.

In a preferred embodiment, said host target site is a target site of a mammalian cell, more preferably of a human cell, more preferably cells which naturally or by way of genetic recombination, express IGF-1R.

In an additional embodiment, said host target site is a target site of a cell of patient, preferably human, having a cancer, preferably an IGF-1R expressing cancer, or IGF-1R related cancers.

IGF-1R expressing cancers or IGF-1R related cancers include particularly cancers wherein the tumoral cells express or over-express whole or part of the IGF-1R at their surface.

IGF-1R antibodies that can be used as binding unit in the present invention are described in particular in WO2015/162291, WO2015/162292 or WO2015/162293.

Linker Molecule

The linker of formula (I) according to the present invention, preferably in which q=2, is useful for covalently linking a drug to a binding unit, such as an antibody (e.g, a monoclonal antibody) or an antigen binding fragment thereof.

For that, the sulfomaleimide moiety of the linker can react with thiol moieties present on the binding unit, whereas the $X_3$ end of the linker can react with a functional group present on the drug (QH or Q-OH).

The linker molecule can be prepared according to various synthesis methods which are exemplified in the experimental part.

When $X_1$ and $X_2$ are independently chosen among H and Cl, at least one being Cl, the linker according to the invention can be prepared from a disulphide compound of formula L-NHCO—CH$_2$CH$_2$—S—S—CH$_2$CH$_2$—CONH-L, with L representing $L_1$-(CO)$_c$—(W)$_w$—(Y)$_y$—X$_3$, optionally in a protected form, by reaction with a chlorinating agent such as SO$_2$Cl$_2$.

When $X_1$ and $X_2$ are independently chosen among H and Br, at least one being Br, the linker according to the invention can be prepared from a compound of formula

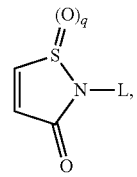

with L representing $L_1$-(CO)$_c$—(W)$_w$—(Y)$_y$—X$_3$, optionally in a protected form, by reaction with a brominating agent such as Br$_2$.

When at least one of $X_1$ and $X_2$ is a (C$_1$-C$_6$)alkoxy, an aryloxy optionally substituted, or —O—(CH$_2$CH$_2$O)$_r$H, the linker according to the invention can be prepared from the corresponding linker of formula (I) with at least one of $X_1$ and $X_2$ being Cl or Br, optionally in a protected form, by a nucleophilic substitution reaction with an alcohol of formula $R_a$—OH with $R_a$ representing a (C$_1$-C$_6$)alkyl, an aryl optionally substituted, or —(CH$_2$CH$_2$O)$_r$H.

It can be envisaged also to form the sulfomaleimide moiety with a truncated linker moiety (e.g, with L=$L_1$-(CO)$_c$—X$_6$ with $X_6$ functional group such as NH$_2$, OH or a leaving group, optionally in a protected form) grafted on it and to complete the linker synthesis after the formation of the sulfomaleimide moiety, as illustrated notably below for the synthesis of the drug-linker conjugate.

Moreover, a step of oxidation can be performed to convert the S(O)$_q$ group in the required oxidation state (i.e, preferably q=2). Such an oxidation step is well-known to the one skilled in the art. The oxidant used can be mCPBA. RuO$_4$ or RuCl$_3$/NaIO$_4$ for example.

Further protection/deprotection steps can be carried out in the processes described above, such steps and their reaction conditions being well known to the one skilled in the art.

The linker obtained can be separated from the reaction medium by methods well known to the person skilled in the art, such as by extraction, evaporation of the solvent or by precipitation or crystallisation (followed by filtration).

The linker can also be purified if necessary by methods well known to the person skilled in the art, such as by recrystallisation, by distillation, by chromatography on a column of silica gel or by high performance liquid chromatography (HPLC).

Drug-Linker Conjugates

The drug-linker conjugate of formula (II) according to the present invention, preferably in which q=2, is useful for covalently linking a drug to a binding unit, such as an antibody (e.g, a monoclonal antibody) or an antigen binding fragment thereof.

For that, the sulfomaleimide moiety of the drug-linker conjugate can react with thiol moieties present on the binding unit.

The drug-linker conjugates can be prepared according to various synthesis methods. Indeed, the linker of formula (I) can react with the drug (QH or Q-OH) in order to form the conjugate. However, other possibilities can be envisaged in which the linker is formed progressively on the drug molecule, i.e, a first part of the linker is first grafted on the drug, the resulting compound being reacted with a truncated linker molecule to form the drug-linker conjugate.

The following non-limitative synthetic routes can thus be used for the preparation of the drug-linker conjugates of formula (II) according to the present invention, even if other synthetic routes could be considered.

In all these synthetic routes, further protection/deprotection/substitution steps can be carried out, such steps and their reaction conditions being well known to the one skilled in the art.

The drug-linker conjugate obtained can be separated from the reaction medium by methods well known to the person skilled in the art, such as by extraction, evaporation of the solvent or by precipitation or crystallisation (followed by filtration).

The drug-linker conjugate can also be purified if necessary by methods well known to the person skilled in the art, such as by recrystallisation, by distillation, by chromatography on a column of silica gel or by high performance liquid chromatography (HPLC).

Synthetic Route I Represented on Scheme I reaction can be performed in a solvent such as DCM, notably at a temperature between 0° C., and room temperature.

3-(2-Chlorocarbonyl-ethyldisulfanyl)-propionyl chloride can be prepared from 3,3'-dithiodipropionic acid by a well-known method to form an acyl chloride such as by reaction with $(COCl)_2$. The reaction can be performed in a solvent such as DCM, notably at room temperature. A catalytic amount of DMF can be added.

It can be envisaged also to react the 3-(2-chlorocarbonyl-ethyldisulfanyl)-propionyl chloride with a molecule of formula $H_2N$-$L_1$-$(CO)_c$—$X_3$ optionally in a protected form, for example, and to complete the synthesis of the linker moiety grafted with Q in a later step, notably according to one of the other synthetic routes described below.

Step 2

The molecule obtained in step 1 can be cyclized and chlorinated in the presence of $SO_2Cl_2$, present notably in a

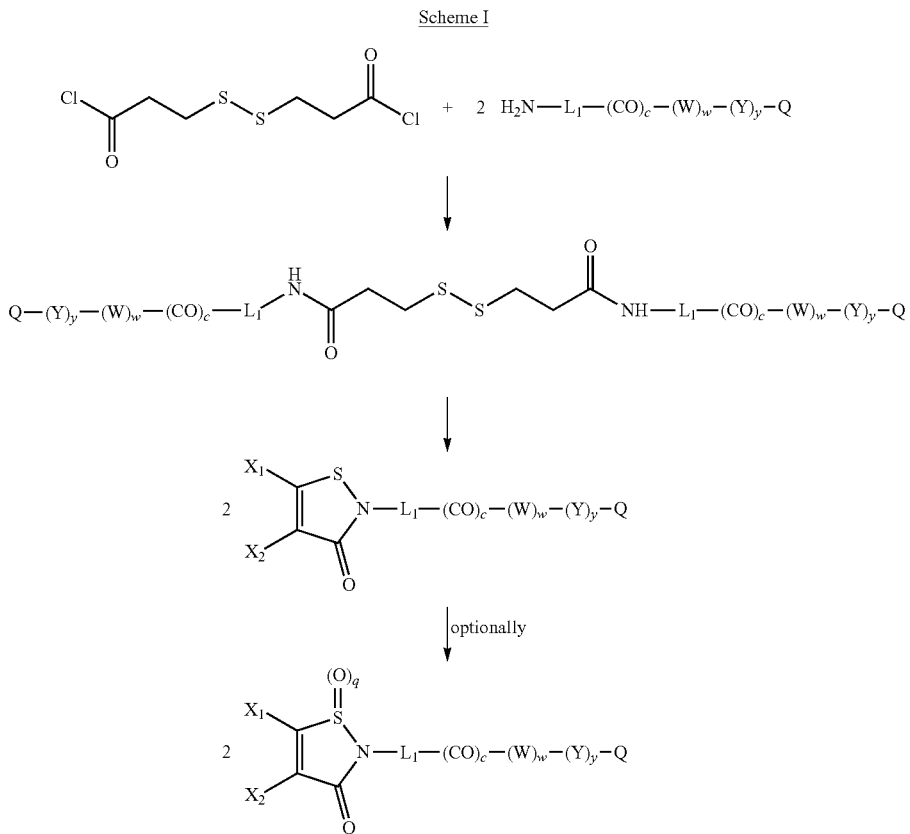

The terminal sulfomaleimide moiety can be formed from a group already present on the drug grafted with a precursor of the linker moiety, as detailed below.

Step 1

3-(2-Chlorocarbonyl-ethyldisulfanyl)-propionyl chloride is reacted with a molecule of formula $H_2N$-$L_1$-$(CO)_c$—$(W)_w$—$(Y)_y$-Q (i.e. a drug molecule on which a part of the linker has already been grafted). Such a reaction can be performed in the presence of a base such as trimethylamine. The large excess (for ex. 5 to 10 eq., such as about 9 eq.). The reaction can be performed in a solvent such as DCM, notably at room temperature.

The chlorine atom can be converted into another $X_1$ or $X_2$ group (other than H) by well-known methods, such as by a nucleophilic substitution.

Step 3

If necessary, the molecule obtained in step 2 will be oxidized to obtain a drug-linker of formula (IIa). Such an oxidation step can be performed in conditions well-known to the one skilled in the art, notably in the presence of mCPBA (for ex. 10 eq.). The reaction can be performed in a solvent such as DCM, notably at room temperature.

Synthetic Route II Represented on Scheme II

Scheme II

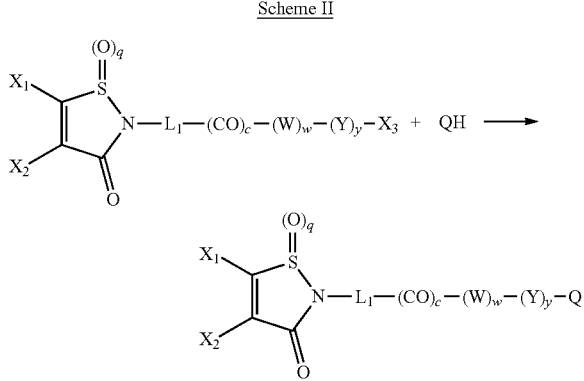

A direct coupling between a drug (QH or Q-OH) and the linker of formula (I) can be performed, the conditions of which depending on the nature of $X_3$ and of the functional group present on the drug.

This coupling can be a substitution, such as a nucleophilic substitution or a Mitsunobu reaction, the reaction conditions of such chemical reactions being well-known to the one skilled in the art.

When $X_3$=OH and at least y=1, w≠0 or c=1 (i.e, the terminal functional group of the linker of formula (I) is COOH) and QH comprises a NH function, the coupling between the linker of formula (I) and the drug (QH) can be a peptide coupling well-known to the one skilled in the art. The terminal COOH function can also be converted into an acyl chloride COCl, which could then react with a nucleophilic function present on the drug (QH) (e.g. NH or OH).

When $X_3$=NH$_2$: or $X_3$=H, y=z=1 and Z=—NR$_4$—(CH$_2$)$_u$—NR$_5$—; or $X_3$=H, c=w=y=0, z'=1 and Z' is —NR$_4$—(CH$_2$)$_u$—NR$_5$— (i.e, the terminal functional group of the linker of formula (I) is NH) and Q-OH comprises a COOH function, the coupling between the linker of formula (I) and the drug (Q-OH) can be a peptide coupling well-known to the one skilled in the art. The terminal COOH function of the drug can also be converted into an acyl chloride COCl, which could then react with the NH function.

If necessary, an additional step of oxidation can be performed to convert the S(O)$_q$ group in the required oxidation state (i.e, preferably q=2). Such an oxidation step is well-known to the one skilled in the art. The oxidant used can be mCPBA, RuO$_4$ or RuCl$_3$/NaIO$_4$ for example.

Synthetic Route III Represented on Schemes IIIa and IIIb

Scheme IIIa (with c = 1)

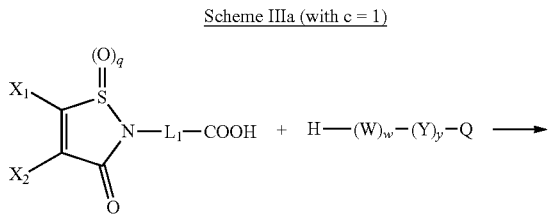

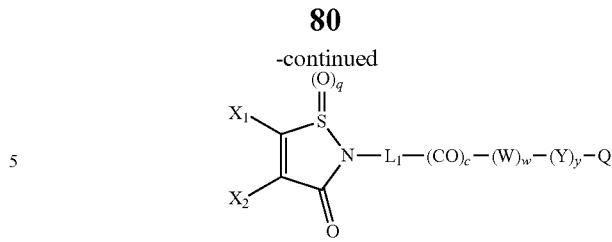

Scheme IIIb (with w ≠ 0)

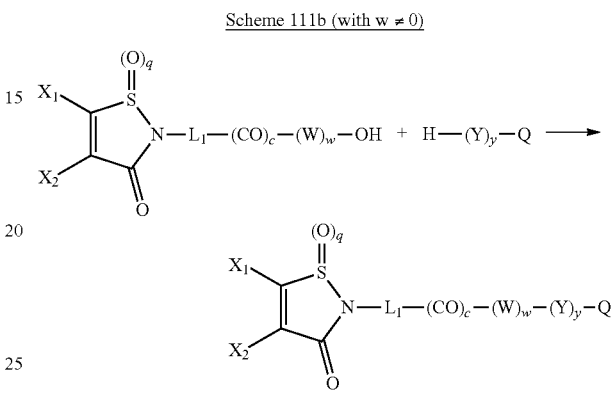

A peptide coupling can also be performed between a truncated linker bearing a COOH function and a drug moiety grafted with the other part of the linker as illustrated on Schemes IIIa and IIIb. The terminal COOH function of the truncated linker can also be converted into an acyl chloride COCl, which could then react with the NH function of the other reactant. The reaction conditions of such reactions are well known to the one skilled in the art.

If necessary, an additional step of oxidation can be performed to convert the S(O)$_q$ group in the required oxidation state (i.e, preferably q=2), for example in the presence of mCPBA, RUO$_4$ or RuCl$_3$/NaIO$_4$.

Synthetic Route IV Represented on Scheme IV

Scheme IV

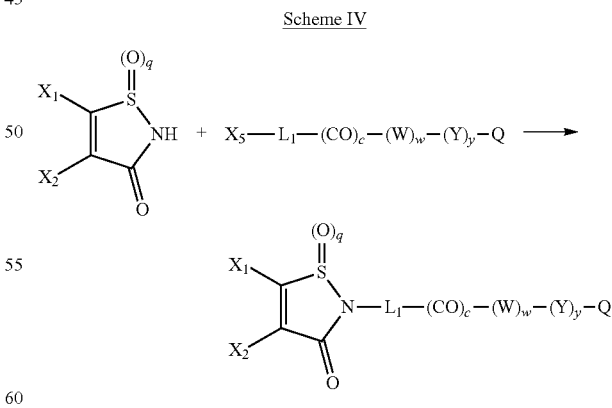

A coupling between the sulfomaleimide moiety and the drug on which the rest of the linker has already been grafted can also be performed as illustrated on Scheme IV on which $X_5$ represents OH or a leaving group as defined previously.

The coupling can be a substitution, such as a nucleophilic substitution.

If necessary, an additional step of oxidation can be performed to convert the $S(O)_q$ group in the required oxidation state (i.e, preferably q=2), for example in the presence of mCPBA, $RUO_4$ or $RuCl_3/NaIO_4$.

Synthetic Route V Represented on Schemes Va and Vb

Scheme Va

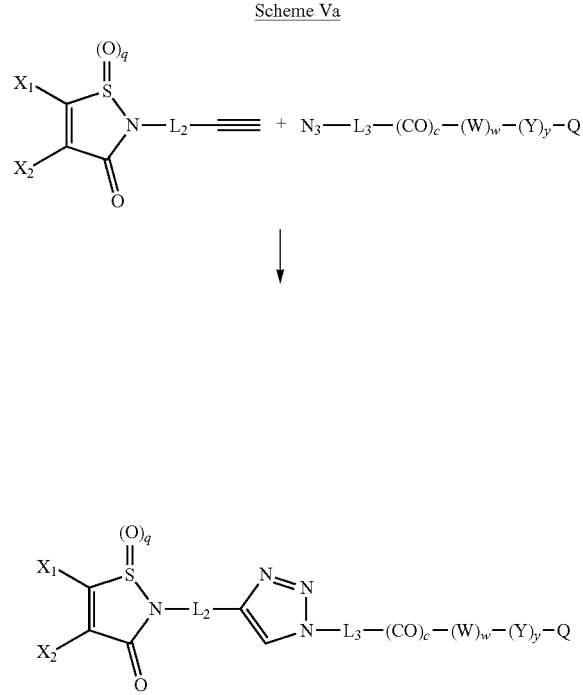

Scheme Vb

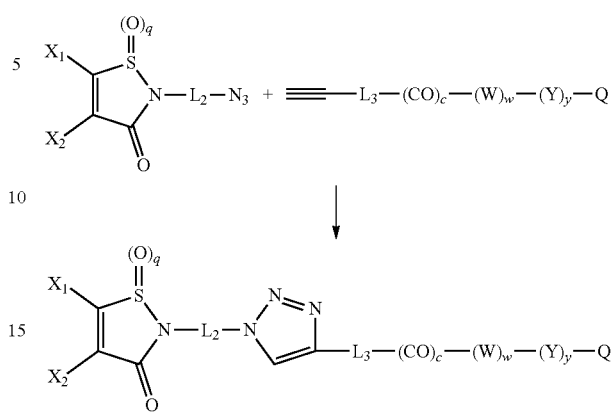

When the linker comprises a heteroarylene moiety with is a bivalent 1H-1,2,3-triazole, this heteroarylene group can be formed by click chemistry between an azide and an alkyne in conditions well known to the one skilled in the art as illustrated on Schemes Va and Vb above where $L_2$ represents —$(CH_2)_n$— or —$(CH_2CH_2O)_m$—$CH_2$—$CH_2$— and $L_3$ represents —$(CH_2)_p$— or —$(CH_2CH_2O)_m$—$CH_2$—$CH_2$—, $L_2$ and $L_3$ being not at the same time a group —$(CH_2CH_2O)_m$—$CH_2$—$CH_2$—.

If necessary, an additional step of oxidation can be performed to convert the $S(O)_q$ group in the required oxidation state (i.e, preferably q=2), for example in the presence of mCPBA, $RUO_4$ or $RuCl_3/NaIO_4$.

Binding Unit-Drug Conjugates

The binding unit-drug conjugates, such as antibody-drug conjugates, can be prepared by:
1) forming thiol functions on the binding unit, notably by reduction of disulphide bond(s); and
2) reacting said binding unit bearing thiol functions with drug-linker conjugate(s) so as to covalently link drug moiety/ies onto the binding unit by reacting the sulfomaleimide function with thiol functions.

Such a method is illustrated on Scheme VI below.

Scheme VI

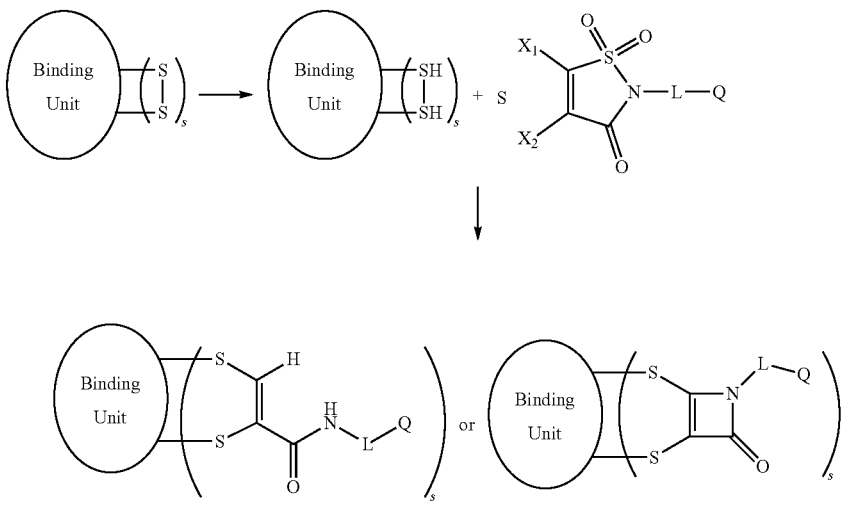

Pharmaceutical Composition

A pharmaceutical composition according to the present invention comprises a binding unit-drug conjugate of formula (III) or (IV) and at least one pharmaceutically acceptable excipient.

The pharmaceutical compositions of the invention can be intended to enteral (e.g, oral) or parenteral (e.g, intravenous) administration, preferably oral or intravenous administration. The active ingredient can be administered in unit forms for administration, mixed with conventional pharmaceutical excipients, to animals, preferably mammals including humans.

For oral administration, the pharmaceutical composition can be in a solid or liquid (solution or suspension) form.

A solid composition can be in the form of tablets, gelatin capsules, powders, granules and the like. In tablets, the active ingredient can be mixed with pharmaceutical vehicle(s) such as gelatin, starch, lactose, magnesium stearate, talc, gum arabic and the like before being compressed. The tablets may be further coated, notably with sucrose or with other suitable materials, or they may be treated in such a way that they have a prolonged or delayed activity. In powders or granules, the active ingredient can be mixed or granulated with dispersing agents, wetting agents or suspending agents and with flavor correctors or sweeteners. In gelatin capsules, the active ingredient can be introduced into soft or hard gelatin capsules in the form of a powder or granules such as mentioned previously or in the form of a liquid composition such as mentioned below.

A liquid composition can contain the active ingredient together with a sweetener, a taste enhancer or a suitable coloring agent in a solvent such as water. The liquid composition can also be obtained by suspending or dissolving a powder or granules, as mentioned above, in a liquid such as water, juice, milk, etc. It can be for example a syrup or an elixir.

For parenteral administration, the composition can be in the form of an aqueous suspension or solution which may contain suspending agents and/or wetting agents. The composition is advantageously sterile. It can be in the form of an isotonic solution (in particular in comparison to blood).

Such parenteral compositions will contain advantageously a physiologically acceptable medium, generally based on an isotonic saline solution, i.e. 0.9% NaCl aqueous solution (normal saline). Non-aqueous water miscible co-solvent, such as ethanol, glycerin, propylene glycol or n-lactamide, can also be used.

The parenteral composition of the invention can also comprise one or more additive(s), such as suspending agents, wetting agents, preservatives, antioxidants, chelating agents, buffering agents, tonicity adjusting agents, etc. Such additives are conventional to those of skill in the art.

Suspending agents can be an alginate, sodium carboxymethyl cellulose, methyl cellulose, hydroxyl methyl cellulose, hydroxyl ethyl cellulose, hydroxylpropyl methyl cellulose, microcrystalline cellulose, a gum such as acacia, tragacanth or xanthan gum, gelatin, a carrageenan, polyvinyl pyrrolidone, etc.

Wetting agents can be glycerin, propylene glycol or also nonionic surfactants such as a lecithin, a polysorbate or a poloxamer.

Preservatives can be benzyl alcohol, phenol, cresol, chlorobutanol, a paraben such as methylparaben, propylparaben or propylparaben, benzalkonium chloride, benzethonium chloride, etc.

Antioxidants can be ascorbic acid, citric acid, acetylcysteine, sulfurous acid salts (bisulfite, metabisulfite), monothioglycerol, sodium formaldehyde sulfoxylate, thiourea, tocopherol, etc.

Chelating agents can be an ethylene diamine tetraacetic acid (EDTA) salt.

Buffering agents can be acetate, citrate, tartrate, phosphate, triethanolamine (TRIS), etc.

Tonicity adjusting agents can be dextrose, glycerol, sodium chloride, glycerin, mannitol, etc.

The binding unit-drug conjugate of the invention can be used in a pharmaceutical composition at a dose ranging from 0.01 mg to 1000 mg a day, administered in only one dose once a day or in several doses along the day, for example twice a day in equal doses. The daily administered dose is advantageously comprised between 5 mg and 500 mg, and more advantageously between 10 mg and 200 mg. However, it can be necessary to use doses out of these ranges, which could be noticed by the person skilled in the art.

Cancer Treatment

The binding unit-drug conjugate of formula (III) or (IV) or a pharmaceutical composition comprising a binding unit of formula (III) or (IV) can be used for the treatment of cancer, in particular when it comprises a drug moiety (Q) which is a residue of a drug (QH) useful in the treatment of cancer, such as a cytotoxic agent.

Binding unit-drug conjugates, such as antibody-drug conjugates (ADCs) combine the binding specificity of a binding unit, such as an antibody, with the potency of drugs such as, for example, cytotoxic agents.

The use of binding unit-drug conjugates, such as ADCs, allows the local delivery of drugs which, if administered as unconjugated drugs, may result in unacceptable levels of toxicity to normal cells. In other words, maximal efficacy with minimal toxicity is sought thereby.

The cancer can be exemplified by, but not limited to, prostate cancer, osteosarcoma, lung cancer, breast cancer, endometrial cancer, glioblastoma, colon, cancer, gastric cancer, renal cancer, pancreas cancer, head and neck cancer or any other cancer associated with expression of the antigen targeted by the antibody on the tumor cells.

The present invention is illustrated by the following non-limitative examples and figures.

FIGURES

Figure 12:
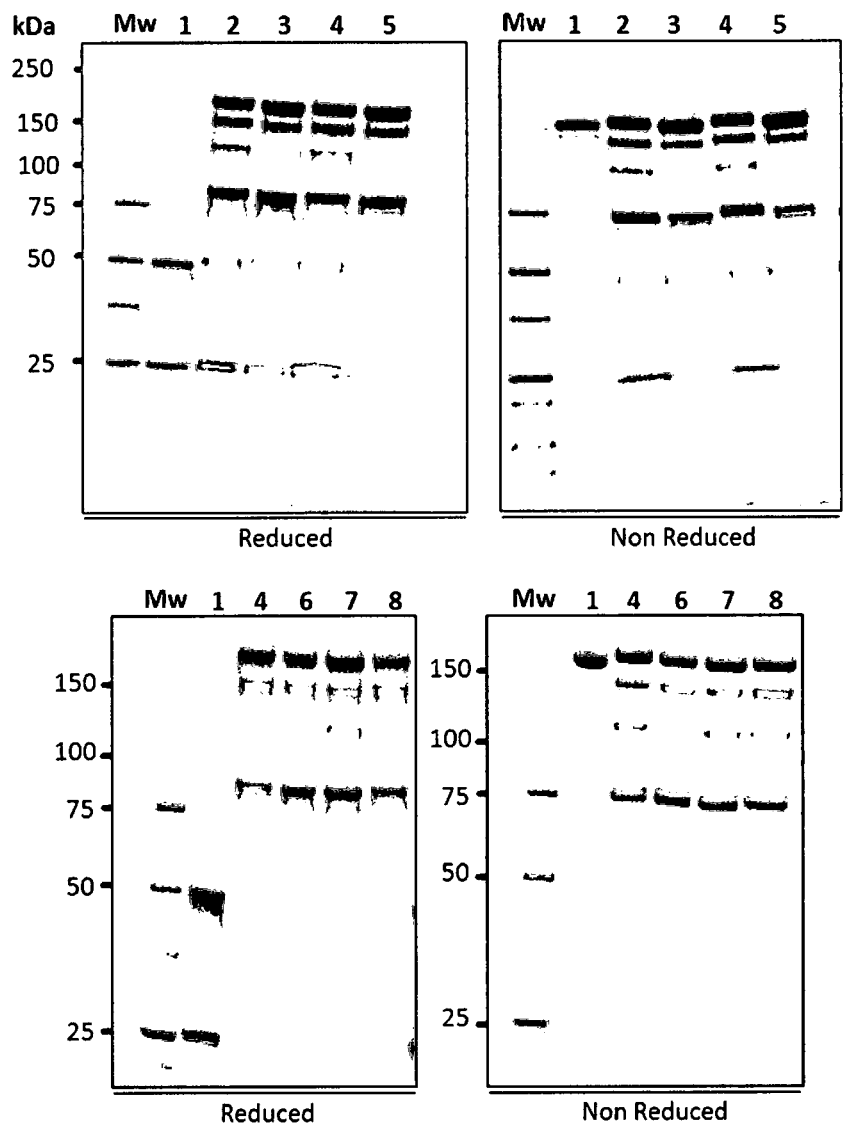

FIG. 12 represents the SDS-PAGE analysis of the Ab1 antibody (I) and purified ADCs according to the invention (ADC1-A (2), ADC1-B (3), ADC1-C (4), ADC1-D (5). ADC1-E (6). ADC 1-F (7) and ADC 1-G (8)) under reducing and non-reducing conditions. The bands observed on the gels correspond to completely bridged antibody (i.e. LHHL); partially bridged (i.e. HHL, HH, HL) and no bridging (i.e. H and L).

Figure 13:
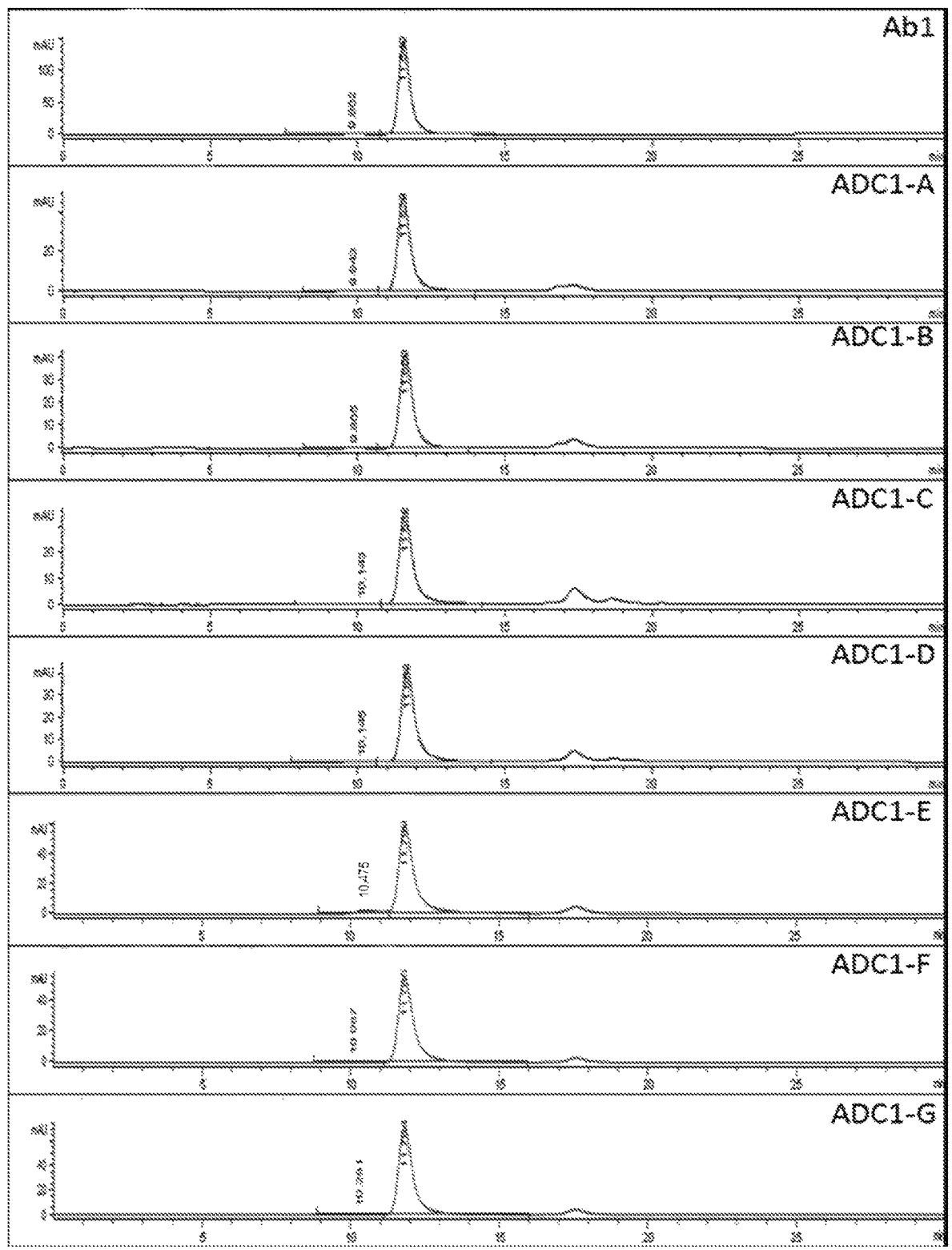
Figure 14A:
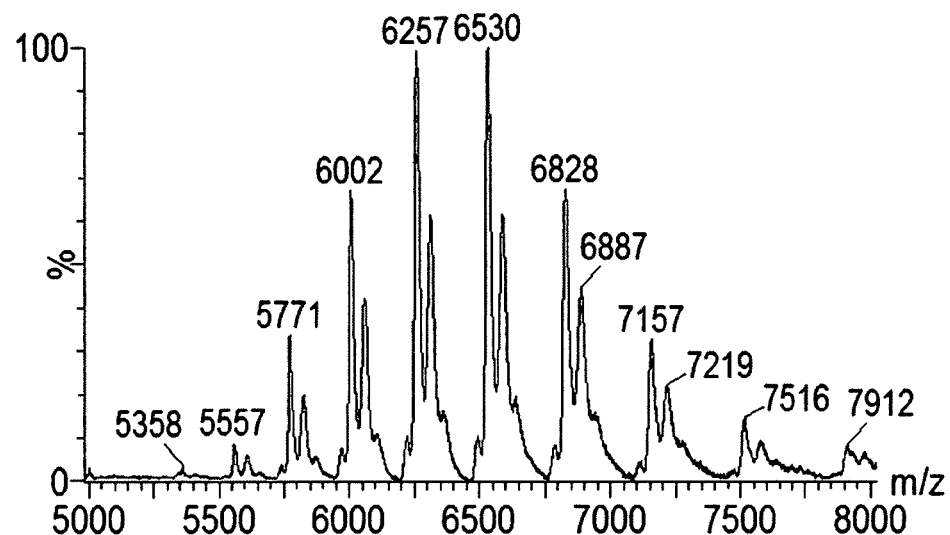
Figure 14B:
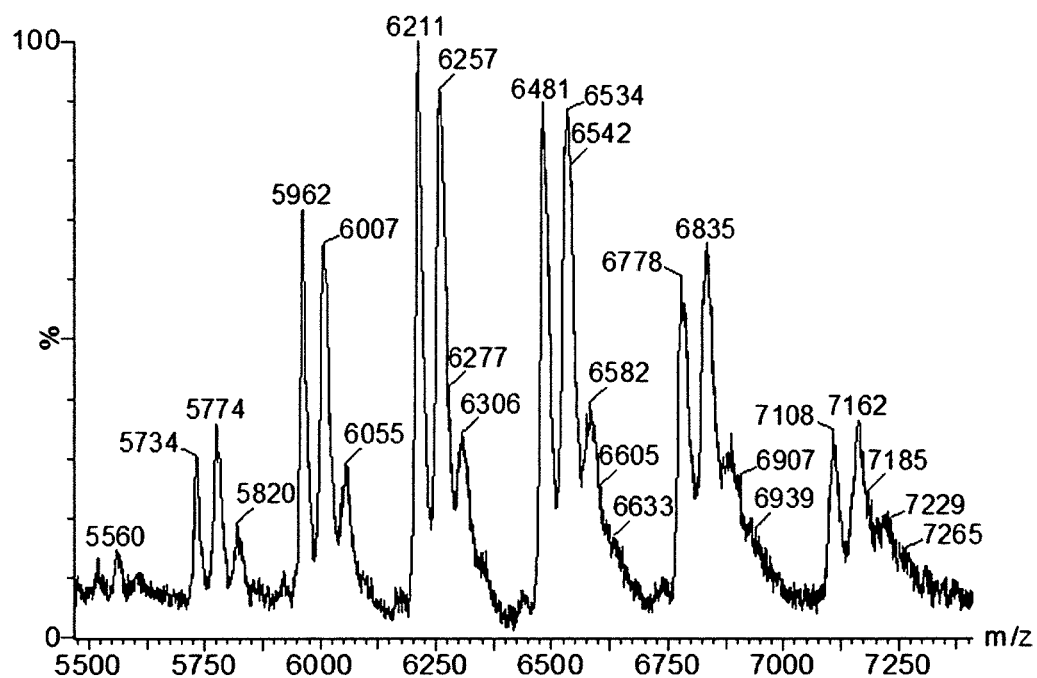
Figure 14C:
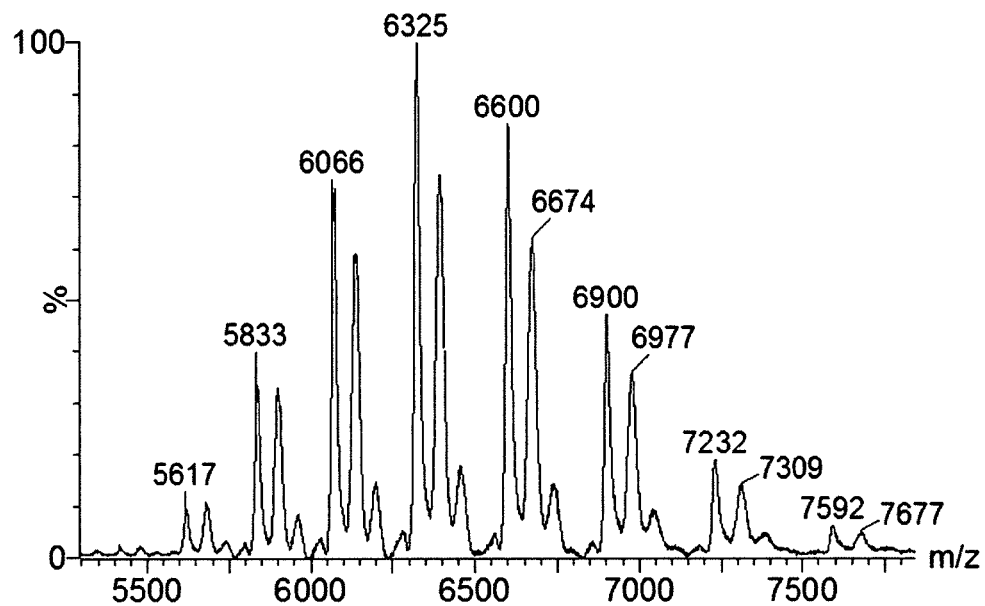
Figure 14D:
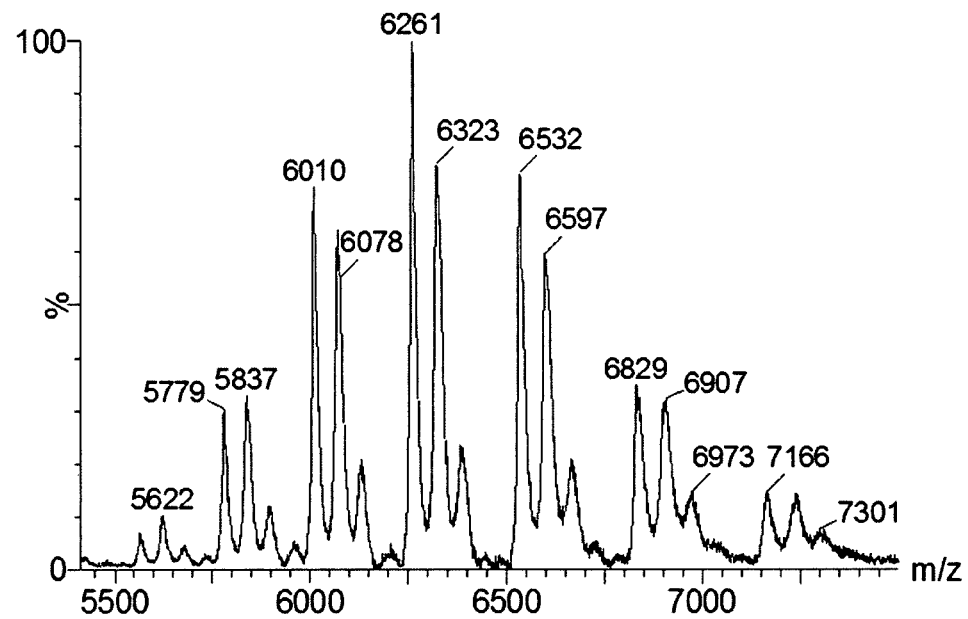

FIG. 13 represents the SEC analysis of the Ab1 antibody and ADCs according to the invention (ADC1-A, ADC1-B, ADC1-C, ADC1-D, ADC1-E, ADC1-F and ADC1-G).

FIGS. 14A, 14B, 14C and 14D represent ADC m/z spectra before deconvolution of ADCs according to the invention: (A) ADC1-A, (B) ADC1-B, (C) ADC1-C and (D) ADC-1D respectively.

Figure 15A:
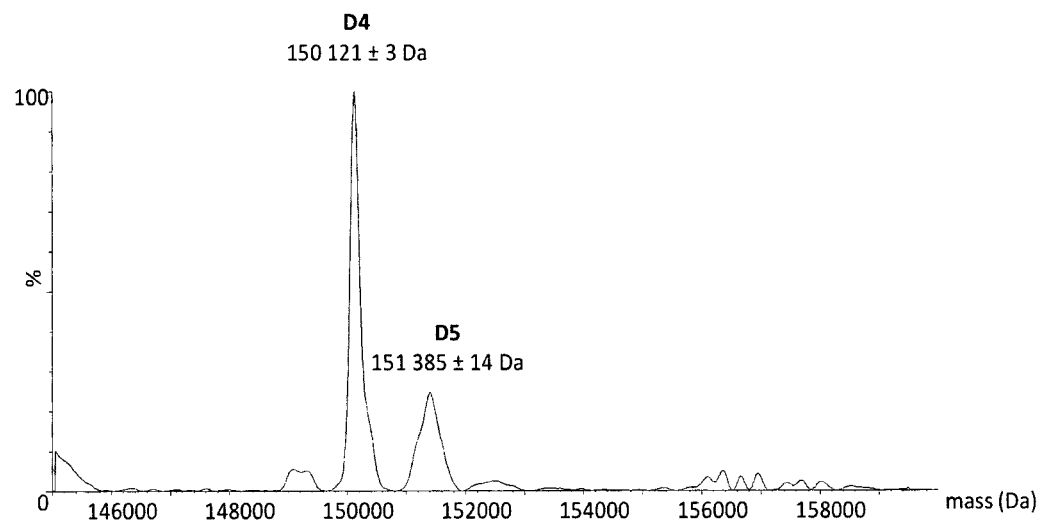
Figure 15B:
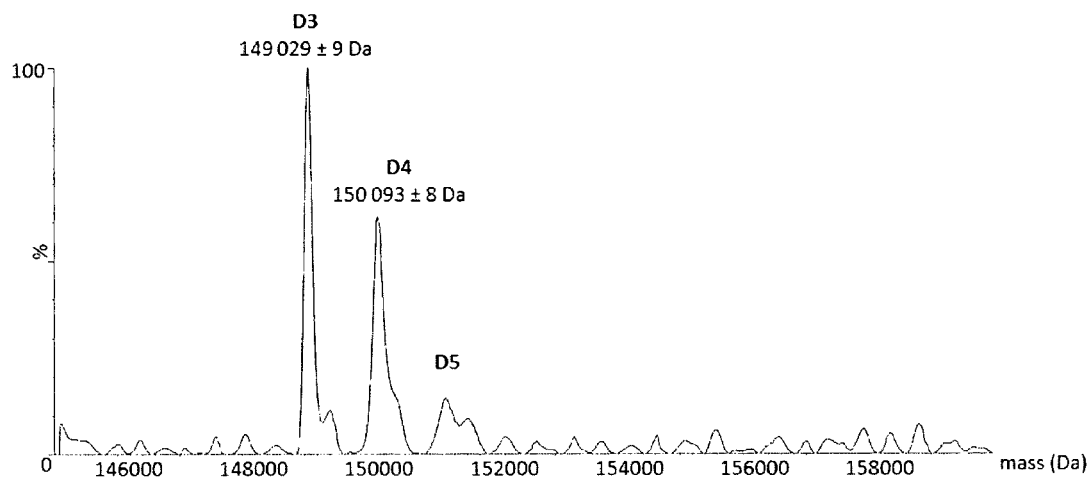
Figure 15C:
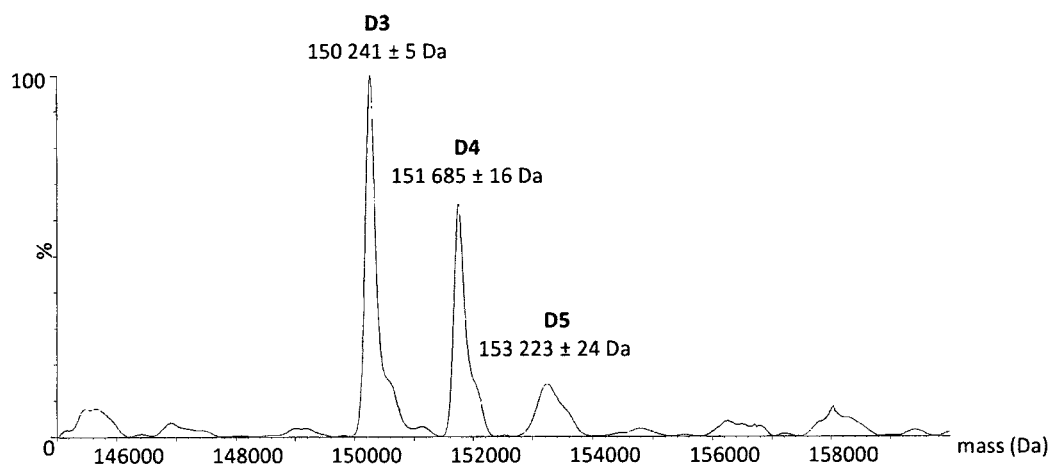

FIGS. 15A, 15B and 15C represent DAR distribution after Maxent deconvolution for (A) ADC1-A, (B) ADC1-B and (C) ADC1-D respectively.

Figure 16A:
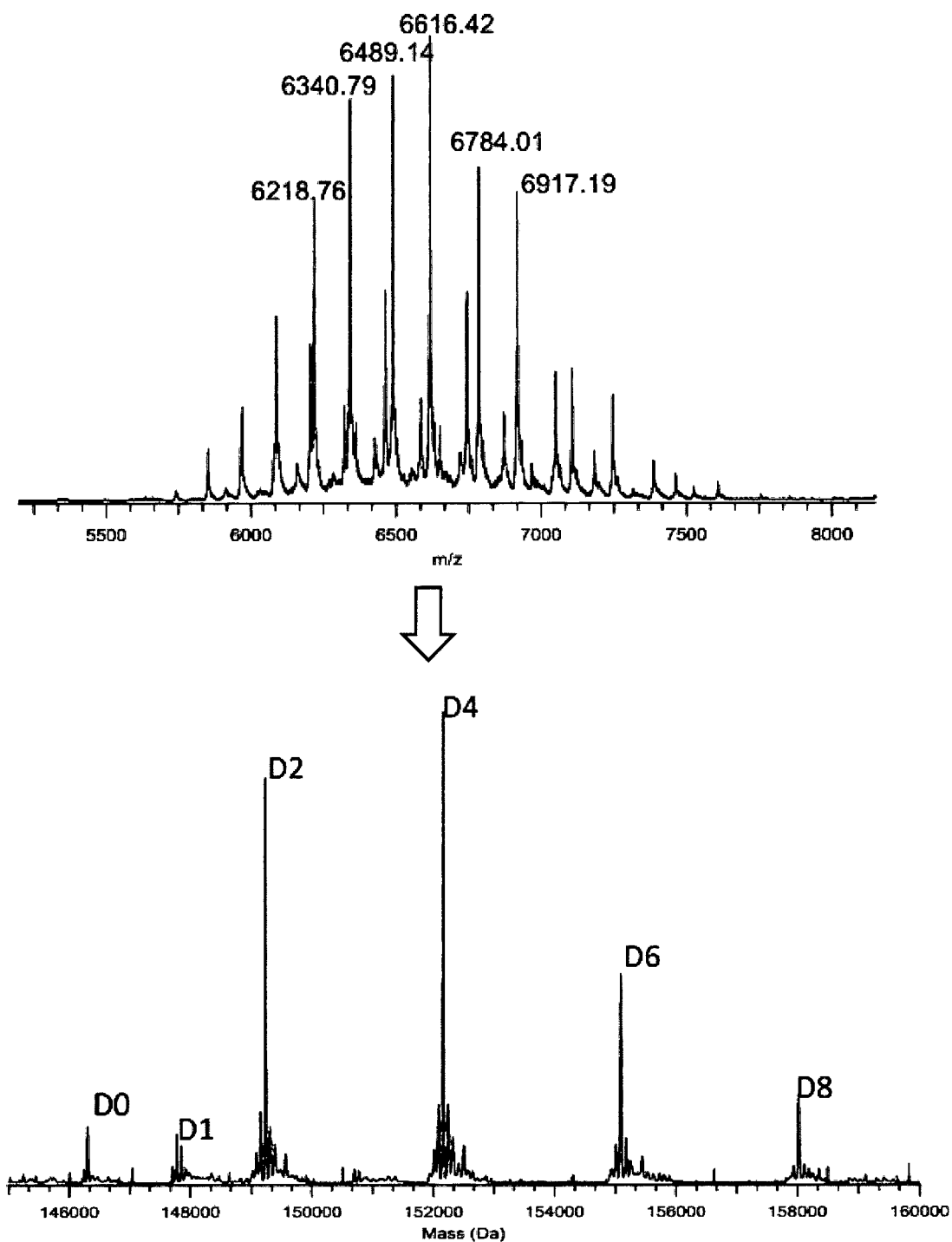
Figure 16B:
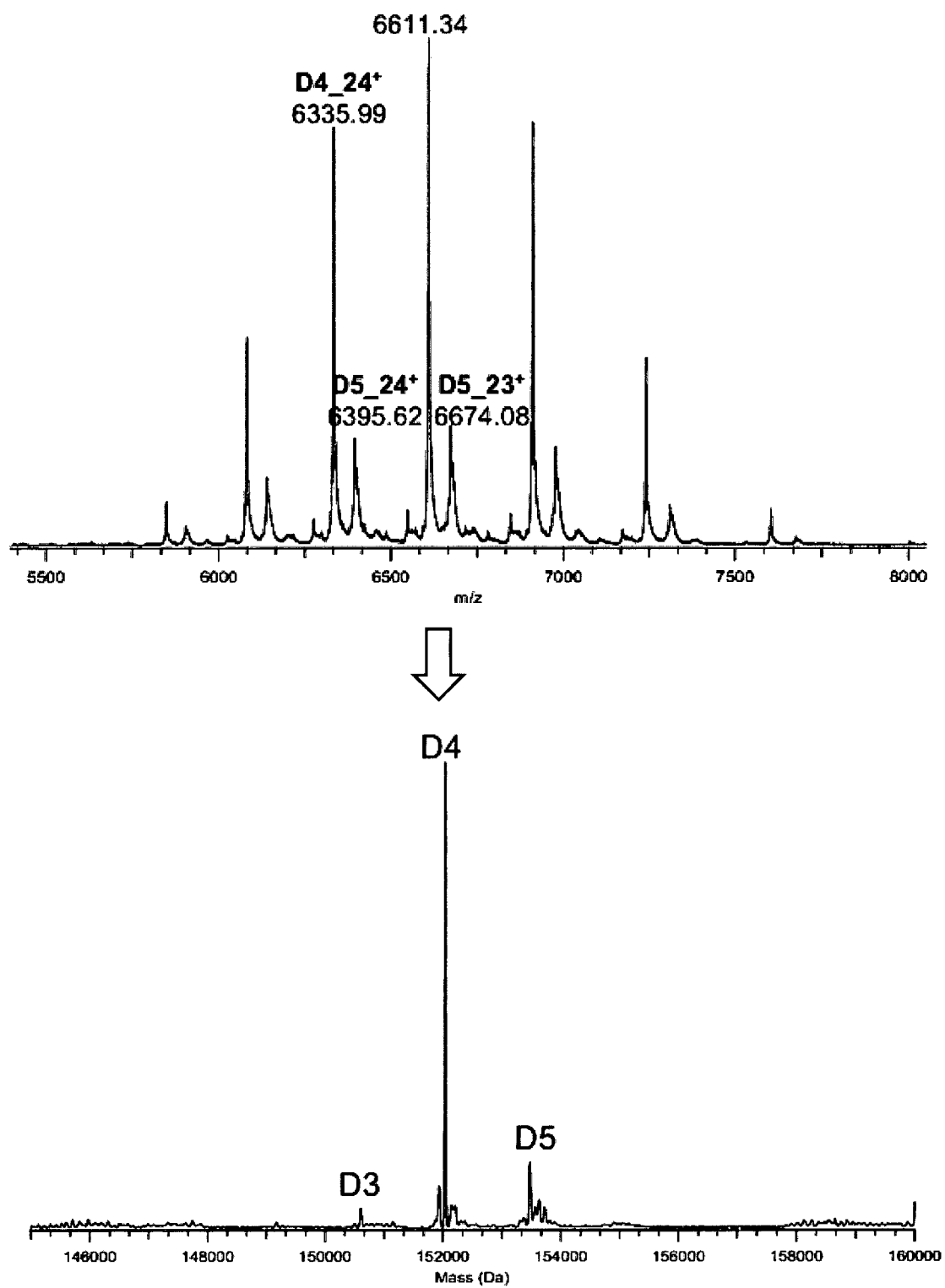

FIGS. 16A and 16B represent an analysis by native mass spectrometry of ADCs: (A) a reference ADC Ref-A and (B) ADC1-C according to the invention.

Figure 17A:
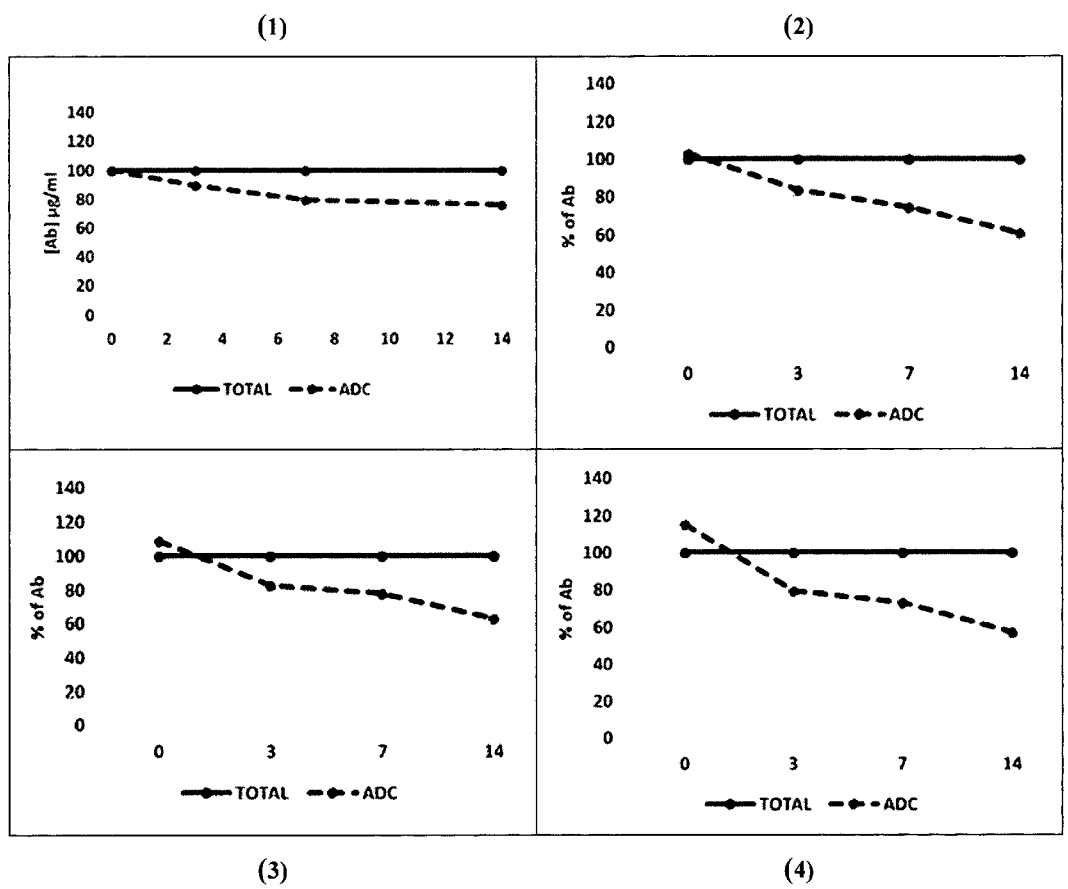
Figure 17B:
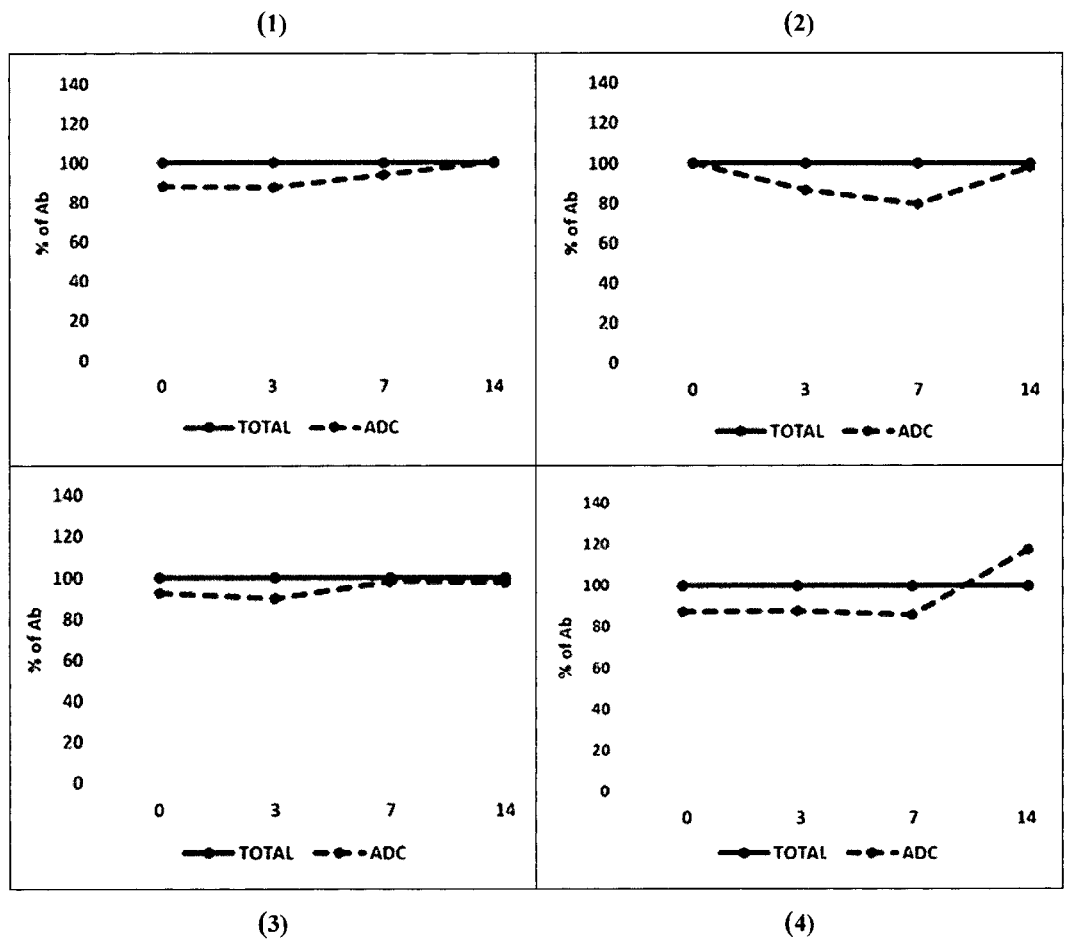
Figure 17C:
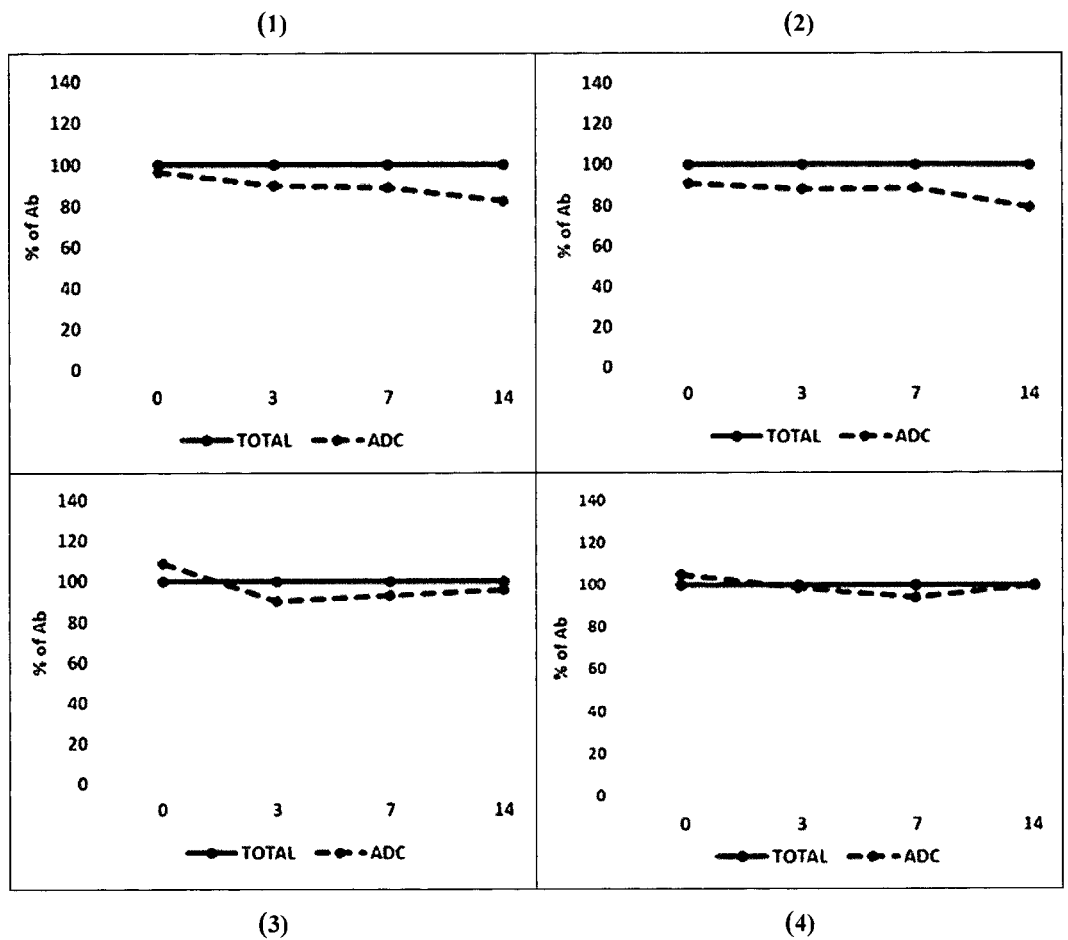

FIGS. 17A, 17B and 17C represent the results of the in vitro stability study by presenting the percentage of total antibody (100%) and ADC at each timepoint (D0, D3, D7 and D14) in (1) human, (2) cynomolgus, (3) mouse and (4) rat sera for (A) a reference ADC Ref-B, (B) ADC1-C and (C) ADC1-E respectively.

Figure 18A:
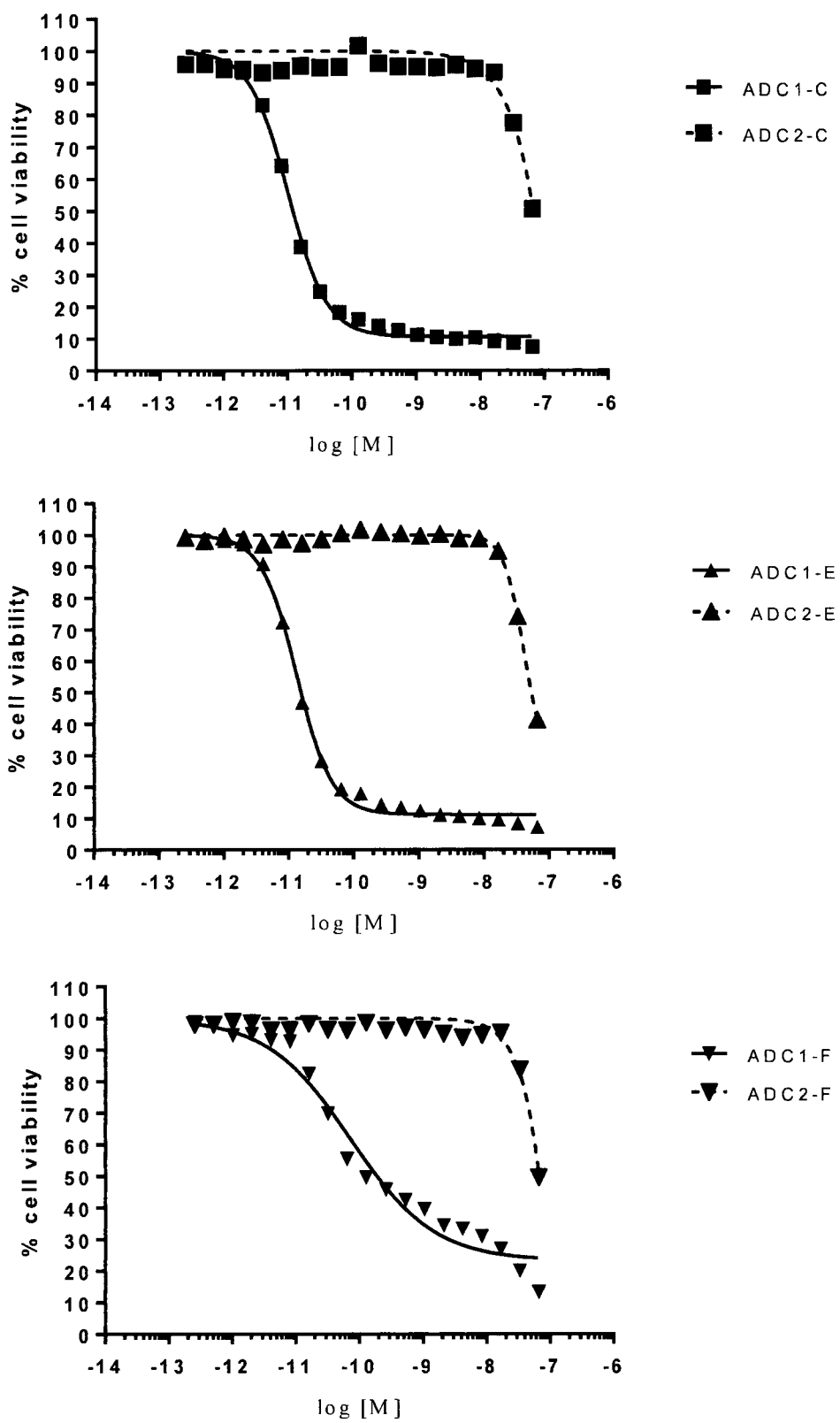
Figure 18B:
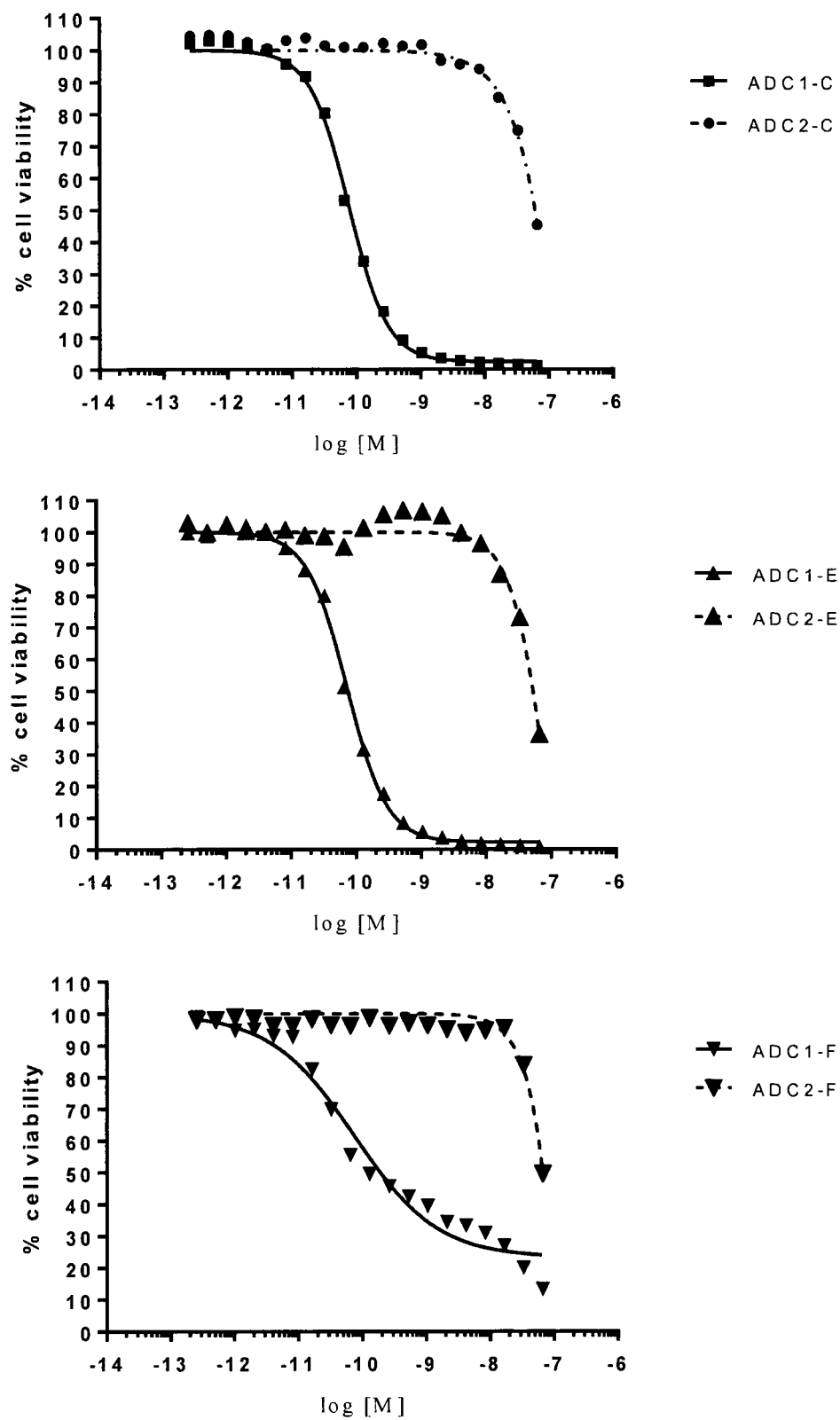

FIGS. 18A and 18B represent the in vitro cell cytotoxicity evaluation of different ADCs in NCI-H2122 (A) and MCF-7 (B) cells respectively.

Figure 19:
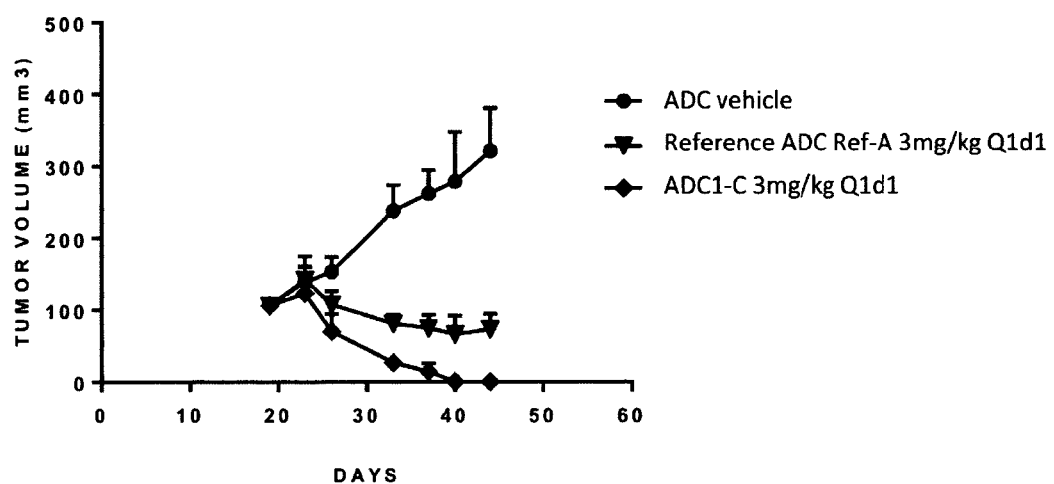
Figure 20:
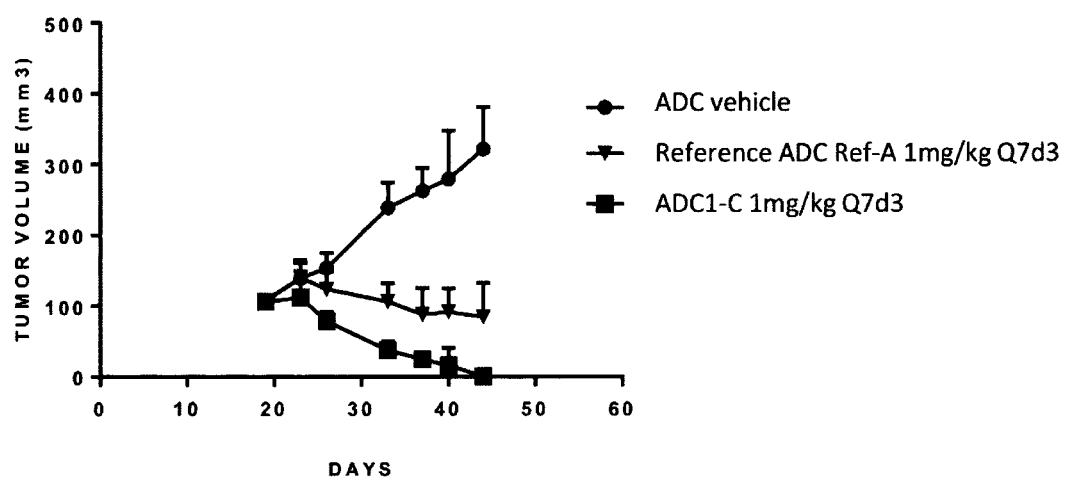

FIGS. 19 and 20 represent the in vivo activity of ADC1-C and reference ADC Ref-A in an ovarian cancer model.

Figure 22A:
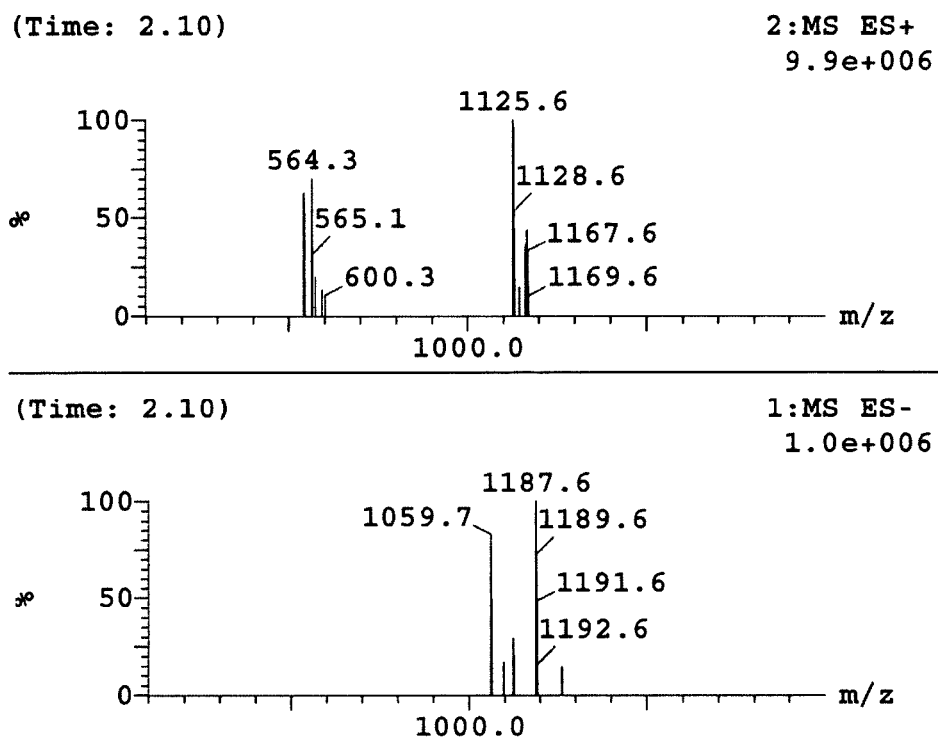
Figure 22B:
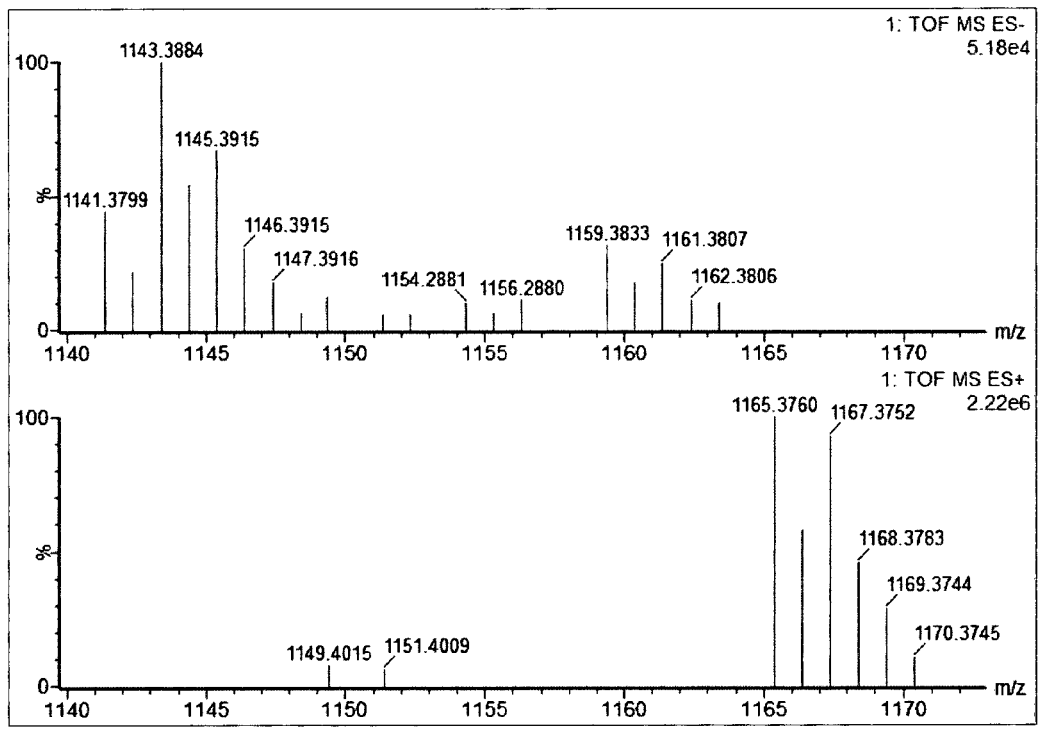

FIG. 22B represents a TOF-MS spectrum of a drug-linker conjugate according to the invention.

Figure 23A:
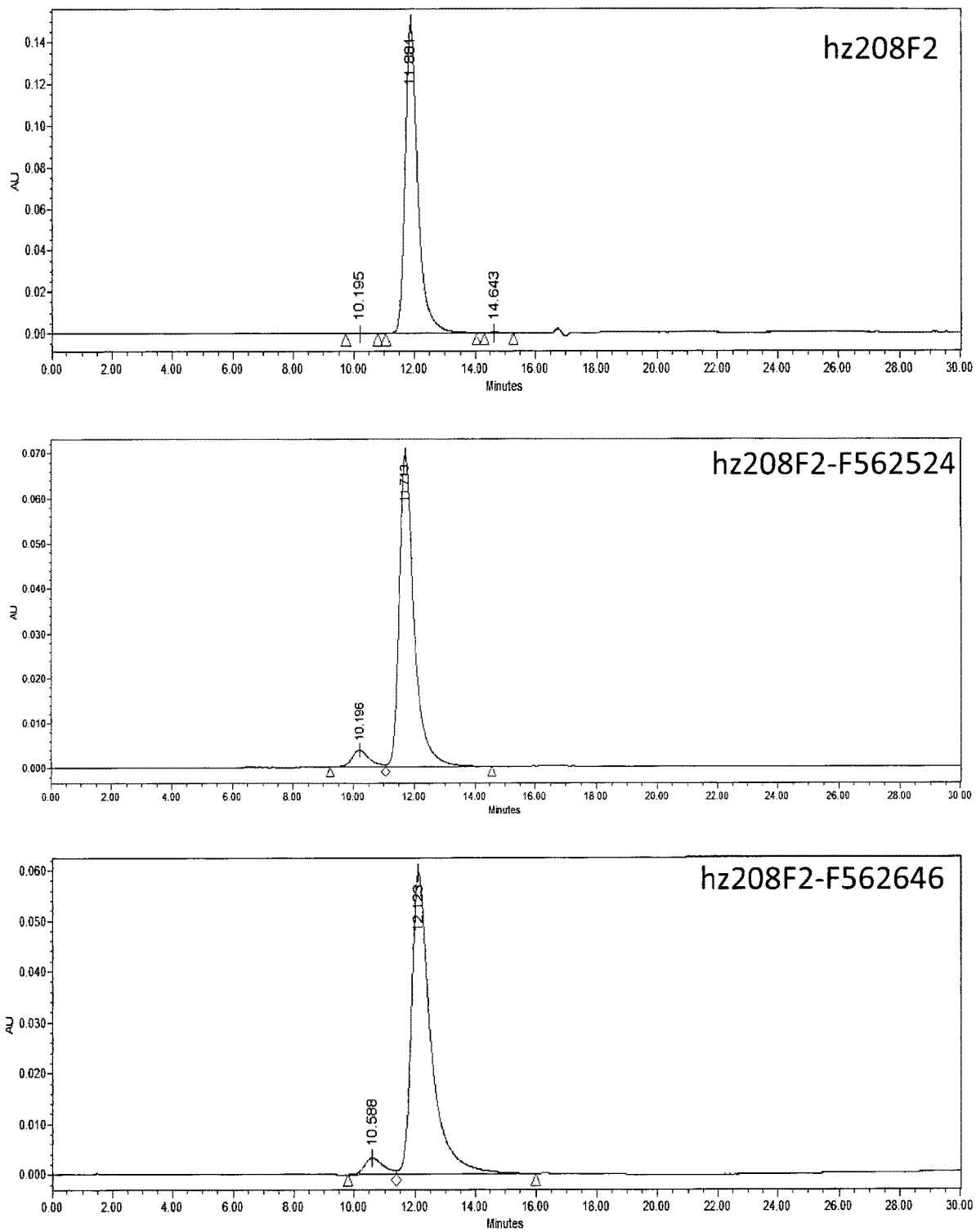

FIG. 23A represents the SEC analysis of the Ab1 antibody and ADCs according to the invention which are synthesized with the PNU-159682 derivatives.

Figure 23B:
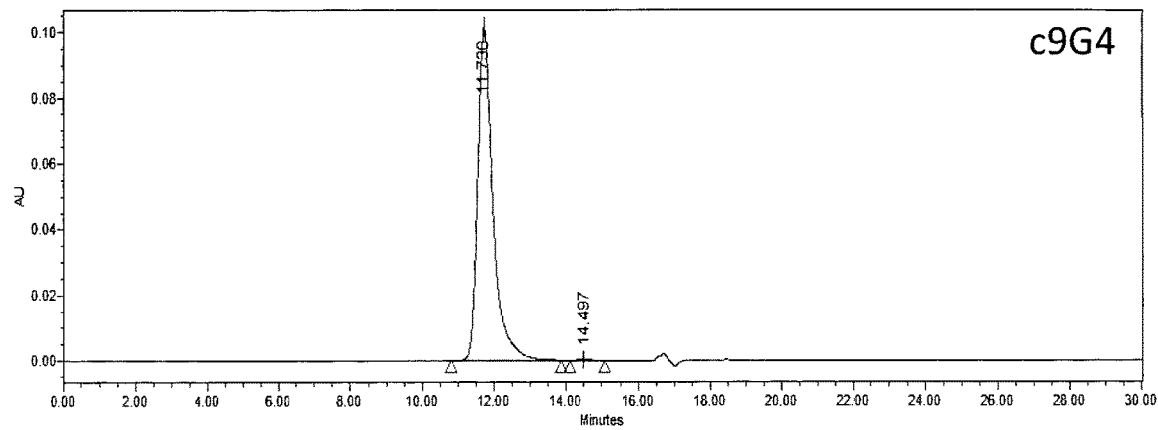
Figure 23B:
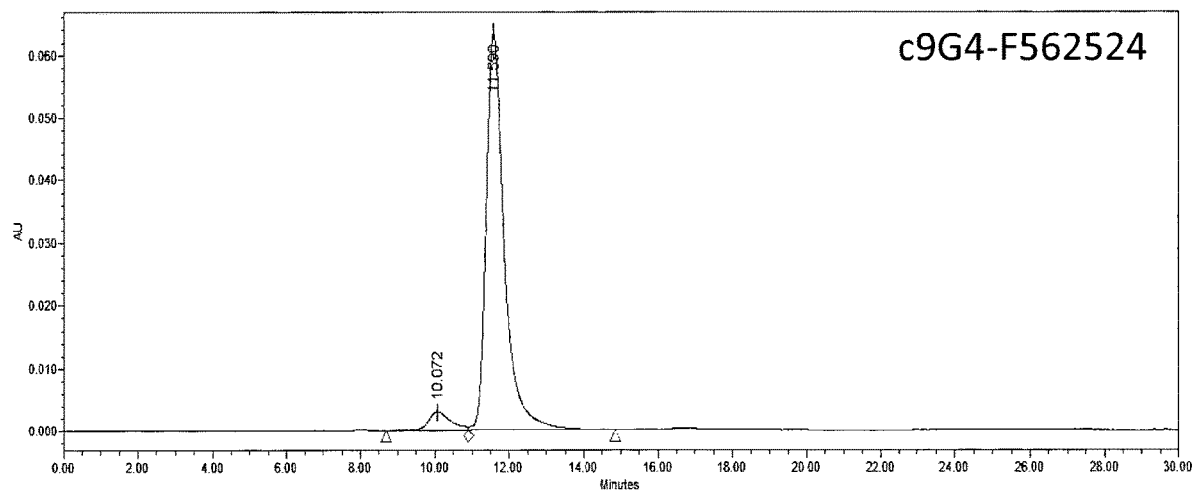
Figure 23B:
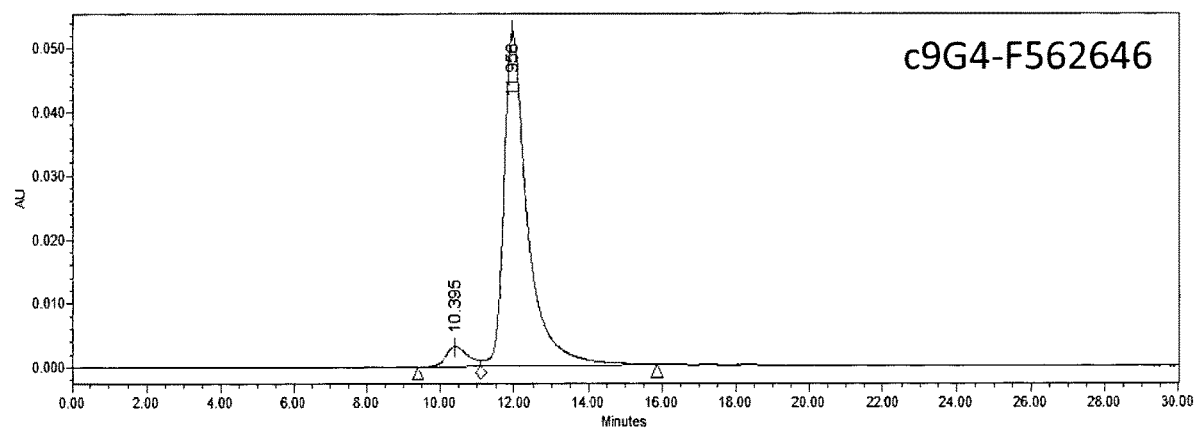
Figure 24A:
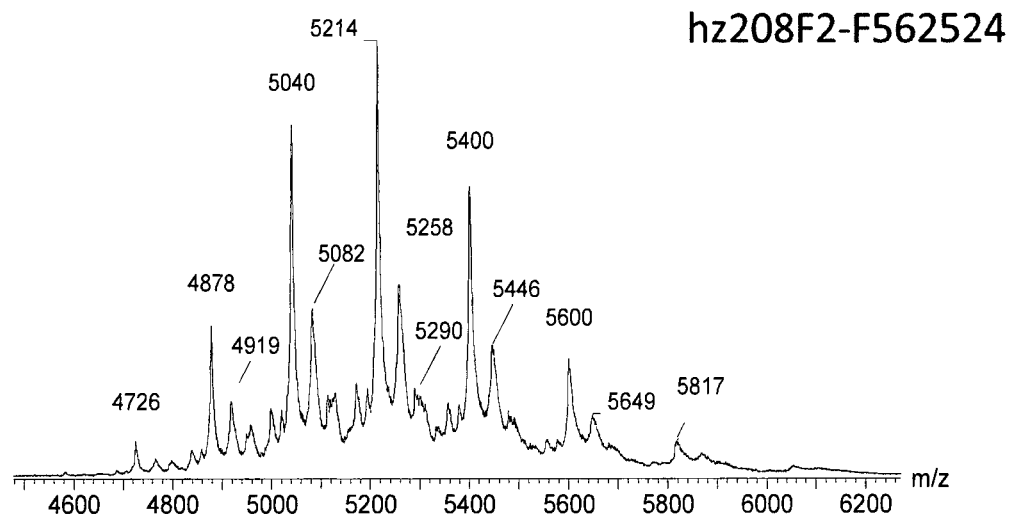
Figure 24B:
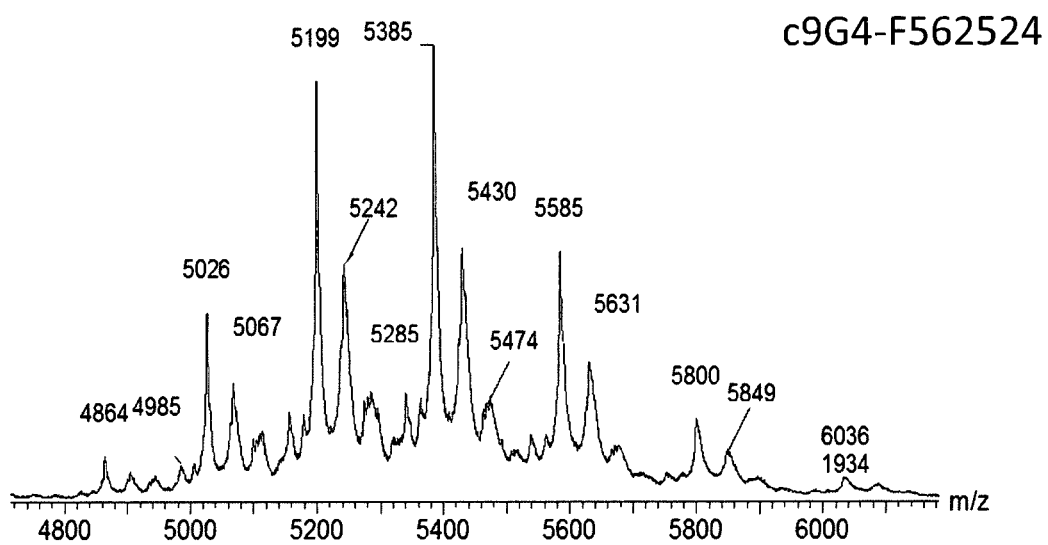
Figure 24C:
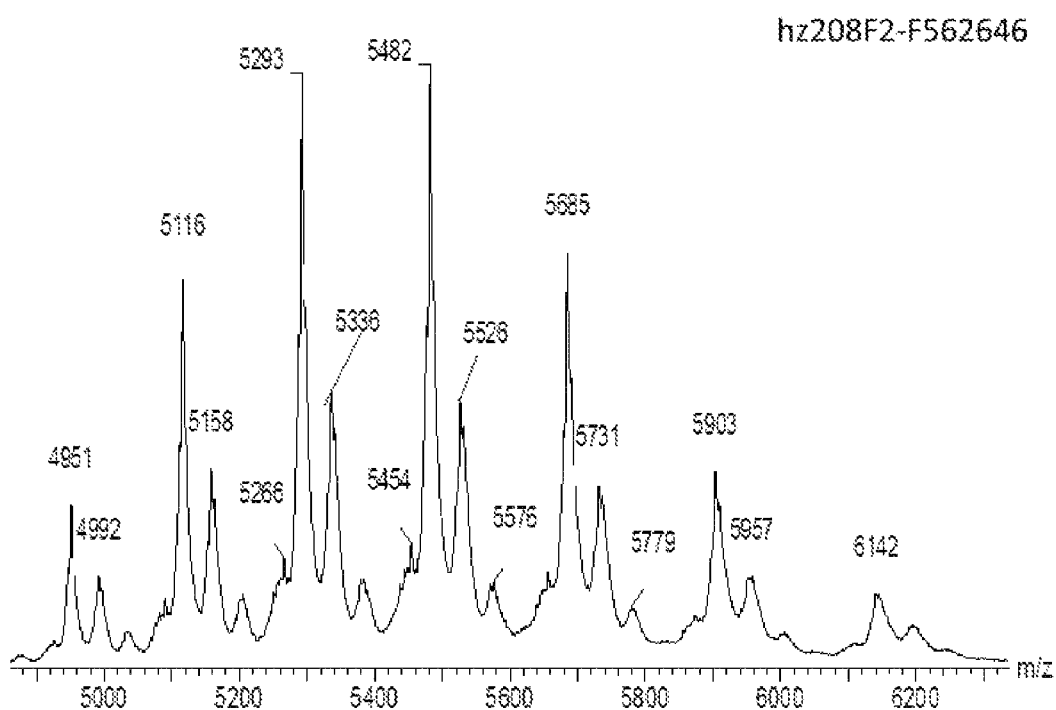
Figure 24D:
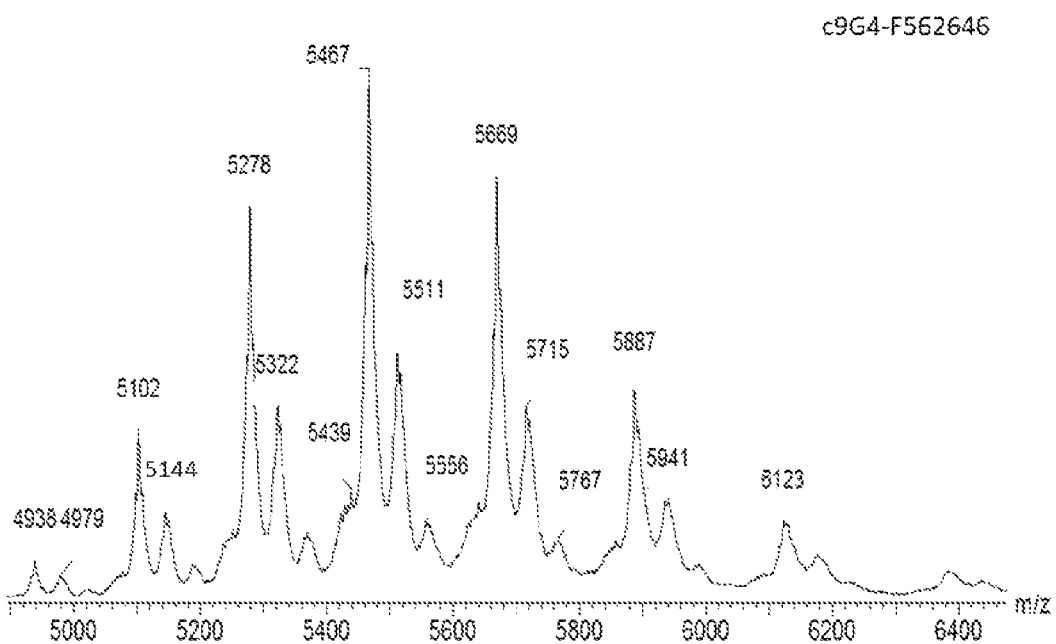
Figure 25A:
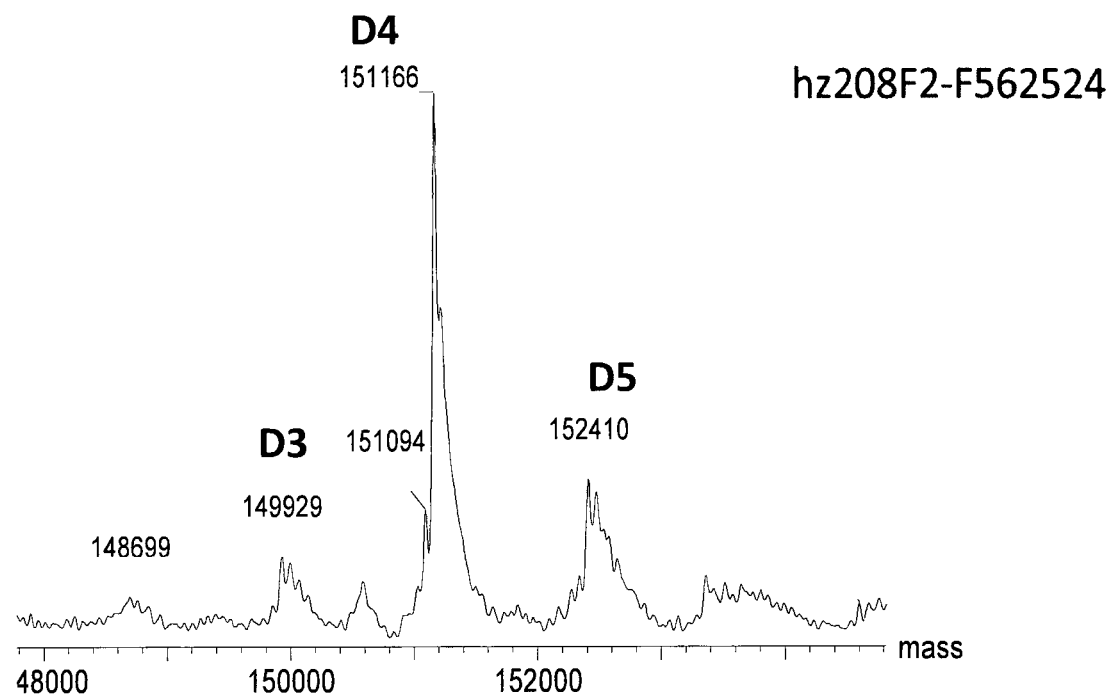
Figure 25B:
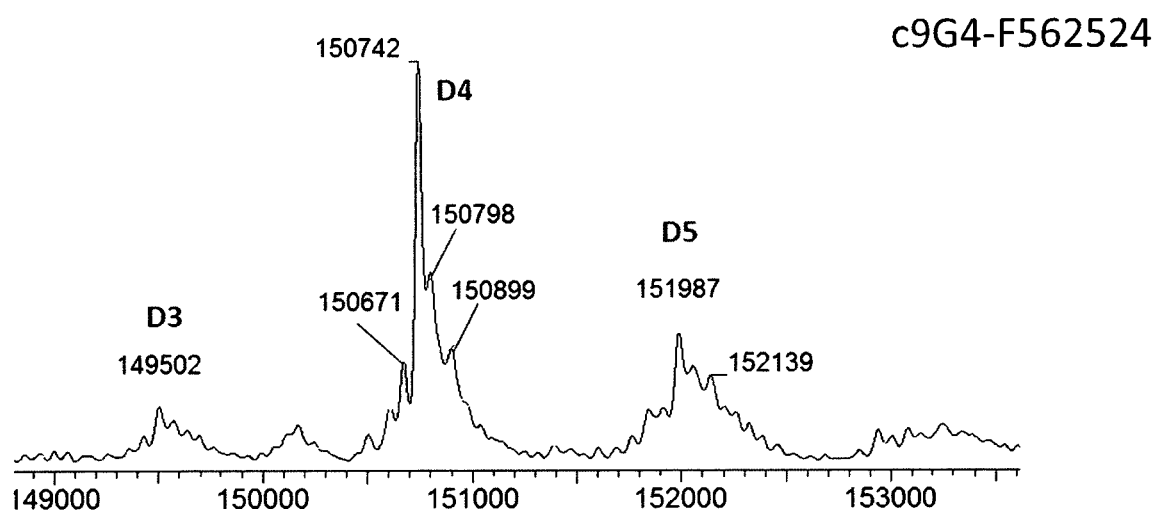
Figure 25C:
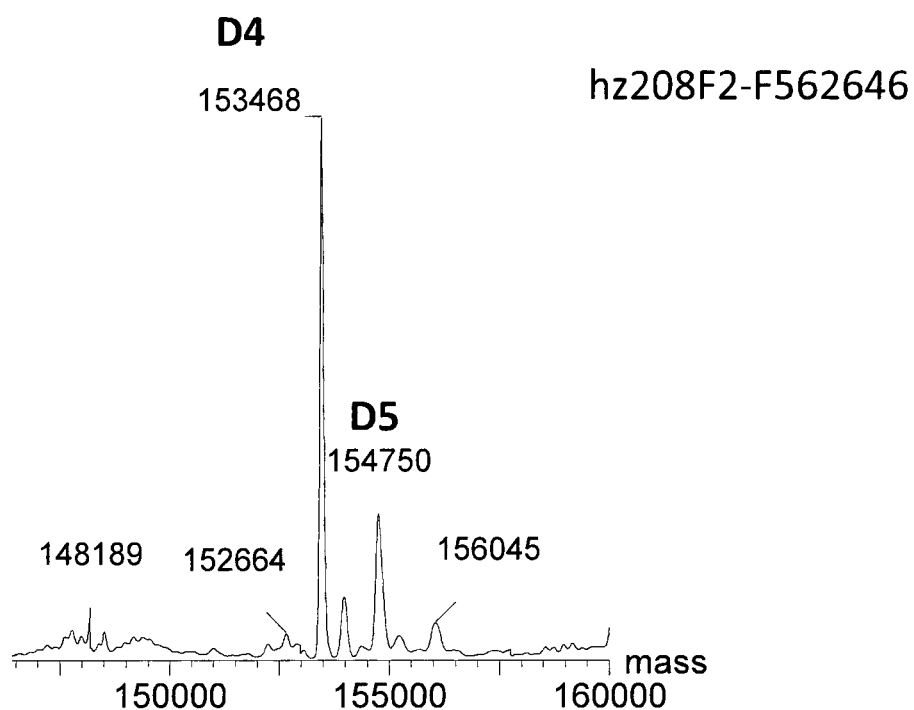
Figure 25D:
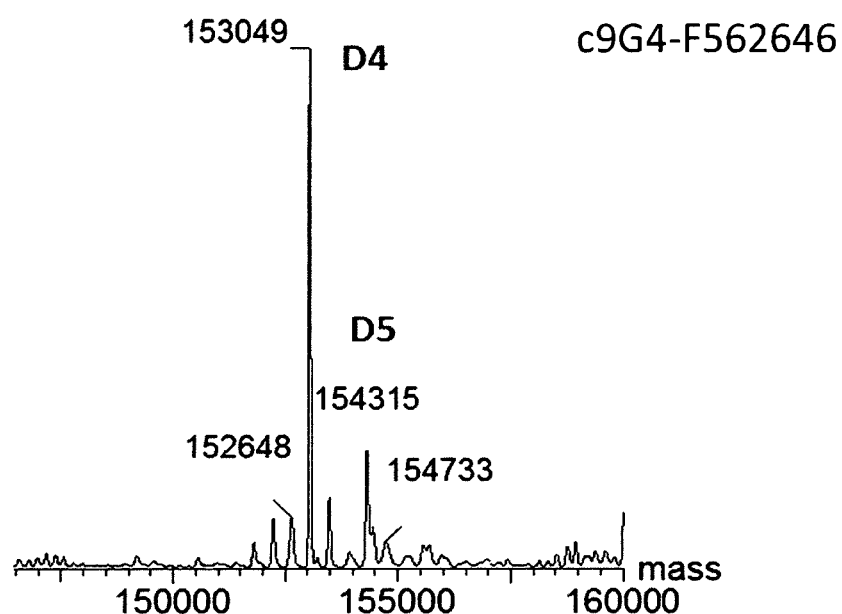

FIG. 23B represents the SEC analysis of the Ab2 antibody and ADCs according to the invention which are synthesized with the PNU-159682 derivatives.

FIGS. 24: 24A, 24B, 24C and 24D represent ADC m/z spectra before deconvolution of the ADCs according to the invention: (A) hz208F2-F562524, (B) c9G4-F562524, (C) hz208F2-F562616 and (D) c9G4-F562646 respectively.

FIGS. 25: 25A, 25B, 25C and 25D represent DAR distribution, after Maxent deconvolution, for ADCs according to the invention: (A) hz208F2-F562524, (B) c9G4-F562524, (C) hz208F2-F562616 and (D) c9G4-F562646 respectively.

Figure 26A:
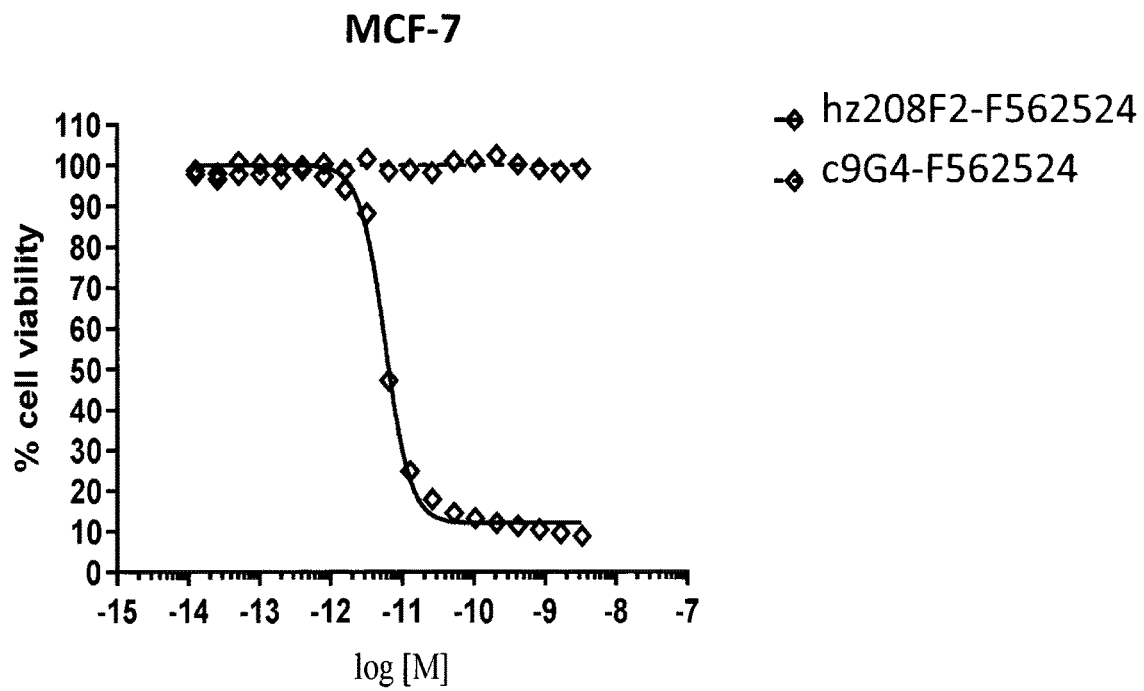
Figure 26B:
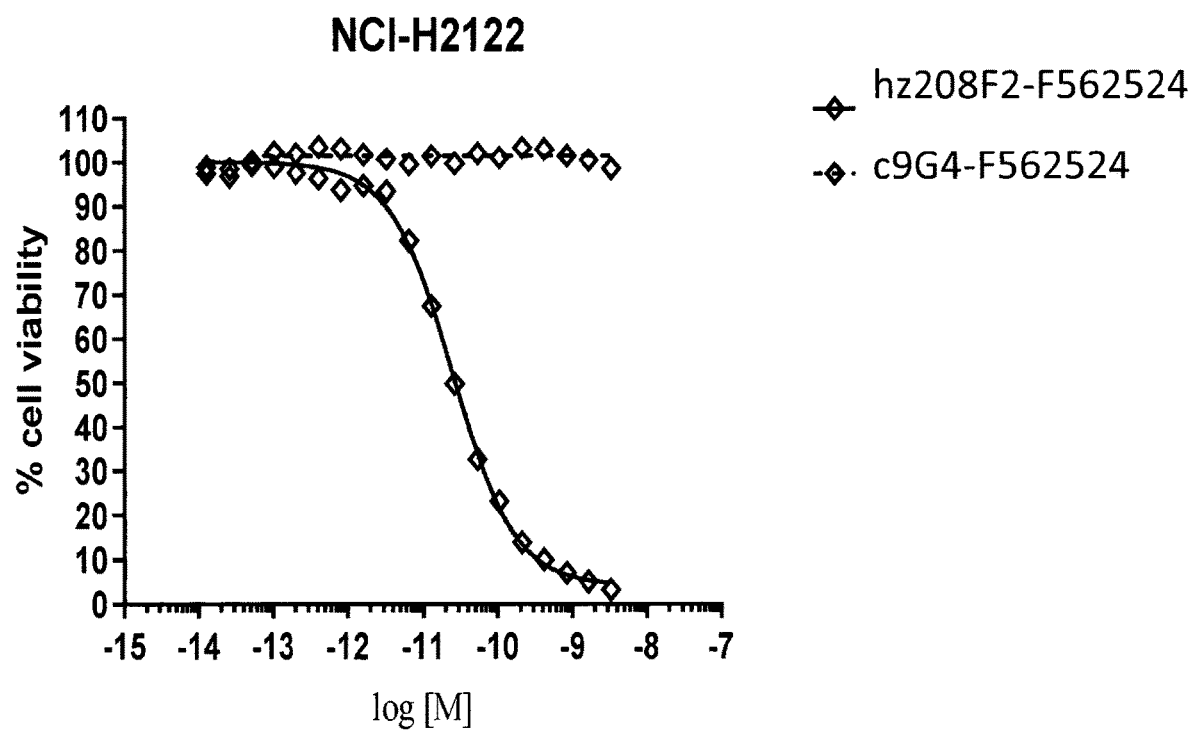

FIGS. 26: 26A and 26B represent the in vitro cell cytotoxicity evaluation of the ADC hz208F2-F562524, and the corresponding control ADC c9G4-F562524, in NCI-H2122 (A) and MCF-7 (B) cells respectively.

Figure 27A:
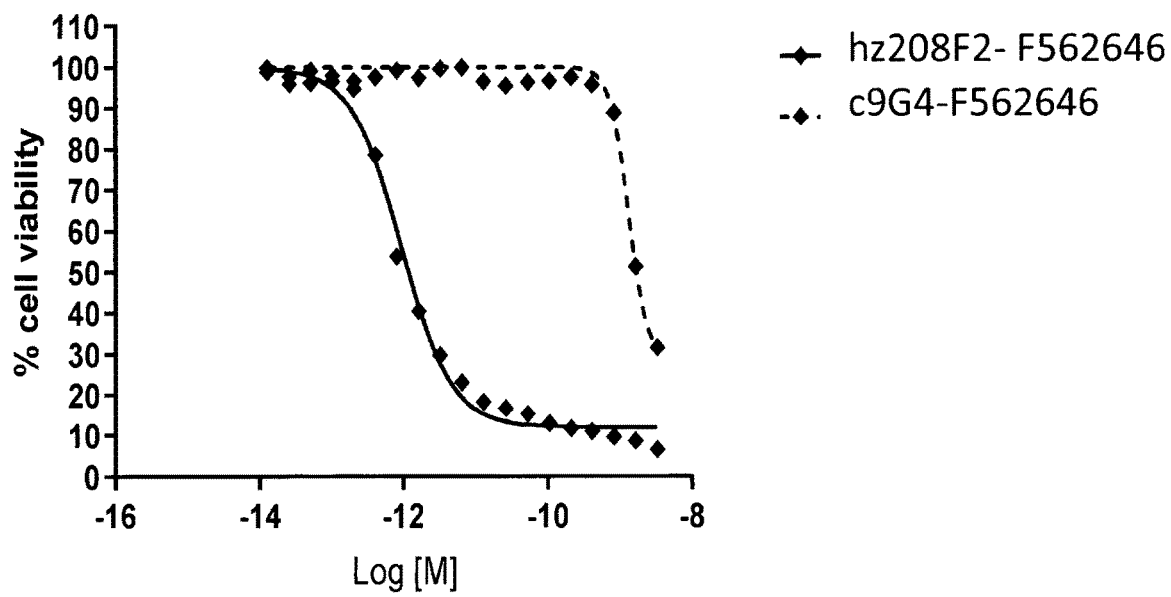
Figure 27B:
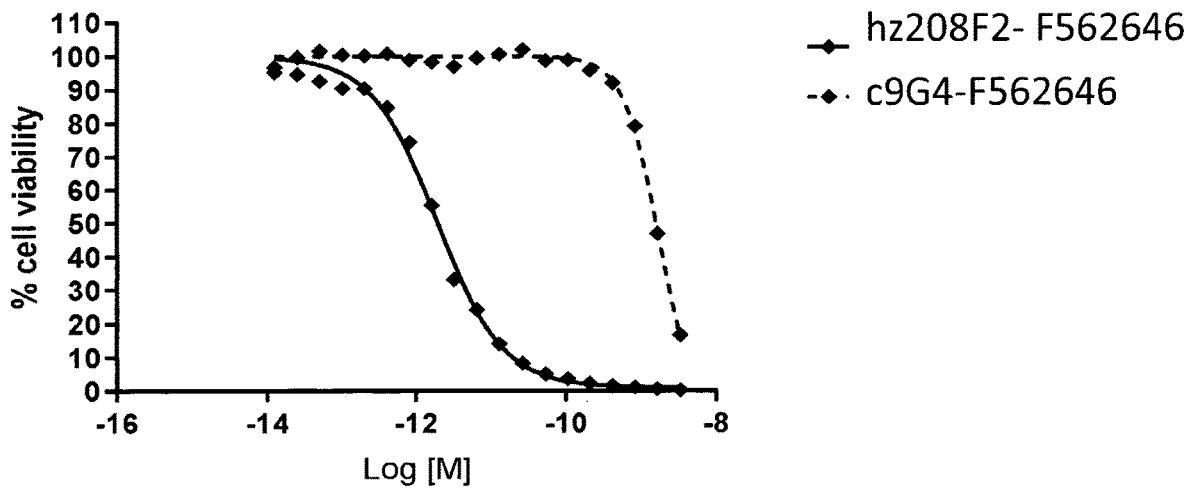

FIGS. 27: 27A and 27B represent the in vitro cell cytotoxicity evaluation of the ADC hz208F2-F562646, and the corresponding control ADC c9G4-F562646, in NCI-H2122 (A) and MCF-7 (B) cells respectively.

Figure 28:
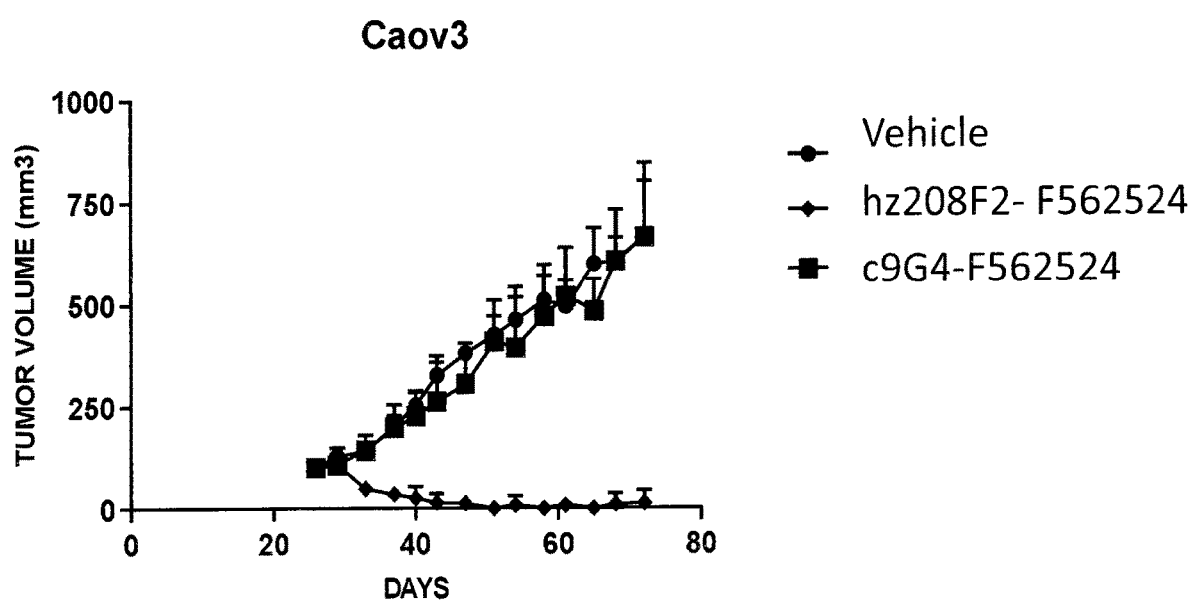

FIG. 28 represents the in vivo activity of the ADC hz208F2-F562524, and the corresponding control ADC c9G4-F562524, in an ovarian cancer model.

EXAMPLES

Abbreviations

ACN: Acetonitrile
ADC: Antibody-Drug Conjugate
aq: aqueous
BBO: Broadband Observe
BCA: Bicinchoninic acid
CDR: Complementarity Determining Region
DAR: Drug-to-Antibody Ratio
DCM: Dichloromethane
DIPEA: N,N-Diisopropylethylamine
DMF: Dimethylformamide
DMSO: Dimethylsulfoxide
EDCI: 1-Ethyl-3-(3-dimethylaminopropyl)carbodiimide
EDTA: Ethylenediaminetetraacetic acid
eq: equivalent
ES: Electrospray
ESI: Electrospray ionisation
HATU: 1-[Bis(dimethylamino)methylene]-1H-1,2,3-triazolo[4,5-b]pyridinium 3-oxid hexafluorophosphate
HOBt: 1-Hydroxybenzotriazole
HIC: Hydrophobic Interaction Chromatography
HPLC: High Performance Liquid Chromatography
HRMS: High Resolution Mass Spectrometry
LBA: Ligand Binding Assay
LC: Liquid Chromatography
LCMS: Liquid Chromatography-Mass Spectrometry
mCPBA: meta-Chloroperoxybenzoic acid
Ms: Mesyl
MS: Mass Spectrum
NMR: Nuclear Magnetic Resonance
PBS: Phosphate buffered saline
Q-TOF: Quadrupole-time-of-flight
Rf: Retardation factor
rt: Room Temperature
sat.: saturated
SDS-PAGE: Sodium Dodecyl Sulfate-PolyAcrylamide Gel Electrophoresis
SEC: Size Exclusion Chromatography
TBME: Tert-butyl methyl ether
TCEP: Tris(2-carboxyethyl)phosphine
TEA: Triethylamine
TFA: Trifluoroacetic acid
THF: Tetrahydrofuran
TLC: Thin Layer Chromatography
TOF: Time of Flight
Ts: Tosyl
UV: Ultraviolet

EXPERIMENTAL PROCEDURES

All reactions requiring anhydrous conditions were conducted in oven-dried apparatus under an atmosphere of nitrogen. Anhydrous solvents were received in sealed bottles under inert atmosphere. All reagents were used as received. Column chromatography was carried out on puriFlash® Columns with silica gel (50 µm) on an Interchim puri-Flash®430 and a Grace Reveleris® $X_2$. TLC was performed on aluminum sheets pre-coated with silica (Merck silica gel 60 $F_{254}$) which were visualized with an UV-Lamp 254 nm. Proton ($^1$H) and carbon ($^{13}$C) NMR spectra were recorded in CDCl$_3$ and DMSO at room temperature with Bruker 500 MHz Ascend™ equipped with a BBO Prodigy probe (5 mm). Spectra were interpreted using Topspin™ 3.2 software. Chemical shifts ($\delta_H$ and $\delta_C$) are reported in parts per million (ppm) and are referenced relative to either CDCl$_3$ ($^1$H NMR 7.26, $^{13}$C NMR 77.0, central signal of triplet) or DMSO ($^1$H NMR 2.50, $^{13}$C NMR 37.9, central signal of septuplet). Assignments were aided by COSY and HSQC experiments. Coupling constants (J: vicinal protons, $J_{cis}$: vicinal protons in cis position, $J_o$: proton in ortho position, $J_m$: proton in meta position) are given in Hertz to the nearest ±0.1 Hz. Multiplicities are given as singular (s), doublet (d), triplet (t), quartet (q), triplet of triplet (t. of t.), multiplet (m) and broad (b) where applicable. Mass spectra (w/z) were recorded on a Waters® ZQ Mass Detector spectrometer using the technique of electrospray ionization (ES+), source temperature: 120° C., dessolvatation temperature: 350° C., capillary voltage: 3.20 kV, cone voltage: 25 V, extractor voltage: 5 V, Rf lens voltage: 0.5 V, MS Scan range: 100-2000. HPLC analysis were performed using a Waters® X-Bridge Shield RP18 3.5 µm (3.0 mm×30 mm) column and a Waters® X-Bridge Shield RP18 3.5 µm (3.0 mm×20 mm)

pre-column on a HPLC Waters® Alliance 2695 with Mass-Lynx 4.1 software and a Waters 2996 PDA Detector UV/vis at the appropriate wavelength for the sample under analysis. Retention times ($R_t$) are given in 10 minutes to the nearest 0.01 min. Two methods of elution were used:

TABLE 7

Method 1 of elution for LC

| Time (min.) | Solvent A (Water + 0.1% formic acid) % | Solvent B (ACN + 0.1% formic acid) % |
| --- | --- | --- |
| 0.00 | 97.0 | 3.0 |
| 2.25 | 0.0 | 100.0 |
| 2.50 | 0.0 | 100.0 |
| 2.60 | 97.0 | 3.0 |
| 3.00 | 97.0 | 3.0 |

TABLE 8

Method 2 of elution for LC

| Time (min.) | Solvent A (Water + 0.1% formic acid) % | Solvent B (ACN + 0.1% formic acid) % |
| --- | --- | --- |
| 0.00 | 50.0 | 50.0 |
| 2.10 | 25.0 | 75.0 |
| 2.25 | 0.0 | 100.0 |
| 2.50 | 0.0 | 100.0 |
| 2.75 | 97.0 | 3.0 |
| 3.00 | 97.0 | 3.0 |

Retention times given by Method 1 are indicated by $R_{t,1}$ and ones given by Method 2 by $R_{t,2}$.

1. SYNTHESIS OF THE LINKERS

Example of a Synthetic Path for Oxoisothiazolones

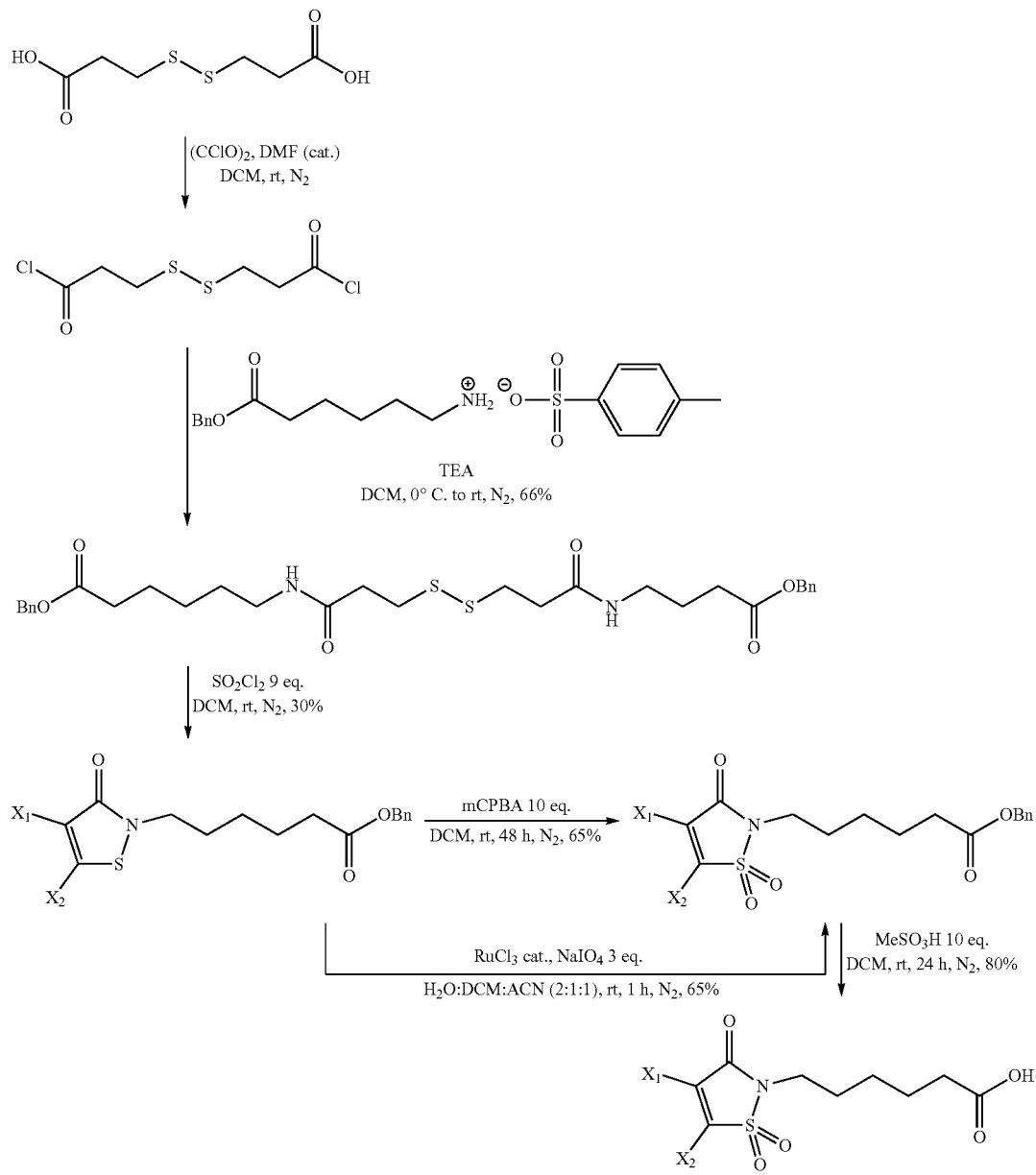

I.1. 3,3'-disulfanediyldipropanoyl Chloride

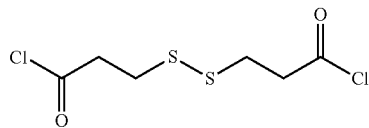 [SMILES: O=C(Cl)CCSSCCC(=O)Cl]

I.2. 3,3'-disulfanediyldipropionic acid (4 g, 0.019 mol, 1 eq.) was suspended in anhydrous DCM (100 mL) and anhydrous DMF (300 μL) was added, followed by oxalyl chloride (7.24 g, 0.057 mol, 3 eq.) at 0° C., under inert atmosphere. The solution clarified. The mixture was left for 3 h at rt until it clarified and no gas formation was longer observed. The crude was evaporated and kept under reduced pressure for another 30 min to remove remnants of oxalyl chloride. A yellow oil (4.70 g, 100%) was obtained. The crude was used without further purification; $R_{f,1}$ (in MeOH): 2.13; MS ES+ m/z: 206.86.

I.3. Dibenzyl 6,6'-((3,3'-disulfanediylbis(propanoyl))bis(azanediyl))dihexanoate

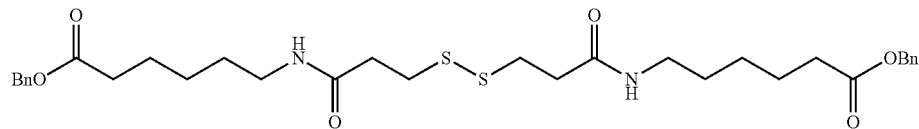 [SMILES: O=C(CCSSCCC(=O)NCCCCCC(=O)OCc1ccccc1)NCCCCCC(=O)OCc1ccccc1]

6-(benzyloxy)-6-oxohexan-1-aminium 4-methylbenzenesulfonate (12.20 g, 0.031 mol, 2.2 eq.) was suspended under vigorous stirring in anhydrous DCM (75 mL) in an ice bath at 0° C., under inert atmosphere. TEA (15.72 mL, 0.113, 8 eq.) was added to the solution. A solution of freshly prepared 3,3'-disulfanediyldipropanoyl chloride (3.88 g, 0.014 mol, 1 eq.) in DCM (25 mL) was slowly dropped into the solution maintained at 0° C. Stirring was continued for 24 hours while the solution was let to come to rt. Water was added (50 mL) and the mixture transferred to a separatory funnel. The organic layer was separated and washed with brine (1×100 mL) then washed with HCl 1M (1×100 mL), saturated solution of $NaHCO_3$ salt (2×100 mL) and brine (1×100 mL) again. The combined aqueous layers were extracted with DCM (2×100 mL). The organic layers were dried with $MgSO_4$, filtered and evaporated to dryness affording a yellow solid which was triturated in MeOH to give Dibenzyl 6,6'-((3,3'-disulfanediylbis(propanoyl)) bis(azanediyl))dihexanoate as a light yellow powder (6.0 g, 66%). $^1$H NMR (500 MHz, $CDCl_3$), δ 7.35 (m, 10H), 6.0 (s, 2H), 5.11 (s, 4H), 3.25 (q, J=5.9 Hz, 4H), 3.00 (t, J=7.0 Hz, 4H), 2.55 (t, J=7.10 Hz, 4H), 2.36 (t, J=7.30 Hz, 4H), 1.66 (t of t., J=8.10 Hz, 4H), 1.52 (t of t., J=8.10 Hz, 4H), 1.35 (t of t, J=8.52 Hz, 4H); $^{13}$C NMR (500 MHz, $CDCl_3$), δ 173.5 (2-NH—C=O), 170.9 (—O—C=O), 136.0 (2 $C_{quat}$ from aromatic cycles), 128.6 (2H—$C_{aromatic}$), 128.3 (H—$C_{aromatic}$), 128.2 (2H—$C_{aromatic}$), 66.2 (2-$CH_2$—O—), 39.4 (2-$CH_2$—N), 35.8 (2-$CH_2$—COO—), 34.3 (2-CH—S—), 34.1 (2-$CH_2$—CNO—), 29.1 (2C), 26.3 (2C), 24.4 (2C); $R_{f,1}$ (in MeOH): 2.50; MS ES+ M/Z: 617.00.

I.4. Benzyl 6-(5-chloro-3-oxoisothiazol-2(3H)-yl)hexanoate

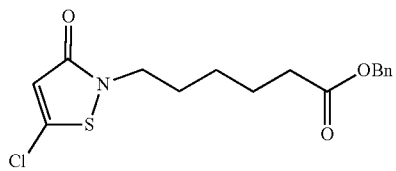 [SMILES: O=C(CCCCCn1sc(Cl)cc1=O)OCc1ccccc1]

Dibenzyl 6,6'-((3,3'-disulfanediylbis(propanoyl))bis(azanediyl))dihexanoate (2.50 g, 4.05 mmol, 1 eq.) was dissolved in anhydrous DCM (20.3 mL). $SO_2Cl_2$ (pur. 97%, 2.96 mL, 0.036 mol, 9 eq.) was added dropwise to the solution, and the mixture was stirred at rt for 5 h under inert atmosphere. The solution clarified and became pale yellow. Subsequently, the solution was washed with water (2×100 mL) and brine (1×100 mL). The combined aqueous layers were extracted with DCM (2×100 mL). The organic layers were dried with $MgSO_4$ and filtered, then concentrated under reduced pressure and purified using a chromatography column. Benzyl 6-(5-chloro-3-oxoisothiazol-2(3H)-yl) hexanoate (0.824 g, 29.9%) was obtained as a light yellow oil along with benzyl 6-(3-oxoisothiazol-2(3H)-yl)hexanoate. $^1$H NMR ($CDCl_3$), δ 7.35 (m, 5H), 6.25 (s, 1H), 5.11 (s, 2H), 3.72 (t, J=7.34 Hz, 2H), 2.37 (t, J=7.39 Hz, 2H), 1.69 (m, 4H), 1.38 (m, 2H); $^{13}$C NMR (500 MHz, $CDCl_3$), δ 173.2 (—O—C=O), 166.9 (—N—C=O), 145.6 (Cl—HC=CH—), 136.0 ($C_{quat}$ from aromatic cycle), 128.6-128.3 (5H—$C_{aromatic}$), 114.8 (Cl—HC=CH—), 66.2 (—$CH_2$—O—), 43.5 (—$CH_2$—N—), 34.0 (—$CH_2$—C=O), 29.4, 25.9, 24.4; $R_{f,1}$ (in ACN): 2.35; MS ES+ m/z: 339.84.

I.5. Benzyl 6-(5-chloro-1-oxido-3-oxoisothiazol-2(3H)-yl)hexanoate

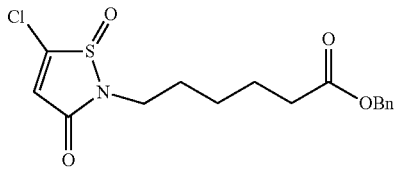 [SMILES: O=C(CCCCCN1C(=O)C=C(Cl)S1=O)OCc1ccccc1]

Benzyl 6-(5-chloro-3-oxoisothiazol-2(3H)-yl)hexanoate (802 g, 3.58 mmol) was diluted in anhydrous DCM (25 mL), 3-chlorobenzoperoxoic acid (1.2 eq.) is added. The solution was stirred for 48 h at rt under inert atmosphere. The solution was then diluted with DCM and treated by 10% aq. $Na_2S_2O_3$. The organic phase was then extracted successively by a saturated solution of $NaHCO_3$ salt (2×100 mL), followed by brine (1×100 mL). The combined aqueous layers were extracted with DCM (2×100 mL). The organic layers were dried over MgSO$_4$, filtered, then concentrated under reduced pressure and purified using a chromatography column. Benzyl 6-(5-chloro-1-oxido-3-oxoisothiazol-2(3H)-yl)hexanoate was then obtained (753 mg) as a colorless oil.

I.6. Benzyl 6-(5-chloro-1,1-dioxido-3-oxoisothiazol-2(3H)-yl)hexanoate

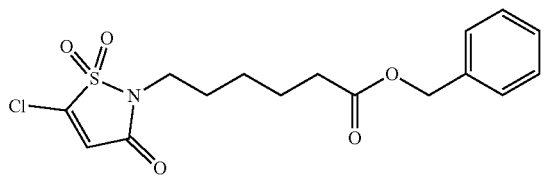 [SMILES: O=C(CCCCCN1C(=O)C=C(Cl)S1(=O)=O)OCc1ccccc1]

Standard Procedure for the Oxidation of Mono-Chloride Compounds:

Benzyl 6-(5-chloro-3-oxoisothiazol-2(3H)-yl)hexanoate (1.11 g, 0.0036 mol, 1 eq.) was diluted in anhydrous DCM (7 mL), 3-chlorobenzoperoxoic acid (2.69 g, 0.0109 mol, 3 eq.) is added. The solution was stirred for 48 h at rt under inert atmosphere. The solution was then diluted with DCM and treated by 10% aq. Na$_2$S$_2$O$_3$. The organic phase was then extracted successively by a saturated solution of NaHCO$_3$ salt (2×100 mL), followed by brine (1×100 mL). The combined aqueous layers were extracted with DCM (2×100 mL). The organic layers were dried over MgSO$_4$, filtered, then concentrated under reduced pressure and purified using a chromatography column. Benzyl 6-(5-chloro-1,1-dioxido-3-oxoisothiazol-2(3H)-yl)hexanoate was obtained as a light yellow oil (0.760 g, 64.3%). $^1$H NMR (CDCl$_3$), δ 7.36 (m, 5H), 6.68 (s, 1H), 5.11 (s, 2H), 3.67 (t, J=7.68 Hz, 2H), 2.37 (t, J=7.27 Hz, 2H), 1.78 (t of t, J=7.73 Hz, 2H), 1.70 (t of t, J=7.38 Hz, 2H), 1.40 (m, 2H); $^{13}$C NMR (500 MHz, CDCl$_3$), δ 173.2 (—O—CO), 157.0 (—N—CO), 144.6 (Cl—HC=CH—), 136.0 (C$_{quat}$ from aromatic cycle), 128.6-128.2 (H—C$_{aromatic}$), 123.6 (Cl—HC=CH—), 66.2 (—CH$_2$—O), 40.3 (—CH$_2$—N—), 34.0 (—CH$_2$—C=O), 27.9, 26.0, 24.2; R$_{t,1}$ (in ACN): 2.49; MS ES+ M/Z: 371.83.

Example 1. 6-(5-Chloro-1,1-dioxido-3-oxoisothiazol-2(3H)-yl)hexanoic Acid

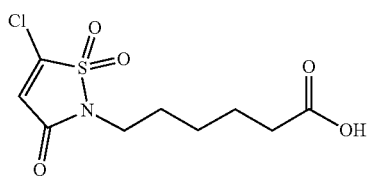 [SMILES: O=C(O)CCCCCN1C(=O)C=C(Cl)S1(=O)=O]

6-(5-Chloro-1,1-dioxido-3-oxoisothiazol-2(3H)-yl)hexanoic acid was obtained as a light white powder following the standard procedure of deprotection of benzyl esters starting from Benzyl 6-(5-chloro-1,1-dioxido-3-oxoisothiazol-2(3H)-yl)hexanoate (0.445 g, 77%). $^1$H NMR (CDCl$_3$), δ 10.89 (br, s, 1H), 6.70 (s, 1H), 3.70 (t, J=7.43 Hz, 2H), 2.38 (t, J=7.38 Hz, 2H), 1.81 (t of t, J=7.60 Hz, 2H), 1.69 (t of t, J=7.71 Hz, 2H), 1.43 (splitted t of t, J=7.75 Hz, J=3.31 Hz, 2H); $^{13}$C NMR (500 MHz, CDCl$_3$), δ 178.7 (O=C—OH), 157.1 (—N—C=O), 144.7 (Cl—HC=CH—), 123.6 (Cl—HC=CH—), 40.2 (—CH$_2$—N), 33.5 (—CH$_2$—C=O), 27.9, 25.9, 23.9; R$_{t,1}$ (in ACN): 1.98; MS ES+ m/z: 349.89.

I.7. Benzyl 6-(4,5-dichloro-3-oxoisothiazol-2(3H)-yl)hexanoate

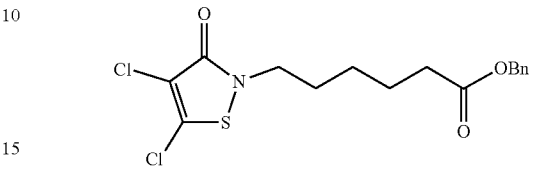

Dibenzyl 6,6'-((3,3'-disulfanediylbis(propanoyl))bis(azanediyl))dihexanoate (3.21 g, 0.0052 mol, 1 eq.) was dissolved in anhydrous DCM (26 mL). SO$_2$Cl$_2$ (pur. 97%, 3.80 mL, 0.047 mol, 9 eq.) was added dropwise to the solution, and the mixture was stirred at rt for 24 h under inert atmosphere. The solution clarified and became pale yellow. Subsequently, the mixture was washed with water (2×100 mL) and brine (1×100 mL). The combined aqueous layers were extracted with DCM (2×100 mL). The organic layers were dried with MgSO$_4$ and filtered then concentrated under reduced pressure and purified using a chromatography column. Benzyl 6-(4,5-dichloro-3-oxoisothiazol-2(3H)-yl)hexanoate was obtained as a light yellow oil (1.391 g, 35.7%). $^1$H NMR (CDCl$_3$), δ 7.35 (m, 5H), 5.11 (s, 2H), 3.79 (t, J=7.18 Hz, 2H), 2.37 (t, J=7.33 Hz, 2H), 1.70 (m, 4H), 1.38 (m, 2H); $^{13}$C NMR (500 MHz, CDCl$_3$), δ 173.2 (—O—C=O), 161.9 (—N—C=O), 138 (—CH$_2$—O—), 0.3 (Cl—C—S—), 135.6 (C$_{quat}$ from aromatic cycle), 128.6-128.3 (5H—C$_{aromatic}$), 115.1 (Cl—C—C=O), 66.2, 44.9 (—CH$_2$—N—), 33.9 (—CH$_2$—C=O), 29.1, 25.9, 24.3; R$_{t,1}$ (in ACN): 2.50; MS ES+ m/z: 373.75.

I.8. Benzyl 6-(4,5-dichloro-1,1-dioxido-3-oxoisothiazol-2(3H)-yl)hexanoate

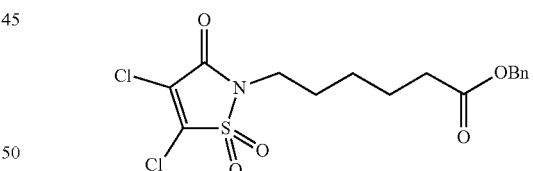

Standard Procedure for the Oxidation of Di-Chloride Compounds:

Ruthenium trichloride monohydrated (16 mg, 0.07 mmol, 0.013 eq.) was added in one portion to a stirred solution of Benzyl 6-(4,5-dichloro-3-oxoisothiazol-2(3H)-yl)hexanoate (1.94 g, 0.0052 mol, 1 eq.) in water:DCM:ACN (2:1:1, 1 ml). Sodium periodate (3.33 g, 0.0156 mol, 3 eq.) was then added over 5 min and the resulting mixture stirred at rt for 90 minutes under inert atmosphere. The solids were filtered and the filtrate was diluted with water (50 mL), extracted with EtOAc (2×100 mL), dried with MgSO$_4$, filtered, and concentrated under reduced pressure. The grey solid obtained was then purified using a chromatography column and Benzyl 6-(4,5-dichloro-1,1-dioxido-3-oxoisothiazol-2(3H)-yl)hexanoate was obtained as a pale yellow oil (0.930 g, 44.2%). $^{1}$H NMR (CDCl$_3$), δ 7.36 (m, 5H), 5.12 (s, 2H), 3.72 (t, J=7.53 Hz, 2H), 2.73 (t, J=7.50 Hz, 2H), 1.80 (t of t, J=7.53 Hz, 2H), 1.70 (t of t, J=7.70 Hz), 1.41 (m, 2H); $^{13}$C NMR (500 MHz, CDCl$_3$), δ 173.1 (—O—C=O—), 154.1 (N—C=O), 138.0 (Cl—C—SO$_2$—), 136.0 (C$_{quat}$ from aromatic cycle), 130.7 1 (Cl—C—C=O), 128.6-128.3 (5H—C$_{aromatic}$), 66.2 (—CH$_2$—O—), 41.1 (—CH$_2$—N—), 33.9 (—CH$_2$—C=O), 27.9, 26.0, 24.2; R$_{t,1}$ (in ACN): 2.59; MS ES+ m/z: 405.76.

Example 2. 6-(4,5-Dichloro-1,1-dioxido-3-oxoisothiazol-2(3H)-yl)hexanoic Acid

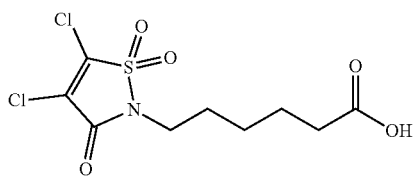 [SMILES: O=C(O)CCCCCN1C(=O)C(Cl)=C(Cl)S1(=O)=O]

Standard Procedure of Deprotection of Benzyl Esters:

Benzyl 6-(4,5-dichloro-1,1-dioxido-3-oxoisothiazol-2(3H)-yl)hexanoate (0.930 g, 2.23 mmol, 1 eq.) was diluted in anhydrous DCM (11.5 mL). Methanesulfonic acid (1.5 mL, 0.023 mol, 10 eq.) was added. The solution was stirred for 24 h at rt under inert atmosphere. The solution was then diluted with DCM, and treated with water (50 mL). The organic layer was extracted with water (2×100 mL) then brine (1×100 mL). The combined aqueous layers were extracted with DCM (2×100 mL). The organic layers were dried over MgSO$_4$ and concentrated under reduced pressure, then purified using a chromatography column. 6-(4,5-Dichloro-1,1-dioxido-3-oxoisothiazol-2(3H)-yl)hexanoic acid was obtained as a light white powder (0.563 g, 78%). $^{1}$H NMR (500 MHz, CDCl$_3$), δ=3.76 (t, J=7.34 Hz, 2H), 2.38 (t, J=7.32 Hz, 2H), 1.83 (t of t, J=7.65 Hz, 2H), 1.70 (t of t, J=1.11 Hz, 2H), 1.45 (t of t, J=7.54 Hz, J=3.31 Hz, 2H); $^{13}$C NMR (500 MHz, CDCl$_3$), δ 178.2 (O=C—OH), 154.2 (N—C=O), 138.1 (Cl—C—SO$_2$—), 130.9 (Cl—C—C=O), 41.1 (—CH$_2$—N—), 33.4 (—CH$_2$—C=O), 27.9, 25.9, 23.9: R$_{t,1}$ (in ACN): 2.09; MS ES+m/z: 315.76.

I.9. Benzyl 6-(4-bromo-1,1-dioxido-3-oxoisothiazol-2(3H)-yl)hexanoate

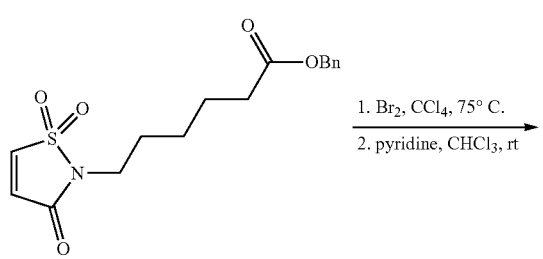

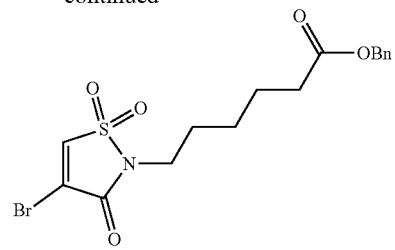

To a solution of benzyl 6-(1,1-dioxido-3-oxoisothiazol-2(3H)-yl)hexanoate (obtained following the standard procedure for the oxidation of mono-chloride compounds starting from benzyl 6-(3-oxoisothiazol-2(3H)-yl)hexanoate) (3 g, 8.89 mmol, 1.00 equiv) in CCl$_4$ (40 mL) was added Br: (1.2 mL, 19.58 mmol, 2.2 equiv) dropwise with stirring at ambient temperature over 30 min and stirred overnight at 75° C. The reaction mixture was concentrated under vacuum and diluted with CHCl$_3$ (40 mL), which was followed by the addition of pyridine (0.9 g). The resulting solution was stirred for 30 min at ambient temperature and then quenched by the addition of 50 ml saturated NaHCO$_3$ solution. The resulting mixture was washed with saturated sodium carbonate (2×50 mL) and 50 mL of brine. The resulting mixture was concentrated under vacuum and the residue was purified by a silica gel column with ethyl acetate/petroleum ether (1:5) to afford 0.4 g (10.8%) of benzyl 6-(4-bromo-1,1-dioxido-3-oxoisothiazol-2(3H)-yl)hexanoate as a light yellow oil. LC-MS (ES, m/z): 416 [M+H]$^+$, 433 [M+NH$_4$]$^+$; $^1$H-NMR (400 MHz, Chloroform-d) δ 7.42-7.28 (m, 2H), 5.12 (s, 1H), 3.69 (t, J=7.4 Hz, 1H), 2.38 (t, J=7.4 Hz, 1H), 1.86-1.64 (m, 2H), 1.47-1.34 (m, 1H).

Example 3. 6-(4-bromo-1,1-dioxido-3-oxoisothiazol-2(3H)-yl)hexanoic Acid

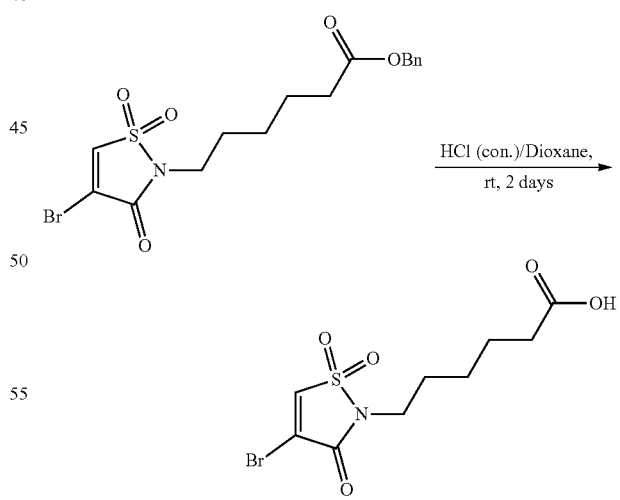

To a solution of benzyl 6-(4-bromo-1,1-dioxido-3-oxoisothiazol-2(3H)-yl)hexanoate (1 g, 2.40 mmol, 1.00 equiv) in dioxane (10 mL) was added 4N HCl (10 mL) dropwise with stirring at 0'C. The resulting solution was stirred for 2 days at room temperature. The resulting mixture was concentrated under vacuum and extracted with dichloromethane (3×50 mL). The combined organic layer was washed with brine (2×100 mL), dried over anhydrous sodium sulfate and concentrated under vacuum. The residue was purified via a silica gel column with DCM/MeOH (10:1) to afford 100 mg (13%) of 6-(4-bromo-1,1-dioxido-3-oxoisothiazol-2(3H)-yl)hexanoic acid as a white solid. LC-MS (ES, m/z): 308 [M+NH$_4$]$^+$, 326/328 [M+H]$^+$; $^1$H-NMR (300 MHz, Chloroform-d) δ 7.58 (s, 1H), 3.75 (t, J=7.4 Hz, 2H), 2.41 (t, J=7.4 Hz, 2H), 1.78 (dq, J=34.6, 7.4 Hz, 4H), 1.47 (t, 0.7=7.7 Hz, 2H).

Example of a Synthetic Path for the Synthesis of a Linker with X$_1$=OR

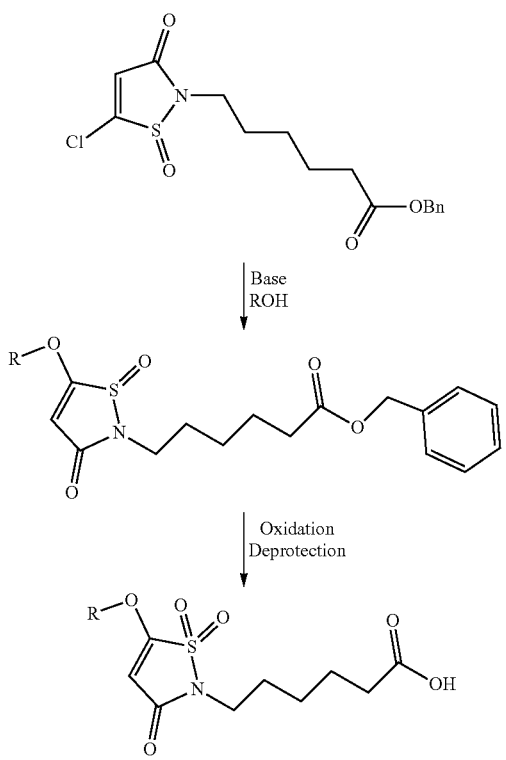

I.10. Benzyl 6-(5-(4-cyanophenoxy)-1-oxido-3-oxoisothiazol-2(3H)-yl)hexanoate

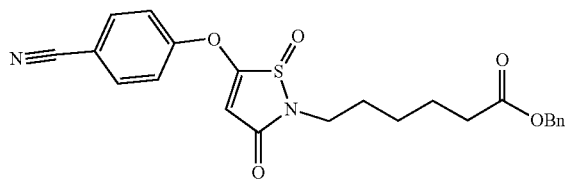 [SMILES: N#Cc1ccc(OC2=CC(=O)N(CCCCCC(=O)OCc3ccccc3)S2=O)cc1]

A solution of 4-hydroxybenzenecarbonitrile (76 mg, 0639 mmol) in THF (2 mL) was added at 0° C., to a mixture of NaH (0.639 mmol) in THF (2 mL). After 30 minutes under stirring, benzyl 6-(5-chloro-1-oxido-3-oxoisothiazol-2(3H)-yl)hexanoate (250 mg, 0,703 mmol) in THF (2 mL) was added. The reaction mixture was then stirred at room temperature for 18 h. The reaction mixture was diluted with AcOEt and NH$_4$Cl (10% aqueous) was added. The organic phase was then washed with brine and dried over MgSO4, filtered and concentrated. The crude product was purified over silica gel column using DCM/MeOH mixture (80/20) to afford Benzyl 6-(5-(4-cyanophenoxy)-1-oxido-3-oxoisothiazol-2(3H)-yl)hexanoate (210 mg, 75% yield) as a colorless oil. LC-MS (ES, m/z): 439.0 [M+H]+; $^1$H-NMR (300 MHz, Chloroform-d) δ 7.79 (m, 2H), 7.35 (m, 7H), 5.59 (s, 1H), 5.12 (s, 2H), 3.69 (m, 2H), 2.37 (m, 2H), 1.71 (m, 4H), 1.39 (m, 2H).

I.11. Benzyl 6-(5-(4-cyanophenoxy)-1,1-dioxido-3-oxoisothiazol-2(3H)-yl)hexanoate

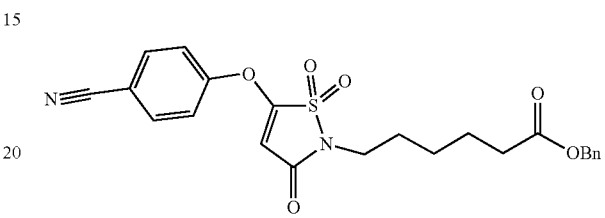

Obtained as a colorless oil following the standard procedure for the oxidation of mono-chloride compounds (136 mg, 48% yield) starting from Benzyl 6-(5-(4-cyanophenoxy)-1-oxido-3-oxoisothiazol-2(3H)-yl)hexanoate. LC-MS (ES, m/z): 455.0 [M+H]+; $^1$H-NMR (300 MHz, Chloroform-d) δ 7.82 (m, 2H), 7.40 (m, 2H), 7.35 (m, 5H), 5.63 (s, 1H), 5.12 (s, 2H), 3.65 (m, 2H), 2.38 (m, 2H), 1.79 (m, 2H), 1.70 (m, 2H), 1.41 (m, 2H).

Example 4. 6-(5-(4-cyanophenoxy)-1,1-dioxido-3-oxoisothiazol-2(3H)-yl)hexanoic Acid

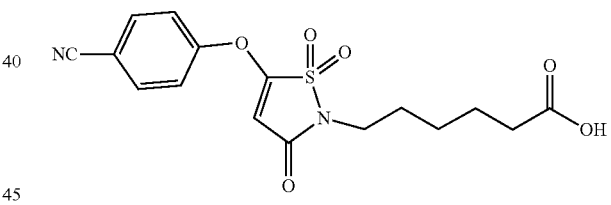

Obtained as a white solid following the standard procedure for deprotection of benzyl esters (38 mg, 35% yield) starting from Benzyl 6-(5-(4-cyanophenoxy)-1,1-dioxido-3-oxoisothiazol-2(3H)-yl)hexanoate. LC-MS (ES, m/z): 365.0 [M+H]+; $^1$H-MR (300 MHz, Chloroform-d) 7.82 (m, 2H), 7.41 (m, 2H), 5.65 (s, 1H), 3.67 (m, 2H), 2.38 (m, 2H), 1.80 (m, 2H), 1.69 (m, 2H), 1.44 (m, 2H).

I.12. Benzyl 6-(5-methoxy-1-oxido-3-oxoisothiazol-2(3H)-yl)hexanoate

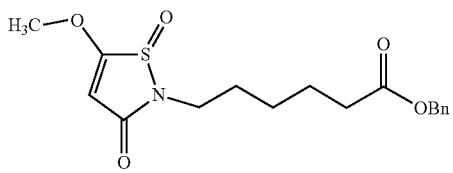 [SMILES: COC1=CC(=O)N(CCCCCC(=O)OCc2ccccc2)S1=O]

A mixture of benzyl 6-(5-chloro-1-oxido-3-oxoisothiazol-2(3H)-yl)hexanoate (270 mg, 0,759 mmol) in methanol (5 mL) and triethylamine (113 µl, 0,835 mmol) was stirred at room temperature for 18 h. Volatiles were then removed under vacuum and the residue purified over a silica column cyclohexane/AcOEt (1/1) to afford Benzyl 6-(5-methoxy-1-oxido-3-oxoisothiazol-2(3H)-yl)hexanoate (107 mg, 40%) as a yellow oil. LC-MS (ES, m/z): 352.0 [M+H]+; $^1$H-NMR (300 MHz, Chloroform-d) δ 7.36 (m, 5H), 5.57 (s, 1H), 5.11 (s, 2H), 4.04 (s, 3H), 3.60 (m, 2H), 2.37 (m, 2H), 1.75 (m, 2H), 1.69 (m, 2H), 1.39 (m, 2H).

I.13. Benzyl 6-(5-methoxy-1,1-dioxido-3-oxoisothiazol-2(3H)-yl)hexanoate

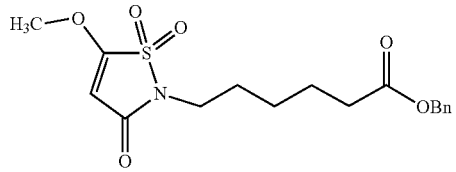 [SMILES: COC1=CC(=O)N(CCCCCC(=O)OCc2ccccc2)S1(=O)=O]

Obtained as a white solid following the standard procedure for the oxidation of mono-chloride compounds (62 mg, 36% yield) starting from benzyl 6-(5-methoxy-1-oxido-3-oxoisothiazol-2(3H)-yl)hexanoate. LC-MS (ES, m/z): 368.0 [M+H]+; $^1$H-NMR (300 MHz, Chloroform-d) δ 7.36 (m, 5H), 5.57 (s, 1H), 5.11 (s, 2H), 4.04 (s, 3H), 3.60 (m, 2H), 2.37 (m, 2H), 1.75 (m, 2H), 1.69 (m, 2H), 1.39 (m, 2H).

Example 5. 6-(5-Methoxy-1,1-dioxido-3-oxoisothiazol-2(3H)-yl)hexanoic Acid

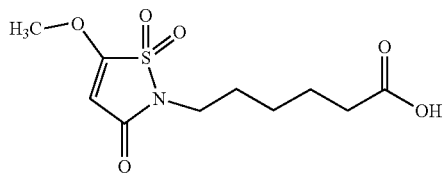 [SMILES: COC1=CC(=O)N(CCCCCC(=O)O)S1(=O)=O]

Obtained as a white solid following the standard procedure for deprotection of benzyl esters (37 mg, 67% yield) starting from benzyl 6-(5-methoxy-1,1-dioxido-3-oxoisothiazol-2(3H)-yl)hexanoate. HRMS (ES, m/z): [M+H] found 278.0691 for 278.0698 calculated; $^1$H-NMR (300 MHz, Chloroform-d) δ 5.60 (s, 1H), 4.05 (s, 3H). 3.62 (m, 2H), 2.36 (m, 2H), 1.77 (m, 2H), 1.68 (m, 2H), 1.42 (m, 2H).

I.14. Benzyl 4-(aminomethyl)cyclohexane-1-carboxylate 4-methylbenzeaesulfonate

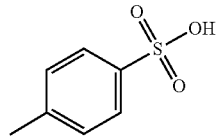

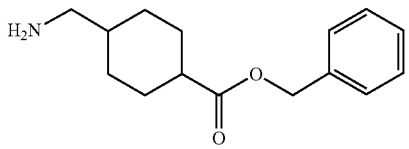

A mixture of 4-(aminomethyl)cyclohexanecarboxylic acid (10 g, 63.61 mmol, 1 eq), phenylmethanol (55.03 g, 508.87 mmol, 52.91 mL, 8 eq) and TsOH·H$_2$O (12.70 g, 66.79 mmol, 1.05 eq) in toluene (50 mL) was stirred at 140° C., for 16 hours using a Dean and Stark apparatus to collect the water of condensation and from the toluene sulphonic acid monohydrate. The reaction turned to clear after refluxing for several hours. The clear reaction mixture was poured into TBME (500 mL) and the resultant white solid Altered off, washed with TBME (200 mL) and dried in vacuum. Benzyl 4-(aminomethyl)cyclohexanecarboxylate; 4-methylbenzenesulfonic acid (26.6 g, 63.40 mmol, 99.68% yield) was obtained as a white solid; $^1$H NMR (400 MHz, METHANOL-d4) δ ppm 7.71 (d, J=8.16 Hz, 2H) 7.28-7.40 (m, 5H) 7.23 (d, J=7.94 Hz, 2H) 5.11 (s, 2H) 2.77 (d, J=7.06 Hz, 2H) 2.29-2.39 (m, 4H) 1.99-2.08 (m, 2H) 1.85 (br d, J=11.25 Hz, 2H) 1.53-1.65 (m, 1H) 1.43 (qd, J=12.97, 3.20 Hz, 2H) 1.06 (qd, J=12.75, 3.20 Hz, 2H).

I.15. Dibenzyl 4,4'-(((3,3'-disulfanediylbis(propanoyl))bis(azanediyl))bis(methylene))bis (cyclohexane-1-carboxylate)

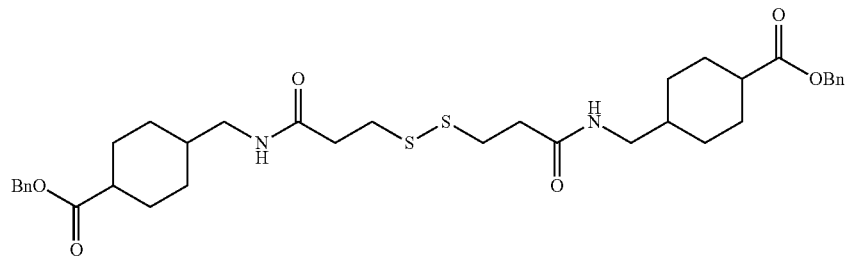 [SMILES: O=C(CCSSCCC(=O)NCC1CCC(C(=O)OCc2ccccc2)CC1)NCC1CCC(C(=O)OCc2ccccc2)CC1]

To a solution of 3-(2-carboxyethyldisulfanyl)propanoic acid (6.64 g, 31.58 mmol, 1 eq), HOBt (9.39 g, 69.48 mmol, 2.2 eq) and TEA (12.78 g, 126.33 mmol, 17.58 mL, 4 eq) in DCM (300 mL) was added EDCI (13.32 g, 69.48 mmol, 2.2 eq) at 0° C. Then benzyl 4-(aminomethyl)cyclohexanecarboxylate; 4-methylbenzenesulfonic acid (26.5 g, 63.17 mmol, 2 eq) was added at this temperature. The mixture was stirred at 0-20° C., for 4 hrs. TLC (Petroleum ether:Ethyl acetate=2:1. R$_f$=0.5) indicated the reaction was completed. The mixture was poured into sat. NaHCO$_3$ (100 mL) and H$_2$O (100 mL) and the organic layer was separated. The aqueous layer was extracted with DCM (200 mL). The combined organic layers were washed with H$_2$O (100 mL), brine (100 mL), dried over Na$_2$SO$_4$, filtered and concentrated in vacuum. The residue was dissolved into DCM (50 mL), added petroleum ether very slowly until the white precipitate was formed. Filtered and washed with petroleum ether, dried over vacuum. Benzyl 4-[[3-[[3-[(4-benzyloxycarbonylcyclohexyl)methylamino]-3-oxo-propyl]disulfanyl]propanoylamino]methyl]cyclohexanecarboxylate (19 g, 28.40 mmol, 89.94% yield) was obtained as a white solid; $^1$H NMR (400 MHz, CHLOROFORM-d) δ ppm 7.27-7.41 (m, 10H) 6.05 (br s, 2H) 5.11 (d, J=1.54 Hz, 4H) 3.10-3.17 (m, 4H) 2.96-3.02 (m, 4H) 2.54-2.63 (m, 4H) 2.30 (td, J=12.24, 1.76 Hz, 2H) 2.04 (br d, J=12.57 Hz, 4H) 1.85 (br d, J=12.79 Hz, 4H) 1.38-1.54 (m, 6H) 0.99 (q, J=12.72 Hz, 4H).

I.16. Benzyl 4-((5-chloro-3-oxoisothiazol-2(3H)-yl)methyl)cyclohexane-1-carboxylate

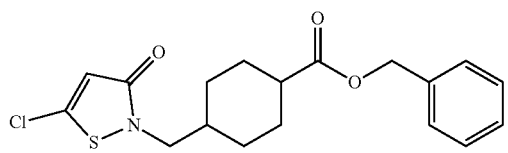 [SMILES: O=C(OCc1ccccc1)C1CCC(Cn2sc(Cl)cc2=O)CC1]

I.17. Benzyl 4-((4,5-dichloro-3-oxoisothiazol-2(3H)-yl)methyl)cyclohexane-1-carboxylate

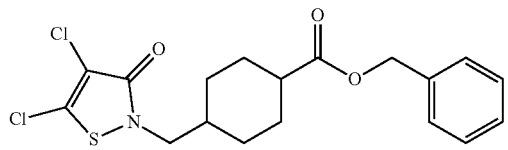 [SMILES: O=C(OCc1ccccc1)C1CCC(Cn2sc(Cl)c(Cl)c2=O)CC1]

To a solution of benzyl 4-[[3-[[3-[(4-benzyloxycarbonylcyclohexyl)methylamino]-3-oxo-propyl] disulfanyl]propanoylamino]methyl]cyclohexanecarboxylate (10 g, 14.95 mmol, 1 eq) in DCM (100 mL) was added dropwise sulfuryl chloride (10.09 g, 74.75 mmol, 7.47 mL, 5 eq) at 0° C. The mixture was stirred at 0-20° C., for 12 hrs. The clear solution was obtained after the addition of the sulfuryl chloride. TLC (Petroleum ether:Ethyl acetate=2:1, Rf. (major)=0.5) indicated the reaction was completed. The mixture was poured into H$_2$O (30 mL), extracted with DCM (50 mL*2). The combined organic layers were washed with H$_2$O (50 mL), brine (50 mL), dried over Na$_2$SO$_4$, filtered and concentrated in vacuum. Purification over silica gel column afforded Benzyl 4-[(3-oxoisothiazol-2-yl)methyl]cyclohexanecarboxylate (2.1 g, 3.42 mmol, 11.44% yield, S4% purity) obtained as a brown solid. Benzyl 4-[(5-chloro-3-oxo-isothiazol-2-yl)methyl]cyclohexanecarboxylate (7.1 g, 18.82 mmol, 62.96% yield, 97% purity) obtained as an off-white solid and Benzyl 4-[(4,5-dichloro-3-oxo-isothiazol-2-yl)methyl]cyclohexanecarboxylate (0.4 g, 869.31 umol, 2.91% yield, 87% purity) obtained as a brown oil.

I.18. Benzyl 4-((5-chloro-1,1-dioxido-3-oxoisothiazol-2(3H)-yl)methyl)cyclohexane-1-carboxylate

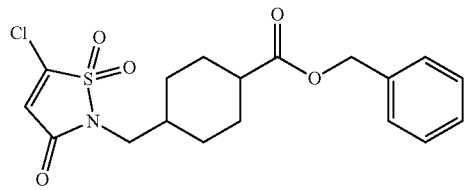 [SMILES: O=C(OCc1ccccc1)C1CCC(CN2C(=O)C=C(Cl)S2(=O)=O)CC1]

To a mixture of benzyl 4-[(5-chloro-3-oxo-isothiazol-2-yl)methyl]cyclohexanecarboxylate (2 g, 5.01 mmol, 1 eq) in H$_2$O (20 mL), ACN (10 mL) and DCM (10 mL) was added RuCl$_3$·H$_2$O (22.58 mg, 100.14 umol, 0.02 eq) and NaIO$_4$ (6.43 g, 30.04 mmol, 1.66 mL, 6 eq) in one portion at 0° C., under N$_2$. The mixture then heated to 20° C., and stirred for 16 hours. TLC showed the reaction was completed (Petroleum ether:Ethyl acetate=2:1, Rf-pl=0.6). The mixture was filtered, the filtrate was concentrated by nitrogen flow, and the solid that appeared again was filtered, the filtrate was concentrated by nitrogen. The residue was purified by preparative TLC (column height: 250 mm, diameter: 100 mm, 100-200 mesh silica gel. Petroleum ether:Ethyl acetate=2:1) to afford benzyl 4-[(5-chloro-1,1,3-trioxo-isothiazol-2-yl) methyl]cyclohexanecarboxylate (1.4 g, 3.17 mmol, 63.25% yield, 90% purity) as white solid.

Example 6. 4-((5-chloro-1,1-dioxido-3-oxoisothiazol-2(3H)-yl)methyl)cyclohexane-1-carboxylic Acid

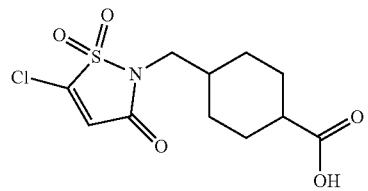 [SMILES: O=C(O)C1CCC(CN2C(=O)C=C(Cl)S2(=O)=O)CC1]

To a mixture of benzyl 4-[(5-chloro-1,1,3-trioxo-isothiazol-2-yl)methyl]cyclohexanecarboxylate (0.1 g, 226.20 umol, 1 eq) in DCM (S mL) was added MsOH (217.39 mg, 2.26 mmol, 161.03 uL, 10 eq) in one portion at 30° C., under N$_2$. The mixture was stirred at 30° C., for 16 hours. TLC showed the reaction was completed. LCMS (ET17992-54-P1A) showed desired MS detected. The mixture was poured into ice-water (5 mL) and stirred for 5 min. The aqueous phase was extracted with DCM (3 mL*2). The combined organic phase was washed with brine (3 mL), dried with anhydrous Na$_2$SO$_4$, filtered and concentrated in vacuum. The residue was purified by preparative TLC (column height: 250 mm, diameter: 100 mm, 100-200 mesh silica gel, Petroleum ether/Ethyl acetate=2:1) to afford 4-[(5-chloro-1,1,3-trioxo-isothiazol-2-yl)methyl]cyclohexanecarboxylic acid (0.02 g, 64.99 umol, 28.73% yield) as colorless oil; LC-MS (ES, m/z): 306.0 [M−H]$^-$; $^1$H-NMR (300 MHz, DMSO-D6) δ 12.01 (bs, 1H), 7.62 (s, 1H), 3.45 (m, 2H), 2.11 (m, 1H), 1.90 (m, 2H), 1.76 (m, 2H), 1.73 (m, 1H), 1.23 (m, 2H), 0.96 (m, 2H).

I.19 Benzyl 4-((4,5-dichloro-1,1-dioxido-3-oxoisothiazol-2(3H)-yl)methyl)cyclohexane-1-carboxylate

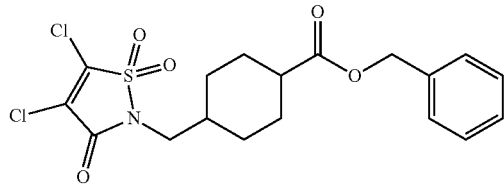 [SMILES: O=C(OCc1ccccc1)C1CCC(CN2C(=O)C(Cl)=C(Cl)S2(=O)=O)CC1]

To a mixture of benzyl 4-[(4,5-dichloro-3-oxo-isothiazol-2-yl)methyl]cyclohexanecarboxylate (1.2 g, 2.70 mmol, 1 eq) in H$_2$O (20 mL), DCM (10 mL) and ACN (10 mL) was added RuCl$_3$·H$_2$O (12.16 mg, 53.96 umol, 0.02 eq) and NaIO$_4$ (3.46 g, 16.19 mmol, 896.96 uL, 6 eq) in one portion at 0° C., under N$_2$. The mixture was stirred at 20° C., for 2 hours. TLC showed the reaction was completed (Petroleum ether:Ethyl acetate=2:1, Rf-pl=0.7). The mixture was poured into ice-water (30 mL) and stirred for 5 min. The aqueous phase was extracted with ethyl acetate (20 mL*2). The combined organic phases were washed with brine (20 mL), dried with anhydrous Na$_2$SO$_4$, filtered and concentrated in vacuum. The residue was purified by silica gel chromatography (column height: 250 mm, diameter: 100 mm, 100-200 mesh silica gel, Petroleum ether:Ethyl acetate=5:1 to 3:1) to afford benzyl 4-[(4,5-dichloro-1,1,3-trioxo-isothiazol-2-yl) methyl]cyclohexanecarboxylate (0.8 g, 1.67 mmol, 61.73% yield, 90% purity) as white solid.

Example 7. 4-((4,5-dichloro-1,1-dioxido-3-oxoisothiazol-2(3H)-yl)methyl)cyclohexane-1-carboxylic Acid

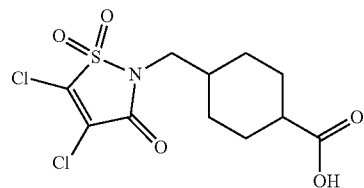 [SMILES: O=C(O)C1CCC(CN2C(=O)C(Cl)=C(Cl)S2(=O)=O)CC1]

To a mixture of benzyl 4-[(4,5-dichloro-1,1,3-trioxo-isothiazol-2-yl)methyl]cyclohexanecarboxylate (0.8 g, 1.67 mmol, 1 eq) in DCM (20 mL) was added MsOH (1.60 g, 16.65 mmol, 1.19 mL, 10 eq) in one portion at 30° C., under N$_2$. The mixture was stirred at 30° C., for 16 hours. LCMS showed the reaction was completed. The mixture was poured into ice-water (5 mL) and concentrated under reduced pressure then a solid appeared. The solution was filtered and trituration by EtOAc (2 mL*3) and the filter cake was dried in vacuum to afford 4-[(4,5-dichloro-1,1,3-trioxo-isothiazol-2-yl)methyl]cyclohexanecarboxylic acid (0.170 g, 486.86 umol, 29.23% yield, 98% purity) as white solid; LC-MS (ES, m/z): 364.0 [M+Na]$^+$; $^1$H-NMR (300 MHz, DMSO-D6) δ 11.99 (bs, 1H), 3.49 (m, 2H), 2.11 (m, 1H), 1.88 (m, 2H), 1.79 (m, 2H), 1.66 (m, 1H), 1.23 (m, 2H), 0.96 (m, 2H).

I.20 Dibenzyl 3,3'-(((3,3'-disulfanediylbis(propanoyl))bis(azanediyl))bis(4,1-phenylene))dipropionate

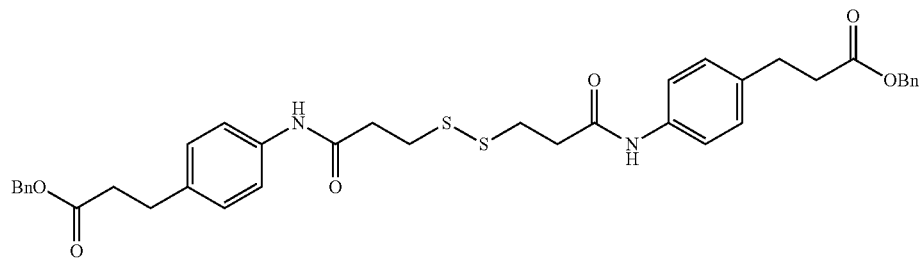 [SMILES: O=C(CCSSCCC(=O)Nc1ccc(CCC(=O)OCc2ccccc2)cc1)Nc1ccc(CCC(=O)OCc2ccccc2)cc1]

To a solution of 3-(2-carboxyethyldisulfanyl)propanoic acid (651.56 mg, 3.10 mmol, 1 eq), HOBt (921.15 mg, 6.82 mmol, 2.2 eq) and TEA (1.25 g, 12.39 mmol, 1.73 mL, 4 eq) in DCM (50 mL) was added EDCI (1.31 g, 6.82 mmol, 2.2 eq) at 0° C. Then benzyl 4-(aminomethyl)cyclohexanecarboxylate; 4-methylbenzenesulfonic acid (2.6 g, 6.20 mmol, 2 eq) was added at this temperature. The mixture was stirred at 0-20° C., for 12 hrs. TLC (Petroleum ether:Ethyl acetate=2:1, Rf=0.5) indicated the reaction was completed. The mixture was poured into sat. NaHCO$_3$ (20 mL) and H$_2$O (20 mL) and the organic layer was separated. The aqueous layer was extracted with DCM (50 mL). The combined organic layers were washed with H$_2$O (50 mL), brine (50 mL), dried over Na$_2$SO$_4$, filtered and concentrated in vacuum. Benzyl 4-[[3-[[3-[(4-benzyloxycarbonylcyclohexyl)methylamino]-3-oxo-propyl]disulfanyl]propanoyl amino]methyl]cyclohexanecarboxylate (1.1 g, 1.64 mmol, S3.07% yield) was obtained as a white solid; $^1$H NMR (400 MHz, CHLOROFORM-d) δ ppm 7.28-7.41 (m, 10H) 5.96 (br s, 2H) 5.10 (s, 4H) 3.13 (t, J=6.39 Hz, 4H) 2.98 (t, J=6.84 Hz, 4H) 2.57 (t, J=6.95 Hz, 4H) 2.23-2.34 (m, 2H) 2.03 (br d, J=12.79 Hz, 4H) 1.84 (br d, J=12.13 Hz, 4H) 1.37-1.63 (m, 6H) 0.91-1.05 (m, 4H).

I.21. Benzyl 3-(4-(5-chloro-3-oxoisothiazol-2(3H)-yl)phenyl)propanoate

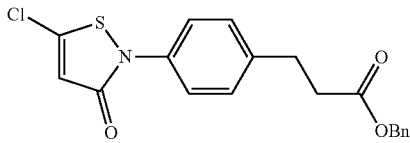 [SMILES: O=C(CCc1ccc(-n2sc(Cl)cc2=O)cc1)OCc1ccccc1]

To a solution of benzyl 3-[4-[3-[[3-[4-(3-benzyloxy-3-oxo-propyl)amino]-3-oxo-propyl]disulfanyl]propanoylamino]phenyl]propanoate (10 g, 14.60 mmol, 1 eq) in DCM (200 mL) was added sulfuryl chloride (5.91 g, 43.80 mmol, 4.38 mL, 3 eq) dropwise at 25° C., under N₂. The solution was stirred at 25° C., for 8 hours. The color of solution changed from colorless to black when sulfuryl chloride was added and then changed to yellow after 1 hour. TLC (Petroleum ether:Ethyl acetate=2:1, Rf=0.60) showed starting material was consumed and two new main spots were generated. The residue was poured into ice-water (200 ml) and then concentrated in vacuum to remove DCM. After concentration, the aqueous phase was extracted with ethyl acetate (200 mL*3) and then the combined organic phase was washed with water (200 mL*l), dried with anhydrous Na₂SO₄, filtered and concentrated in vacuum. The residue was purified by column chromatography (SiO2, Petroleum ether:Ethyl acetate=5:1 to 1:1) to get benzyl 3-[4-(3-oxoisothiazol-2-yl)phenyl]propanoate (2.5 g, 7.37 mmol, 50.47% yield) ¹H NMR (400 MHz, METHANOL-d4) δ=8.56 (d, J=6.2 Hz, 1H), 7.44-7.39 (m, 2H), 7.37-7.26 (m, 7H), 6.30 (d, J=6.4 Hz, 1H), 5.09 (s, 2H), 2.98 (t, J=7.4 Hz, 2H), 2.78-2.66 (m, 2H); and benzyl 3-[4-(5-chloro-3-oxo-isothiazol-2-yl)phenyl]propanoate (5 g, 13.37 mmol, 91.60% yield) was a yellow solid; ¹H NMR (ET17992-22-P2A) confirmed ET17992-22-P2. ¹H NMR (400 MHz, METHANOL-d4) δ=7.42-7.36 (m, 2H), 7.35-7.25 (m, 7H), 6.49-6.45 (m, 1H), 5.08 (s, 2H), 2.99-2.91 (m, 2H), 2.69 (t. J=7.5 Hz, 2H).

I.22. Benzyl 3-(4-(5-chloro-1,1-dioxido-3-oxoisothiazol-2(3H)-yl)phenyl)propanoate To a mixture of benzyl 3-[4-(5-chloro-3-oxo-isothiazol-2-yl)phenyl]propanoate (1.4 g, 3.74 mmol, 1 eq) in H2O (12 mL), DCM (6 mL) and ACN (6 mL) was added NaIO₄ (4.81 g, 22.47 mmol, 1.25 mL, 6 eq) in one portion at 25° C., and then the mixture was purged with N₂ three times. Then, RuCl₃·H₂O (42.21 mg, 187.24 umol, 0.05 eq) was added under N₂. The mixture was stirred at 25° C., for 12 hrs. The mixture turned turbidity and the color become to gray. The residue was poured into Ethyl acetate (100 ml) and then filtered. The filtrate was concentrated in vacuum. The residue was purified by column chromatography (SiO₂, Petroleum ether:Ethyl acetate=10:1 to 4:1) to give benzyl 3-[4-(5-chloro-1,1,3-trioxo-isothiazol-2-yl)phenyl]propanoate (460 mg, 1.08 mmol, 28.75% yield, 95% purity) as a yellow solid; ¹H NMR (ET17992-63-P1A) confirmed ET17992-63-P1. ¹H NMR (400 MHz, CHLOROFORM-d) δ=7.41-7.30 (m, 7H), 6.84 (s, 1H), 5.13 (s, 2H), 3.04 (t, J=7.6 Hz, 2H), 2.72 (t, J=7.7 Hz, 2H).

Example 8. 3-(4-(5-chloro-1,1-dioxido-3-oxoisothiazol-2(3H)-yl)phenyl)propanoic Acid

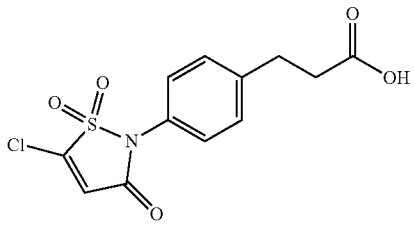

A solution of benzyl 3-[4-(5-chloro-1,1,3-trioxo-isothiazol-2-yl)phenyl]propanoate (460 mg, 1.13 mmol, 1 eq) in DCM (15 mL) was added methanesulfonic acid (1.09 g, 11.33 mmol, 806.87 uL, 10 eq) dropwise at 10° C. Then, the solution was heated to 35° C., and stirred for 12 hrs. The residue was washed with water (15 ml*3), dried with anhydrous Na₂SO₄, filtered and concentrated in vacuum. The residue was poured into water (20 ml) and then filtered. The filter cake was dissolved in DCM (S ml) and then petroleum ether (30 ml) was poured into the residue, the solution was stirred at 10° C., for 2 min, and then filtered, the filter cake was dried in vacuum to give 3-[4-(5-chloro-1,1,3-trioxo-isothiazol-2-yl)phenyl]propanoic acid (162 mg, 501.81 umol, 44.27% yield, 97.8% purity) as a white solid; LC-MS (ES, m/z): 313.9 ¹H-NMR (300 MHz, DMSO-D6) δ 12.18 (bs, 1H), 7.81 (s, 1H), 7.45 (m, 2H), 7.37 (m, 2H), 2.89 (m, 2H), 2.58 (m, 2H).

I.23. Benzyl 3-(4-(4,5-dichloro-3-oxoisothiazol-2(3H)-yl)phenyl)propanoate

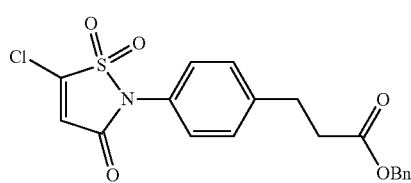 [SMILES: O=C(CCc1ccc(N2C(=O)C=C(Cl)S2(=O)=O)cc1)OCc1ccccc1] 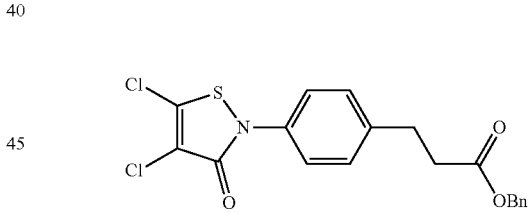

To a mixture of benzyl 4-[(3-oxoisothiazol-2-yl)methyl]cyclohexanecarboxylate (1.2 g, 3.32 mmol, 1 eq) in H₂O (20 mL). ACN (10 mL) and DCM (10 mL) was added RuCl₃·H₂O (14.95 mg, 66.33 umol, 0.02 eq) and NaIO₄ (4.26 g, 19.90 mmol, 1.10 mL, 6 eq) in one portion at 0° C., under N₂. The mixture then heated to 20° C., and stirred for 16 hours. The mixture was filtered, and the filtrate was concentrated by nitrogen flow, and a solid appeared again and filtered, the filtrate was concentrated by nitrogen. The residue was purified by prep-TLC (column height: 250 mm, diameter: 100 mm, 100-200 mesh silica gel, Petroleum ether:Ethyl acetate=2:1) to afford benzyl 4-[(1,1,3-trioxoisothiazol-2-yl)methyl]cyclohexanecarboxylate (0.45 g, 1.11 mmol, 33.60% yield, 90% purity) as a colorless oil; ¹H NMR (400 MHz, CHLOROFORM-d) δ=7.53 (dd, J=3.2, 8.7 Hz, 2H), 7.17 (ddd, J=3.2, 7.6, 9.0 Hz, 2H), 6.97-6.89 (m, 2H), 5.56 (br s, 1H), 4.12-4.06 (m, 4H), 3.92 (s, 5H), 3.55 (q, J=5.1 Hz, 5H).

I.24. Benzyl 3-(4-(4,5-dichloro-1,1-dioxido-3-oxoisothiazol-2(3H)-yl)phenyl)propanoate

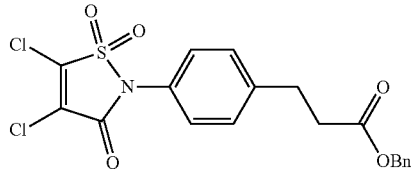 [SMILES: O=C(CCc1ccc(N2C(=O)C(Cl)=C(Cl)S2(=O)=O)cc1)OCc1ccccc1]

To a mixture of benzyl 3-[4-(4,5-dichloro-3-oxo-isothiazol-2-yl)phenyl]propanoate (650 mg, 1.59 mmol, 1 eq) and NaIO$_4$ (1.36 g, 6.37 mmol, 352.86 uL, 4 eq) in H$_2$O (10 mL), DCM (5 mL), ACN (5 mL) was added RuCl$_3$·H$_2$O (7.18 mg, 31.84 umol, 0.02 eq) in one portion at 0° C., under N$_2$. The mixture was stirred at 20° C., for 2 hrs. The residue was extracted with ethyl acetate (30 mL*2). The combined organic phase was dried with anhydrous Na$_2$SO$_4$, filtered and concentrated in vacuum. The residue was purified by column chromatography (SiO$_2$, Petroleum ether:Ethyl acetate=30:1 to 5:1) to give benzyl 3-[4-(4,5-dichloro-1,1,3-trioxo-isothiazol-2-yl)phenyl]propanoate (180 mg, 25.68% yield) as a yellow solid; $^1$H NMR (400 MHz, CHLOROFORM-d) δ=7.43-7.29 (m, 9H), 5.13 (s, 2H), 3.05 (t, J=7.6 Hz, 2H), 2.73 (t, J=7.6 Hz, 2H).

Example 9. 3-(4-(4,5-dichloro-1,1-dioxido-3-oxoisothiazol-2(3H)-yl)phenyl)propanoic Acid

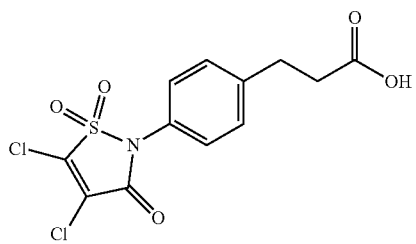 [SMILES: O=C(O)CCc1ccc(N2C(=O)C(Cl)=C(Cl)S2(=O)=O)cc1]

A solution of benzyl 3-[4-(4,5-dichloro-1,1,3-trioxo-isothiazol-2-yl)phenyl]propanoate (180 mg, 408.81 umol, 1 eq) in DCM (5 mL) was added methanesulfonic acid (392.89 mg, 4.09 mmol, 291.03 uL, 10 eq) dropwise at 10° C. The solution was stirred at 35° C., for 12 hrs. The residue was poured into water (5 ml) and then filtered. The filter cake was washed with water (10 ml*3) and then dried in vacuum. The residue was dissolved into Dichloromethane:Methanol (5.5 ml, v/v=10:1) and then purified by prep-TLC (Ethyl acetate, Rf=0.26) to give 3-[4-(4,5-dichloro-1,1,3-trioxo-isothiazol-2-yl)phenyl]propanoic acid (S7.64 mg, 156.83 umol, 38.36% yield, 95.278% purity) as a white solid; LC-MS (ES, m/z): 347.9 [M−H]−; $^1$H NMR (400 MHz, DMSO-d6) δ=12.22 (br s, 1H), 7.51-7.40 (m, 4H), 2.90 (br t, J=7.6 Hz, 2H), 2.60 (br t, J=7.6 Hz, 2H).

I.25. Dibenzyl 4,4'-((3,3'-disulfanediylbis(propanoyl))bis(azanediyl))dibenzoate

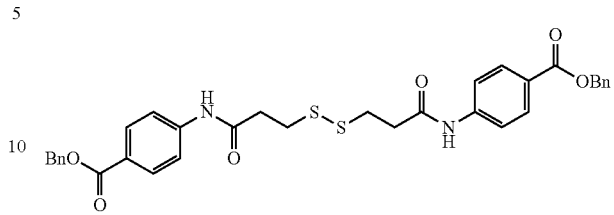

To a solution of 3-(2-carboxyethyldisulfanyl)propanoic add (6.01 g, 28.60 mmol, 1 eq) and pyridine (14.93 g, 188.77 mmol, 15.24 mL, 6.6 eq) in DMF (120 mL) was added EDO (12.06 g, 62.92 mmol, 2.2 eq) and benzyl 4-aminobenzoate (13 g, 57.20 mmol, 2 eq) at 10° C. Then, the mixture was stirred at 50° C., for 12 hrs. The residue was poured into ice-water (200 mL) and stirred for 20 min. The aqueous phase was extracted with ethyl acetate (200 mL*3). The combined organic phase was washed with sat. NaCl (200 mL*3), dried with anhydrous Na$_2$SO$_4$, filtered and concentrated in vacuum. Then, the residue was recrystallized from Petroleum ether:DCM=50:1 to get the solid. The solid was washed petroleum three times (150 ml*3), and then dried in vacuum to give benzyl 4-[3-[[3-(4-benzyloxycarbonylamino)-3-oxo-propyl]disulfanyl]propanoylamino]benzoate (14 g, crude) as a white solid; $^1$H NMR (400 MHz, DMSO-d6) 5=10.37 (s, 2H), 8.02-7.83 (m, 4H), 7.72 (d, J=8.8 Hz, 4H), 7.48-7.32 (m, 10H), 5.31 (s, 4H), 3.05-2.98 (m, 4H), 2.81-2.75 (m, 4H).

I.26. Benzyl 4-(5-chloro-3-oxoisothiazol-2(3H)-yl)benzoate

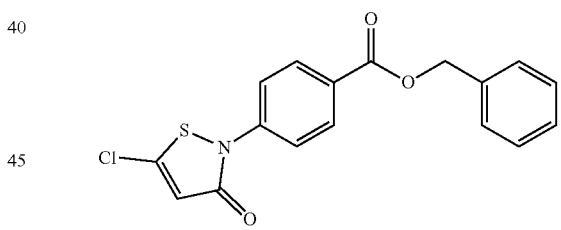

I.27. Benzyl 4-(4,5-dichloro-3-oxoisothiazol-2(3H)-yl)benzoate

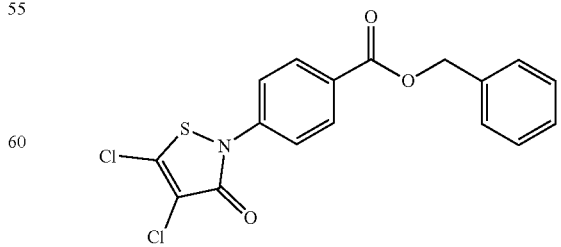

To a solution of benzyl 4-[3-[[3-(4-benzyloxycarbonylamino)-3-oxo-propyl]disulfanyl]propanoylamino]benzoate (9.4 g, 14.95 mmol, 1 eq) in DCM (120 mL) was added dropwise sulfuryl chloride (10.09 g, 74.75 mmol, 7.47 mL, 5 eq) at 0° C. The mixture was stirred at 0-20° C., for 12 hrs. The mixture turned to clear after stirring for several minutes. TLC (Petroleum ether:Ethyl acetate=2:1) indicated the reaction was completed. The mixture was poured into $H_2O$ (200 mL), extracted with DCM (200 mL*2). The combined organic layers were washed with $H_2O$ (200 mL*2), dried over $Na_2SO_4$, filtered and concentrated in vacuum. The residue was purified by column chromatography on silica gel (Petroleum ether:Ethyl acetate=5:1 to 1:1) to give benzyl 4-(3-oxoisothiazol-2-yl)benzoate (1.2 g, 3.43 mmol, 11.47% yield, 89% purity) was obtained as an off-white solid; $^1$H NMR (400 MHz, CHLOROFORM-d) δ ppm 8.09-8.27 (m, 3H) 7.63-7.82 (m, 2H) 7.32-7.52 (m, 5H) 6.34 (br d, J=6.36 Hz, 1H) 5.39 (s, 2H); Benzyl 4-(5-chloro-3-oxo-isothiazol-2-yl)benzoate (3.5 g, 10.01 mmol, 33.49% yield, 98.92% purity) was obtained as an off-white solid; $^1$H NMR (400 MHz, CHLOROFORM-d) δ ppm 8.15 (d, J=8.60 Hz, 2H) 7.69 (d, J=8.82 Hz, 2H) 7.33-7.49 (m, 4H) 6.38 (s, 1H) 5.38 (s, 2H) and Benzyl 4-(4,5-dichloro-3-oxo-isothiazol-2-yl) benzoate (2.8 g, 7.19 mmol, 24.06% yield, 97.68% purity) was obtained as an off-white solid; $^1$H NMR (400 MHz, CHLOROFORM-d) δ ppm 8.18 (d, J=8.60 Hz, 2H) 7.71 (d, J=8.60 Hz, 2H) 7.33-7.50 (m, 4H) 5.39 (s, 2H).

I.28. Benzyl 4-(5-chloro-1,1-dioxido-3-oxoisothiazol-2(3H)-yl)benzoate

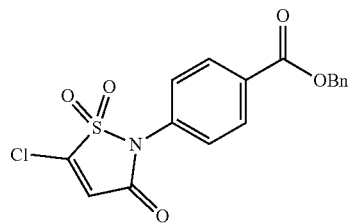 [SMILES: O=C(OCc1ccccc1)c1ccc(N2C(=O)C=C(Cl)S2(=O)=O)cc1]

To a mixture of benzyl 4-(5-chloro-3-oxo-isothiazol-2-yl) benzoate (1 g, 2.89 mmol, 1 eq) in $H_2O$ (10 mL), ACN (5 mL) and DCM (5 mL) was added $RuCl_3 \cdot H_2O$ (13.04 mg, 57.84 umol, 0.02 eq) and $NaIO_4$ (2.47 g, 11.57 mmol, 640.97 uL, 4 eq) in one portion at 0° C., under $N_2$. The mixture then heated to 20° C., and stirred for 2 hours. The residue was filtered and the filtrate was poured into water (40 ml). The aqueous phase was extracted with ethyl acetate (50 mL*1). The organic phase was washed with sat. NaCl (30 mL*3), dried with anhydrous $Na_2SO_4$, filtered and concentrated in vacuum. The residue was purified by column chromatography (SiO$_2$, Petroleum ether:Ethyl acetate=15:1 to 5:1) to give benzyl 4-(5-chloro-1,1,3-trioxo-isothiazol-2-yl)benzoate (500 mg, 1.32 mmol, 45.77% yield) as a yellow oil; $^1$H NMR (400 MHz, CHLOROFORM-d) δ=8.27-8.21 (m, 2H), 7.61-7.55 (m, 2H), 7.49-7.34 (m, 5H), 6.87 (s, 1H), 5.40 (s, 2H).

Example 10. 4-(5-chloro-1,1-dioxido-3-oxoisothiazol-2(3H)-yl)benzoic Acid

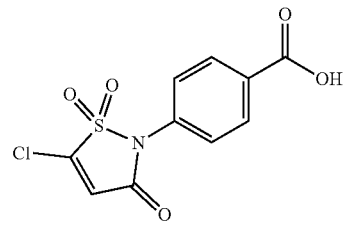 [SMILES: O=C(O)c1ccc(N2C(=O)C=C(Cl)S2(=O)=O)cc1]

A solution of benzyl 4-(5-chloro-1,1,3-trioxo-isothiazol-2-yl)benzoate (450 mg, 1.19 mmol, 1 eq) in DCM (20 mL) was added methanesulfonic acid (1.14 g, 11.91 mmol, 847.94 uL, 10 eq) dropwise at 10° C. The solution was stirred at 35° C., for 10 hrs. The residue was concentrated in vacuum to remove DCM. Then, the residue was dissolved into Ethyl acetate (10 ml) and then the organic phase was washed with water (20 mL*5), dried with anhydrous $Na_2SO_4$, filtered and concentrated in vacuum. The residue was dissolved into methanol (3 ml) and then petroleum ether (30 ml) was poured into the residue, the solution was stirred at 10° C., for 2 min, and then filtered, the filter cake was dried in vacuum to give 4-(5-chloro-1,1,3-trioxo-isothiazol-2-yl)benzoic acid (112.56 mg, 379.48 umol, 31.86% yield, 96.986% purity) as a white solid; LC-MS (ES, m/z): 285.9 [M−H]−; $^1$H NMR (400 MHz, DMSO-d6) δ=13.33 (br s, 1H), 8.17-8.11 (m, 2H), 7.87 (d, J=1.5 Hz, 1H), 7.67-7.61 (m, 2H).

I.29. Benzyl 4-(4,5-dichloro-1,1-dioxido-3-oxoisothiazol-2(3H)-yl)benzoate

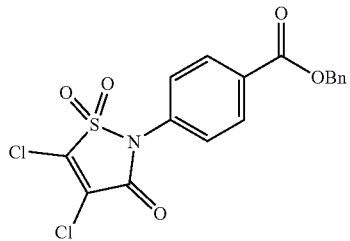 [SMILES: O=C(OCc1ccccc1)c1ccc(N2C(=O)C(Cl)=C(Cl)S2(=O)=O)cc1]

To a mixture of benzyl 4-(4,5-dichloro-3-oxo-isothiazol-2-yl)benzoate (1 g, 2.63 mmol, 1 eq) in $H_2O$ (10 mL), ACN (5 mL) and DCM (5 mL) was added $RuCl_3 \cdot H_2O$ (11.86 mg, 52.60 umol, 0.02 eq) and $NaIO_4$ (2.25 g, 10.52 mmol, 582.91 uL, 4 eq) in one portion at 0° C., under $N_2$. The mixture then heated to 20° C., and stirred for 2 hours. The residue was filtered and the filtrate was concentrated in vacuum. The residue was purified by column chromatography (SiO$_2$, Petroleum ether:Ethyl acetate=20:1 to 5:1) to give benzyl 4-(4,5-dichloro-1,1,3-trioxo-isothiazol-2-yl) benzoate (130 mg, 315.35 umol, 11.99% yield) as a white solid; $^1$H NMR (400 MHz, CHLOROFORM-d) δ=8.25 (d, J=8.6 Hz, 2H), 7.58 (d, J=8.8 Hz, 2H), 7.49-7.34 (m, 5H), 5.41 (s, 2H).

Example 11. 4-(4,5-dichloro-1,1-dioxido-3-oxoiso-thiazol-2(3H)-yl)benzoic Acid

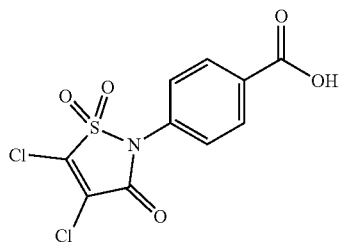 [SMILES: O=C(O)c1ccc(N2C(=O)C(Cl)=C(Cl)S2(=O)=O)cc1]

A solution of benzyl 4-(4,5-dichloro-1,1,3-trioxo-isothiazol-2-yl)benzoate (130 mg, 315.35 umol, 1 eq) in DCM (5 mL) was added methanesulfonic acid (303.07 mg, 3.15 mmol, 224.49 uL, 10 eq) dropwise at 10° C. The solution was stirred at 10° C., for 5 min, then the solution was heated to 35° C., and stirred for 10 hours. The color of solution changed from colorless to yellow. The reaction solution was poured into water (20 ml) and then filtered. The filter cake was washed with water (10 ml*3) and DCM (10 ml*3) three times respectively. Then the filter cake was dried in vacuum. The residue was dispersed with DCM (10 ml) and then petroleum ether (30 ml) was poured into the residue, the mixture was stirred at 10° C., for 2 min, and then filtered, the filter cake was dried in vacuum to give 4-(4,5-dichloro-1,1,3-trioxo-isothiazol-2-yl)benzoic acid (93.4 mg, 282.97 umol, 89.73% yield, 97.590% purity) as a white solid; LC-MS (ES, m/z): 319.9 [M−H]−; $^1$H NMR (400 MHz, DMSO-d6) δ=8.16 (d, J=8.4 Hz, 2H), 7.68 (d, J=8.4 Hz, 2H).

I.30. Benzyl 3-(2-(2-(2-aminoethoxy)ethoxy)ethoxy)propanoate 4-methylbenzenesulfonate

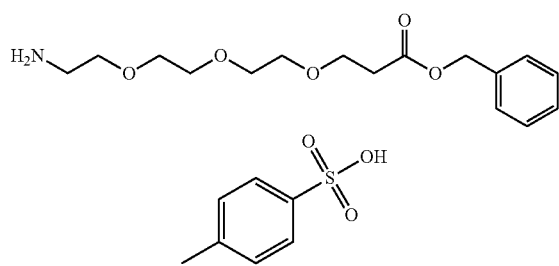

A mixture of 3-[2-[2-(2-aminoethoxy)ethoxy]ethoxy]propanoic acid (4 g, 18.08 mmol, 1 eq), phenylmethanol (15.64 g, 144.63 mmol, 15.04 mL, 8 eq) and TsOH·H$_2$O (3.61 g, 18.98 mmol, 1.05 eq) in toluene (30 mL) was stirred at 140° C., for 8 hours using a Dean and Stark apparatus to collect the water of condensation. The reaction turned to clear after refluxing for several hours. TLC (Dichloromethane:Methanol=10:1, Rf=0.3) indicated the reaction was complete. The clear reaction mixture was poured into TBME:Petroleum ether (1:1, 50 mL) and removed the clear solution. The residue was washed with TBME:Petroleum ether (1:1, 50 mL) for 2 times and dried in vacuum. The crude product Benzyl 3-[2-[2-(2-aminoethoxy)ethoxy]ethoxy]propanoate; 4-methylbenzenesulfonic acid (8.9 g, crude) was obtained as a yellow oil; $^1$H NMR (400 MHz, CHLOROFORM-d) δ ppm 7.76 (br d, J=8.07 Hz, 2H) 7.33-7.38 (m, 5H) 7.15 (d, J=7.95 Hz, 2H) 5.11 (s, 2H) 3.72 (q, J=6.11 Hz, 4H) 3.53-3.64 (m, 8H) 3.11-3.24 (m, 2H) 2.53-2.69 (m, 2H) 2.30-2.41 (m, 1H) 2.34 (s, 3H).

I.31. Benzyl 3-[2-[2-[2-[3-[[3-[2-[2-[2-(3-benzyloxy-3-oxo-propoxy)ethoxy]ethoxy]ethyl amino]-3-oxopropyl]disulfanyl]propanoylamino]ethoxy]ethoxy]ethoxy]propanoate

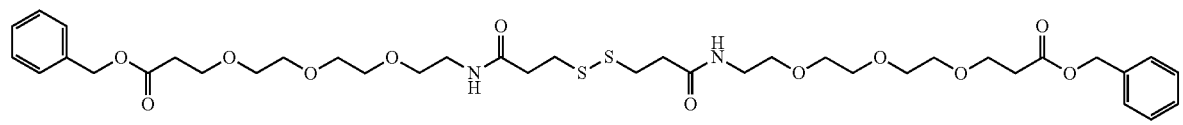 [SMILES: O=C(CCSSCCC(=O)NCCOCCOCCOCCC(=O)OCc1ccccc1)NCCOCCOCCOCCC(=O)OCc1ccccc1]

To a mixture of 3-(2-carboxyethyldisulfanyl)propanoic acid (1.90 g, 9.04 mmol, 1 eq), HOBt (2.69 g, 19.88 mmol, 2.2 eq) and TEA (4.57 g, 45.18 mmol, 6.29 mL, 5 eq) in DCM (100 mL) was added EDCI (3.81 g, 19.88 mmol, 2.2 eq) at 20° C. Then benzyl 3-[2-[2-(2-aminoethoxy)ethoxy]ethoxy]propanoate; 4-methylbenzenesulfonic acid (8.74 g, 18.07 mmol, 2 eq) was added to the above solution. The mixture was stirred at 20° C., for 12 hours. TLC (Petroleum ether:Ethyl acetate=2:1, Rf=0.25) indicated that the reaction was complete. MeOH was added and the solution was concentrated under reduced pressure and dried over vacuum. The residue was poured into H$_2$O (20 mL), extracted with EtOAc (50 mL). The organic layer was dried over Na$_2$SO$_4$, filtered and concentrated in vacuum. The crude product was purified by prep-TLC (Petroleum ether:Ethyl acetate=1:1, Rf=0.5) to give Benzyl 3-[2-[2-[2-[3-[[3-[2-[2-[2-(3-benzyloxy-3-oxo-propoxy)ethoxy]ethoxy]ethylamino]-3-oxopropyl]disulfanyl]propanoyl amino]ethoxy]ethoxy]ethoxy]propanoate (6.52 g, 7.94 mmol, 87.81% yield, 97% purity) as a yellow oil; $^1$H NMR (400 MHz, CHLOROFORM-d) δ ppm 7.29-7.42 (m, 10H) 6.42 (br s, 2H) 5.15 (s, 4H) 3.79 (t, J=6.42 Hz, 4H) 3.53-3.69 (m, 18H) 2.92-3.00 (m, 4H) 2.62-2.71 (m, 4H) 2.53-2.62 (m, 4H).

I.32. Benzyl 3-(2-(2-(2-(5-chloro-3-oxoisothiazol-2(3H)-yl)ethoxy)ethoxy)ethoxy)propanoate

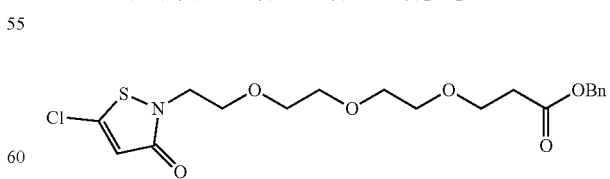

To a solution of benzyl 3-[2-[2-[2-[3-[[3-[2-[2-[2-(3-benzyloxy-3-oxo-propoxy)ethoxy]ethoxy]ethylamino]-3-oxopropyl]disulfanyl]propanoylamino]ethoxy]ethoxy]ethoxy]propanoate (6.4 g, 8.03 mmol, 1 eq) in DCM (50 mL) was added dropwise the solution of sulfuryl chloride (4.34 g, 32.12 mmol, 3.21 mL, 4 eq) in DCM (10 mL) at 0° C. The mixture was stirred at 0-10° C., for 12 hrs. TLC (Petroleum ether:Ethyl acetate=0:1, Rf=0.15, 0.35) indicated the reaction was complete. The mixture was poured into ice/water (100 mL), extracted with DCM (200 mL*2). The combined organic layers were washed with H₂O (100 mL*2), brine (100 mL), dried over Na₂SO₄. Filtration and concentrated in vacuum. The residue was purified by column chromatography on silica gel (Petroleum ether:Ethyl acetate=1:1 to 0:1) to give Benzyl 3-[2-[2-[2-(3-oxoisothiazol-2-yl)ethoxy]ethoxy]ethoxy]propanoate (820 mg, 1.66 mmol, 10.33% yield, 80% purity) as a brown oil; ¹H NMR (400 MHz, CHLOROFORM-d) δ ppm 8.06 (d, J=6.17 Hz, 1H) 7.30-7.41 (m, 5H) 6.24 (d, J=6.39 Hz, 1H) 5.15 (s, 2H) 3.95-4.03 (m, 2H) 3.79 (t, J=6.39 Hz, 2H) 3.68-3.75 (m, 2H) 3.59-3.68 (m, 8H) 2.63-2.70 (m, 2H) and Benzyl 3-[2-[2-[2-(5-chloro-3-oxo-isothiazol-2-yl)ethoxy]ethoxy]ethoxy]propanoate (2.5 g, 4.30 mmol, 26.79% yield, 74% purity) as a colorless oil; ¹H NMR (400 MHz, CHLOROFORM-d) δ ppm 7.28-7.43 (m, 5H) 6.25 (s, 1H) 5.15 (s, 2H) 3.92-3.98 (m, 2H) 3.77-3.81 (m, 2H) 3.59-3.71 (m, 10H) 2.66 (t, J=6.39 Hz, 2H).

I.33. Benzyl 3-(2-(2-(2-(5-chloro-1,1-dioxido-3-oxoisothiazol-2(3H)-yl)ethoxy)ethoxy)ethoxy)propanoate

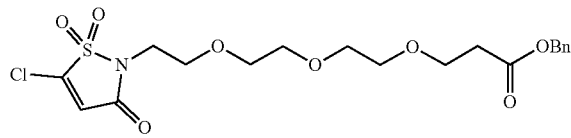 [SMILES: O=C(CCOCCOCCOCCN1C(=O)C=C(Cl)S1(=O)=O)OCc1ccccc1]

To a mixture of benzyl 3-[2-[2-[2-(5-chloro-3-oxo-isothiazol-2-yl)ethoxy]ethoxy]ethoxy]propanoate (I g, 2.33 mmol, 1 eq) and NaIO₄ (1.99 g, 9.30 mmol, 515.57 uL, 4 eq) in H₂O (20 mL), DCM (10 mL), ACN (10 mL) was added RuCl₃·H₂O (26.22 mg, 116.30 umol, 0.05 eq) in one portion at 20° C., under N₂. Then, the mixture was stirred at 20° C., for 1 hr. The residue was extracted with ethyl acetate (20 mL*2). The combined organic phase was dried with anhydrous Na₂SO₄, filtered and concentrated in vacuum. The residue was purified by column chromatography (SiO₂, Petroleum ether:Ethyl acetate=5:1 to 1:1) to give benzyl 3-[2-[2-[2-(5-chloro-1,1,3-trioxo-isothiazol-2-yl)ethoxy]ethoxy]ethoxy]propanoate (560 mg, 1.21 mmol, 52.12% yield, 100% purity) as a purple oil: ¹H NMR (400 MHz, CHLOROFORM-d) δ=7.42-7.29 (m, 5H), 6.70 (s, 1H), 5.15 (s, 2H), 3.92-3.86 (m, 2H), 3.77 (td, J=6.0, 11.9 Hz, 4H), 3.68-3.58 (m, 8H), 2.67 (t, J=6.5 Hz, 2H).

Example 12. 3-(2-(2-(2-(5-chloro-1,1-dioxido-3-oxoisothiazol-2(3H)-yl)ethoxy)ethoxy)ethoxy)propanoic Acid

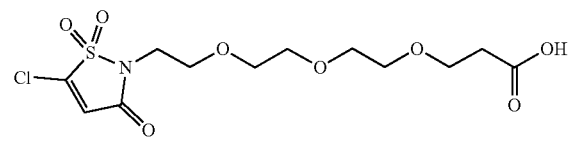 [SMILES: O=C(O)CCOCCOCCOCCN1C(=O)C=C(Cl)S1(=O)=O]

A solution of benzyl 3-[2-[2-[2-(5-chloro-1,1,3-trioxo-isothiazol-2-yl)ethoxy]ethoxy]ethoxy]propanoate (560 mg, 1.21 mmol, 1 eq) in DCM (30 mL) was added methanesulfonic acid (1.17 g, 12.12 mmol, 863.06 uL, 10 eq) dropwise at 10° C. The mixture was heated to 35° C., and stirred for 10 hrs. The color of solution turned to yellow. The residue was washed with water (30 ml*3) and then the organic phase was dried with anhydrous Na₂SO₄, filtered and concentrated in vacuum. The residue was purified by prep-TLC (Ethyl acetate:Ethyl acetate:Methanol:Acetic acid=40:8:1, Rf=0.77) to give 3-[2-[2-[2-(5-chloro-1,1,3-trioxo-isothiazol-2-yl)ethoxy]ethoxy]ethoxy] propanoic acid (95.61 mg, 240.16 umol, 19.81% yield, 93.389% purity) as a colorless oil; LC-MS (ES, m/z): 372.1 [M+H]⁺; ¹H NMR (400 MHz, DMSO-d6) δ=12.13 (br s, 1H), 7.64 (s, 1H), 3.86-3.74 (m, 2H), 3.61 (td, J=6.0, 16.9 Hz, 4H), 3.54-3.46 (m, 8H), 2.43 (t, J=6.4 Hz, 2H).

I.34. Benzyl 3-(2-(2-(2-(4,5-dichloro-3-oxoisothiazol-2(3H)-yl)ethoxy)ethoxy)ethoxy)propanoate

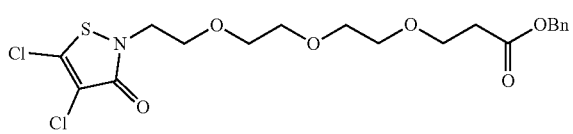 [SMILES: O=C(CCOCCOCCOCCn1sc(Cl)c(Cl)c1=O)OCc1ccccc1]

To a solution of benzyl 3-[2-[2-[2-(5-chloro-3-oxo-isothiazol-2-yl)ethoxy]ethoxy]ethoxy] propanoate (1.6 g, 3.72 mmol, 1 eq) in DCM (30 mL) was added dropwise sulfuryl chloride (1.00 g, 7.44 mmol, 744.17 uL, 2 eq) at 0° C. The mixture was stirred at 0-10° C., for 12 hrs. A clear pale yellow solution was obtained after the addition of sulfuryl chloride. TLC (Ethyl acetate:Petroleum ether=2:1, Rf=0.5) indicated the reaction was complete. The mixture was concentrated in vacuum to give a crude product. The residue was poured into H₂O (50 mL), extracted with DCM (50 mL*2). The combined organic layers were washed with H₂O (50 mL), dried over Na₂SO₄, filtered and concentrated in vacuum. The residue was purified by column chromatography on silica gel (Ethyl acetate:Petroleum ether=1:2 to 2:1) to give Benzyl 3-[2-[2-[2-(4,5-dichloro-3-oxo-isothiazol-2-yl)ethoxy]ethoxy]ethoxy] propanoate (1.06 g, 1.76 mmol, 47.17% yield, 76.9% purity) as a colorless oil; ¹H NMR (400 MHz, CHLOROFORM-d) δ ppm 7.28-7.40 (m, 4H) 5.13 (s, 2H) 3.98-4.04 (m, 2H) 3.77 (t, J=6.39 Hz, 2H) 3.67-3.72 (m, 2H) 3.57-3.67 (m, 8H) 2.65 (t, J=6.39 Hz, 2H).

I.35. Benzyl 3-(2-(2-(2-(4,5-dichloro-1,1-dioxido-3-oxoisothiazol-2(3H)-yl)ethoxy)ethoxy) ethoxy)propanoate

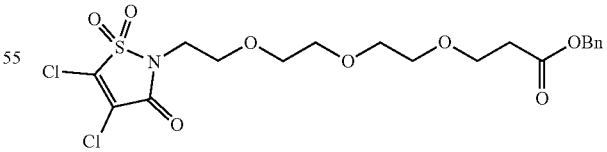

To a mixture of benzyl 3-[2-[2-[2-(4,5-dichloro-3-oxo-isothiazol-2-yl)ethoxy]ethoxy]ethoxy] propanoate (1 g, 2.15 mmol, 1 eq) and NaIO₄ (1.84 g, 8.61 mmol, 477.32 uL, 4 eq) in H₂O (20 mL), CH₃CN (10 mL) and DCM (10 mL) was added RuCl₃·H₂O (7.28 mg, 32.30 umol, 0.015 eq) under N₂ at 0° C. The mixture was stirred at 0-10 for 2 hrs. TLC indicated the reaction was complete. The mixture was diluted with EtOAc (50 mL), filtered to remove the unsoluble solid. The organic layer was separated and concentrated in vacuum. The residue was purified by prep-TLC (Petroleum ether:Ethyl acetate=1:1, Rf=0.6) to give Benzyl 3-[2-[2-[2-(4,5-dichloro-1,1,3-trioxo-isothiazol-2-yl)ethoxy]ethoxy]ethoxy]propanoate (830 mg, 1.61 mmol, 74.96% yield, 96.533% purity) as a colorless oil; $^1$H NMR (400 MHz, CHLOROFORM-d) δ ppm 7.28-7.41 (m, 5H) 5.15 (s, 2H) 3.91-3.97 (m, 2H) 3.75-3.83 (m, 4H) 3.59-3.68 (m, 8H) 2.66 (t, J=6.50 Hz, 2H).

Example 13. 3-(2-(2-(2-(4,5-dichloro-1,1-dioxido-3-oxoisothiazol-2(3H)-yl)ethoxy)ethoxy)ethoxy)propanoic Acid

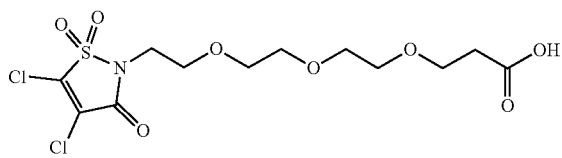 [SMILES: O=C(O)CCOCCOCCOCCN1C(=O)C(Cl)=C(Cl)S1(=O)=O]

A solution of benzyl 3-[2-[2-[2-(4,5-dichloro-1,1,3-trioxo-isothiazol-2-yl)ethoxy]ethoxy]ethoxy]propanoate (820.00 mg, 1.65 mmol, 1 eq) in DCM (10 mL) was added methanesulfonic acid (1.59 g, 16.52 mmol, 1.18 mL, 10 eq) dropwise at 10° C. Then, the solution was heated at 35° C., and stirred for 10 hrs. The residue was diluted by DCM (20 ml) and then the solution was washed with water (15 ml*3), the organic phase was dried with anhydrous Na$_2$SO$_4$, filtered and concentrated in vacuum. The residue was purified by prep-TLC (Ethyl acetate:Acetic acid=250:1, Rf=0.55) to 3-[2-[2-[2-(4,5-dichloro-1,1,3-trioxo-isothiazol-2-yl)ethoxy]ethoxy]ethoxy]propanoic acid (249.4 mg, 602.76 umol, 36.49% yield, 98.180% purity) as a yellow oil; LC-MS (ES, m/z): 406.0 [M+H]$^+$; $^1$H NMR (400 MHz, DMSO-d6) δ=12.16 (br s, 1H), 3.85 (t, J=5.5 Hz, 2H), 3.65 (br t, J=5.4 Hz, 2H), 3.61-3.45 (m, 10H), 2.43 (t, J=6.3 Hz, 2H).

I.36. Benzyl 1-amino-3,6,9,12,15,18-hexaoxahenicosan-21-oate 4-methylbenzenesulfonate

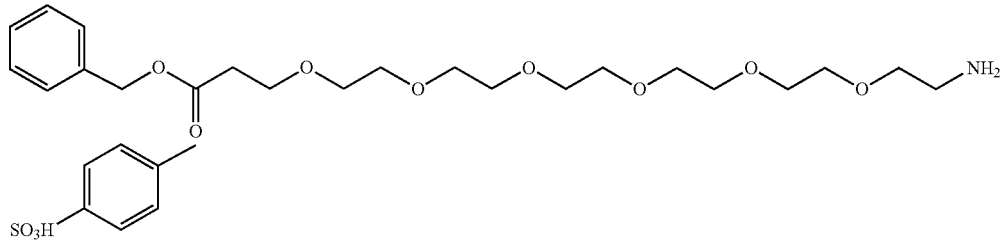

A mixture of phenylmethanol (2.45 g, 22.64 mmol, 2.35 mL, 8 eq), 3-[2-[2-[2-[2-[2-(2-aminoethoxy)ethoxy]ethoxy]ethoxy]ethoxy]propanoic acid (1 g, 2.83 mmol, 1 eq) and TsOH·H$_2$O (565.16 mg, 2.97 mmol, 1.05 eq) in toluene (30 mL) was stirred at 140° C., with a Dean-Stark trap for 14 hrs. The mixture was changed from turbidity to clearly several hours later. The residue was concentrated in vacuum to remove toluene, and then TBME (50 ml) was poured into the residue and stirred for 1 min. Then, supernatant was remove and dried to give benzyl 3-[2-[2-[2-[2-[2-(2-aminoethoxy)ethoxy]ethoxy]ethoxy]ethoxy]propanoate; 4-methylbenzene sulfonic acid (1.45 g, crude) as a yellow oil; $^1$H NMR (400 MHz, CHLOROFORM-d) δ=7.80 (d, J=8.1 Hz, 2H), 7.67-7.46 (m, 2H), 7.39-7.31 (m, 5H), 7.15 (d, J=7.8 Hz, 2H), 5.13 (s, 2H), 3.96-3.83 (m, 2H), 3.75-3.50 (m, 22H), 3.24-3.14 (m, 2H), 2.63 (t, J=6.2 Hz, 2H), 2.34 (s, 3H).

I.37. Dibenzyl 23,30-dioxo-4,7,10,13,16,19,34,37,40,43,46,49-dodecaoxa-26,27-dithia-22,31-diazadopentacontanedioate

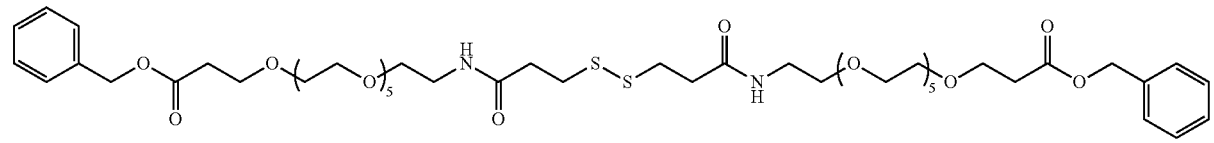

To a mixture of 3-(2-carboxyethyldisulfanyl)propanoic acid (47.41 mg, 225.47 umol, 1 eq) and TEA (91.26 mg, 901.86 umol, 125.53 uL, 4 eq), HOBt (91.40 mg, 676.40 umol, 3 eq), EDCI (129.67 mg, 676.40 umol, 3 eq) in DCM (5 mL) was added benzyl 3-[2-[2-[2-[2-[2-(2-aminoethoxy)ethoxy]ethoxy]ethoxy]ethoxy]propanoate; 4-methyl benzenesulfonic acid (277.65 mg, 450.93 umol, 2 eq) dropwise at 25° C. After addition, the mixture was stirred at 25° C., for 8 hours. TLC (Ethyl acetate:Methanol=3:1, Rf=0.33) showed starting material was consumed and a new main spot was generated. The residue was poured into sat. NaCl (10 ml) and stirred for 2 min. Then, the aqueous phase was extracted with DCM (5 mL*3). The combined organic phase was washed with sat. NaCl (10 mL*2), dried with anhydrous $Na_2SO_4$, filtered and concentrated in vacuum. The residue was purified by prep-HPLC (column: Waters Xbridge 150*25 5u; mobile phase: [water (10 mM NH4HCO3)-ACN]; B %: 32%-62%, 12 min) to give benzyl 3-(2-[2-[2-[2-[2-[2-[3-[[3-[2-[2-[2-[2-[2-(3-benzyloxy-3-oxo-propoxy)ethoxy)ethoxy]ethoxy]ethoxy]ethoxy]ethylamino]-3-oxo-propyl]disulfanyl]propanoylamino]ethoxy]ethoxy]ethoxy]ethoxy]ethoxy]ethoxy] propanoate (70 mg, 65.96 umol, 29.25% yield) as a colorless oil: $^1$H NMR (400 MHz, CHLOROFORM-d) δ=7.41-7.29 (m, 10H), 6.50 (br s, 2H), 5.14 (s, 4H), 3.78 (t, J=6.5 Hz, 4H), 3.67-3.61 (m, 40H), 3.59-3.55 (m, 4H), 3.45 (q, J=5.1 Hz, 4H), 2.97 (t, J=7.2 Hz, 4H), 2.66 (t, J=6.5 Hz, 4H), 2.60 (t, J=7.1 Hz, 4H).

I.38. Benzyl 1-(5-chloro-3-oxoisothiazol-2(3H)-yl)-3,6,9,12,15,18-hexaoxahenicosan-21-oate

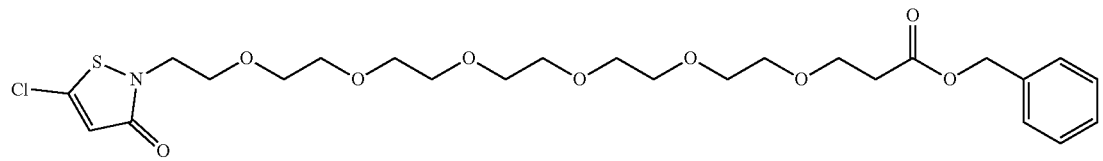 [SMILES: O=C(CCOCCOCCOCCOCCOCCOCCn1sc(Cl)cc1=O)OCc1ccccc1]

To a solution of benzyl 3-[2-[2-[2-[2-[2-[2-[3-[[3-[2-[2-[2-[2-[2-[2-(3-benzyloxy-3-oxo-propoxy)ethoxy]ethoxy]ethoxy]ethoxy]ethoxy]ethylamino]-3-oxo-propyl]disulfanyl]propanoylamino]ethoxy]ethoxy]ethoxy]ethoxy]ethoxy]ethoxy]-propanoate (5.5 g, 5.18 mmol, 1 eq) in DCM (60 mL) was added dropwise sulfuryl chloride (3.50 g, 25.91 mmol, 2.59 mL, 5 eq) at 0° C. The mixture was stirred at 0-20° C., for 12 hrs. TLC (Ethyl acetate:Methanol=10:1, Rf=0.3, 0.5) indicated the reaction was completed. The mixture was poured into ice/water (10 mL), extracted with DCM (20 mL*2). The combined organic layers were washed with $H_2O$ (20 mL*2), brine (20 mL), dried over $Na_2SO_4$. Filtration and concentrated in vacuum. The residue was purified by column chromatography on silica gel (Petroleum ether:Ethyl acetate=1:1 to 0:1) to give Benzyl 3-[2-[2-[2-[2-[2-[2-(3-oxoisothiazol-2-yl)ethoxy]ethoxy]ethoxy]ethoxy]ethoxy]ethoxy]propanoate (1.4 g, 2.29 mmol, 22.05% yield, 86.148% purity) as a brown oil; $^1$H NMR (400 MHz, CHLOROFORM-d) δ ppm 8.02 (d, J=6.17 Hz, 1H) 7.22-7.32 (m, 5H) 6.17 (br d, J=6.17 Hz, 1H) 5.07 (s, 2H) 3.92 (br t, J=4.30 Hz, 2H) 3.51-3.73 (m, 24H) 2.58 (t, J=6.39 Hz, 2H) and Benzyl 3-[2-[2-[2-[2-[2-[2-(5-chloro-3-oxo-isothiazol-2-yl)ethoxy]ethoxy]ethoxy]ethoxy]ethoxy]ethoxy]propanoate (3.1 g, 4.44 mmol, 42.85% yield, 80.532% purity) as a colorless oil: $^1$H NMR (400 MHz, CHLOROFORM-d) δ ppm 7.30-7.40 (m, 5H) 6.26 (s, 1H) 5.15 (s, 2H) 3.93-3.99 (m, 2H) 3.78 (t, J=6.50 Hz, 2H) 3.60-3.72 (m, 23H) 2.66 (t, J=6.50 Hz, 2H).

I.39 Benzyl 1-(5-chloro-1,1-dioxido-3-oxoisothiazol-2(3H)-yl)-3,6,9,12,15,18-hexaoxahenicosan-21-oate

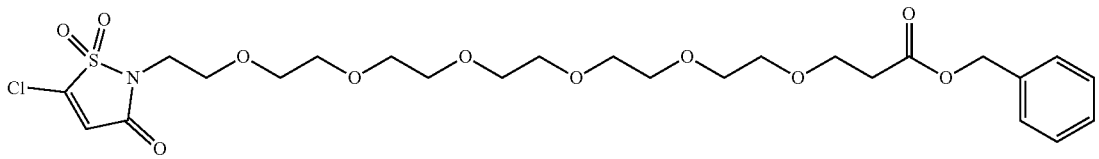 [SMILES: O=C(CCOCCOCCOCCOCCOCCOCCN1C(=O)C=C(Cl)S1(=O)=O)OCc1ccccc1]

To a mixture of benzyl 3-[2-[2-[2-[2-[2-[2-(5-chloro-3-oxo-isothiazol-2-yl)ethoxy]ethoxy]ethoxy]ethoxy]ethoxy]propanoate (1 g, 1.78 mmol, 1 eq) and NaIO$_4$ (1.52 g, 7.12 mmol, 394.34 uL, 4 eq) in H$_2$O (20 mL), DCM (10 mL), ACN (10 mL) was added RuCl$_3$·H$_2$O (20.05 mg, 88.96 umol, 0.05 eq) in one portion at 20° C., under N$_2$. Then, the mixture was stirred at 20° C., for 1 hr. The residue was extracted with ethyl acetate (20 mL*2). The combined organic phase was dried with anhydrous Na$_2$SO$_4$, filtered and concentrated in vacuum. The residue was purified by column chromatography (SiO$_2$, Petroleum ether:Ethyl acetate=1:1 to Ethyl acetate:Methanol=10:1) to give benzyl 3-[2-[2-[2-[2-[2-[2-(5-chloro-1,1,3-trioxo-isothiazol-2-yl)ethoxy]ethoxy]ethoxy]ethoxy]ethoxy]propanoate (S20 mg, 849.06 umol, 47.72% yield, 97% purity) as a yellow oil: $^1$H NMR (400 MHz, CHLOROFORM-d) δ=7.44-7.29 (m, 5H), 6.72 (s, 1H), 5.14 (s, 2H), 3.92-3.86 (m, 2H), 3.80-3.73 (m, 4H), 3.69-3.59 (m, 20H), 2.66 (t, J=6.4 Hz, 2H).

Example 14, 1-(5-chloro-1,1-dioxido-3-oxoisothiazol-2(3H)-yl)-3,6,9,12,15,18-hexaoxahenicosan-21-oic Acid

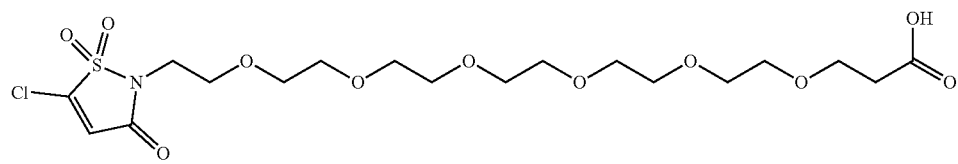 [SMILES: O=C(O)CCOCCOCCOCCOCCOCCOCCN1C(=O)C=C(Cl)S1(=O)=O]

A solution of benzyl 3-[2-[2-[2-[2-[2-[2-(5-chloro-1,1,3-trioxo-isothiazol-2-yl)ethoxy]ethoxy]ethoxy]ethoxy]ethoxy]propanoate (520 mg, 875.32 umol, 1 eq) in DCM (30 mL) was added methanesulfonic acid (841.23 mg, 8.75 mmol, 623.13 uL, 10 eq) dropwise at 10° C. The solution was heated to 35° C., and stirred for 10 hrs. The residue was washed with water (30 ml*3) and then the organic phase was dried with anhydrous Na$_2$SO$_4$, filtered and concentrated in vacuum. The residue was purified by prep-TLC (Ethyl acetate:Methanol:Acetic acid=40:8:1, Rf=0.58). The residue was purified again by prep-HPLC (column: Nano-micro Kromasil C18 100*30 mm 5 μm; mobile phase: [water (0.05% HCl)-ACN]; B %: 1%-30%, 10 min) to give 3-[2-[2-[2-[2-[2-[2-(5-chloro-1,1,3-trioxo-isothiazol-2-yl)ethoxy]ethoxy]ethoxy]ethoxy]ethoxy]ethoxy]propanoic acid (55.93 mg, 106.24 umol, 12.14% yield, 95.726% purity) as a colorless oil; LC-MS (ES, m/z): 504.2 [M+H]$^+$; $^1$H NMR (400 MHz, DMSO-d6) δ=12.30-11.96 (m, 1H), 7.64 (s, 1H), 3.83-3.76 (m, 2H), 3.65-3.58 (m, 4H), 3.54-3.52 (m, 2H), 3.52-3.48 (m, 18H), 2.44-2.42 (m, 2H).

I.40 Benzyl 3-[2-[2-[2-[2-[2-[2-(4,5-dichloro-3-oxo-isothiazol-2-yl)ethoxy]ethoxy]ethoxy] ethoxy]ethoxy]ethoxy]propanoate

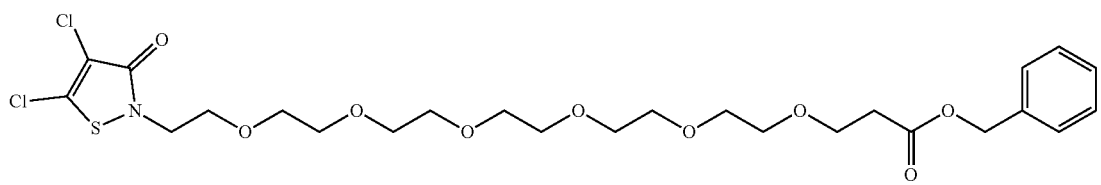 [SMILES: O=C(CCOCCOCCOCCOCCOCCOCCn1sc(Cl)c(Cl)c1=O)OCc1ccccc1]

A solution of benzyl 3-[2-[2-[2-[2-[2-[2-(5-chloro-3-oxo-isothiazol-2-yl)ethoxy]ethoxy]ethoxy]ethoxy]ethoxy]propanoate (1.3 g, 2.31 mmol, 1 eq) in DCM (30 mL) was added sulfuryl chloride (624.34 mg, 4.63 mmol, 462.47 uL, 2 eq) dropwise at 20° C. The solution was stirred at 20° C., for 2 hrs. The solution turned to yellow. The residue was poured into ice-water (30 ml) and stirred for 30 min. The DCM phase was washed with water (50 mL*6), dried with anhydrous Na2SO4, filtered and concentrated in vacuum. The residue was purified by prep-TLC (Ethyl acetate:Methanol=10:1, Rf=0.50) to give benzyl 3-[2-[2-[2-[2-[2-[2-(4,5-dichloro-3-oxo-isothiazol-2-yl)ethoxy]ethoxy]ethoxy]ethoxy]ethoxy]propanoate (800 mg, 1.21 mmol, 52.19% yield, 90% purity) as a yellow oil; $^1$H NMR (400 MHz, CHLOROFORM-d) δ=7.40-7.29 (m, 5H), 5.15 (s, 2H), 4.04 (t, J=4.7 Hz, 2H), 3.78 (t, J=6.4 Hz, 2H), 3.72 (t, J=4.7 Hz, 2H), 3.69-3.63 (m, 16H), 3.62 (s, 4H), 2.66 (t, J=6.5 Hz, 2H).

I.41 Benzyl 1-(4,5-dichloro-1,1-dioxido-3-oxoisothiazol-2(3H)-yl)-3,6,9,12,15,18-hexaoxahenicosan-21-oate

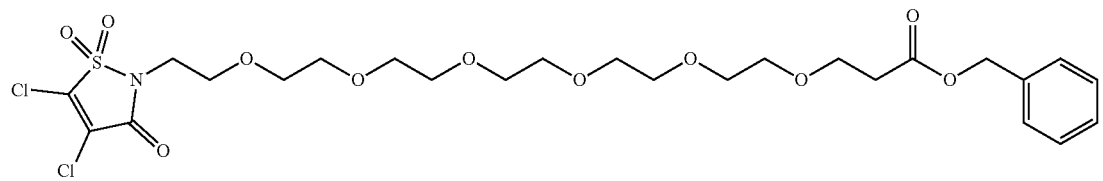 [SMILES: O=C(CCOCCOCCOCCOCCOCCOCCN1C(=O)C(Cl)=C(Cl)S1(=O)=O)OCc1ccccc1]

To a mixture of benzyl 3-[2-[2-[2-[2-[2-[2-(4,5-dichloro-3-oxo-isothiazol-2-yl)ethoxy]ethoxy]ethoxy]ethoxy]ethoxy]propanoate (600 mg, 1.01 mmol, 1 eq) and NaIO$_4$ (860.56 mg, 4.02 mmol, 222.94 uL, 4 eq) in H$_2$O (20 mL), DCM (10 mL), ACN (10 mL) was added RuCl$_3$·H$_2$O (11.34 mg, 50.29 umol, 0.05 eq) in one portion at 0° C., under N$_2$. The mixture was stirred at 0° C., for 2 min, then heated to 25° C., and stirred for 1 hour. The residue was poured into Ethyl acetate (30 ml), and then filtered. The filtrate was extracted with ethyl acetate (30 mL*3). The combined organic phase was concentrated in vacuum. The residue was purified by prep-TLC (Ethyl acetate, Rf=0.50) to give benzyl 3-[2-[2-[2-[2-[2-[2-(4,5-dichloro-1,1,3-trioxo-isothiazol-2-yl)ethoxy]ethoxy]ethoxy]ethoxy]ethoxy]propanoate (220 mg, 350.03 umol, 34.80% yield, 100% purity) as a colorless oil; $^1$H NMR (400 MHz, CHLOROFORM-d) δ=7.40-7.27 (m, 4H), 5.15 (s, 2H), 3.99-3.90 (m, 2H), 3.78 (t, J=6.2 Hz, 4H), 3.70-3.58 (m, 20H), 2.66 (t, J=6.4 Hz, 2H).

Example 15, 1-(4,5-dichloro-1,1-dioxido-3-oxoisothiazol-2(3H)-yl)-3,6,9,12,15,18-hexaoxahenicosan-21-oic Acid

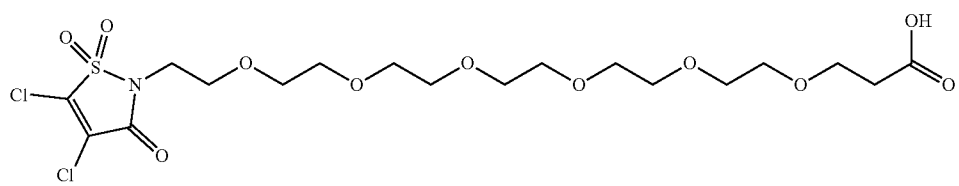 [SMILES: O=C(O)CCOCCOCCOCCOCCOCCOCCN1C(=O)C(Cl)=C(Cl)S1(=O)=O]

A solution of benzyl 3-[2-[2-[2-[2-[2-[2-(4,5-dichloro-1,3-trioxo-isothiazol-2-yl)ethoxy]ethoxy]ethoxy]ethoxy]ethoxy]ethoxy]propanoate (220 mg, 350.03 umol, 1 eq) in DCM (5 mL) was added methanesulfonic acid (504.60 mg, 5.25 mmol, 373.78 uL, eq) dropwise at 10° C. Then, the solution was heated to 40° C., and stirred for 20 hrs. The residue was diluted by DCM (20 ml) and then the solution was washed with water (15 ml*3), the organic phase was dried with anhydrous $Na_2SO_4$, filtered and concentrated in vacuum. The residue was purified by prep-HPLC (column: Nano-micro Kromasil C18 100*30 mm 5 um; mobile phase: [water (0.05% HCl)-ACN]; B %: 25%-55%, 10 min) to give 3-[2-[2-[2-[2-[2-[2-(4,5-dichloro-1,1,3-trioxo-isothiazol-2-yl)ethoxy]ethoxy]ethoxy]ethoxy]ethoxy]ethoxy]propanoic acid (53.79 mg, 98.63 umol, 28.18% yield, 98.724% purity) as a yellow oil: LC-MS (ES, m/z): 538.2 $[M+H]^+$; 1H NMR (400 MHz, DMSO-d6) δ=12.13 (br s, 1H), 3.89-3.81 (m, 2H), 3.65 (t, J=5.5 Hz, 2H), 3.59 (t, J=6.4 Hz, 2H), 3.56-3.48 (m, 20H), 2.43 (t, J=6.4 Hz, 2H).

Example 16

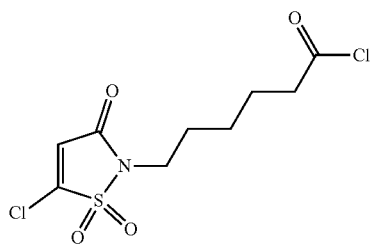 [SMILES: O=C(Cl)CCCCCN1C(=O)C=C(Cl)S1(=O)=O]

In a flask under argon was added product 6-(5-chloro-1,1-dioxido-3-oxoisothiazol-2(3H)-yl) hexanoic acid (12.58 mg, 0.045 mmol), DCM (2 mL) and DMF (10 μl). The mixture was cooled to 0° C., then oxalyl dichloride (11.65 μl, 0.136 mmol) was added dropwise. The mixture was warmed up to rt and was stirred until complete conversion was observed by LCMS (follow-up by LCMS by adding to the aliquot dry MeOH to form the methyl ester). The crude was evaporated under vacuo. The residue was taken in DCM and dried again under vacuo to give a yellow solid. The crude material was used without further purification for the next step.

2. SYNTHESIS OF THE DRUG-LINKER CONJUGATES

Example A. ((2R,3R)-3-((S)-1-((3R,4S,5S)-4-((S)-2-((S)-2-<(4-(6-(5-chloro-1,1-dioxido-3-oxoisothiazol-2(3H)-yl)-N-methylhexanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine

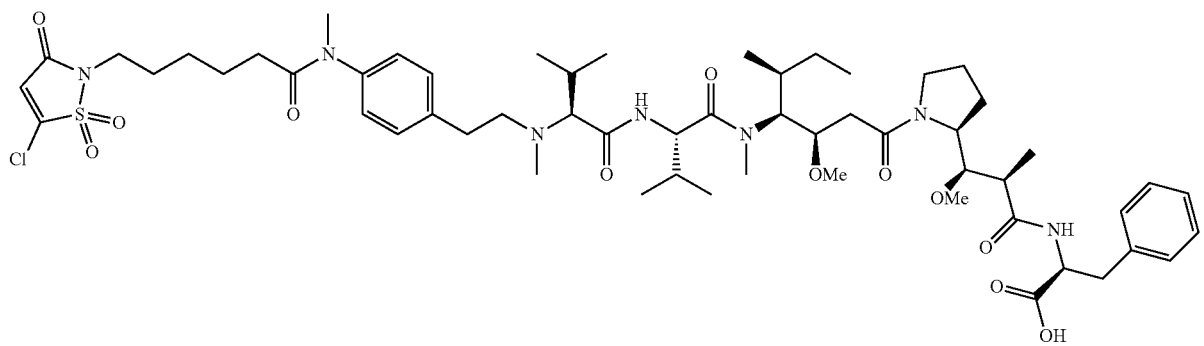 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)CCCCCN2C(=O)C=C(Cl)S2(=O)=O)cc1)C(C)C]

Figure 1A:
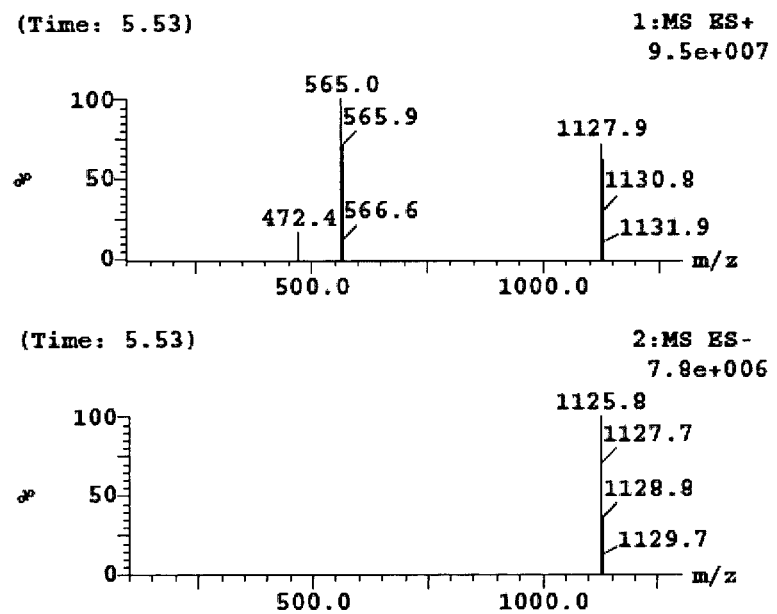
FIGS. 1A, 2, 3A, 4A, 5A, 6A, 7A, 21 and 22A represent mass spectra of drug-linker conjugates according to the invention.
Figure 1B:
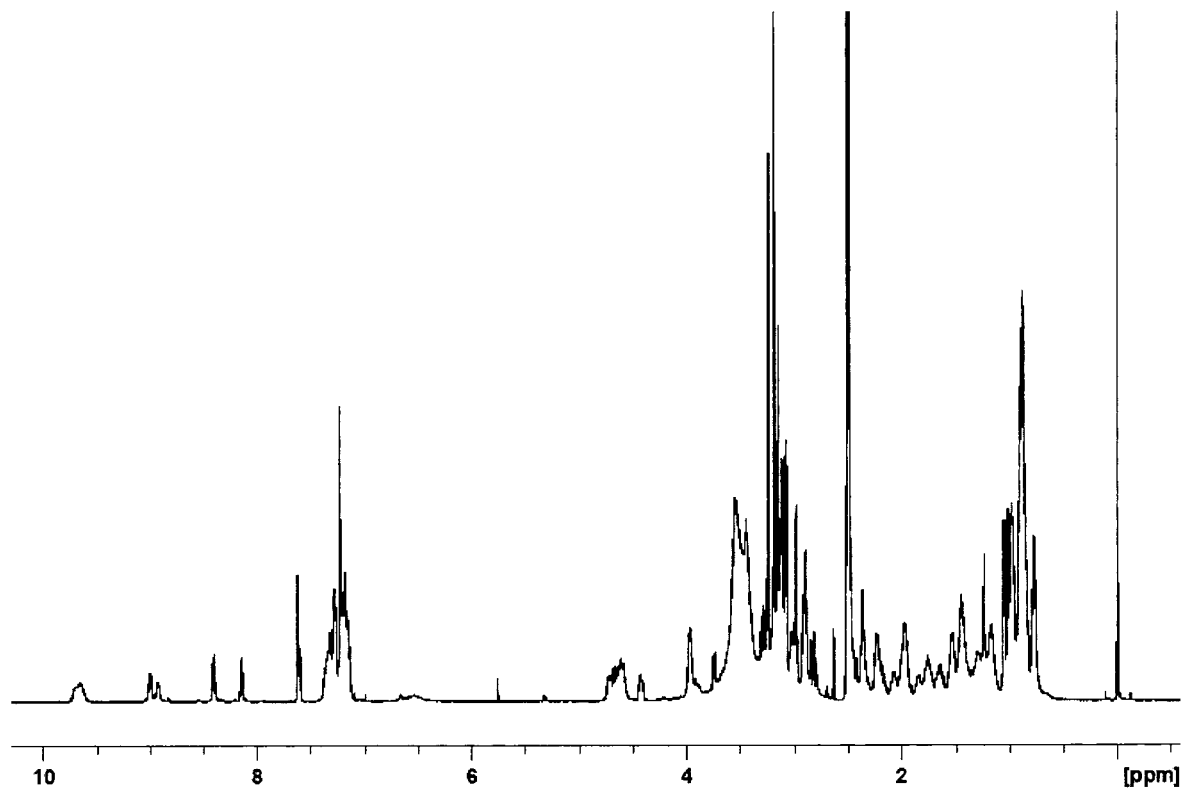
FIGS. 1B, 3B, 4B, 5B, 6B, 7B, 8 and 9 represent $^1$H-NMR spectra of drug-linker conjugates according to the invention.

Standard Procedure for the Synthesis of Drug-Linkers:

In a flask under nitrogen, were added at rt 6-(5-chloro-1,1-dioxido-3-oxoisothiazol-2(3H)-yl)hexanoic acid (205 mg, 0.73 mmol) (Example 1), dichloromethane (10 mL) and DMF (100 µl). The mixture was cooled to 0° C., using an ice bath, then oxalyl chloride was added (190.4 µl, 2.18 mmol). The mixture was warmed up to rt and was stirred for 2 h. The reaction mixture was evaporated under vacuum. The residue was taken in CH$_2$Cl$_2$ and dried again under vacuum to give 6-(5-chloro-1,1-dioxido-3-oxoisothiazol-2(3H)-yl)hexanoyl chloride as a yellow solid. In a vial under N$_2$ at rt were introduced (S)-2-((2R,3R)-3-((S)-1-((3R,4S,5S)-4-((S)—N,3-dimethyl-2-((S)-3-methyl-2-(methyl(4-(methylamino)phenethyl)amino)butanamido)butanamido)-3-methoxy-5-methylheptanoyl)pyrrolidin-2-yl)-3-methoxy-2-methylpropanamido)-3-phenylpropanoic acid, (S)-2-((2R,3R)-3-((S)-1-((3R,4S,5S)-4-((S)—N,3-dimethyl-2-((S)-3-methyl-2-(methyl(4-(methy)amino)phenethyl)amino)butanamido)butanamido)-3-methoxy-5-methylheptanoyl)pyrrolidin-2-yl)-3-methoxy-2-methylpropanamido)-3-phenylpropanoic acid compound with 2,2,2-trifluoroacetic acid (1:1) (111 mg, 0.102 mmol) and dichloromethane (3.7 mL). The mixture was cooled to 0° C., and DIPEA (70.9 µl, 0.406 mmol) was added. The reaction mixture was stirred for 10 min at 0° C., then 6-(5-chloro-1,1-dioxido-3-oxoisothiazol-2(3H)-yl)hexanoyl chloride (36.6 mg, 0.122 mmol) was added dropwise as a solution in DCM (248 mg of acid chloride in 2 mL of DCM). The mixture was stirred at 0° C., for 1 h 15. The reaction was stopped by adding trifluoroacetic acid (32.9 µl, 0,426 mmol), acetonitrile (2.1 mL) and water (0.3 mL) into the mixture at 0° C. The crude material was concentrated in vacuum and the residue purified by preparative HPLC (Column X-Bridge C18 (100*30) using a gradient of ACN and water with 0.1% TFA as a mobile phase) to give ((2R,3R)-3-((S)-1-((3R,4S,5S)-4-((S)-2-((S)-2-((4-(6-(5-chloro-1,1-dioxido-3-oxoisothiazol-2(3H)-yl)-N-methylhexanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine. The mass spectrum and the $^1$H-NMR spectrum of this drug-linker conjugate are represented respectively on FIGS. 1A and 1B.

Example B. ((2R,3R)-3-((S)-1-((3R,4S,5S)-4-((S)-2-((S)-2-((4-(6-(4,5-dichloro-1,1-dioxido-3-oxoisothiazol-2(3H)-yl)-N-methylhexanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine

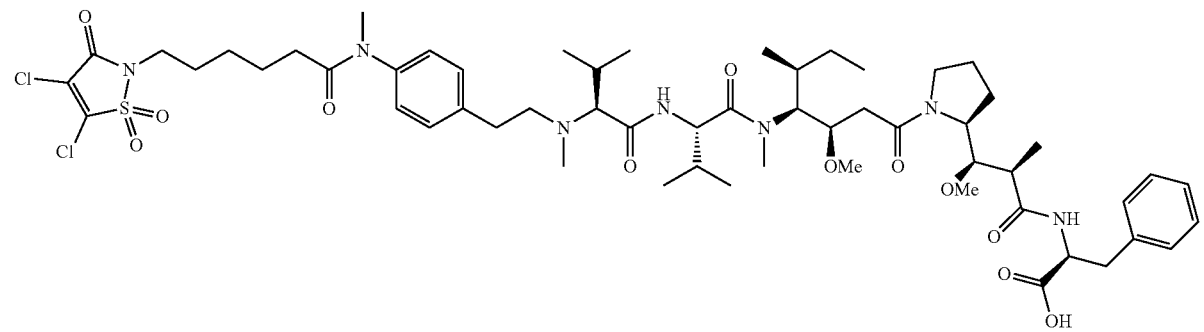 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)CCCCCN2C(=O)C(Cl)=C(Cl)S2(=O)=O)cc1)C(C)C]

It was synthesized following the standard procedure for the synthesis of drug-linkers using 6-(4,5-dichloro-1,1-dioxido-3-oxoisothiazol-2(3H)-yl)hexanoic acid (Example 2) and ((2R,3R)-3-((S)-1-((3R,4S,5S)-4-((S)—N,3-dimethyl-2-((S)-3-methyl-2-(methyl(4-(methylamino)phenethyl)amino)butanamido)butanamido)-3-methoxy-5-methylheptanoyl)pyrrolidin-2-yl)-3-methoxy-2-methylpropanoyl)-L-phenylalanine compound with 2,2,2-trifluoroacetic acid (1:1) as starting materials.

Figure 2:
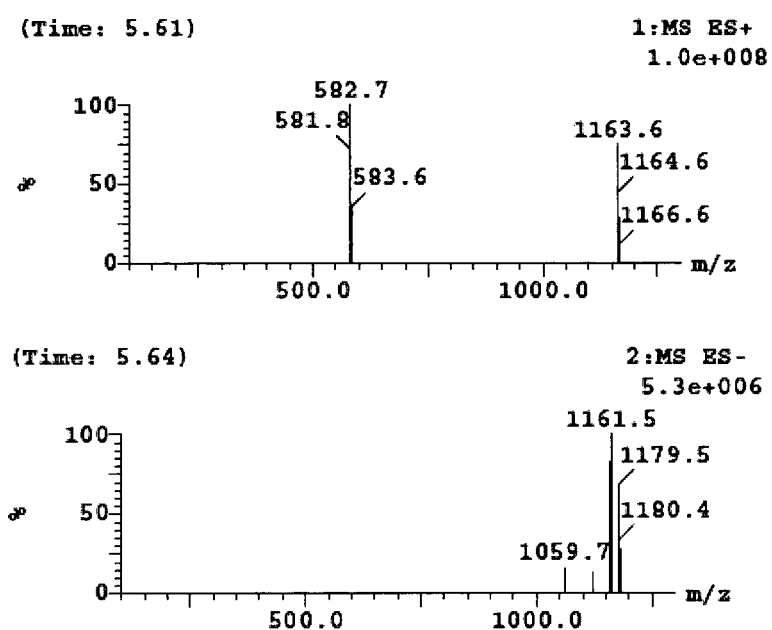

The mass spectrum of this drug-linker conjugate is represented on FIG. 2.

Example C. ((2R,3R)-3-((S)-1-<(3R,4S,5S)-4-((S)-2-((S)-2-((4-((((4-((S)-2-((S)-2-(6-(5-chloro-1,1-dioxido-3-oxoisothiazol-2(3H)-yl)hexanamido)-3-methylbutanamido)-5-ureidopentanamido)beazyl)oxy)carbonyl)(metliyl)amino)pheaethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine

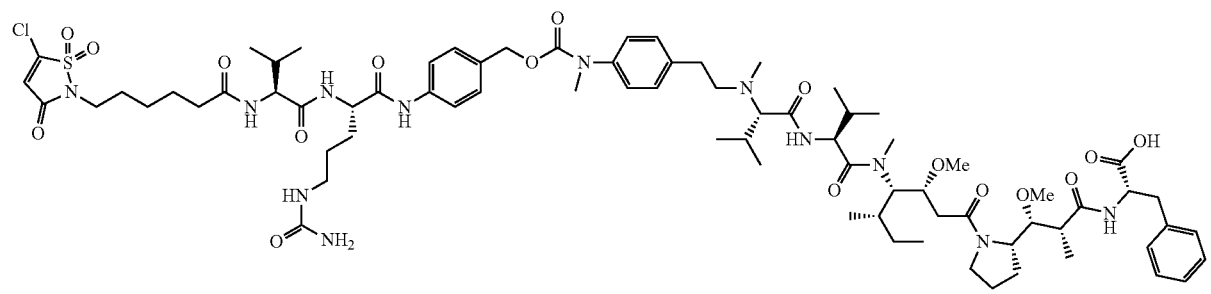 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)OCc2ccc(NC(=O)[C@H](CCCNC(N)=O)NC(=O)[C@@H](NC(=O)CCCCCN3C(=O)C=C(Cl)S3(=O)=O)C(C)C)cc2)cc1)C(C)C]

It was obtained following the standard procedure for drug-linker synthesis using 6-(5-chloro-1,1-dioxido-3-oxoisothiazol-2(3H)-yl)hexanoic acid (Example 1) and ((2R,3R)-3-((S)-1-((3R,4S,5S)-4-((S)-2-((S)-2-((4-((((4-((S)-2-((S)-2-amino-3-methylbutanamido)-5-ureidopentanamido)benzyl)oxy)carbonyl) (methyl)amino)phenethyl)(methyl)amino)-3-methylbutanamido)-N3-dimethylbutanamido)-3-methoxy-5-methylheptanoyl)pyrrolidin-2-yl)-3-methoxy-2-methylpropanoyl)-L-phenylalanine as starting materials.

Figure 3A:
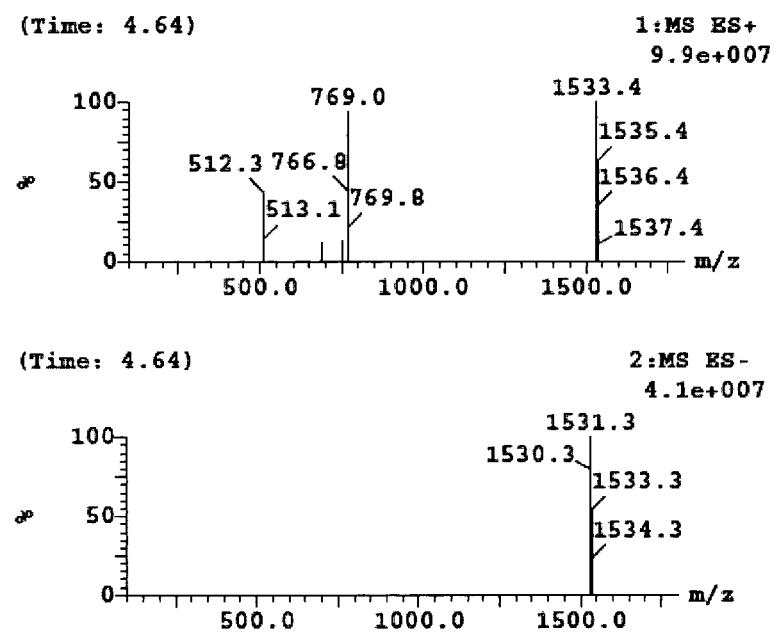
Figure 3B:
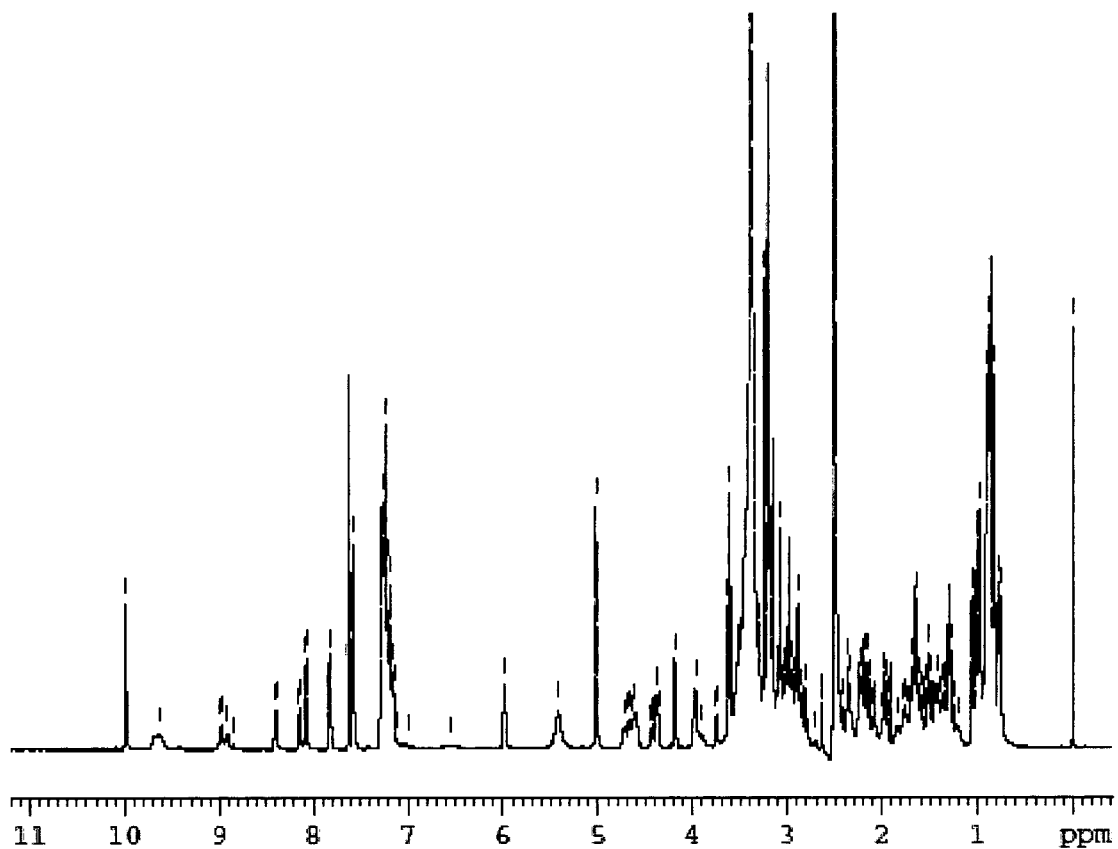

The mass spectrum and the $^1$H-NMR spectrum of this drug-linker conjugate are represented respectively on FIGS. 3A and 3B.

Example D. ((2R,3R)-3-((S)-1-((3R,4S,5S)-4-((S)-2-((S)-2-((4-((((4-((S)-2-((S)-2-(6-(4,5-dichloro-1,1-dioxido-3-oxoisothiazol-2(3H)-yl)hexanamido)-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine

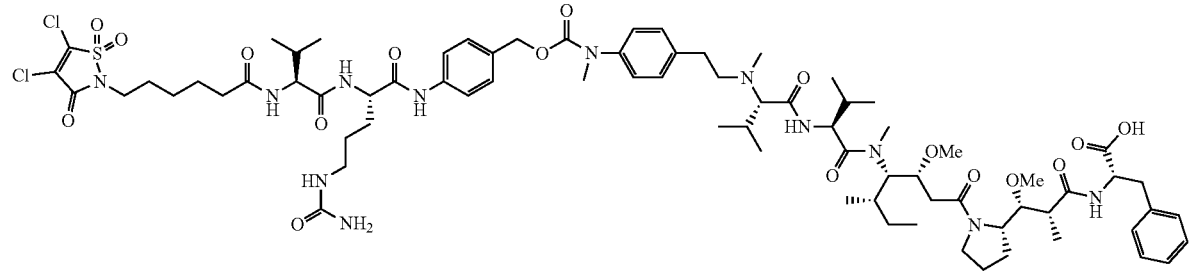 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)OCc2ccc(NC(=O)[C@H](CCCNC(N)=O)NC(=O)[C@@H](NC(=O)CCCCCN3C(=O)C(Cl)=C(Cl)S3(=O)=O)C(C)C)cc2)cc1)C(C)C]

It was obtained following the standard procedure for drug-linker synthesis using 6-(4,5-dichloro-1,1-dioxido-3-oxoisothiazol-2(3H)-yl)hexanoic acid (Example 2) and ((2R,3R)-3-((S)-1-((3R,4S,5S)-4-((S)-2-((S)-2-((4-((((4-((S)-2-((S)-2-amino-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine as starting materials.

Figure 4A:
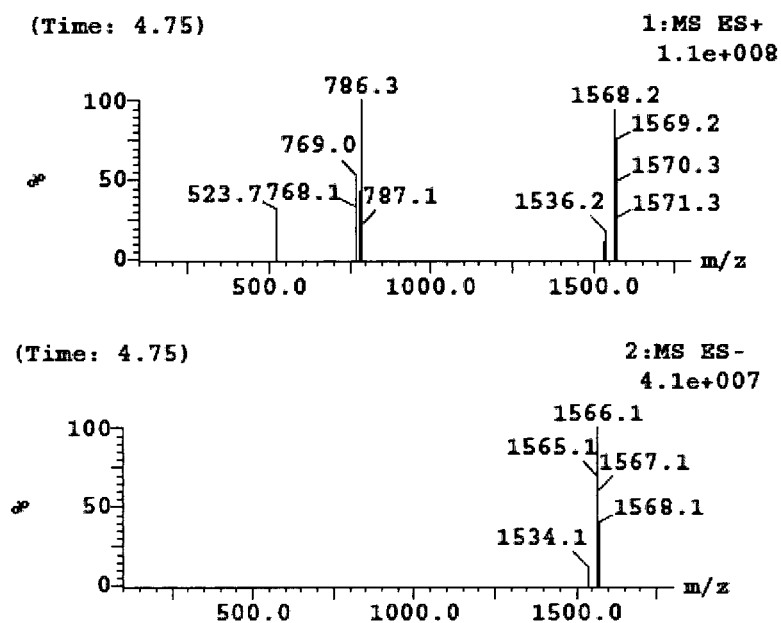
Figure 4B:
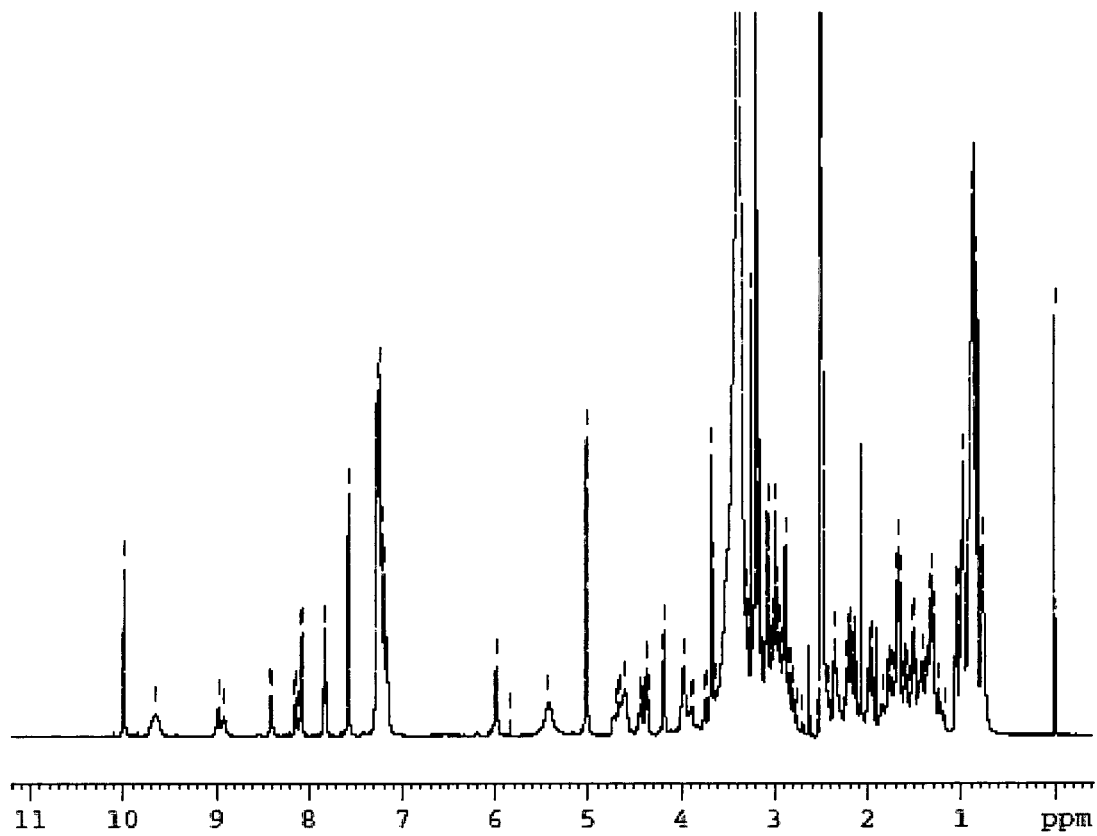

The mass spectrum and the ¹H-NMR spectrum of this drug-linker conjugate are represented respectively on FIGS. 4A and 4B.

Example E. ((2R,3R)-3-((S)-1-((3R,4S,5S)-4-((S)-2-((S)-2-((4-((((4-((S)-2-((S)-2-(3-(2-(2-(2-(5-chloro-1,1-dioxido-3-oxoisothiazol-2(3H)-yl)ethoxy)ethoxy)ethoxy)propanamido)-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetic Acid Salt

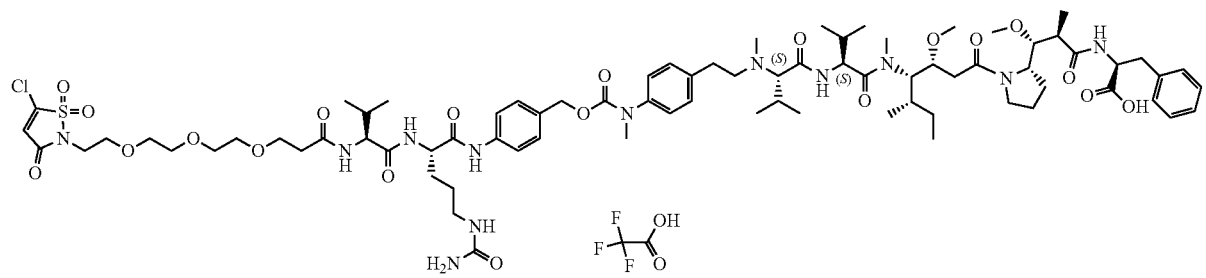

Synthesized following the standard procedure for the synthesis of drug-linkers using 3-(2-(2-(2-(5-chloro-1,1-dioxido-3-oxoisothiazol-2(3H)-yl)ethoxy)ethoxy)ethoxy)propanoic acid (Example 12) and (S)-2-((2R,3R)-3-((S)-1-((3R,4S,5S)-4-((S)-2-((S)-2-((4-((((4-((S)-2-((S)-2-amino-3-methylbutanamido)-5 ureidopentanamido)benzyl)oxy)carbonyl)(methyl)amino)phenethyl)(methyl)amino)-3-methylbutanamido)-N3-dimethylbutanamido)-3-methoxy-5-methylheptanoyl)pyrrolidin-2-yl)-3-methoxy-2-methylpropanamido)-3-phenylpropanoic acid as starting materials.

Figure 5A:
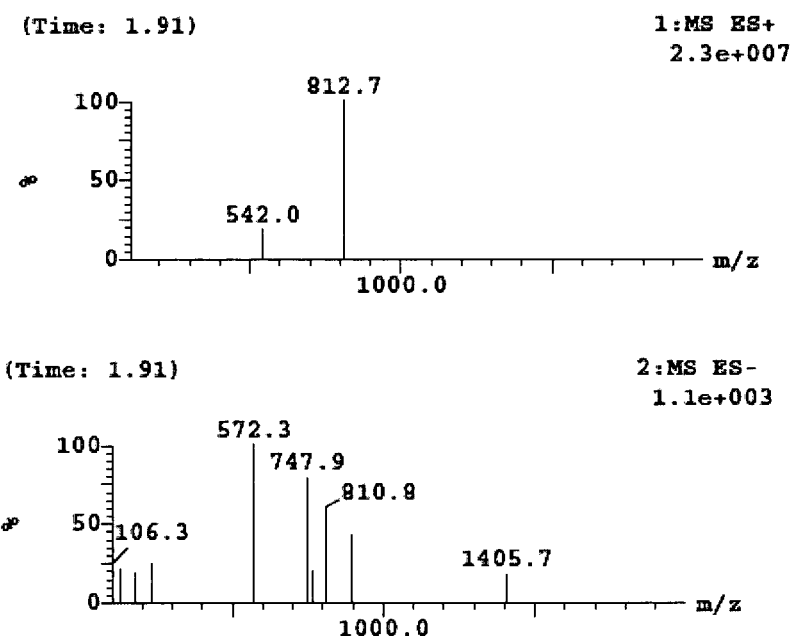
Figure 5B:
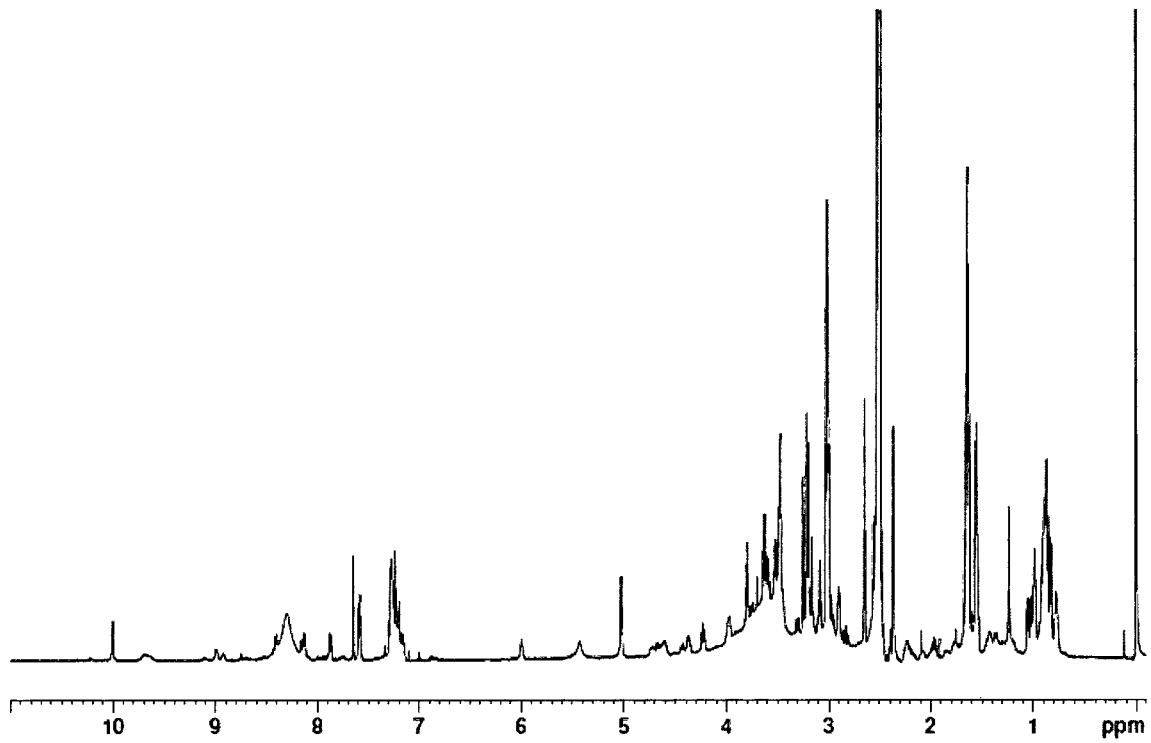

The mass spectrum and the ¹H-NMR spectrum of this drug-linker conjugate are represented respectively on FIGS. 5A and 5B.

Example F. ((2R,3R)-3-(1-((3R,4R,5S)-4-((S)-2-((S)-2-((4-((S)-2-((S)-2-(3-(2-(2-(2-(5-chloro-1,1-dioxido-3-oxoisothiazol-2(3H)-yl)ethoxy)ethoxy)ethoxy)propanamido)-3-methylbutanamido)-N-methylpropanamido)plienethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-D-phenylalanine

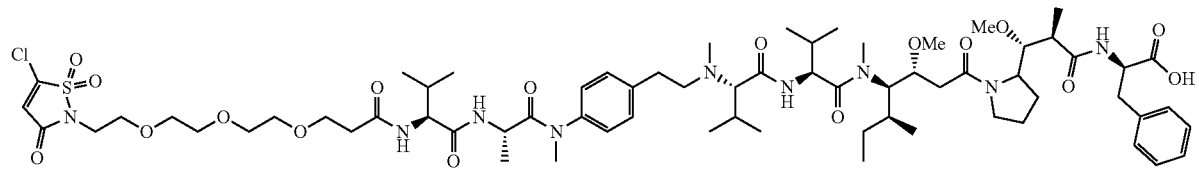 [SMILES: CC[C@H](C)[C@H]([C@@H](CC(=O)N1CCCC1[C@H](OC)[C@@H](C)C(=O)N[C@H](Cc1ccccc1)C(=O)O)OC)N(C)C(=O)[C@@H](NC(=O)[C@H](C(C)C)N(C)CCc1ccc(N(C)C(=O)[C@H](C)NC(=O)[C@@H](NC(=O)CCOCCOCCOCCN2C(=O)C=C(Cl)S2(=O)=O)C(C)C)cc1)C(C)C]

Synthesized following the standard procedure for the synthesis of drug-linkers using 3-(2-(2-(2-(5-chloro-1,1-dioxido-3-oxoisothiazol-2(3H)-yl)ethoxy)ethoxy)ethoxy)propanoic acid (Example 12) and ((2R,3R)-3-(1-((3R,4R,5S)-4-((S)-2-((S)-2-((4-((S)-2-((S)-2-amino-3-methylbutanamido)-N-methylpropanamido)phenethyl)(methyl)amino)-3-methylbutanamido)-N3-dimethylbutanamido)-3-methoxy-5-methylheptanoyl)pyrrolidin-2-yl)-3-methoxy-2-methylpropanoyl)-D-phenylalanine as starting materials.

Figure 6A:
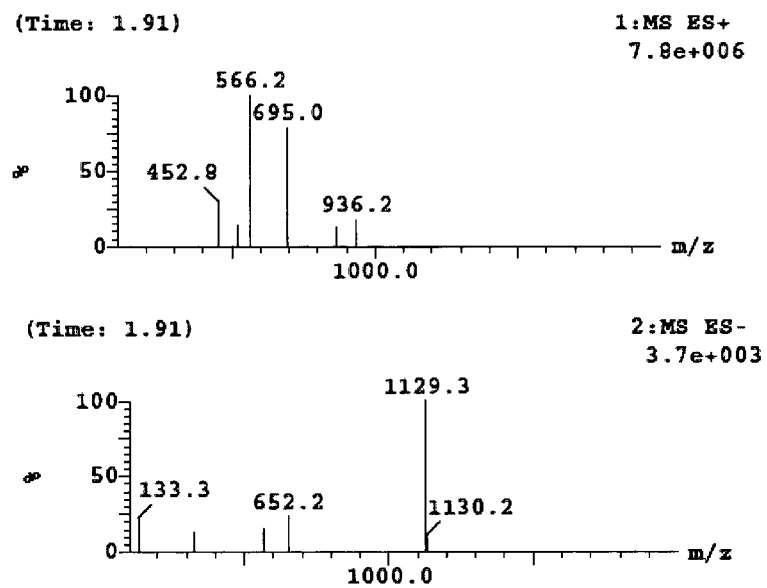
Figure 6B:
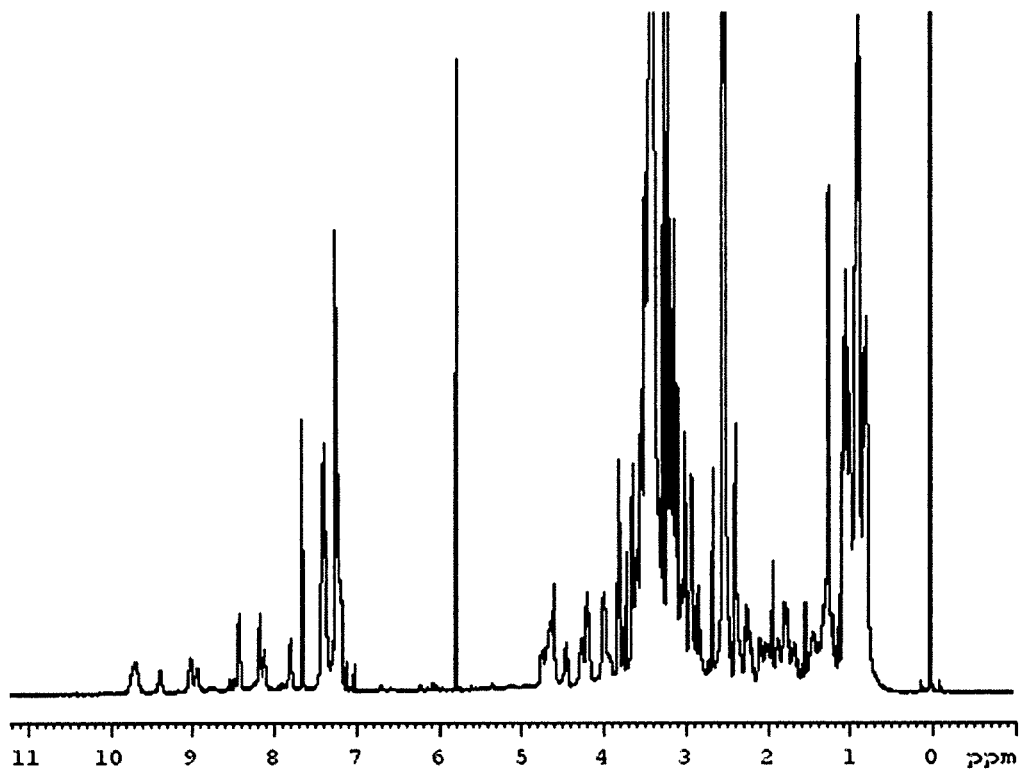

The mass spectrum and the $^1$H-NMR spectrum of this drug-linker conjugate are represented respectively on FIGS. 6A and 6B.

Example G. ((2R,3R)-3-(1-((3R,4R,5S)-4-((S)-2-((S)-2-((4-((S)-2-((S)-2-(6-(5-chloro-1,1-dioxido-3-oxoisothiazol-2(3H)-yl)hexanamido)-3-methylbutanamido)-N-methylpropanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-D-phenylalanine

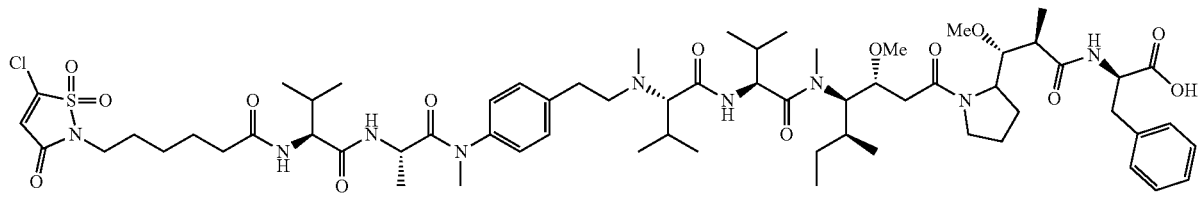 [SMILES: CC[C@H](C)[C@H]([C@@H](CC(=O)N1CCCC1[C@H](OC)[C@@H](C)C(=O)N[C@H](Cc1ccccc1)C(=O)O)OC)N(C)C(=O)[C@@H](NC(=O)[C@H](C(C)C)N(C)CCc1ccc(N(C)C(=O)[C@H](C)NC(=O)[C@@H](NC(=O)CCCCCN2C(=O)C=C(Cl)S2(=O)=O)C(C)C)cc1)C(C)C]

Synthesized following the standard procedure for the synthesis of drug-linkers using 6-(5-chloro-1,1-dioxido-3-oxoisothiazol-2(3H)-yl)hexanoic acid (Example 1) and ((2R,3R)-3-(1-((3R,4R,5S)-4-((S)-2-((S)-2-((4-((S)-2-((S)-2-amino-3-methylbutanainido)-N-methylpropaiiamido)phenethyl)(niethyl)amino)-3-methylbutanamido)-N,3-dimethylbutanamido)-3-methoxy-5-methylheptanoyl)pyrrolidin-2-yl)-3-methoxy-2-methylpropanoyl)-D-phenylalanine as starting materials.

Figure 7A:
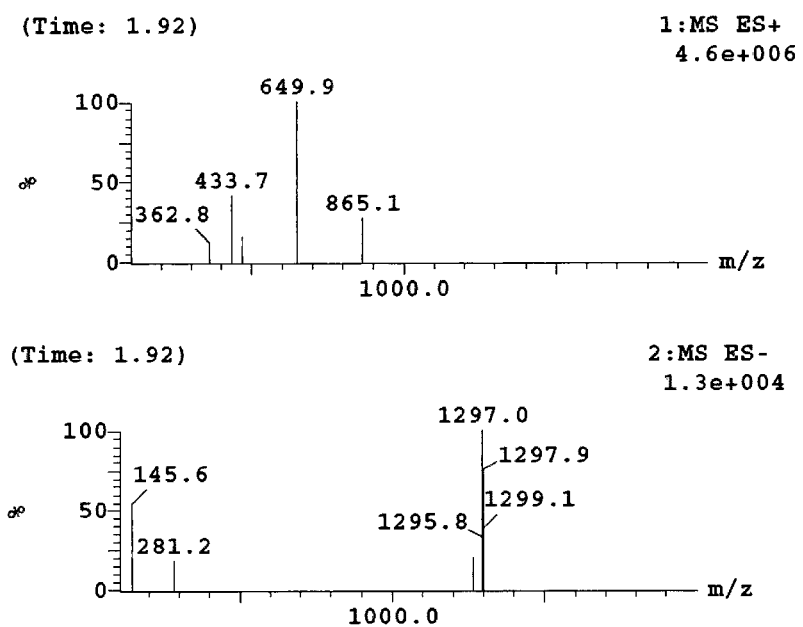
Figure 7B:
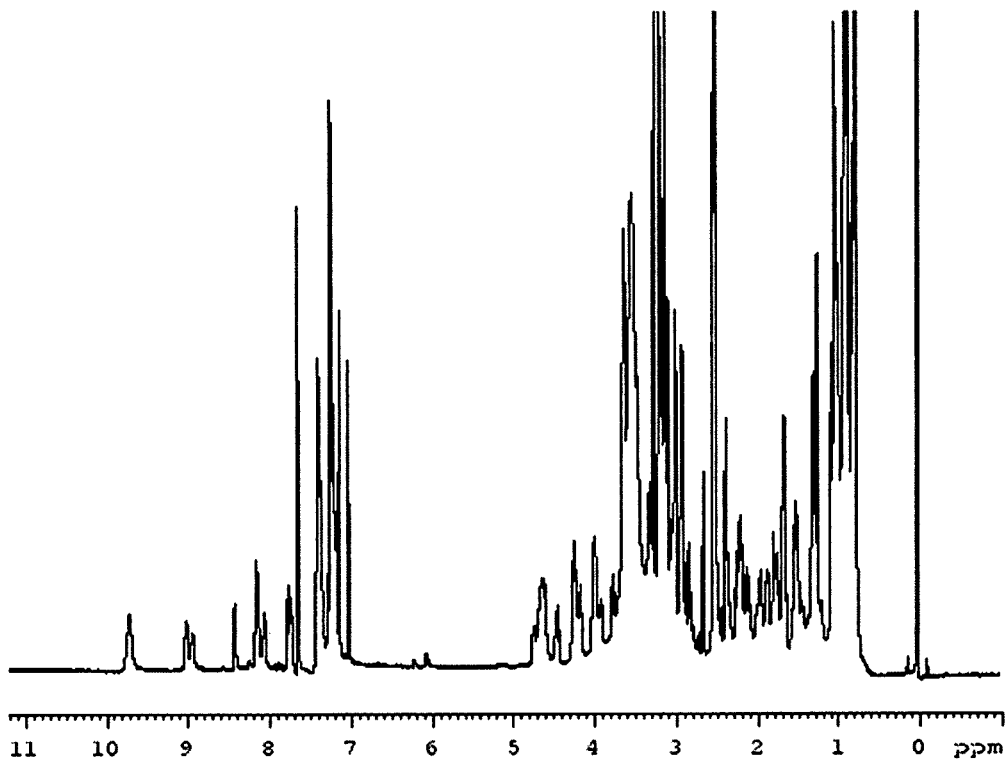

The mass spectrum and the $^1$H-NMR spectrum of this drug-linker conjugate are represented respectively on FIGS. 7A and 7B.

Example H. 4-((S)-2-((S)-2-(6-(5-chloro-1,1-dioxido-3-oxoisothiazol-2(3H)-yl)hexanamido)-3-methylbutanamido)-5-ureidopentanamido)benzyl (2-((2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-6,11-dioxo-1,2,3,4,6,11-hexahydrotetracene-2-carboxamido)ethyl)carbamate

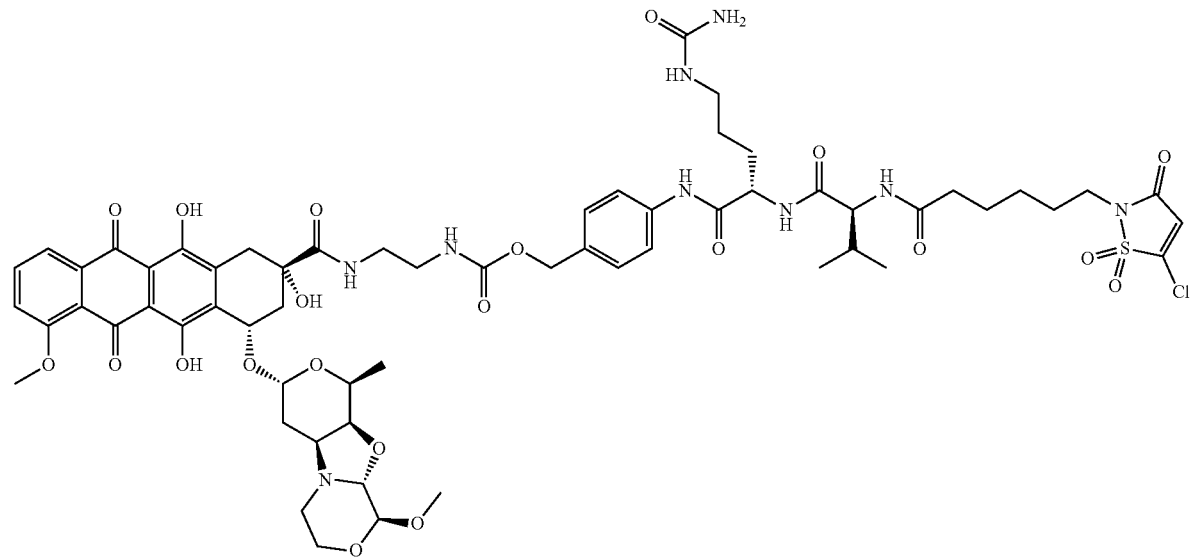

Example H has been synthesized according to the following synthetic path:
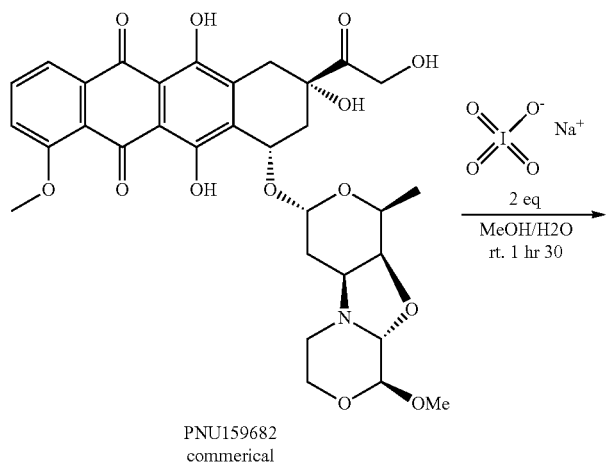
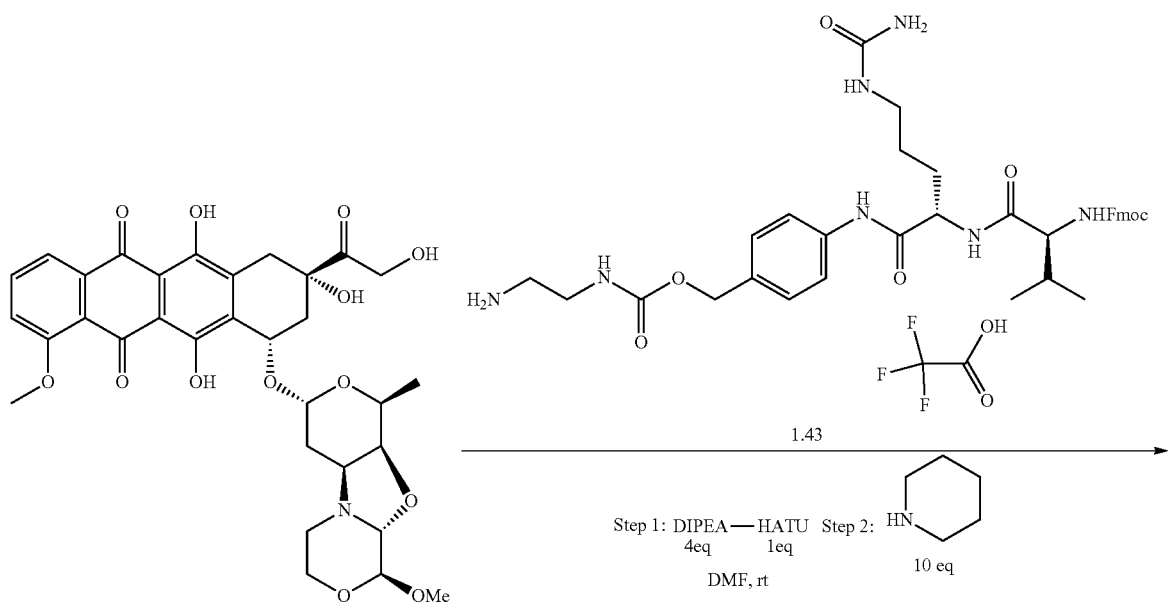

-continued
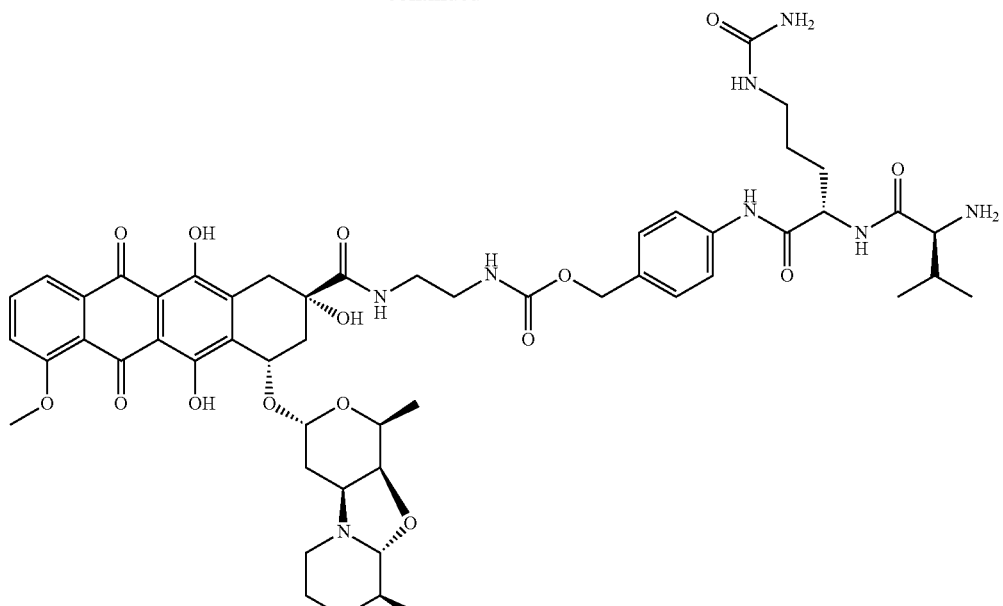
I.44
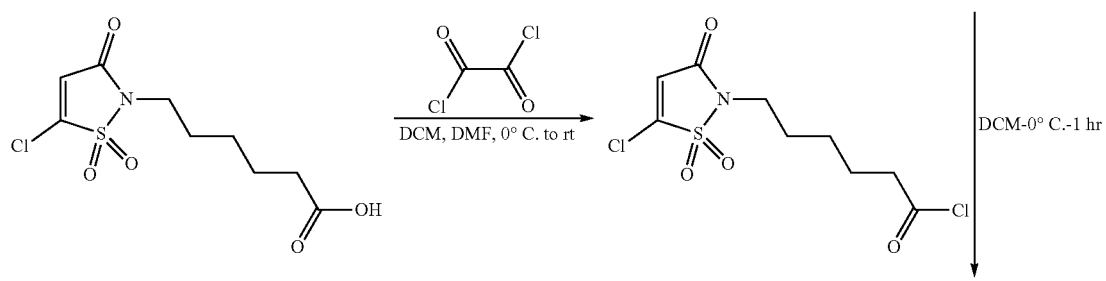
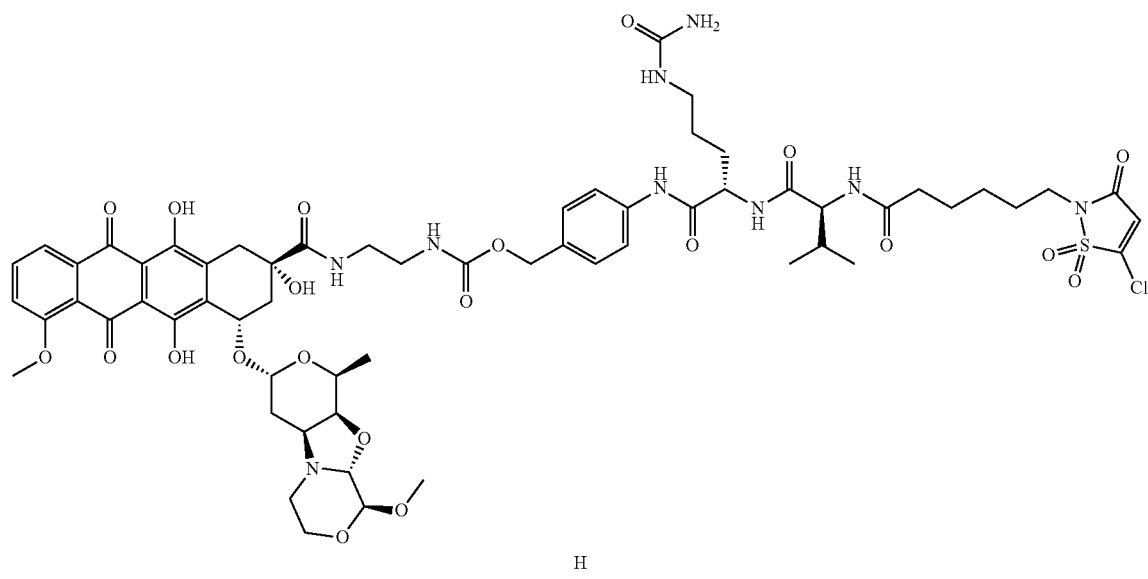
H

I.42. (2S,4S)-2,5,12-trihydroxy-7-methoxy-4-(((1S, 3R,4aS,9S,9aR,10aS)-9-methoxy-1-methyloctahydro-1H-pyrano[4',3':4,5]oxazolo[2,3-c][1,4] oxazin-3-yl)oxy)-6,11-dioxo-1,2,3,4,6,11-hexahydrotetracene-2-carboxylic Acid In a flask was added PNU-159682 (52 mg, 0.081 mmol) in a mixture of methanol (15 mL) and water (10 mL). A solution of NaIO$_4$ (34.7 mg, 0.162 mmol) in water (5 mL) was added. The reaction mixture was stirred at rt until complete conversion was observed by LCMS. The solvents were removed under vacuo to give 1.42 as a red solid which was used directly in the next step.

I.43 (9H-fluoren-9-yl)methyl ((S)-1-(((S)-1-((4-((((2-aminoethyl)carbamoyl)oxy) methyl)phenyl) amino)-1-oxo-5-ureidopentan-2-yl)amino)-3-methyl-1-oxobutan-2-yl)carbamate In a flask under argon were added (9H-fluoren-9-yl) methyl ((S)-1-(((S)-1-((4-(hydroxymethyl)phenyl)amino)-1-oxo-5-ureidopentan-2-yl)amino)-3-methyl-1-oxobutan-2-yl)carbamate (1 g, 1.662 mmol) and bis(4-nitrophenyl) carbonate (1.011 g, 3.32 mmol) in DMF (0.443 mol/L). Then, the mixture was cooled at 0° C., and DIPEA (639 µL, 3.66 mmol) was added dropwise. The reaction mixture was warmed up to rt and stirred for 18 h. The crude mixture was concentrated under vacuo. The crude product was taken in 1:1 mixture of Et$_2$O/EtOAc and filtered. The precipitate was washed with Et$_2$O, citric acid 5%, H$_2$O then Et$_2$O again to obtain a yellow solid. This solid was purified by automatic column chromatography silica gel (100 DCM:0 MeOH to 80 DCM:20 MeOH) to give 345 mg of (9H-fluoren-9-yl)methyl ((S)-3-methyl-1-(((S)-1-((4-((((4-nitrophenoxy)carbonyl) oxy)methyl)phenyl)amino)-1-oxo-5-ureidopentan-2-yl) amino)-1-oxobutan-2-yl)carbamate (white solid), 27.1% yield.

To a solution of the previous product (150 mg, 0.196 mmol) in DMF (6 mL) were added HOBt (34.4 mg, 0.254 mmol) and pyridine (63.3 µl, 0.782 mmol) at 0° C. After 5 min, tert-butyl (2-aminoethyl)carbamate 1-2 (40.7 mg, 0.254 mmol) in DMF (1.5 mL) was added to the mixture, followed by DIPEA (102 µl, 0.587 mmol). The mixture was warmed to rt and stirred for 2 h. The crude was concentrated under vacuo to give a white solid which was purified by automatic column chromatography silica gel (100 DCM:0 MeOH to 80 DCM:20 MeOH) to give 129 mg of 4-((S)-2-((S)-2-((((9H-fluoren-9-yl)methoxy)carbonyl)amino)-3-methylbutanamido)-5-ureidopentanamido)benzyl tert-butyl ethane-1,2-diyldicarbamate (white solid), 84% yield.

In a flask was placed the previous product (154 mg, 0.195 mmol) in DCM (6 mL). The mixture was cooled at 0° C., and TFA (753 µL, 9.77 mmol) was added and the mixture was stirred at 0° C., until complete conversion was observed by LCMS. The crude mixture was concentrated in vacuo to give 1.43 as a white solid (quantitative yield).

I.44 4-((S)-2-((S)-2-amino-3-methylbutanamido)-5-ureidopentanamido)benzyl (2-((2S,4S)-2,5,12-trihydroxy-7-methoxy-4-(((1S,3R,4aS,9S,9aR,10aS)-9-methoxy-1-methyloctahydro-1H-pyrano[4',3':4,5] oxazolo[2,3-c][1,4]oxazin-3-yl)oxy)-6,11-dioxo-1,2, 3,4,6,11-hexahydrotetracene-2-carboxamido)ethyl) carbamate In a flask were added 1.42 (50.9 mg, 0.081 mmol), 1.43 (78.0 mg, 0.097 mmol) and DMF (8 mL) followed by HATU (30.8 mg, 0.081 mmol) and DIPEA (56.7 µl, 0.324 mmol). The reaction mixture was stirred at rt for 18 h. To this mixture was then added piperidine (80 µl, 0.811 mmol). The reaction mixture was stirred for 1 h (until complete conversion was observed by LCMS). The mixture was concentrated under vacuo. The crude product obtained was immediately purified by automatic column chromatography silica gel (100 DCM:0 MeOH/NH$_3$ aq to 85 DCM:25 MeOH/ NH$_3$aq) to give 20 mg of 1.44 (red oil), 23% yield.

Example H

In a flask under N$_2$ was added 6-(5-Chloro-1,1-dioxido-3-oxoisothiazol-2(3H)-yl)hexanoic acid (example 1) (7.86 mg, 0.028 mmol) in DCM (1 mL) and DMF (10 µl). The mixture was cooled at 0° C., then oxalyl chloride (7.28 µl, 0.085 mmol) was added dropwise. The mixture was warmed up to rt and was stirred until complete conversion was observed by LCMS (follow-up by LCMS by adding to the aliquot dry MeOH to form the methyl ester). The crude mixture was evaporated under vacuo. The residue was taken in DCM and dried again under vacuo to give 6-(5-chloro-1,1-dioxido-3-oxoisothiazol-2(3H)-yl)hexanoyl chloride as a yellow solid (yield quantitative). The crude material was used without further purification for the next step.

In a flask under N$_2$ were introduced at rt 1.44 (20 mg, 0.019 mmol) in DCM (2 mL). The mixture was cooled to 0° C., and DIPEA (12.96 µl, 0.074 mmol) was added. The mixture was stirred at 0° C., for 10 min then the product of previous step (8.40 mg, 0.028 mmol) diluted in DCM (1 mL) was added. The mixture was then stirred at 0° C., for 2 h (until complete conversion was observed by LCMS). The crude mixture was concentrated under vacuo and purified by automatic column chromatography, silica gel (100 DCM:0 MeOH to 85 DCM: 15 MeOH) to give 6.85 mg of example H (also named compound F562524) as a red solid, 27% yield.

Figure 8:
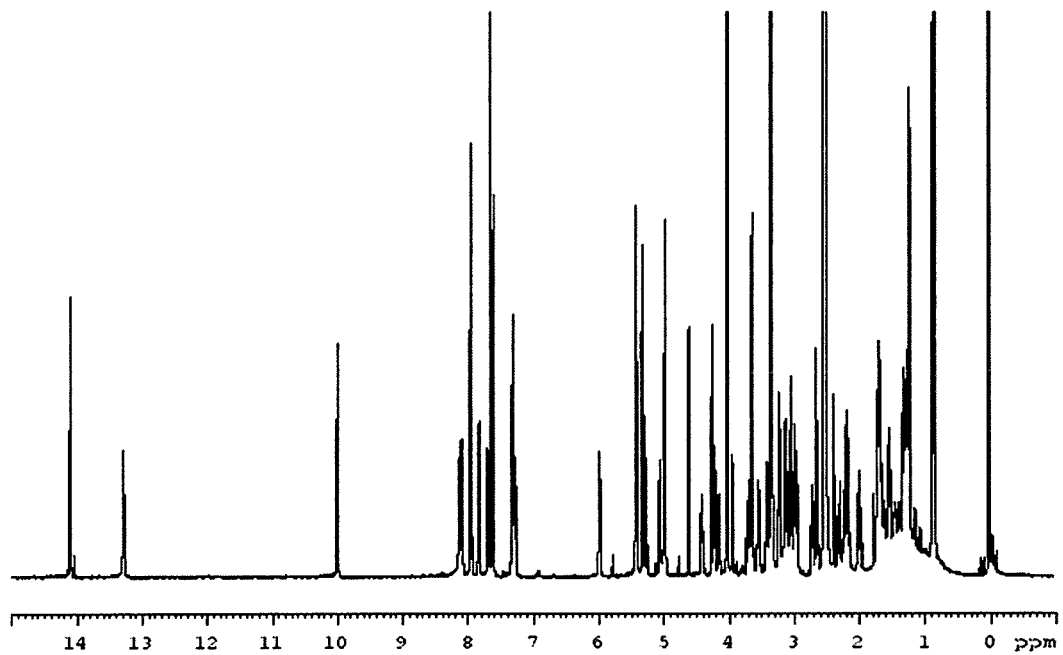

The $^1$H-NMR spectrum of this drug-linker conjugate is represented on FIG. 8.

Example I. 4-((S)-2-((S)-2-(6-(5-chloro-1,1-dioxido-3-oxoisothiazol-2(3H)-yl)hexanamido)-3-methylbutanamido)-5-ureidopentanamido)benzyl (2-oxo-2-((2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-6,11-dioxo-1,2,3,4,6,11-hexahydrotetracen-2-yl)ethyl) ethane-1,2-diylbis(methylcarbamate)
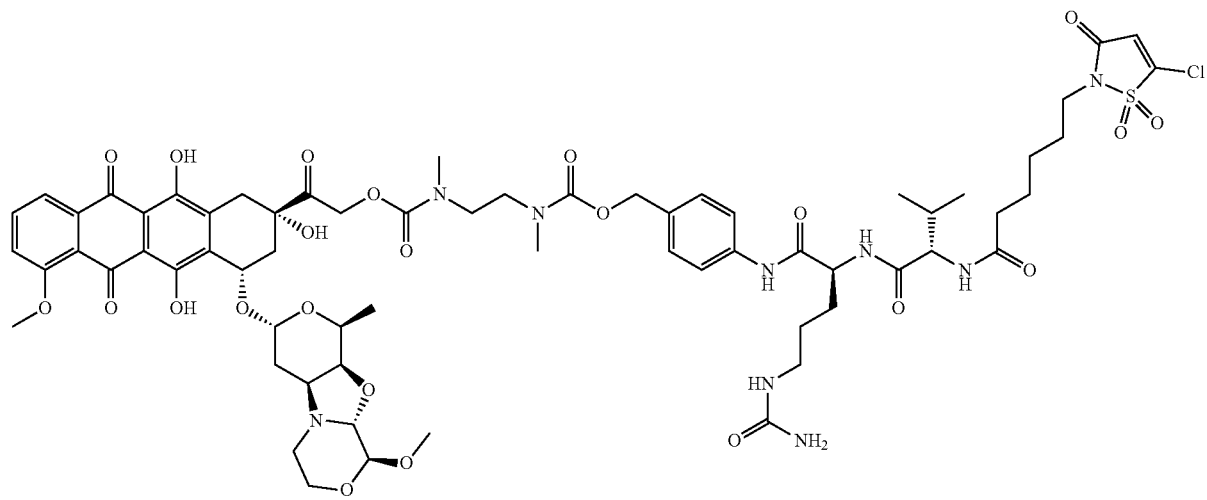 [SMILES: COc1cccc2c1C(=O)c1c(O)c3c(c(O)c1C2=O)C[C@@](O)(C(=O)COC(=O)N(C)CCN(C)C(=O)OCc1ccc(NC(=O)[C@H](CCCNC(N)=O)NC(=O)[C@@H](NC(=O)CCCCCN2C(=O)C=C(Cl)S2(=O)=O)C(C)C)cc1)C[C@@H]3O[C@H]1C[C@H]2[C@H](O[C@@H]3[C@@H](OC)OCCN32)[C@H](C)O1]
Example I has been synthesized according to the following synthetic path:
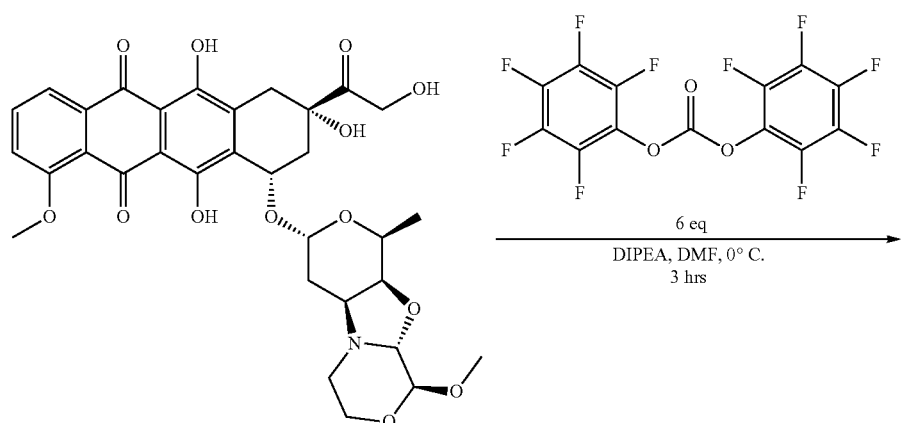

141
-continued
142
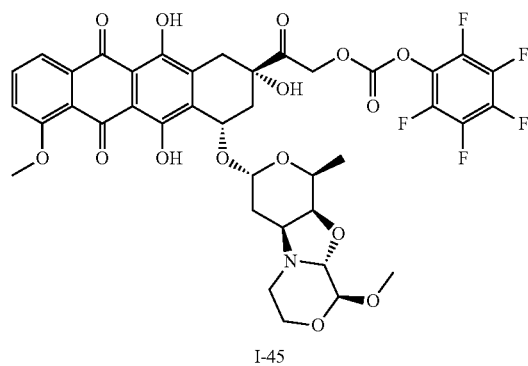
I-45
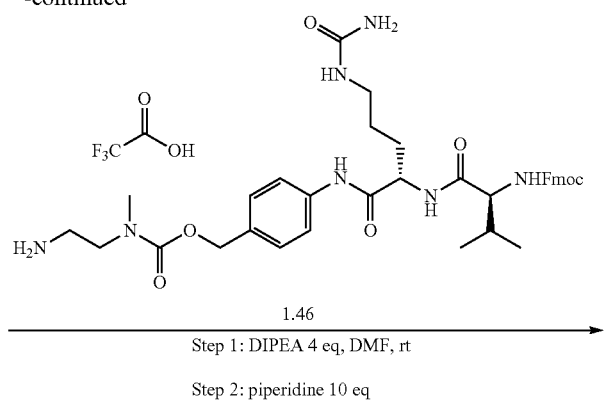
1.46
Step 1: DIPEA 4 eq, DMF, rt
Step 2: piperidine 10 eq
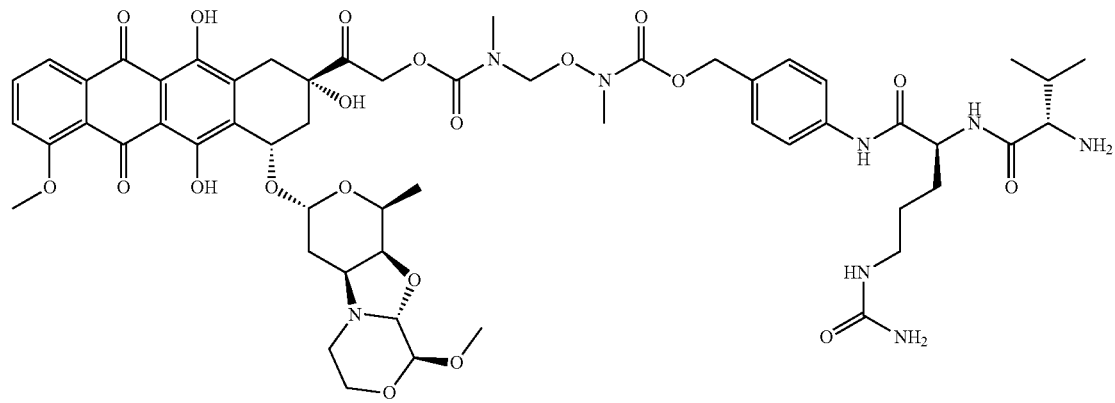
I.47
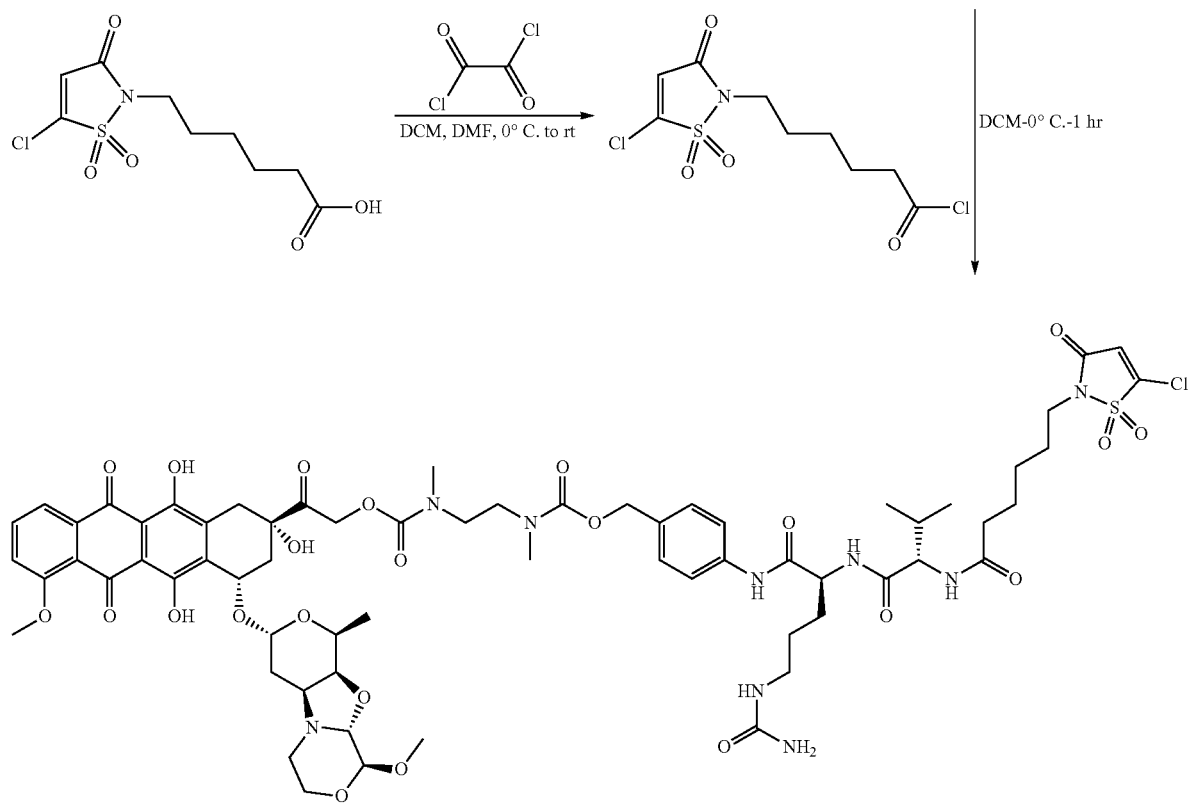

I.45 2-oxo-2-((2S,4S)-2,5,12-trihydroxy-7-methoxy-4-(((1S,3R,4aS,9S,9aR,10aS)-9-methoxy-1-methyl-octahydro-1H-pyrano[4',3':4,5]oxazolo[2,3-c][1,4]oxazin-3-yl)oxy)-6,11-dioxo-1,2,3,4,6,11-hexahydrotetracen-2-yl)ethyl (Perfluorophenyl) Carbonate In a flask under argon were added PNU-159682 (12 mg, 0.0180 mmol) and DMF (1.5 mL). The mixture was cooled at 0° C., and bis(perfluorophenyl) carbonate (36.9 mg, 0.094 mmol) was added. Then a solution of DIPEA (9.80 µl, 0.056 mmol) in DMF (0.5 mL) was slowly added over a period of 5 min. The mixture was finally stirred for 3 h at 0° C. (conversion observed by LCMS). The crude mixture was concentrated in vacuo and purified by automatic column chromatography, silica gel (100 DCM:0 [80 DCM:20 MeOH] to 50 DCM:50 [80 DCM:2 0 MeOH]) to give 5.52 mg of I.45 as a red oil, 36% yield.

I.46 (9H-fluoren-9-yl)methyl ((S)-3-methyl-1-(((S)-1-((4-((((4-nitrophenoxy)carbonyl) oxy)methyl)phenyl)amino)-1-oxo-5-ureidopentan-2-yl)amino)-1-oxobutan-2-yl)carbamate 2,2,2-trifluoroacetate In a flask under argon were added (9H-fluoren-9-yl)methyl ((S)-1-(((S)-1-((4-(hydroxymethyl)phenyl)amino)-1-oxo-5-ureidopentan-2-yl)amino)-3-methyl-1-oxobutan-2-yl)carbamate (I g, 1.662 mmol) and bis(4-nitrophenyl) carbonate (1.011 g, 3.32 mmol) in DMF (0.443 mol/L). Then, the mixture was cooled at 0° C., and DIPEA (639 µL, 3.66 mmol) was added dropwise. The reaction mixture was warmed up to rt and stirred for 18 h. The crude mixture was concentrated under vacuo, taken in Et$_2$O/EtOAc (1/1) and filtered. The precipitate was washed with Et:0, citric acid 5%, H$_2$O then Et$_2$O again to obtain a yellow solid. This solid was purified by automatic column chromatography, silica gel (100 DCM:0 MeOH to 80 DCM:20 MeOH) to give 345 mg of a white solid, 27.1% yield. To a solution of this compound (118 mg, 0.154 mmol) in DMF (6 mL) were added HOBt (27.0 mg, 0.200 mmol) and pyridine (49.8 µl, 0.616 mmol) at 0° C. After 5 min, tert-butyl methyl(2-(methylamino)ethyl)carbamate (37.7 mg, 0.200 mmol) in DMF (1.5 mL) was added to the mixture, followed by DIPEA (81.0 µl, 0.462 mmol). The mixture was then warmed to rt and stirred for 2 h (until complete conversion was observed by LCMS). The crude mixture was concentrated under vacuo to give a yellow oil which was purified by automatic column chromatography, silica gel (100 DCM:0 MeOH to 80 DCM:20 MeOH) to give 103 mg of a white solid, 82% yield.

In a flask was placed this product (198 mg, 0.243 mmol) in DCM (12 mL). The mixture was cooled to 0° C., and TFA (935 µl, 12.13 mmol) was added and the mixture was stirred for 4 h at 0° C. (until complete conversion was observed by LCMS). The crude mixture was concentrated under vacuo to give 220 mg of 1.46 as a clear yellow solid (quantitative yield).

I.47 4-((S)-2-((S)-2-amino-3-methylbutanamido)-5-ureidopentanamido)benzyl (2-oxo-2-((2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-6,11-dioxo-1,2,3,4,6,11-hexahydrotetracen-2-yl)ethyl) ethane-1,2-diylbis(methylcarbamate)

To a solution of product I.4S (19 mg, 0.022 mmol) in DMF (1 mL) was added at rt a solution of product 1.46 (22.2 mg, 0.027 mmol) and DIPEA (15.59 µl, 0.089 mmol) in DMF (I mL). The reaction mixture was stirred at rt for 3 h (until complete conversion was observed by LCMS). Then, to the mixture was added piperidine (22.09 µl, 0.223 mmol). The reaction mixture was stirred for 1 h (complete conversion observed by LCMS). The crude mixture was concentrated under vacuo and purified by automatic column chromatography, silica gel (100 DCM:0 MeOH/NH$_3$ (9/1) to 75 DCM:25 MeOH/NH$_3$ (9/1)) to give 10 mg of 1.47 as a red oil, 39% yield.

Example I

In a flask under N$_2$ was added 6-(5-Chloro-1,1-dioxido-3-oxoisothiazol-2(3H)-yl)hexanoic acid (example 1) (7.86 mg, 0.028 mmol) in DCM (1 mL) and DMF (10 µl). The mixture was cooled at 0° C., then oxalyl chloride (7.28 µl, 0.085 mmol) was added dropwise. The mixture was warmed up to rt and was stirred until complete conversion was observed by LCMS (follow-up by LCMS by adding to the aliquot dry MeOH to form the methyl ester). The crude mixture was evaporated under vacuo. The residue was taken in DCM and dried again under vacuo to give 6-(5-chloro-1,1-dioxido-3-oxoisothiazol-2(3H)-yl)hexanoyl chloride as a yellow solid (yield quantitative). The crude material was used without further purification for the next step.

In a flask under N$_2$ at rt was introduced product 1.47 (10 mg, 0.0086 mmol) in DCM (2 mL). The mixture was cooled at 0° C., and DIPEA (6.0 µl, 0.034 mmol) was added. The mixture was stirred at 0° C., for 10 min then addition of previous product (3.90 mg, 0.013 mmol) diluted in DCM (1 mL). The mixture was then stirred at 0° C., for 2 h (until complete conversion was observed by LCMS). The crude was concentrated in vacuo and purified by automatic column chromatography, silica gel (100 DCM:0 MeOH to 85 DCM:15 MeOH) to give 2.45 mg of example I as a red solid, 19% yield.

Figure 9:
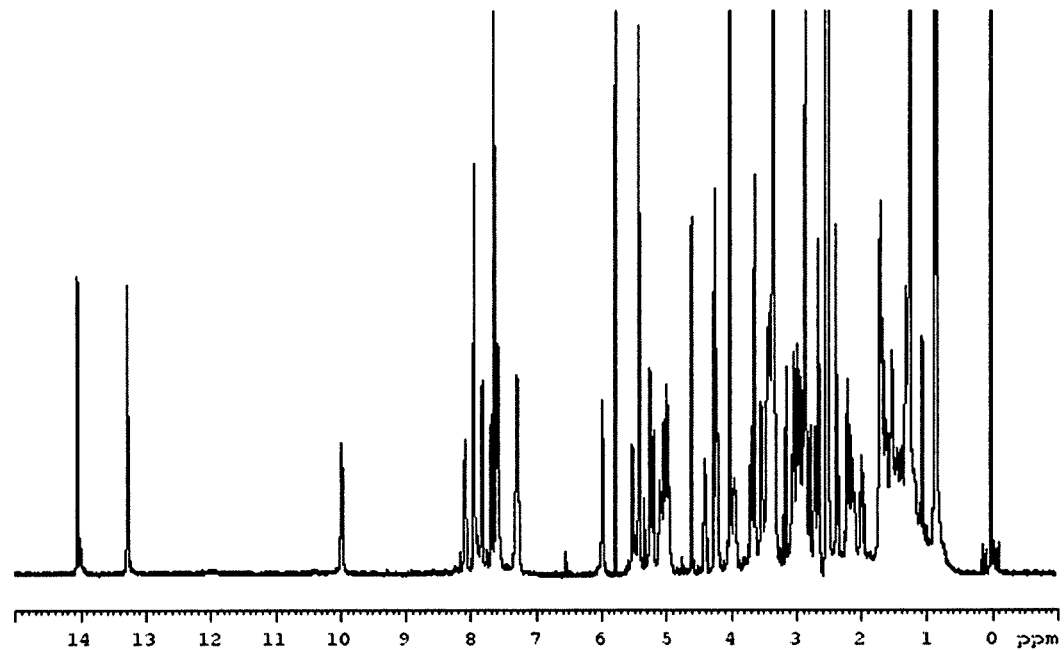

The $^1$H-NMR spectrum of this drug-linker conjugate is represented on FIG. 9.

Example J
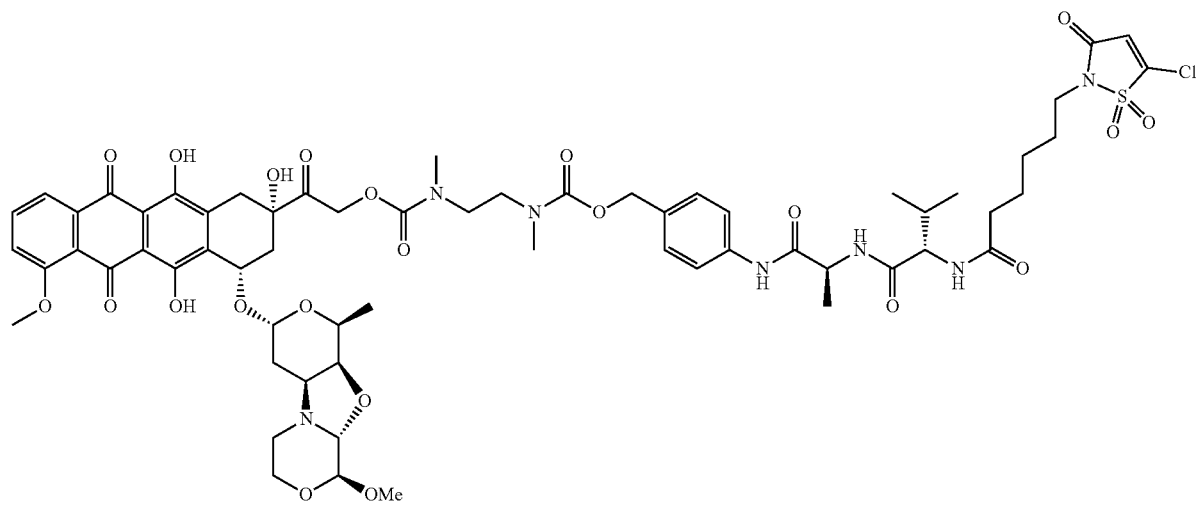 [SMILES: COc1cccc2c1C(=O)c1c(O)c3c(c(O)c1C2=O)C[C@@](O)(C(=O)COC(=O)N(C)CCN(C)C(=O)OCc1ccc(NC(=O)[C@H](C)NC(=O)[C@@H](NC(=O)CCCCCN2C(=O)C=C(Cl)S2(=O)=O)C(C)C)cc1)C[C@@H]3O[C@H]1C[C@H]2[C@H](O[C@@H]3[C@@H](OC)OCCN32)[C@H](C)O1]
Example J has been synthesized according to the following synthetic path:
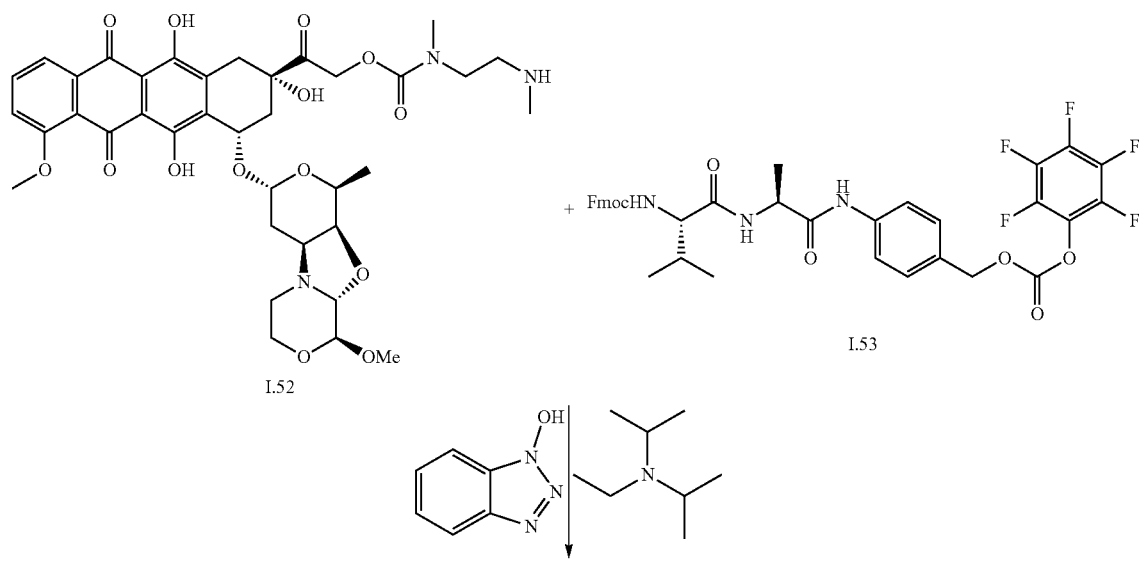

-continued
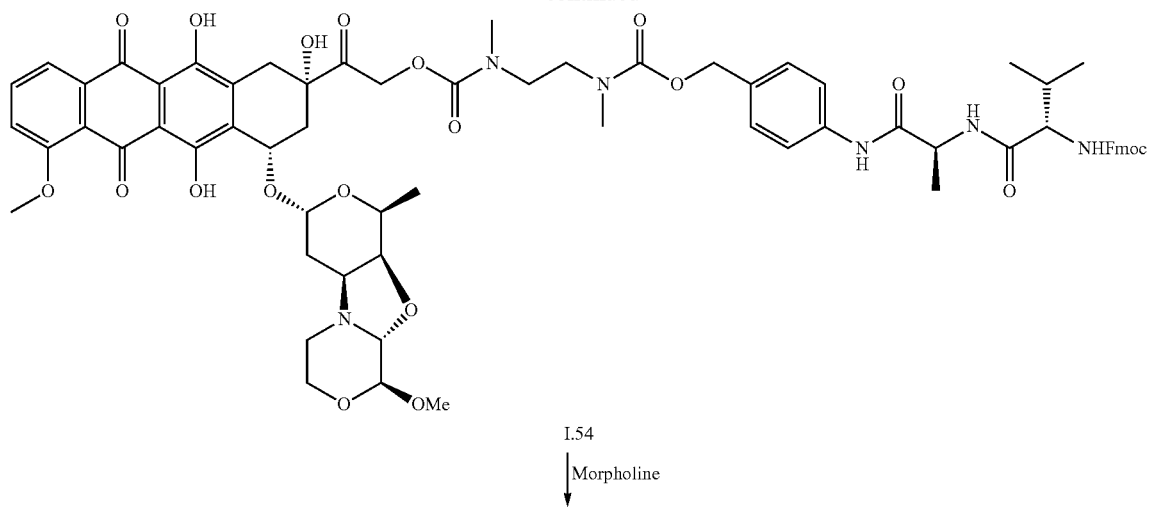
I.54 | Morpholine
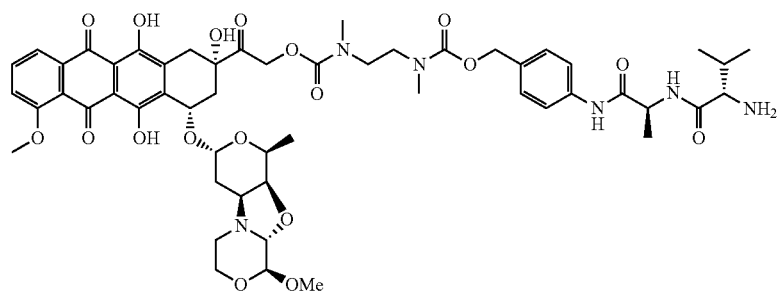
I.55
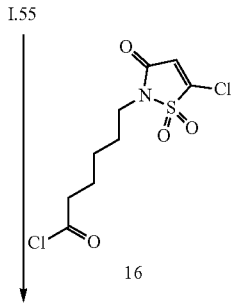
16
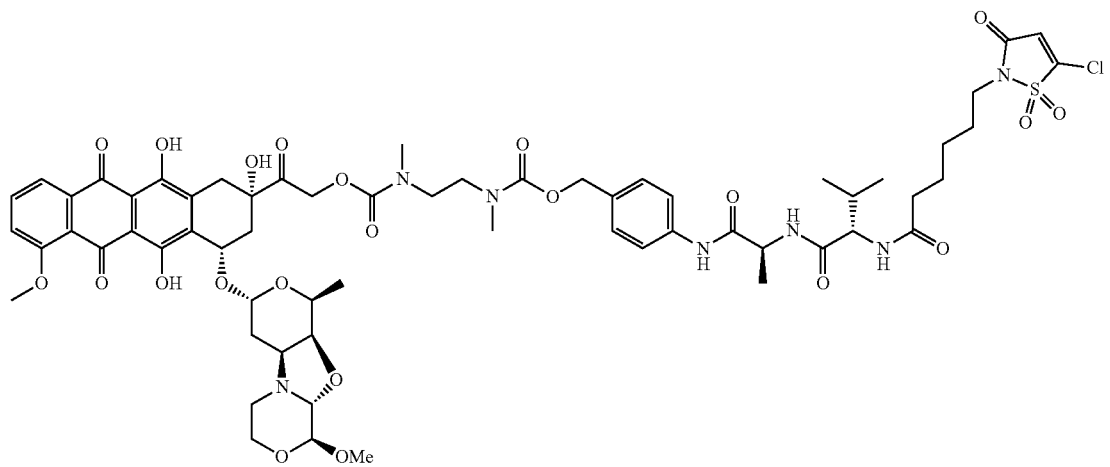
J Compound I.50 has been prepared according to the following synthetic path:

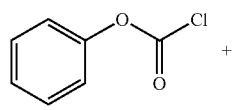

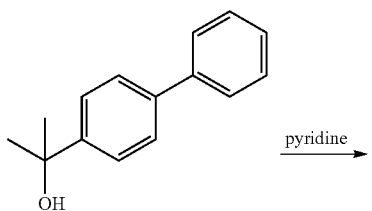

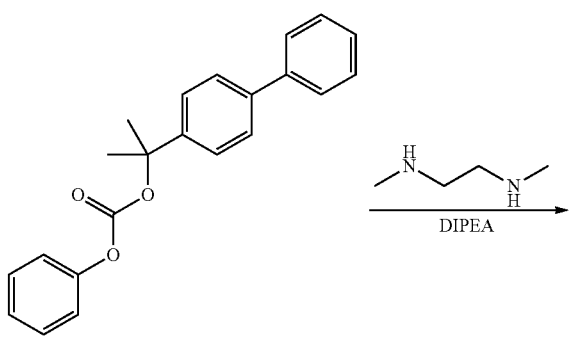

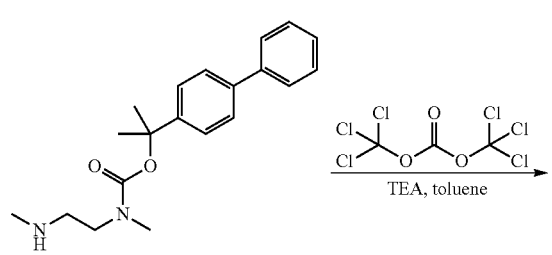

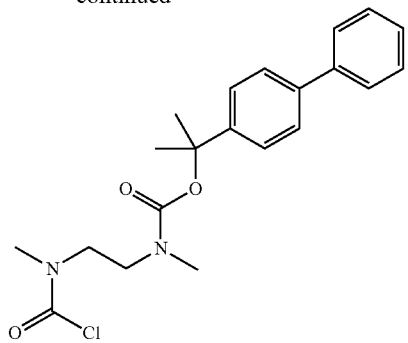

Compound I.48

In a flask under argon were added 2-([1,1'-biphenyl]-4-yl)propan-2-ol (1 g, 4.71 mmol) and pyridine (0.465 ml, 5.75 mmol) in DCM (5 mL). Then, the mixture was cooled to 0° C., and phenyl chloroformate (0.662 ml, 5.28 mmol) in DCM dry (2.4 mL) were added dropwise. The reaction mixture was warmed up to rt and stirred for 18 h (check by LCMS). The crude was concentrated in vacuo. The solid mixture was dissolved in DCM and washed with brine 3 times. The organic layer was dried over $Na_2SO_4$, filtered and concentrated in vacuo to give the desired compound I.48, Yield 880 mg, 56% as white solid. LCMS (ESI): 333.40 (MH+).

Compound I.49

In a flask under argon containing N,N'-dimethyl-1,2-ethanediamine (2791 µl, 26.2 mmol). N-ethyl-N-isopropyl-propan-2-amine (305 µl, 1.748 mmol) and DMF (4 mL), a solution of 2-([1,1'-biphenyl]-4-yl)propan-2-yl phenyl carbonate (581 mg, 1.748 mmol) in DMF (1.5 mL) was added at 0° C. The reaction mixture was warmed up to rt and stirred for 24 h (check by LCMS). The crude was concentrated in vacuo and the residue was purified by automatic column chromatography (Interchim, solid deposit): DCM/MeOH: 9/1. The desired fractions were concentrated in vacuo to give the desired compound I.49, Yield 433 mg, 76% as yellow oil. LCMS (ESI): 327.43 (MH+).

Compound I.50

In a flask under argon containing bis(trichloromethyl) carbonate (157 mg, 0.531 mmol) and toluene (4.3 mL), a solution of 2-([1,1'-biphenyl]-4-yl)propan-2-yl methyl(2-(methylamino)ethyl)carbamate (433 mg, 1,326 mmol) and triethyl amine (368 µl, 2.65 mmol) in toluene (2.9 mL) was added at 0° C. The reaction mixture was warmed up to rt and stirred for 1 h (check by LCMS). The solution was filtered, and the solvent was concentrated in vacuo and the residue was purified by automatic column chromatography (Interchim, solid deposit): cyclohexane/ethyl acetate: 7/3. The desired fractions were concentrated in vacuo to give the desired compound I.50, Yield 166 mg, 33% as white solid. LCMS (ESI): 405.60 (MH+).

Compound I.52 has been prepared according to the following synthetic path:
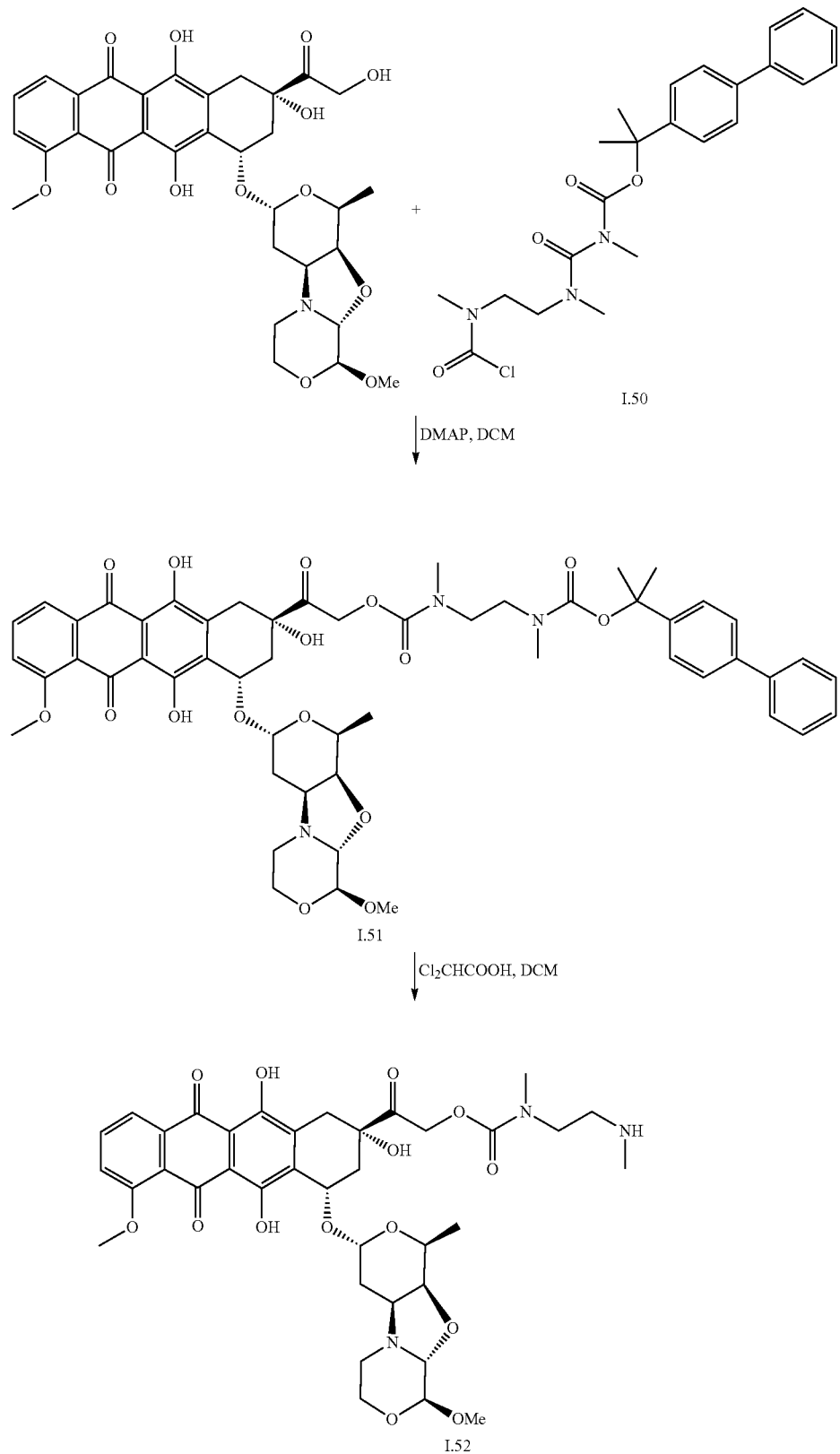

Compound I.51

In a flask under argon containing (8S,10S)-6,8,11-trihydroxy-8-(2-hydroxyacetyl)-1-methoxy-10-(((1S,3R,4aS,9S,9aR,10aS)-9-methoxy-1-methyloctahydro-1H-pyrano[4',3':4,5]oxazolo[2,3-c][1,4]oxazin-3-yl)oxy)-7,8,9,10-tetrahydrotetracene-5,12-dione (50 mg, 0.078 mmol), 4-dimethylaminopyridine (47.6 mg, 0,390 mmol), molecular sieves 0.4 nm (33 mg) and DCM (1 mL), a solution of 2-([1,1'-biphenyl]-4-yl)propan-2-yl (2-((chlorocarbonyl)(methyl)amino)ethyl)(methyl)carbamate (91 mg, 0.234 mmol)) in DCM (0.5 mL) were added. This mixture was stirred in the dark at 25° C., for 5 days. The solution was filtered, and the solvent was concentrated in vacuo and the residue was used without further purification in the next step.

Compound I.52

To a solution of product I.51 in DCM (1 ml) in ice bath, a solution of dichloroacetic acid (96 µl, 1.169 mmol) in 0.5 mL of DCM was added. The solution was stirred at rt for 2 h.

The solvent was concentrated in vacuo and the residue was purified by automatic column chromatography (Interchim, solid deposit): DCM/MeOH: 9/1. The desired fractions were concentrated in vacuo to give the desired compound I.52, Yield 13 mg, 22% as red solid. LCMS (ESI): 756.76 (MH+).

Compound I.53

In a flask under argon were added (9H-fluoren-9-yl)methyl ((S)-1-(((S)-1-((4-(hydroxymethyl)phenyl)amino)-1-oxopropan-2-yl)amino)-3-methyl-1-oxobutan-2-yl)carbamate (250 mg, 0.485 mmol), bis(perfluorophenyl) carbonate (382 mg, 0.970 mmol) and DMF (4 mL). Then, the mixture was cooled to 0° C., and N-ethyl-N-isopropylpropan-2-amine (127 µl, 0.727 mmol) was added dropwise. The reaction mixture was warmed up to rt and stirred for 2 h (check by LCMS). The crude was concentrated in vacuo. The crude was purified by automatic column chromatography (Interchim, solid deposit): DCM/MeOH: 9/1. The desired fractions were concentrated in vacuo to give the desired compound I.53, Yield 281 mg, 80% as yellow oil. LCMS (ESI): 726.65 (MH+).

Compound I.54

In a flask under argon were added 2-oxo-2-((2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-6,11-dioxo-1,2,3,4,6,11-hexahydrotetracen-2-yl)ethyl methyl(2-(methylamino)ethyl)carbamate (78 mg, 0.103 mmol), 1-hydroxybenzotriazole (27.9 mg, 0.206 mmol), N,N'-diisopropylethylamine (35.1 µl, 0.206 mmol) and DMF (2 mL). Then, the mixture was cooled to 0° C., and (9H-fluoren-9-yl)methyl ((S)-3-methyl-1-oxo-1-(((S)-1-oxo-1-((4-(((((perfluorophenoxy)carbonyl)oxy)methyl)phenyl)amino)propan-2-yl)amino)butan-2-yl)carbamate (112 mg, 0.155 mmol) was added dropwise. The reaction mixture was warmed up to rt and stirred for 2 h (check by LCMS). The crude was concentrated in vacuo. The crude was purified by automatic column chromatography (Interchim, solid deposit): DCM/MeOH: 9/1. The desired fractions were concentrated in vacuo to give the desired compound I.54, Yield 77 mg, 58% as red oil. LCMS (ESI): 1298.0 (MH+).

Compound I.55

In a flask under argon were added 4-((S)-2-((S)-2-((((9H-fluoren-9-yl)methoxy)carbonyl)amino)-3-methylbutanamido)propanamido)benzyl (2-oxo-2-((2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-6,11-dioxo-1,2,3,4,6,11-hexahydrotetracen-2-yl)ethyl) ethane-1,2-diylbis(methylcarbamate) (77.7 mg, 0.060 mmol) and DMF (2 mL). Then, the mixture was cooled to 0° C., and morpholine (259 µl, 2.99 mmol) was added dropwise. The reaction mixture was warmed up to rt and stirred for 2 h (check by LCMS). The crude was concentrated in vacuo. The crude was purified by automatic column chromatography (Interchim, solid deposit): DCM/MeOH: 9/1. The desired fractions were concentrated in vacuo to give the desired compound I.55, Yield 32 mg, 50% as red oil. LCMS (ESI): 1075.80 (MH+).

Example J

In a flask under argon at 25° C., were introduced 4-((S)-2-((S)-2-amino-3-methylbutanamido)propanamido) benzyl (2-oxo-2-((2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-6,11-dioxo-1,2,3,4,6,11-hexahydrotetracen-2-yl)ethyl) ethane-1,2-diylbis(methylcarbamate) (32 mg, 0.030 mmol, 1 eq) in dichloromethane (2 mL). The mixture was cooled to 0° C., and N-ethyl-N-isopropylpropan-2-amine (20.74 µl, 0.119 mmol) was added. The mixture was stirred at 0° C., for 10 min then addition of Example 16 diluted in dichloromethane (2 mL). The mixture was then stirred at 0° C., for 2 h (until complete conversion was observed by LCMS). The crude was concentrated in vacuo and purified by automatic column chromatography (Interchim, 12 g, solid deposit): DCM/MeOH: 9/1. The desired fractions were concentrated in vacuo to give the desired Example J (also named compound F562646), Yield 17.4 mg, 40% as red oil. LCMS (ESI): 1338.41 (MH+).

Figure 21:
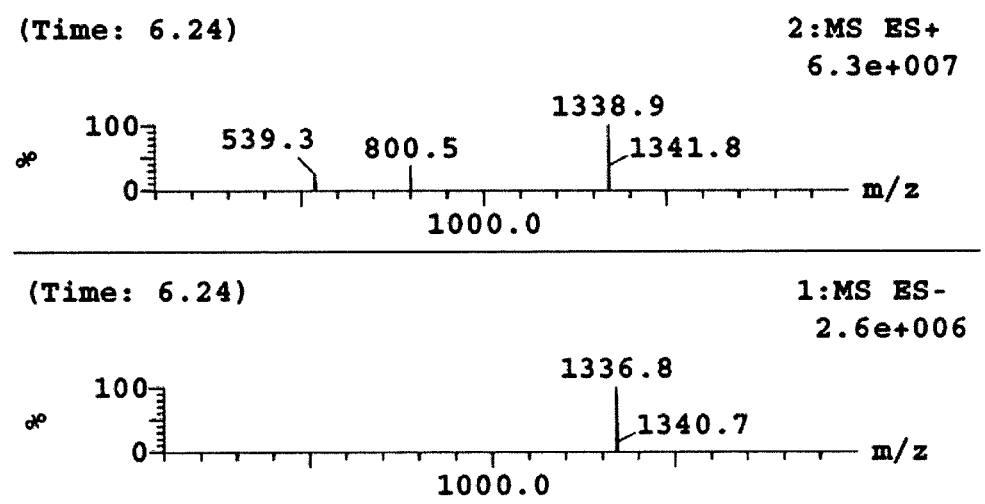

The mass spectrum of this drug-linker conjugate is represented on FIG. 21.

Example K
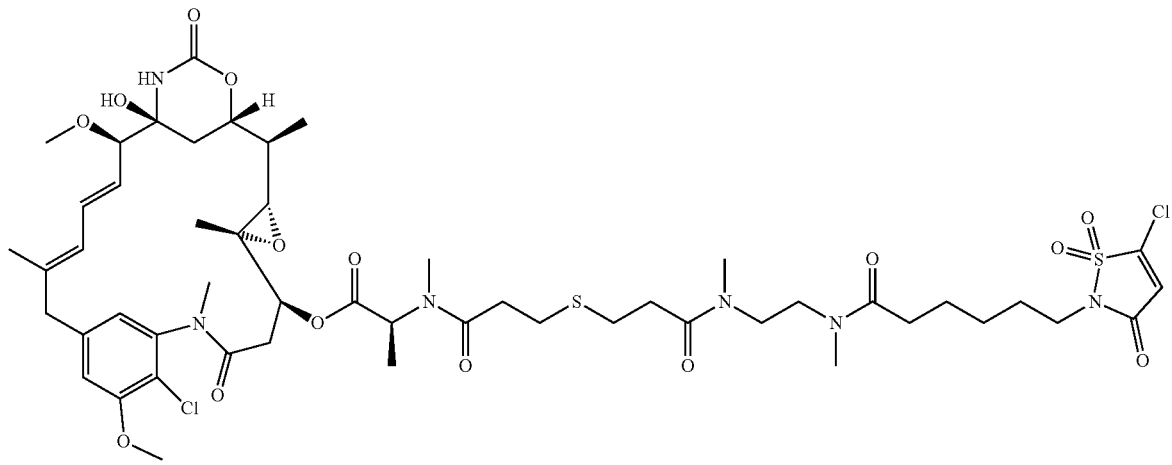
Example K has been synthesized according to the following synthetic path:
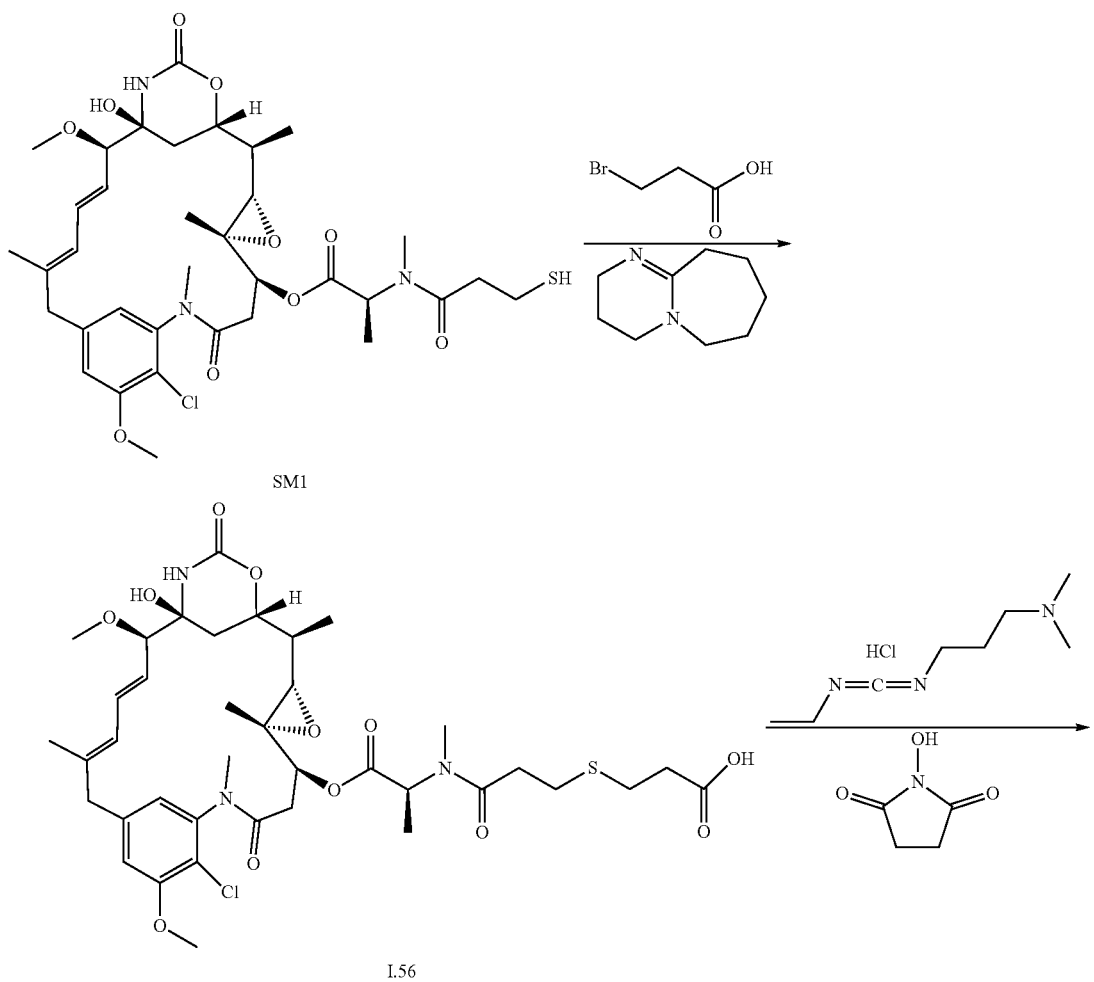

157 158
-continued
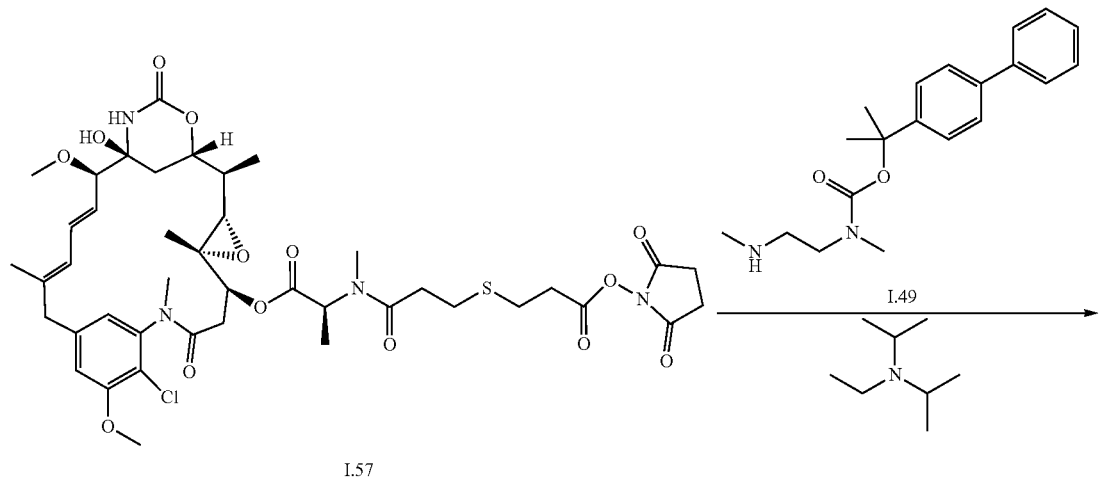
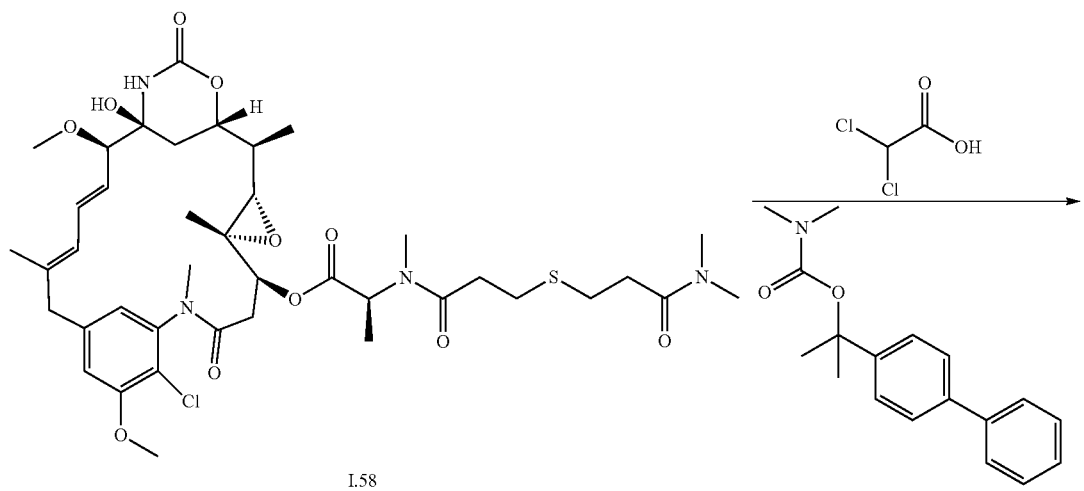
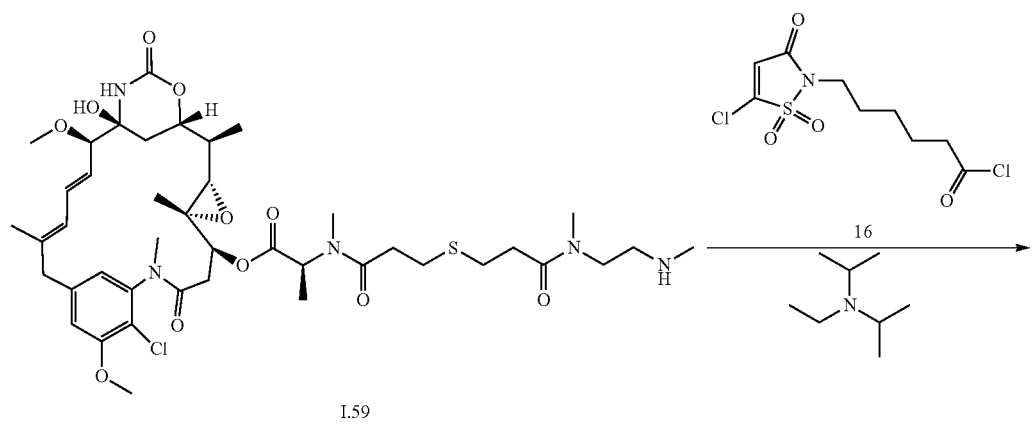

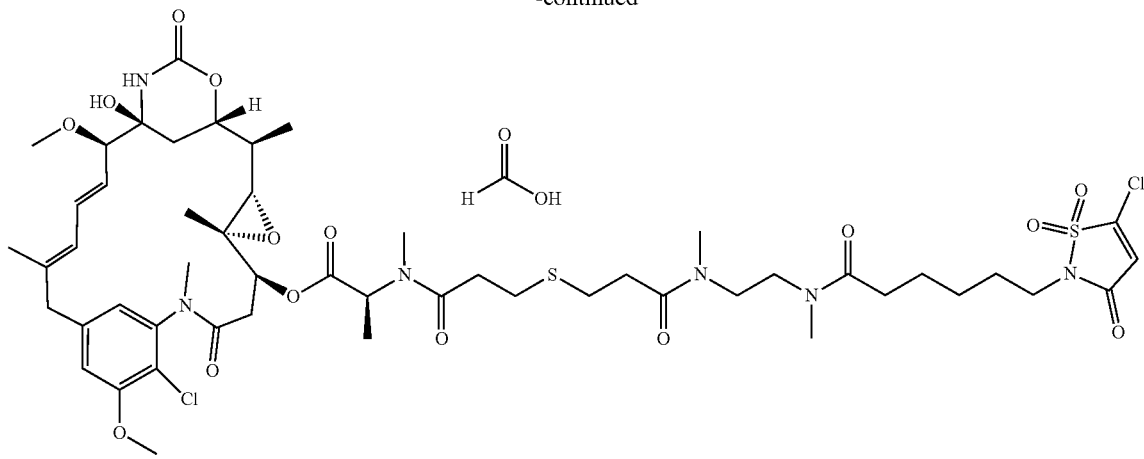

K

Compound I.56

In a flask under argon was added starting material SMI (100 mg, 0.135 mmol) and DMF (1 ml). The mixture was cooled to 0° C., then a solution of 3-bromopropanoic acid (22.79 mg, 0.149 mmol) and 2,3,4,6,7,8,9,10-octahydropyrimido[1,2-a] azepine (40.5 µl, 0.271 mmol) in DMF (0.5 mL) was added dropwise. Then The mixture was warmed up to rt and was stirred until complete conversion was observed by LCMS. The crude was concentrated in vacuo and purified by automatic column chromatography (Interchim, 12 g, solid deposit): DCM/MeOH: 80/20. The desired fractions were concentrated in vacuo to give the desired compound I.56, Yield 108 mg, 98% as white solid. LCMS (ESI): 811.35 (MH+).

Compound I.57

In a flask under argon were added compound I.56 (87.0 mg, 0.107 mmol) and DCM (2 mL). Then, the mixture was cooled to 0° C., N-hydroxysuccinimide (13.59 mg, 0.118 mmol) and 1-(3-dimethylaminopropyl)-3-ethylcarbodiimide hydrochloride (30.9 mg, 0.161 mmol) were added. The reaction mixture was warmed up to rt and stirred for 2 h (CHECK LCMS). The crude was concentrated in vacuo. The crude material was used without further purification for the next step.

Compound I.58

In a flask under argon was added compound I.57 (97 mg, 0.107 mmol) and DCM (1 ml), then a solution of compound I.49 in 1 mL of DCM and N, N'-diisopropylethylamine (37.3 µl, 0.214 mmol) was added dropwise. The mixture was stirred until complete conversion was observed by LCMS. The crude was concentrated in vacuo and used without further purification for the next step.

Compound I.59

In a flask under argon was added compound I.58 (58 mg, 0.052 mmol) and DCM (1 ml). The mixture was cooled to 0° C., then dichloroacetic acid (86 µl, 1.037 mmol) was added dropwise. Then the mixture was warmed up to rt and was stirred until complete conversion was observed by LCMS. The crude was concentrated in vacuo and purified by automatic column chromatography (Interchim, 12 g, solid deposit): DCM/MeOH: 80/20. The desired fractions were concentrated in vacuo to give the desired compound 1.59, Yield 39 mg, 86% as white solid. LCMS (ESI): 882.6 (MH+).

Example K

In a flask under argon at 25° C., were introduced compound I.59 in dichloromethane (1 mL). The mixture was cooled to 0° C., and N-ethyl-N-isopropylpropan-2-amine (15.83 µl, 0.091 mmol) was added. The mixture was stirred at 0° C., for 10 min then addition of Example 16 diluted in dichloromethane (2 mL). The mixture was then stirred at 0° C., for 2 h (until complete conversion was observed by LCMS). The crude was concentrated in vacuo and purified by preparative HPLC (HCOOH conditions) to give the desired Example K, Yield 6 mg, 22% as white solid. LCMS (ESI): 1165.37 (M+Na)$^+$.

The mass spectrum and the TOF-MS spectrum of this drug-linker conjugate are represented respectively on FIGS. 22A and 22B.

3. CONJUGATION WITH SOMATOSTATIN

VI1. Reaction of Somatostatin with Benzyl 6-(5-chloro-1,1-dioxido-3-oxoisothiazol-2(3H)-yl) hexanoate

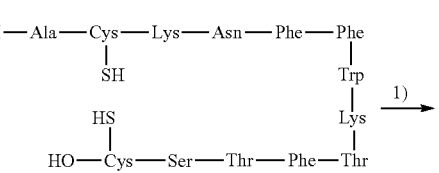

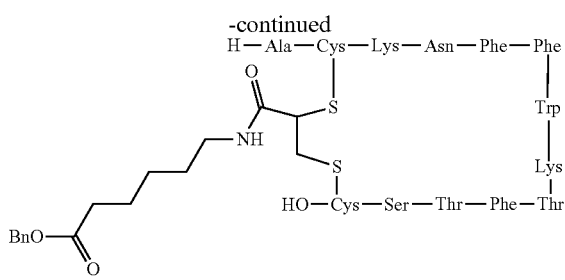

Chemical Formula: $C_{92}H_{123}N_{19}O_{22}S_2$
Exact Mass: 1909.853

1) 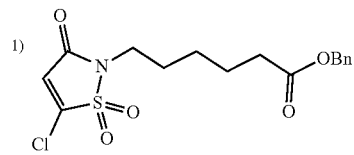

Buffer ($NaH_2PO_4$ 20 mM, pH = 8), 40% MeCN, 2,5% DMF), 37° C.

1 mg of lyophilized somatostatin ($m_{exact}$=1636.72) was solubilized in 4 mL of buffer (57.5% $NaH_2PO_4$ 20 mM, pH 6.5, 40% ACN, 2.5% DMF) to yield a concentration of 153 μM (0.25 mg/mL), 33.5 mg of TCEP were dissolved in 4 mL of buffer (57.5% $NaH_2PO_4$ 20 mM, pH 6.5, 40% ACN, 2.5% DMF). To 300 μL of somatostatin solution (1 eq.) were added 3 μL of TCEP solution (1.1 eq.). The solution is stirred at 37° C., for 1 h. Commercial somatostatin: $R_{t,1}$ (in ACN): 1.57; MS ES+: $M^{+3}/3$=546.4, $M^{+2}/2$=819.2. Reduced disulfide bond somatostatin: $R_{t,1}$ (in ACN): 1.50; MS ES+: $M^{+3}/3$=547.2, $M^{+2}/2$=820.3, 5 mg of Benzyl 6-(5-chloro-1,1-dioxido-3-oxoisothiazol-2(3H)-yl)hexanoate (I.6) were solubilized in 800 μL of ACN. 3 μL of Benzyl 6-(5-chloro-1,1-dioxido-3-oxoisothiazol-2(3H)-yl)hexanoate (1.1 eq.) in solution were added to the somatostatin solution. The solution was stirred at 37° C. $R_{t,1}$ (in ACN): 1.66; MS ES+: $M^{+3}/3$=637.6, $M^{+2}/2$=956.0.

The same reaction was performed in buffer pH 8 (57.5% $NaH_2PO_4$ 20 mM, pH 8, 40% ACN, 2.5% DMF).

Figure 10:
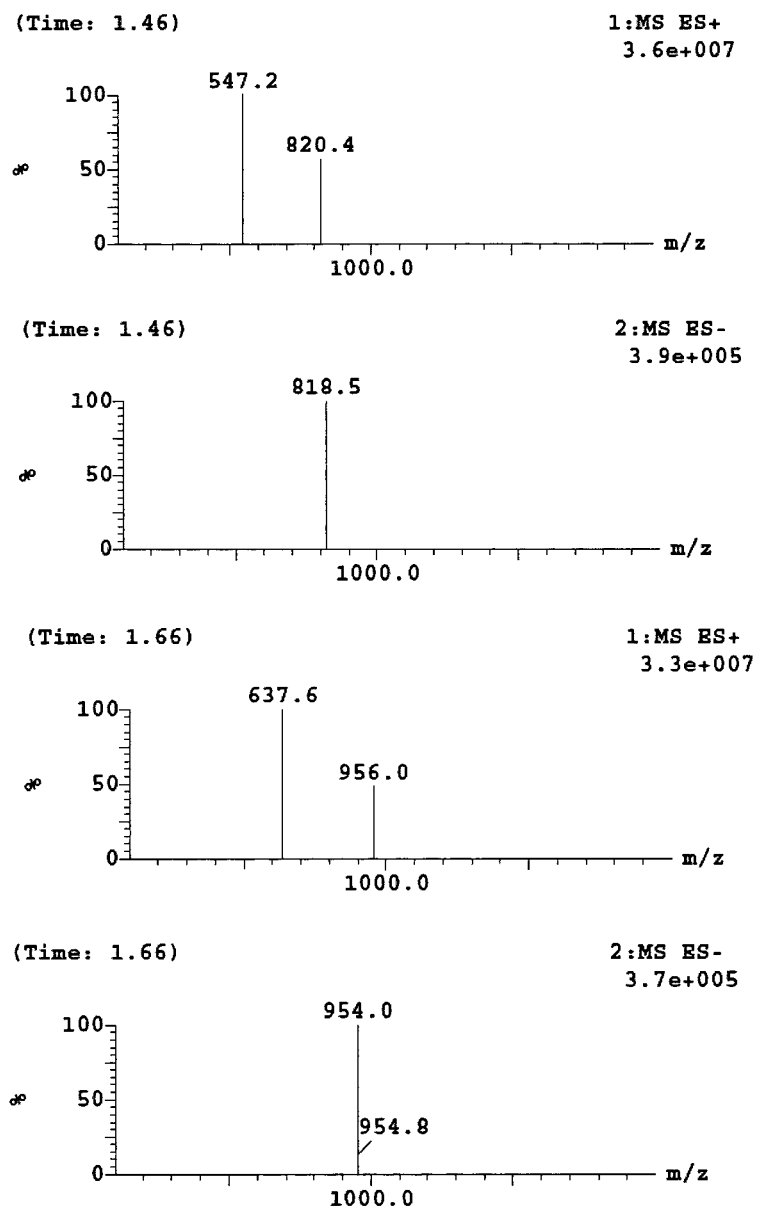
FIGS. 10 and 11 represent mass spectra of drug-somatostatin conjugates according to the invention.

The mass spectrum of the obtained conjugate is represented on FIG. 10.

VI2. Reaction of Somatostatin with Benzyl 6-(4,5-dichloro-1,1-dioxido-3-oxoisothiazol-2(3H)-yl)hexanoate

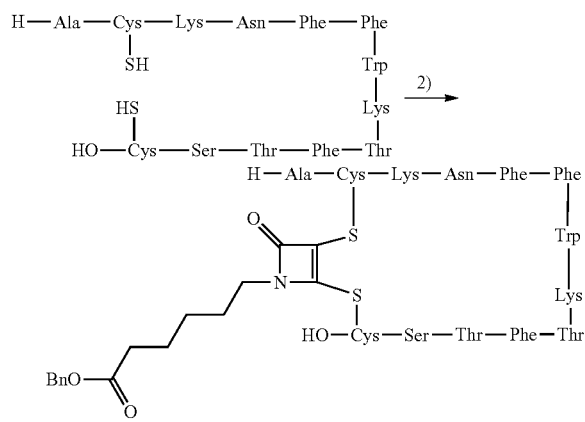

Chemical Formula: $C_{92}H_{121}N_{19}O_{22}S_2$
Exact Mass: 1907.837

2) 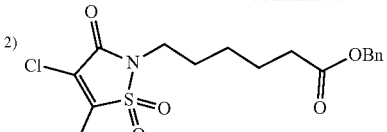

Buffer ($NaH_2PO_4$ 20 mM, pH = 8), 40% MeCN, 2,5% DMF), 37° C.

1 mg of lyophilized somatostatin ($m_{exact}$=1636.72) was solubilized in 4 mL of buffer (57.5% $NaH_2PO_4$ 20 mM, pH 6.5, 40% ACN, 2.5% DMF) to yield a concentration of 153 μM (0.25 mg/mL), 33.5 mg of TCEP were dissolved in 4 mL of buffer (57.5% $NaH_2PO_4$ 20 mM, pH 6.5, 40% ACN, 2.5% DMF). To 300 μL of somatostatin solution (1 eq.) were added 3 μL of TCEP solution (1.1 eq.). The solution is stirred at 37° C., for 1 h. Commercial somatostatin: $R_{t,1}$ (in ACN): 1.57; MS ES+: $M^{+3}/3$=546.4, $M^{+2}/2$=819.2. Reduced disulfide bond somatostatin: $R_{t,1}$ (in ACN): 1.50; MS ES+: $M^{+3}/3$=547.2, $M^{+2}/2$=820.3, 5.4 mg of Benzyl 6-(4,5-dichloro-1,1-dioxido-3-oxoisothiazol-2(3H)-yl)hexanoate (1.7) were solubilized in 800 μL of ACN. 3 μL of Benzyl 6-(4,5-dichloro-1,1-dioxido-3-oxoisothiazol-2(3H)-yl) hexanoate (1.1 eq.) in solution were added to the somatostatin solution. The solution was stirred at 37° C. $R_{t,1}$ (in ACN): 1.65; MS ES+: $M^{+3}/3$=637.3, $M^{+2}/2$=955.5.

The same reaction was performed in buffer pH 8 (57.5% $NaH_2PO_4$ 20 mM, pH 8, 40% ACN, 2.5% DMF).

Figure 11:
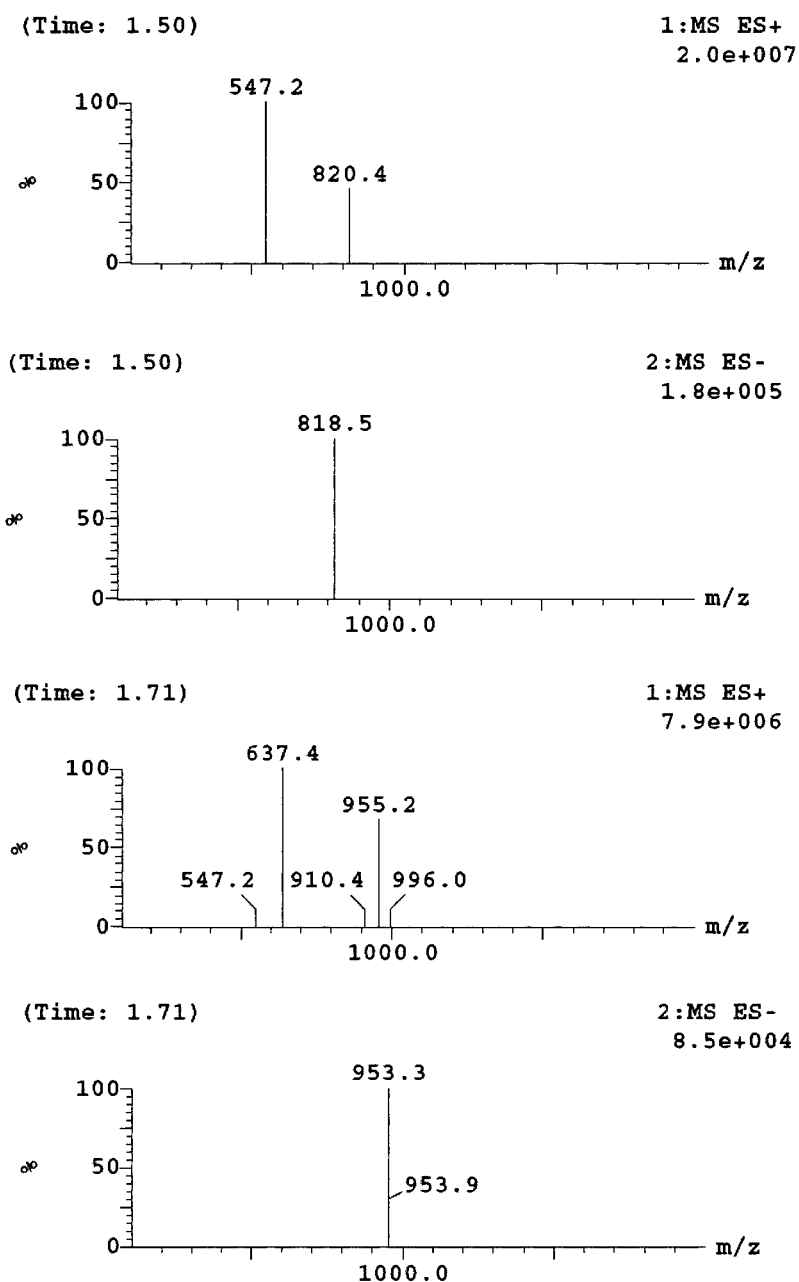

The mass spectrum of the obtained conjugate is represented on FIG. 11.

4. CONJUGATION WITH MONOCLONAL ANTIBODIES

4.1. ADC Synthesis, Purification and Characterization

The procedure described below applies to chimeric, humanized and human IgG1 forms. It must be understood that for any other forms, such as IgG2, IgG4, etc., the person skilled in the art would be capable of adapting this procedure using the general knowledge.

Ab1 antibody is an anti-IGF1R IgG1 monoclonal antibody. This antibody corresponds to antibody 208F2 of WO2015162291 (see table 3, page 36) for which the three light chain CDRs have sequences SEQ ID Nos. 9, 5 and 11; the three heavy chain CDRs have sequences SEQ ID Nos. 7, 2 and 3; the light chain variable domain has sequence SEQ ID No. 18; and the heavy chain variable domain has sequence SEQ ID No. 13.

Ab2 antibody is an irrelevant chimeric (IgG1) antibody directed at a bacterial protein, which is the outer membrane protein A from *E. coli*, and called c9G4 (Haeuw J. F, and Beck A. Proteomics for development of immunotherapies, In Proteomics: Biomedical and Pharmaceutical Applications, Kluwer Academic Publishers, Ed. Hondermarck H., 2014, pages 243-278; WO2015162291).

Antibodies (1-5 mg/ml) were partially reduced with TCEP hydrochloride in 10 mM borate buffer pH 8.4 containing 150 mM NaCl and 2 mM EDTA for 2-4 hours at 37° C. Typically, 6-20 molar equivalents of TCEP were used to target a DAR of around 4. The partial antibody reduction was confirmed by SDS-PAGE analysis under non-reducing conditions. The antibody concentration was then adjusted to 1 mg/ml with 10 mM borate buffer pH 8.4 containing 150 mM NaCl, 2 mM EDTA, 6% sucrose and a 5-20 molar excess of drug-linker conjugate to antibody was added from a 10 mM solution in DMSO. Seven examples of drug-linker conjugate according to the invention were coupled to Ab1:

Example A and Example B giving respectively ADC1-A and ADC1-B (non-cleavable linkers);

Example C, Example D, Example E, Example F and Example G giving respectively ADC1-C, ADC1-D, ADC1-E, ADC1-F and ADC1-G (cleavable linkers).

The final DMSO concentration was adjusted to 10% to maintain the solubility of the drug in the aqueous medium during coupling. The reaction was carried out for 1-4 h at room temperature or 37° C. The drug excess was quenched by addition of 2.5 moles of N-acetylcysteine per mole of drug and incubation for 1 h at room temperature.

After dialysis against 25 mM His buffer pH 6.5 containing 150 mM NaCl and 6% sucrose overnight at 4° C., the re-bridged antibody-drug conjugates were purified by using methods known to persons skilled in the art with commercial chromatography columns and ultrafiltration units. The purified ADCs were stored at 4° C., after sterile filtration on 0.2 µm filter.

They were further analyzed by SDS-PAGE under reducing and non-reducing conditions to confirm drug conjugation and by SEC on analytical TSK G3000 SWXL column to determine the content of monomers and aggregated forms. The content of aggregated forms deduced from the SEC chromatograms (FIG. 13) was lower than 5% as shown in Table 9.

TABLE 9

Content of aggregated forms

| Ab/ADC | % monomer |
|---|---|
| Ab1 | 99.6 |
| ADC1-A | 99.0 |
| ADC1-B | 99.3 |
| ADC1-C | 98.1 |
| ADC1-D | 99.5 |
| ADC1-E | 99.4 |
| ADC1-F | 99.6 |
| ADC1-G | 95.2 |

SDS-PAGE analyses confirm formation of fully bridged antibody H2L2 (FIG. 12). However other species (H2L, H2 and HL), corresponding to partially bridged antibody, were also detected. It's important to note that these species were visible when samples were heat-treated in reducing conditions before the run to ensure full dissociation of heavy and light chains (H and L), not connected by an intact interchain bridge.

The protein concentrations were determined by using the BCA assay with IgG as standard. The DAR was estimated for each purified ADC by HIC using a TSK-Butyl-NPR column. It was comprised between 3.5 and 4.3 (Table 10). HIC profiles revealed that no DAR0 and a major peak of DAR 4 were observed for most of the ADCs synthesised. Indeed, only ADC1-C and E show trace of DAR0. Moreover, for ADC1-A, B. C and G only DAR3, DAR4 and DAR5 were observed. Excepted for ADC1-D, the major peak is a DAR4. Compare to a second-generation ADC, these ADCs are more homogeneous as shown in Table 10.

TABLE 10

DAR distribution estimated by HIC using a TSK-Butyl-NPR column

| | DAR % | | | | | | | | |
|---|---|---|---|---|---|---|---|---|---|
| | DAR 0 | DAR 1 | DAR 2 | DAR 3 | DAR 4 | DAR 5 | DAR 6 | DAR 7 | DAR 8 |
| Adcetris | 6.0 | 1.34 | 25.2 | 3.7 | 32.9 | 0 | 22.5 | 1.5 | 6.9 |
| ADC1-A | 0 | 0 | 0 | 0 | 64.9 | 35.1 | 0 | 0 | 0 |
| ADC1-B | 0 | 0 | 0 | 39.8 | 47.6 | 12.5 | 0 | 0 | 0 |
| ADC1-C | 0.6 | 1.0 | 0.8 | 8.2 | 63.1 | 26.3 | 0 | 0 | 0 |
| ADC1-D | 0 | 0 | 0 | 44.6 | 39.5 | 10.6 | 3.8 | 1.5 | 0 |
| ADC1-E | 2.1 | 4.5 | 4.0 | 11.9 | 56.3 | 21.1 | 0 | 0 | 0 |
| ADC1-F | 0 | 0.5 | 3.2 | 22.6 | 73.7 | 0 | 0 | 0 | 0 |
| ADC1-G | 0.1 | 0.4 | 2.6 | 18.6 | 68.1 | 10.2 | 0 | 0 | 0 |

Adcetris® (brentuximab vedotin) has been used as a reference since it uses a second generation maleimide linker conjugated to the cysteines of the antibody. It is the best representative example of second generation ADC; the technology described in this demand being can be considered as the third generation.

4.2. ADC ANALYSIS BY NATIVE MASS SPECTROMETRY

All chemicals were purchased from Sigma-Aldrich: ammonium acetate (A1542), caesium iodide (21004), 2-propanol (19516). IgGZERO (A0-IZ1-010) enzyme was obtained from Genovis. Aqueous solutions were prepared using an ultra-pure water system (Sartorius, Göttingen, Germany).

ADC1-A to ADC1-G were deglycosylated prior to native MS experiments. This was performed by incubating one unit of IgGZERO per microgram of ADC for 30 min at 37° C. Then, ADCs were buffer exchanged against a 150 mM ammonium acetate solution (pH 6.9) using six cycles of concentration/dilution using a microconcentrator (Vivaspin, 10-kD cutoff, Sartorius, Göttingen, Germany). Protein concentration was determined by UV absorbance using a NanoDrop spectrophotometer (Thermo Fisher Scientific, France). Non-denaturing (native) mass spectrometry of ADCs was performed on a Q-TOF (Synapt G2 HDMS, Waters, Manchester, UK) mass spectrometer operating in the positive ion mode both coupled to an automated chip-based nanoelectrospray device (Triversa Nanomate, Advion, Ithaca, USA). Analyses were performed in the m/z 1000-10 000 range. Samples were diluted in 150 mM NH$_4$OAc at pH 6.9 and infused at 10 µM. External calibration was performed using singly charged ions produced by a 2 g/L solution of caesium iodide in 2-propanol/water (S0/S0 v/v).

The voltage of the nanoelectrospray was set at 1.75 kV and nitrogen nanoflow at 0.75 psi. The cone voltage was set to 180 volts and the backing pressure to 6 mbar.

FIG. 14 presents examples of non-deconvoluted MS spectrum.

The DAR distribution (FIG. 15) was determined after deconvolution using MaxEnt™ algorithm from Mass Lynx 4.1 (Waters, Manchester, UK). The parameters of the software were optimized for each spectrum.

Average DAR values (FIG. 15) were calculated by using the following equation (where j is the maximum number of drug load).

$$DAR = \frac{\left(\sum_{i=0}^{j} i * \text{intensity } Di\right)}{\sum_{i=0}^{j} \text{intensity } Di}$$

The results were derived from the relative peak intensities of each charge states in the raw spectra and are presented in Table 11 below.

TABLE 11

DAR distribution calculated using MaxEnt ™ algorithm from Mass Lynx 4.1

| ADC | DAR0 | DAR1 | DAR2 | DAR3 | DAR4 | DAR5 | DAR6 | DAR7 | DAR8 | Average DAR |
|---|---|---|---|---|---|---|---|---|---|---|
| ADC1-A | 0 | 0 | 0 | 0 | 64 | 36 | 0 | 0 | 0 | 4.4 ± 0.1 |
| ADC1-B | 0 | 0 | 0 | 42 | 39 | 19 | 0 | 0 | 0 | 3.8 ± 0.1 |
| ADC1-D | 0 | 0 | 0 | 47 | 40 | 13 | 0 | 0 | 0 | 3.7 ± 0.1 |

FIG. 16 compares the DAR distribution, determined from raw spectra after mass deconvolution, for 2 different ADCs, i.e.:
- ADC1-C according to the invention prepared from Ab1 antibody and the drug-linker conjugate C (FIG. 16B) and
- a reference ADC Ref-A which is a comparative ADC synthesized from the same antibody (Ab1) and from a drug-linker conjugate corresponding to the drug-linker conjugate C in which the sulfomaleimide moiety

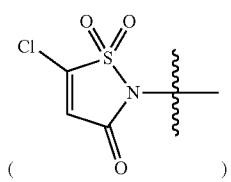 [SMILES: *N1C(=O)C=C(Cl)S1(=O)=O]

has been replaced by a maleimide moiety

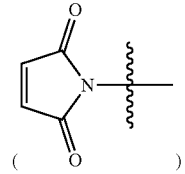

(FIG. 16A).

A heterogeneous distribution from DAR 0 to DAR 8 is observed for the ADC synthesized by using the classical maleimide chemistry to link the drug to the antibody (FIG. 16A), whereas the ADC generated by using the sulfomaleimide chemistry according to the invention is highly homogeneous with 75% of DAR 4 and no DAR 0/2 and 6/8 species (FIG. 16B). These results are summarized in Table 12 below.

TABLE 12

DAR distribution calculated using MaxEnt ™ algorithm from Mass Lynx 4.1

| ADC | DAR0 | DAR1 | DAR2 | DAR3 | DAR4 | DAR5 | DAR6 | DAR7 | DAR8 | Average DAR |
|---|---|---|---|---|---|---|---|---|---|---|
| ADC Ref-A | 6 | 4 | 29 | 0 | 33 | 0 | 18 | 0 | 10 | 3.8 |
| ADC1-C | 0 | 0 | 0 | 5 | 76 | 19 | 0 | 0 | 0 | 4.1 |

4.3. In Vitro Stability Study of ADCs in 4 Mammalian Sera Using a Ligand Binding Assay Method To establish the gain of stability, an in vitro stability study was conducted. It consists in the incubation of the ADCs at 37° C., for a period of 14 days. Samples were collected at day 0, 3, 7 and 14. The various samples (D0, D3, D7 and D14) were then analyzed by LBA to determine the concentration of total antibody versus the concentration of ADC. In practice, a solution of each ADC is prepared at 100 µg/ml in 4 sera (human, cynomolgus, mouse and rat) and incubated at 37° C., for a maximum of 14 days. Then aliquots are collected at D0, D3, D7 and D14, and stored at −80° C., until dosage. For total Ab and ADC quantification, the plates are thawed at room temperature with shaking and both LBA assays are run in parallel. Briefly, standard microtiter plates (MSD, Gaithersburg, USA) are coated using 30 µl of an anti-His antibody solution at 2 µg/ml prepared in PBS 1×. After an overnight incubation at 4° C., assay plates are treated with blocking buffer (3% MSD Blocker A (MSD, Gaithersburg, USA)) for 1 hour at 37° C. Then the recombinant His-taged antigen is added for 1 hour at 37° C., at the concentration of 2.5 µg/ml in assay buffer. After a washing step, samples are analyzed as duplicates at the 1/5000° dilution and incubated for 1 hour at 37° C., while standard ADCs are loaded in duplicate onto the assay plate. The detection step is done using either a goat anti-human Ig Kappa sulfo-tag solution at 1 µg/ml for the detection of total Ab or a mouse monoclonal anti-Drug antibody labelled with sulfotag for ADC detection. After a 1-hour incubation period at 37° C., the detection is realized using 150 µL of a 2×MSD-read T buffer containing surfactant (MSD, Gaithersburg, USA) just before reading using MSD Sector Imager.

The total antibody and ADC concentrations are determined at each timepoint and transformed in percentage, taking 100% as the quantity of total ADCs or antibody at each timepoint.

Data are illustrated in FIGS. 17A, 17B and 17C for 3 ADCs: ADC1-C (FIG. 17B) and ADC1-E (FIG. 17C) in which the drug has been linked to the Ab1 antibody using the sulfomaleimide chemistry according to the invention (by means of the drug-linker conjugate C or E respectively), in comparison to a reference ADC Ref-B in which the drug has been linked to the antibody using a classical maleimide chemistry (FIG. 17A).

Drug-Linker Moiety Used to Prepare Reference ADC Ref-B

As a comparator, a drug-linker using the same payload and a non-cleavable linker was chosen (drug-linker of ADC Ref-B). It was conjugated to the same antibody using a maleimide chemistry. The choice of this comparator limits "the instability" of the reference ADC in the sera by deconjugation from the antibody through a retro-Michael reaction. Compared to our constructs based on a cleavable linker, this comparator is thus favoured which makes the stability improvement of our drug-linkers even more spectacular.

As expected a decrease in ADC concentration is observed for the ADC synthesized using classical maleimide chemistry (ADC Ref-B), whereas the ADCs generated using sulfomaleimide chemistry according to the invention (ADC1-C & ADC1-E) surprisingly are much more stable over the 14-day period.

4.4. In Vitro Cytotoxicity of ADCs

The in vitro cytotoxicity of ADC according to the invention was evaluated. In order to evaluate the non-specific cytotoxicity, the compounds were also coupled to an irrelevant chimeric antibody (Ab2), called c9G4, at the same DAR and using the same drug-linker conjugates to give ADC2-C with Example C, ADC2-E with Example E and ADC2-F with Example F.

MCF-7 and NCI-H2122 cells were plated on 96 well plates (2500 cells per well) in complete growth media. The day after, serial dilutions of the tested ADCs were added to the corresponding wells and incubated at 37° C., for 6 days. Six days after the addition of the ADCs, a Cell Titer Glo assay (PROMEGA) was performed on the plates to check the viability of the cells.

The results obtained, expressed in percentage of viability, are shown in FIGS. 18A and 18B. As expected, the ADCs synthesized with the irrelevant antibody showed no or modest cytotoxic activity on both MCF-7 and NCI-H2122 cells. On the opposite, the ADCs of the invention: ADC1-C, ADC1-E and ADC1-F decreased dramatically cell viability. $EC_{50}$ values of $7.61 \cdot 10^{-11}$, $7.16 \cdot 10^{-11}$ and $3.64 \cdot 10^{-11}$ M were obtained for ADC1-C, ADC1-E and ADC1-F respectively on NCI-H2122 and $EC_{50}$ values of $1.04 \cdot 10^{-11}$, $1.33 \cdot 10^{-11}$ and $7.39 \cdot 10^{-11}$ M were obtained for ADC1-C, ADC1-E and ADC1-F respectively on MCF7, indicating potent cytotoxic activity.

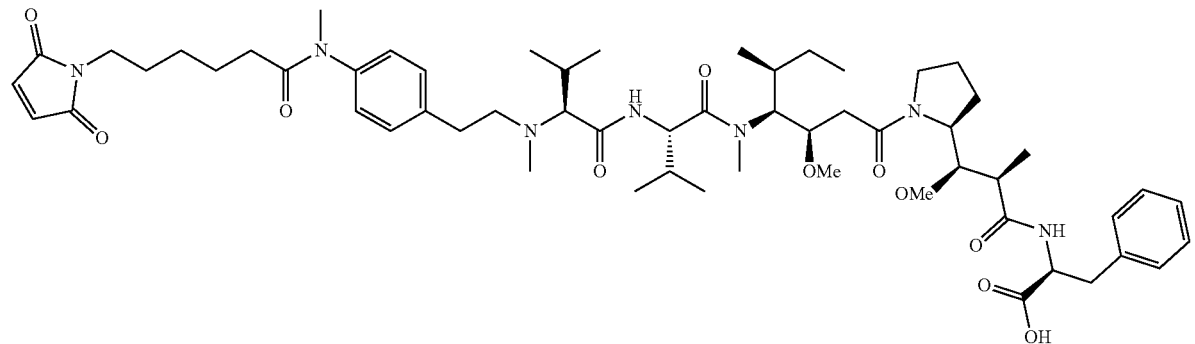 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)CCCCCN2C(=O)C=CC2=O)cc1)C(C)C]

4.5. In Vivo

All experimental protocols were approved by Pierre Fabre's Institutional Animal Care and use Committee.

For ovarian cancer model, 7 weeks old female SCID mice (Charles RIVER Laboratories) were engrafted subcutaneously with $10 \cdot 10^6$ CaoV3 cells (6 animals per groups).

Treatment by intravenous administration of ADC1-C according to the invention, reference ADC Ref-A or ADC vehicle was initiated when tumors reached approximately 150 mm³. The animals were either treated by one injection (Q1d1) or by 3 injections (once weekly) (Q7d3). Tumor volume (Length×width×height×0.52) was measured by electronic caliper at least twice weekly during approximatively 25 days after the first injection. The results are presented on FIG. 19 (animals treated at Q1d1) and FIG. 20 (animals treated at Q7d3).

As can be seen on FIGS. 19 and 20, the ADCs according to the invention have a great efficacy with a complete tumor regression even after a single injection.

5. CONJUGATION OF PNU-159682 DERIVATIVES TO MONOCLONAL ANTIBODIES

5.1. ADC Synthesis, Purification and Characterization

Two PNU-159682 derivatives, namely F562524 (example J) and F562646 (example H), were coupled to the antibodies 208F2 (Ab1) and c9G4 (Ab2), under the conditions previously described in example 4, 208F2 (Ab1) and c9G4 (Ab2) are as disclosed in example 4. Briefly, antibodies (1-5 mg/ml) were partially reduced with 6-20 equivalents of TCEP hydrochloride in 10 mM borate buffer pH 8.4 containing 150 mM NaCl and 2 mM EDTA for 2-4 hours at 37° C. The antibody concentration was then adjusted to 1 mg/ml with 10 mM borate buffer pH 8.4 containing 150 mM NaCl, 2 mM EDTA, 6% sucrose and a 5-20 molar excess of drug-linker conjugate to antibody was added from a 10 mM solution in DMSO. The reaction was carried out for 1-4 h at room temperature or 37° C., in the presence of 10% DMSO. The drug excess was quenched by addition of 2.5 moles of N-acetylcysteine per mole of drug and incubation for 1 h at room temperature. After dialysis against 25 mM His buffer pH 6.5 containing 150 mM NaCl and 6% sucrose overnight at 4° C., the ADCs were purified by chromatography or ultrafiltration. The ADC concentrations were determined by using the BCA assay with IgG as standard and the purified ADCs were stored at 4° C., after sterile filtration on 0.2 µm filter.

ADCs were further analyzed by SDS-PAGE and SEC (TSK G3000 SWXL column), as previously described in example 4, to confirm drug conjugation and rebridging, and to determine the content of monomers and aggregates. The content of monomers was around 95% (FIG. 23 and table 13).

TABLE 13

| Content of monomers | |
|---|---|
| ADC | % of monomers |
| Ab1 (208F2) | 99.8 |
| Ab1- F562524 (208F2-F562524) | 94.1 |
| Ab1- F562646 (208F2-F562646) | 94.8 |
| Ab2 (c9G4) | 99.7 |
| Ab2- F562524 (c9G4-F562524) | 94.4 |
| Ab2- F562646 (c9G4-F562646) | 94.7 |

5.2. ADC Analysis by Native LC-MS

ADCs were analyzed by native liquid chromatography-mass spectrometry on a UPLC Acquity H Class Bio system coupled to a Synapt G2Si mass spectrometer (Waters). LC separation was performed on 2 Polyhydroxyethyl A columns (Poly-LC, 150×1 mm, 300 A, 5 µm) connected in series. Samples were diluted to 0.2 mg/ml with the eluant buffer (150 mM ammonium acetate). Four µg of sample were injected and eluted at a flow rate of 40 µL/min. The mass spectrometer was operated in positive mode with a capillary voltage of 2.9 kV. The sample cone was set at 150 V. Analyses were performed in the range of m/z 1000-8000 with a 1 sec scan time. FIG. 24 shows the m/z spectra before deconvolution. The DAR distribution was determined after deconvolution of MS spectra using MaxEnt™ algorithm from Mass Lynx software (Waters) (FIG. 25). Average DAR values were calculated by using the following equation (where j is the maximum number of drug load):

$$DAR = \frac{(\sum_{i=0}^{j} i * \text{intensity } Di)}{\sum_{i=0}^{j} \text{intensity } Di}$$

The results are presented in the Table 14 below.

TABLE 14

| ADC analysis by native LC-MS analysis: DAR distribution and average DAR | | | | | | | | | | |
|---|---|---|---|---|---|---|---|---|---|---|
| | DAR distribution (%) | | | | | | | | | Average |
| ADC | DAR0 | DAR1 | DAR2 | DAR3 | DAR4 | DAR5 | DAR6 | DAR7 | DAR8 | DAR |
| hz208F2-F562524 | 0 | 0 | 0 | 11 | 68 | 21 | 0 | 0 | 0 | 4.1 |
| hz208F2-F562646 | 0 | 0 | 0 | 0 | 79 | 21 | 0 | 0 | 0 | 4.2 |
| c9G4-F562524 | 0 | 0 | 0 | 11 | 67 | 23 | 0 | 0 | 0 | 4.1 |
| c9G4-F562646 | 0 | 0 | 0 | 0 | 82 | 18 | 0 | 0 | 0 | 4.2 |

5.3. In Vitro Stability

The ADC hz208F2-F562524 was incubated at 200 μg/ml in cynomolgus serum at 37° C., for a period of 14 days. Samples were collected at day 0, 3, 7 and 14, and stored at −80° C., until LC-MS analysis to determine the average DAR.

Before LC-MS analysis, the samples were immunopurified by using Streptavidin magnetic beads (M-280, Invitrogen) coated with a Capture Select anti-human IgG-Biotin conjugate (Life Technologies, 8 μg antibody/200 μL beads). Samples were incubated with the anti-IgG-coated beads for 2 h at room temperature (100 μL sample/200 μL beads) before acidic elution with 40 μL of 0.4% trifluoroacetic acid. The pH was increased by adding 4 μL of a 3 M Tris/HCL pH 8.8 solution. The immunopurified samples were incubated with 2 μL of IgGZero for 30 minutes at 37° C., before LC-MS analysis in native conditions as described above. The DAR distribution was determined after deconvolution of MS spectra using MaxEnt™ algorithm from Mass Lynx software (Waters), and average DAR values were calculated by using the following equation (where j is the maximum number of drug load):

$$DAR = \frac{\left(\sum_{i=0}^{j} i * \text{intensity } Di\right)}{\sum_{i=0}^{j} \text{intensity } Di}$$

The results are presented in the Table 15 below. The ADC hz208F2-F562524 was shown to be highly stable up to 14 days after in vitro incubation in cynomolgus serum.

TABLE 15

In vitro stability study of hz208F2-F562524: DAR distribution and average DAR

| Day | DAR distribution (%) | | | | | | | | | Average DAR |
|---|---|---|---|---|---|---|---|---|---|---|
| | DAR0 | DAR1 | DAR2 | DAR3 | DAR4 | DAR5 | DAR6 | DAR7 | DAR8 | |
| 0 | 0 | 0 | 0 | 18 | 57 | 25 | 0 | 0 | 0 | 4.1 |
| 3 | 0 | 0 | 0 | 19 | 54 | 27 | 0 | 0 | 0 | 4.1 |
| 7 | 0 | 0 | 0 | 18 | 50 | 32 | 0 | 0 | 0 | 4.1 |
| 10 | 0 | 0 | 0 | 19 | 54 | 28 | 0 | 0 | 0 | 4.1 |

5.4. In Vitro Cytotoxicity

The cytotoxicity of the ADCs was evaluated in MCF-7 and NCI-H2122 cells. Cells were plated on 96 well plates (2500 cells per well) in complete growth media. The day after, serial dilutions of the tested ADCs were added to the corresponding wells and incubated at 37° C., for 6 days. Cell viability was determined by measuring ATP using the cell Titer Glo kit (Promega). Luminescence was read using the plate reader Mithras from Berthold Company. The results obtained, expressed in percentage of viability, are shown in FIGS. 26 and 27. The viability in the non-treated wells was considered as 100%.

As expected, the ADCs hz208F2-F562524 and hz208F2-F562646 decreased dramatically cell viability. $EC_{50}$ values of $2.48 \cdot 10^{-11}$ and $1.92 \cdot 10^{-12}$ M were determined on NCI-H2122 cells for hz208F2-F562524 and hz208F2-F562646, respectively, and $EC_{50}$ values of $5.86 \cdot 10^{-12}$ and $9.45 \cdot 10^{-13}$ M were obtained on MCF-7 cells for hz208F2-F562524 and hz208F2-F562646, respectively, indicating potent cytotoxic activity. On the opposite, the corresponding ADCs synthesized with the irrelevant antibody showed a modest cytotoxic activity on both MCF-7 and NCI-H2122 cells.

5.5. In Vivo Anti-Tumoral Activity

Seven weeks old female SCID mice (Charles River Laboratories) were engrafted subcutaneously with 10.106 Caov3 cells (6 animals per groups). Treatment by intravenous administration (Q7d2) of the ADC hz208F2-F562524 (0.3 mg/kg), the corresponding control ADC c9G4-F562524 (0.3 mg/kg), or the vehicle was initiated when tumors reached approximately 150 mm3. Tumor volume (Length×Width×Height×0.52) was measured by electronic caliper twice weekly during approximatively 50 days after the first injection. The results are presented on FIG. 28. A complete tumor regression can be observed after 2 injections of the ADC hz208F2-F562524 whereas no anti-tumoral effect was observed with the control ADC or the vehicle.

5.6. Conclusion

The ADCs synthesized with PNU-159682 derivatives by using the sulfomaleimide-linker technology are highly homogeneous and stable in serum. Their efficacy was demonstrated in different in vitro and in vivo models.

6. OVERALL CONCLUSIONS

Overall, the sulfomaleimide-based linker technology described in this invention give a better stability in the plasma of different species and a better efficacy in in vitro models compared to usual maleimide-based linkers used for compounds in the market such as Adcetris. These properties have translated in a clear improvement of in vivo efficacy in different cell lines and more notably for cell lines with a lower expression of the antigen (CAOV3).

A better tolerability is also expected since the ADCs according to the invention are more stable in the circulation associated with an improved efficacy and safety margin in human treatment.

---

The invention claimed is:

1. A linker-drug conjugate of the following formula (II):

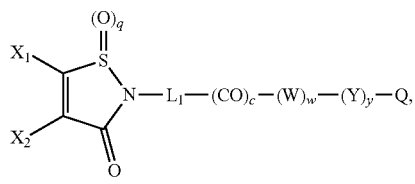

(II)

or a salt thereof,
wherein:
$X_1$ and $X_2$ represent, independently of each other, H, a halogen atom, a ($C_1$-$C_6$)alkoxy, an optionally substituted aryloxy, or —O—($CH_2CH_2O$)$_r$H, provided that $X_1$ and $X_2$ do not represent H at the same time;
$L_1$ represents a group of formula $L_1'$-(CO—$Z'$)$_{z'}$ with $L_1'$ being —($CH_2$)$_n$—, —($CH_2CH_2O$)$_m$—$CH_2$—$CH_2$—, arylene, heteroarylene, cycloalkanediyl, —($CH_2$)$_n$-arylene-, —($CH_2$)$_n$-heteroarylene-, —($CH_2$)$_n$-cycloalkanediyl-, -arylene-($CH_2$)$_p$—, -heteroarylene-($CH_2$)$_p$—, -cycloalkanediyl-($CH_2$)$_p$—, —($CH_2$)$_n$-arylene-($CH_2$)$_p$—, —($CH_2$)$_n$-heteroarylene-($CH_2$)$_p$—, —($CH_2$)$_n$-cycloalkanediyl-($CH_2$)$_p$—, —($CH_2CH_2O$)$_m$—$CH_2$—$CH_2$-arylene-($CH_2$)$_p$—, —($CH_2CH_2O$)$_m$—$CH_2$—$CH_2$-heteroarylene-($CH_2$)$_p$—, —($CH_2CH_2O$)$_m$—$CH_2$—$CH_2$-cycloalkanediyl-($CH_2$)$_p$—, —($CH_2$)$_n$-arylene-$CH_2$—$CH_2$—($OCH_2CH_2$)$_m$—, —($CH_2$)$_n$-heteroarylene-$CH_2$—$CH_2$—($OCH_2CH_2$)$_m$—, or —($CH_2$)$_n$-cycloalkanediyl-$CH_2$—$CH_2$—($OCH_2CH_2$)$_m$—;
each W independently represents an amino acid unit;

Y is PAB-CO—(Z)$_z$—, with PAB being

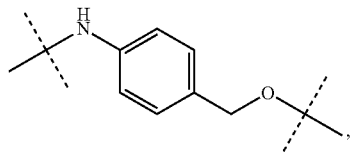

the oxygen of the PAB unit being linked to CO—(Z)$_z$;
Z is —$NR_4$—($CH_2$)$_u$—$NR_5$—, —$NR_4$—($CH_2$)$_u$—$NR_5$—CO—, —$NR_4$—($CH_2$)$_u$—$NR_5$—CO—($CH_2$)$_v$—, or —$NR_4$—($CH_2$)$_u$—$NR_5$—CO—($CH_2$)$_v$—CO—, the $NR_4$ group being linked to the CO group of PAB-CO;
$Z'$ is —$NR_4$—($CH_2$)$_u$—$NR_5$— or —$NR_4$—($CH_2$)$_u$—$NR_5$—CO—($CH_2$)$_v$—, the $NR_4$ group being linked to the CO group of CO—$Z'$;
$R_4$ and $R_5$ are independently H or a ($C_1$-$C_6$)alkyl group;
Q is a residue of an auristatin, an anthracycline, camptothecin, SN-38, a tubulysin, a calicheamicin, a maytansinoid, a duocarmycin, an amanitine, a pyrrolobenzodiazepine, or an activator of immune check point;
c is 0 or 1;
m is an integer from 1 to 15;
n is an integer from 1 to 6;
p is an integer from 1 to 6;
q is 0, 1 or 2;
r is an integer from 1 to 24;
u is an integer from 1 to 6;
v is an integer from 1 to 6;
w is an integer from 0 to 5;
y is 0 or 1;
z is 0 or 1; and
$z'$ is 0 or 1.

2. The linker-drug conjugate according to claim 1, wherein it has the following formula (IIa):

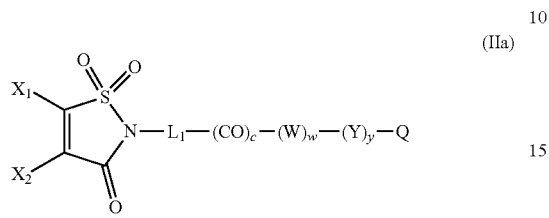

(IIa)

or a salt thereof,
wherein:
y is 0 when w is 0 and y is 0 or 1 when w is an integer from 1 to 5.

3. The linker-drug conjugate according to claim 1, wherein Q is:
a residue of monomethyl auristatin F (MMAF), monomethyl auristatin E (MMAE), or monomethyl dolastatin-10 or a residue of a derivative thereof having the following formula (C):

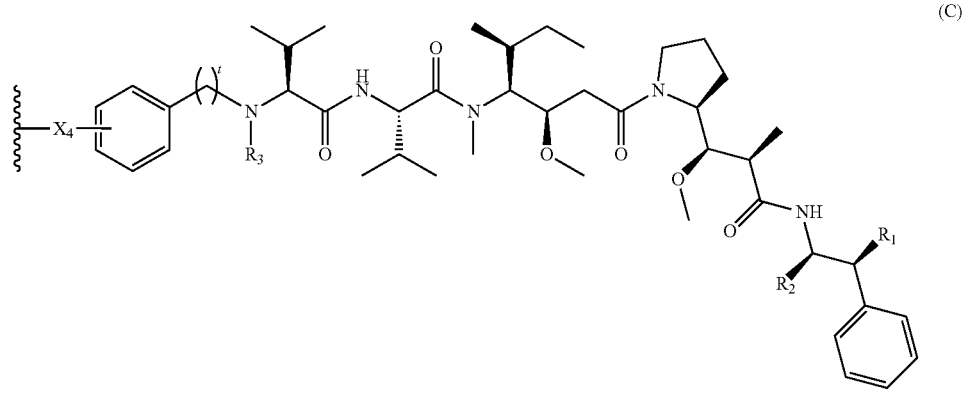

(C)

wherein:
R$_1$ is H or OH,
R$_2$ is a (C$_1$-C$_6$)alkyl, COOH, COO—((C$_1$-C$_6$)alkyl) or a thiazolyl,
R$_3$ is H or a (C$_1$-C$_6$)alkyl,
X$_4$ is O or NR$_9$,
R$_9$ is H or (C$_1$-C$_6$)alkyl, and
t is an integer from 1 and 8;
a residue of daunorubicine, doxorubicine, epirubicine, idarubicine, 2-pyrrolinodoxorubicine, pro-2-pyrrolinodoxorubicine, or PNU-159682 or a residue of following formula (A) or (B):

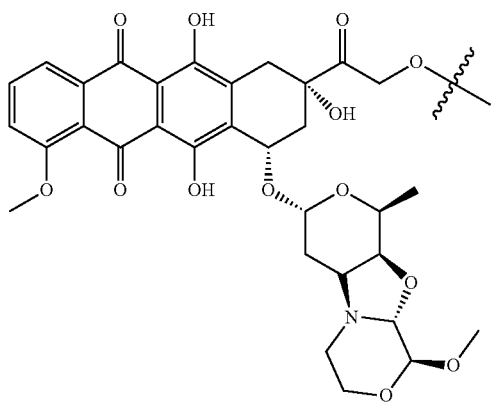

(A)

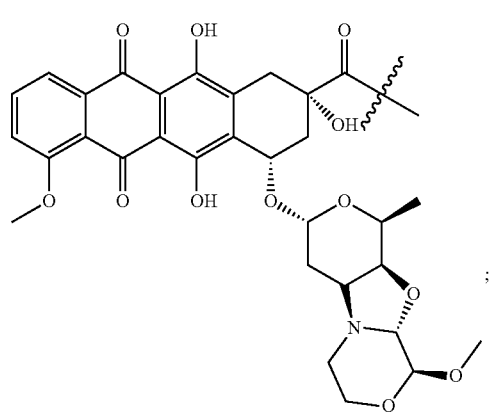

(B)

a residue of camptothecin or SN-38;
a residue of tubulysin A, tubulysin B, tubulysin C or tubulysin D;
a residue of esperamicin, calicheamicin γ1, or N-acetyl dimethyl hydrazide calicheamicin;
a residue of maytansine, DM1 or DM4;
a residue of duocarmycin A, duocarmycin B1, duocarmycin B2, duocarmycin Cl, duocarmycin C2, duocarmycin D duocarmycin SA, or CC-1065;
a residue of α-amanitine, β-amanitine, γ-amanitine or ε-amanitine;
a residue of anthramycin or SGD-1882;

a residue of following formula (D):

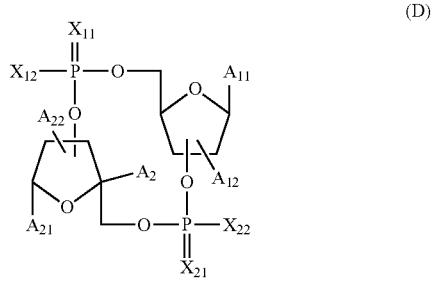

(D)

wherein:
X$_{11}$ and X$_{21}$ are independently O or S,
X$_{12}$ and X$_{22}$ are independently OH, SH, O or S,
A$_{11}$ and A$_{21}$ are independently a group of formula:

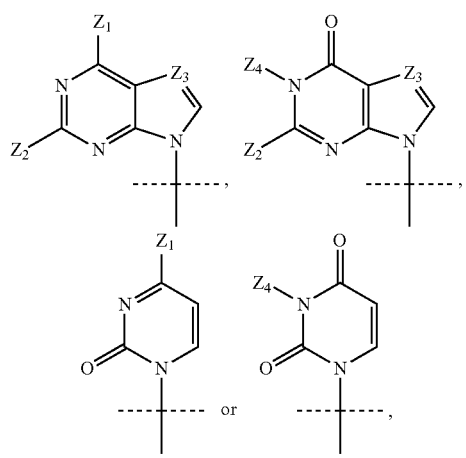

where:
Z$_1$ is OR$_{11}$, NR$_{11}$R$_{12}$, O or NR$_{11}$, with R$_{11}$ and R$_{12}$ being independently H, R$_{13}$ or COR$_{13}$, with R$_{13}$ being (C$_1$-C$_6$)alkyl, aryl or aryl(C$_1$-C$_6$)alkyl,
Z$_2$ is H, NR$_{21}$R$_{22}$ or NR$_{21}$, with R$_{21}$ and R$_{22}$ being independently H, R$_{23}$ or COR$_{23}$, with R$_{23}$ being (C$_1$-C$_6$)alkyl, aryl or aryl(C$_1$-C$_6$)alkyl,
Z$_3$ is N or CR$_{33}$, with R$_{33}$ being H or a halogen atom, and
Z$_4$ is H or a (C$_1$-C$_6$)alkyl,
A$_{12}$ and A$_{22}$ are independently H, OH or F, and
A$_2$ is H or A$_2$ and A$_{22}$ are linked together with A$_2$ being CH$_2$ and A$_{22}$ being 0,
wherein:
when X$_{12}$ is O or S, then X$_{22}$ is not O and is not S, Z$_1$ is not O and is not NR$_{11}$, Z$_2$ is not NR$_{21}$, and the residue of the STING agonist is linked to the rest of the molecule by X$_{12}$;
when X$_{22}$ is O or S, then X$_{12}$ is not O and is not S, Z$_1$ is not O and is not NR$_{11}$, Z$_2$ is not NR$_{21}$, and the residue of the STING agonist is linked to the rest of the molecule by X$_{22}$;
when Z$_1$ is O or NR$_{11}$, then X$_{12}$ is not O and is not S, X$_{22}$ is not O and is not S, Z$_2$ is not NR$_{21}$, and the residue of the STING agonist is linked to the rest of the molecule by Z$_1$;
when Z$_2$ is NR$_{21}$, then X$_{12}$ is not O and is not S, X$_{22}$ is not O and is not S, Z$_1$ is not O and is not NR$_{11}$, and the residue of the STING agonist is linked to the rest of the molecule by Z$_2$.

4. The linker-drug conjugate according to claim 1, wherein Q has:
the following formula (A):
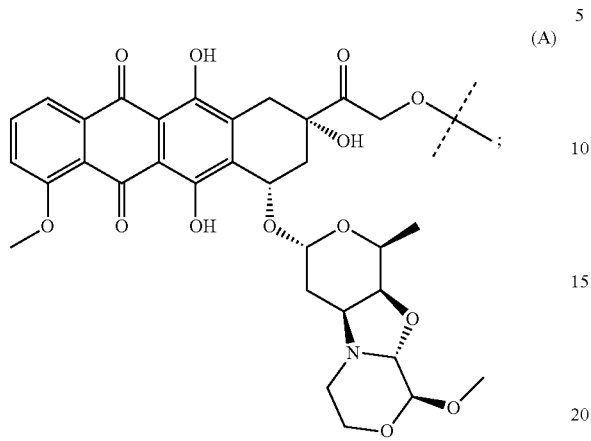
the following formula (B):
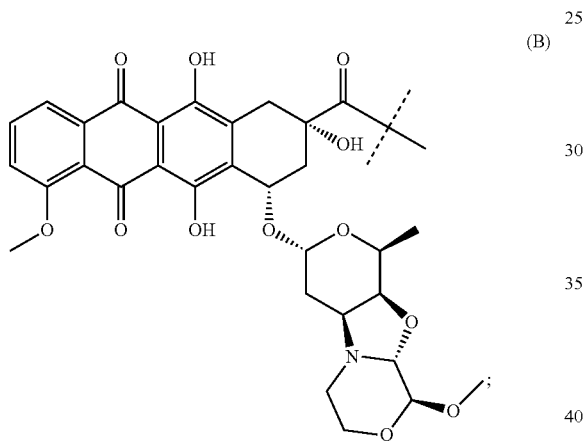
the following formula (C):
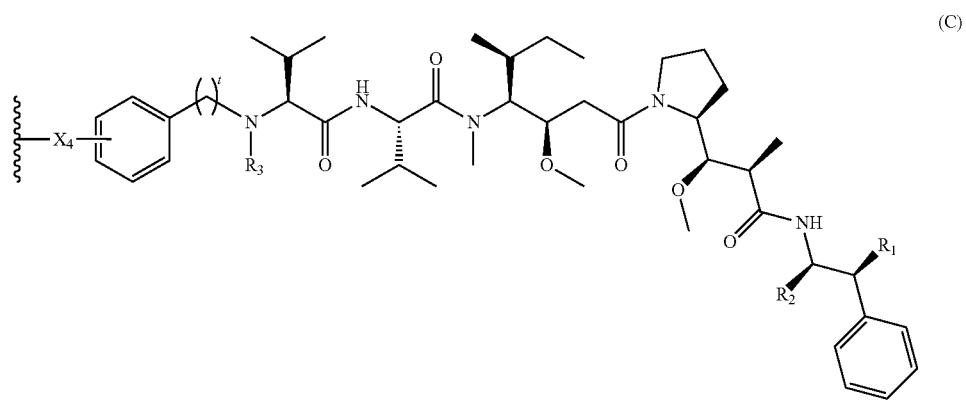

wherein:
R$_1$ is H or OH,
R$_2$ is a (C$_1$-C$_6$)alkyl, COOH, COO—((C$_1$-C$_6$)alkyl) or a thiazolyl,
R$_3$ is H or a (C$_1$-C$_6$)alkyl,
X$_4$ is O or NR$_9$,
R$_9$ is H or (C$_1$-C$_6$)alkyl, and
t is an integer from 1 and 8; or
the following formula (D):

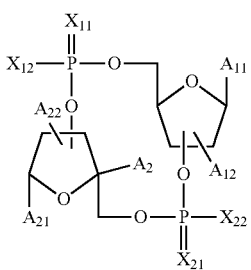
(D)

wherein:
X$_{11}$ and X$_{21}$ are independently O or S,
X$_{12}$ and X$_{22}$ are independently OH, SH, O or S,
A$_{11}$ and A$_{21}$ are independently a group of formula:

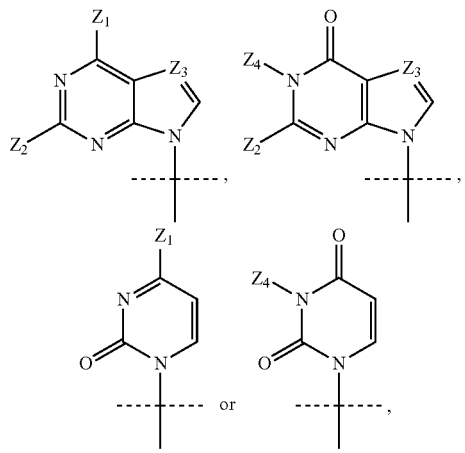

where:
Z$_1$ is OR$_{11}$, NR$_{11}$R$_{12}$, O or NR$_{11}$, with R$_{11}$ and R$_2$ being independently H, R$_{13}$ or COR$_{13}$, with R$_{13}$ being (C$_1$-C$_6$)alkyl, aryl or aryl(C$_1$-C$_6$)alkyl,
Z$_2$ is H, NR$_{21}$R$_{22}$ or NR$_{21}$, with R$_{21}$ and R$_{22}$ being independently H, R$_{23}$ or COR$_{23}$, with R$_{23}$ being (C$_1$-C$_6$)alkyl, aryl or aryl(C$_1$-C$_6$)alkyl,
Z$_3$ is N or CR$_{33}$, with R$_{33}$ being H or a halogen atom, and
Z$_4$ is H or a (C$_1$-C$_6$)alkyl,
A$_{12}$ and A$_{22}$ are independently H, OH or F, and
A$_2$ is H or A$_2$ and A$_{22}$ are linked together with A$_2$ being CH$_2$ and A$_{22}$ being O,
wherein:
when X$_{12}$ is O or S, then X$_{22}$ is not O and is not S, Z$_1$ is not O and is not NR$_{11}$, Z$_2$ is not NR$_{21}$, and the residue of the STING agonist is linked to the rest of the molecule by X$_{12}$;
when X$_{22}$ is O or S, then X$_{12}$ is not O and is not S, Z$_1$ is not O and is not NR$_{11}$, Z$_2$ is not NR$_{21}$, and the residue of the STING agonist is linked to the rest of the molecule by X$_{22}$;
when Z$_1$ is O or NR$_{11}$, then X$_{12}$ is not O and is not S, X$_{22}$ is not O and is not S, Z$_2$ is not NR$_{21}$, and the residue of the STING agonist is linked to the rest of the molecule by Z$_1$;
when Z$_2$ is NR$_{21}$, then X$_{12}$ is not O and is not S, X$_{22}$ is not O and is not S, Z$_1$ is not O and is not NR$_{11}$, and the residue of the STING agonist is linked to the rest of the molecule by Z$_2$.

5. A pharmaceutical composition comprising the linker-drug conjugate according to claim 1 and at least one pharmaceutically acceptable excipient.

6. The linker-drug conjugate according to claim 1, wherein the activator of immune check point is a residue of a stimulator of interferon genes (STING) agonist or a residue of an indoleamine 2,3-dioxygenase (IDO) inhibitor.

7. A method for covalently linking a drug to a binding unit by reacting a linker-drug conjugate according to claim 1 with the binding unit,
wherein the binding unit is an antibody or an antigen binding fragment thereof.

8. The method according to claim 7, wherein q is 2.

9. The linker-drug conjugate according to claim 1, wherein q represents 2.

10. The linker-drug conjugate according to claim 1, wherein at least X$_1$ or X$_2$ represents a halogen atom.

11. The linker-drug conjugate according to claim 1, wherein one of X$_1$ and X$_2$ represents Br or Cl and the other group represents H, Cl or Br.

12. The linker-drug conjugate according to claim 1, wherein q represents 2, one of X$_1$ and X$_2$ represents Br or Cl and the other group represents H, Cl or Br.

13. The linker-drug conjugate according to claim 1, wherein L$_1$' represents —(CH$_2$)$_n$—, —(CH$_2$CH$_2$O)$_m$—CH$_2$—CH$_2$—, arylene, -cycloalkanediyl-, —(CH$_2$)$_n$-arylene-, -arylene-(CH$_2$)$_n$—, —(CH$_2$)$_n$-cycloalkanediyl-, -cycloalkanediyl-(CH$_2$)$_n$—,

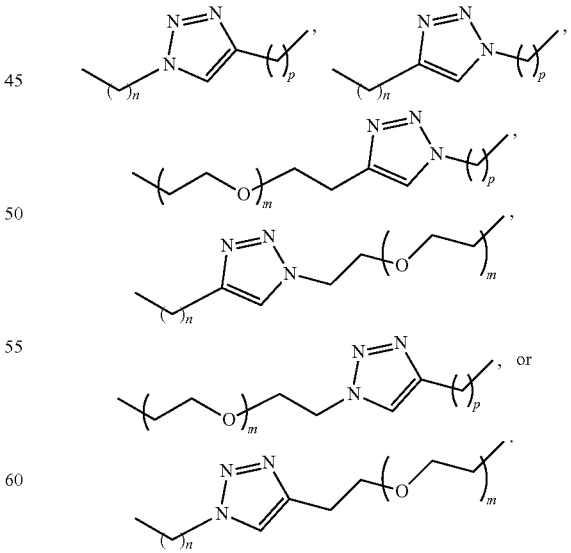

14. The linker-drug conjugate according to claim 1, wherein L$_1$' is —(CH$_2$)$_n$— or —(CH$_2$CH$_2$O)$_m$—CH$_2$—CH$_2$—.

15. The linker-drug conjugate according to claim 1, wherein each W is selected from alanine, valine, leucine, isoleucine, methionine, phenylalanine, tryptophan, proline, lysine, lysine protected with acetyl or formyl, arginine, arginine protected with tosyl or nitro group(s), histidine, ornithine, ornithine protected with acetyl or formyl, and citrulline.

16. The linker-drug conjugate according to claim 1, wherein:
   w=0 and $(W)_w$ is a bond, or
   w=2 and $(W)_w$ is Val-Cit or Val-Ala.

17. The linker-drug conjugate according to claim 1, wherein:
   $X_1$ and $X_2$ are identical and are selected from Cl, Br, $(C_1-C_6)$alkoxy and an aryloxy optionally substituted with one or several groups selected from halogen, CN, $NO_2$ and an aryloxy optionally substituted with one or several halogen atoms, or
   one of $X_1$ and $X_2$ is H and the other is selected from Cl, Br, $(C_1-C_6)$alkoxy and an aryloxy optionally substituted with one or several groups selected from halogen, CN, $NO_2$ and an aryloxy optionally substituted with one or several halogen atoms.

18. The linker-drug conjugate according to claim 1, wherein $X_3$ is H when y=z=1 and Z is —$NR_4$—$(CH_2)_u$—$NR_5$— or when c=w=y=0, z'=1 and Z' is —$NR_4$—$(CH_2)_u$—$NR_5$— and in the other cases, $X_3$ is OH, Cl or N-succinimidyloxy.

* * * * *